US012582767B2

(12) United States Patent
Weber et al.

(10) Patent No.: US 12,582,767 B2
(45) Date of Patent: Mar. 24, 2026

(54) COMPRESSIBLE, MINIMALLY INVASIVE IMPLANTS AND RELATED SYSTEMS AND METHODS

(71) Applicants: Taiyo Weber, Veysonnaz (CH); Paul Weber, Veysonnaz (CH)

(72) Inventors: Taiyo Weber, Veysonnaz (CH); Paul Weber, Veysonnaz (CH)

( * ) Notice: Subject to any disclaimer, the term of this patent is extended or adjusted under 35 U.S.C. 154(b) by 947 days.

(21) Appl. No.: 17/650,459

(22) Filed: Feb. 9, 2022

(65) Prior Publication Data

US 2023/0211076 A1      Jul. 6, 2023

Related U.S. Application Data

(60) Provisional application No. 63/295,068, filed on Dec. 30, 2021.

(51) Int. Cl.
| | |
|---|---|
| *A61M 5/142* | (2006.01) |
| *A61B 5/00* | (2006.01) |
| *A61B 90/90* | (2016.01) |
| *A61N 1/375* | (2006.01) |

(52) U.S. Cl.
CPC ....... *A61M 5/14276* (2013.01); *A61B 5/0031* (2013.01); *A61B 90/90* (2016.02); *A61N 1/3752* (2013.01)

(58) Field of Classification Search
CPC .. A61M 5/14276; A61B 5/0031; A61B 90/90; A61B 5/076; A61B 5/02055; A61B 5/686; A61N 1/3752; A61N 1/375; A61N 1/36007; A61N 1/3605; A61N 1/0504; A61N 1/0558; A61N 1/37518; A61N 1/37205; A61N 1/3787
See application file for complete search history.

(56) References Cited

U.S. PATENT DOCUMENTS

| | | | |
|---|---|---|---|
| 3,760,984 A | 9/1973 | Theeuwes | |
| 3,835,207 A | 9/1974 | Frost | |
| 5,411,537 A | 5/1995 | Munshi | |
| 5,431,682 A | 7/1995 | Hedberg | |
| 5,565,443 A | 10/1996 | Lanquetin | |
| 5,633,000 A | 5/1997 | Grossman | |
| 5,645,583 A | 7/1997 | Villain | |
| 5,990,194 A | 11/1999 | Dunn | |

(Continued)

FOREIGN PATENT DOCUMENTS

| | | | |
|---|---|---|---|
| EP | 2617440 A3 | 2/2013 | |

OTHER PUBLICATIONS

Langer R. "Wireless on-Demand Drug Delivery," Nature Electronics, 2021.

(Continued)

*Primary Examiner* — Mark W. Bockelman
(74) *Attorney, Agent, or Firm* — Matthew D. Thayne; Thayne and Davis LLC

(57) ABSTRACT

Systems and methods involving implants positioned within implant pockets through minimally invasive entrance incisions, along with related implants. In some implementations, implants may be folded, rolled, or otherwise compressed to fit within subcutaneous implant pockets, after which they may be decompressed to fit within an implant pocket having one or more dimensions substantially larger than the entrance incision. Such implants may be used for a variety of purposes, including generating electrical energy for various other implants located throughout the body.

19 Claims, 53 Drawing Sheets

(56) References Cited

U.S. PATENT DOCUMENTS

| | | | |
|---|---|---|---|
| 6,058,330 A | 5/2000 | Borza |
| 6,203,813 B1 | 3/2001 | Goobeman |
| 6,961,619 B2 | 11/2005 | Casey |
| 7,191,007 B2 | 3/2007 | Desai |
| 7,209,784 B2 | 4/2007 | Craig Schmidt |
| 7,214,206 B2 | 5/2007 | Rue |
| 7,295,878 B1 | 11/2007 | Meadows |
| 7,376,466 B2 | 5/2008 | He |
| 7,429,920 B2 | 9/2008 | Smythe |
| 7,485,152 B2 | 2/2009 | Haynes |
| 7,622,405 B1 | 11/2009 | Arvidson |
| 7,642,013 B2 | 1/2010 | Howard |
| 7,684,864 B2 | 3/2010 | Olson |
| 7,776,029 B2 | 8/2010 | Whitehurst |
| 7,803,021 B1 | 9/2010 | Brase |
| 7,867,193 B2 | 1/2011 | McKenna |
| 7,916,013 B2 | 3/2011 | Stevenson |
| 8,119,153 B2 | 2/2012 | Weber |
| 8,357,388 B2 | 1/2013 | Mckay |
| 8,502,192 B2 | 8/2013 | Kwak |
| 8,530,921 B2 | 9/2013 | Ibbeston |
| 8,591,531 B2 | 11/2013 | Buevich |
| 8,652,218 B2 | 2/2014 | Goldfarb |
| 8,697,117 B2 | 4/2014 | Zilberman |
| 8,706,230 B2 | 4/2014 | Rousso |
| 8,751,003 B2 | 6/2014 | Diubaldi |
| 8,795,153 B2 | 8/2014 | Forsell |
| 8,798,752 B2 | 8/2014 | Eder |
| 8,828,311 B2 | 9/2014 | Medina |
| 8,870,967 B2 | 10/2014 | Herr |
| 8,876,795 B2 | 11/2014 | Fiering |
| 8,983,608 B2 | 3/2015 | Pianca |
| 9,050,078 B2 | 6/2015 | Ben Rubi |
| 9,072,886 B2 | 7/2015 | Gaunt |
| 9,107,796 B2 | 8/2015 | Forsell |
| 9,149,370 B2 | 10/2015 | Herr |
| 9,198,999 B2 | 12/2015 | Hall |
| 9,259,578 B2 | 2/2016 | Torgerson |
| 9,278,163 B2 | 3/2016 | Patel |
| 9,283,394 B2 | 3/2016 | Whitehurst |
| 9,362,571 B2 | 6/2016 | Hodgkinson |
| 9,381,299 B2 | 7/2016 | Kuo |
| 9,441,080 B2 | 9/2016 | Trexler |
| 9,486,745 B2 | 11/2016 | Takagi |
| 9,510,849 B2 | 12/2016 | Clark, III |
| 9,570,524 B2 | 2/2017 | Lee |
| 9,763,917 B2 | 9/2017 | Zanella |
| 9,788,978 B2 | 10/2017 | Rojo |
| 9,980,800 B2 | 5/2018 | Koullick |
| 9,987,493 B2 | 6/2018 | Torgerson |
| 10,005,269 B2 | 6/2018 | Hall et al. |
| 10,080,893 B2 | 9/2018 | Meskens |
| 10,107,488 B2 | 10/2018 | Song |
| 10,133,426 B2 | 11/2018 | Den Boer |
| 10,137,011 B2 | 11/2018 | Herr |
| 10,143,570 B2 | 12/2018 | Herr |
| 10,226,417 B2 | 3/2019 | Jarrett |
| 10,251,738 B2 | 4/2019 | Chu |
| 10,251,954 B2 | 4/2019 | Sawhney |
| 10,276,631 B2 | 4/2019 | Gossler |
| 10,285,968 B2 | 5/2019 | Klein |
| 10,297,712 B2 | 5/2019 | Bibl |
| 10,297,719 B2 | 5/2019 | Chen |
| 10,326,109 B2 | 6/2019 | Kim |
| 10,340,546 B1 | 7/2019 | Khan et al. |
| 10,342,961 B2 | 7/2019 | Dalton et al. |
| 10,357,350 B2 | 7/2019 | Astani-Matthies |
| 10,426,970 B2 | 10/2019 | Deisseroth |
| 10,434,261 B2 | 10/2019 | Snyder |
| 10,449,257 B2 | 10/2019 | Hauser |
| 10,568,804 B2 | 2/2020 | Forsell |
| 10,603,101 B2 | 3/2020 | Weber |
| 10,617,402 B2 | 4/2020 | Reddy |
| 10,636,349 B2 | 4/2020 | Shin |
| 10,653,888 B2 | 5/2020 | Oron |

| | | | |
|---|---|---|---|
| 10,765,500 B2 | 9/2020 | Buevich |
| 10,780,275 B2 | 9/2020 | Robinson |
| 10,813,763 B2 | 10/2020 | Schlachter |
| 10,918,875 B2 | 2/2021 | Maile |
| 10,952,786 B2 | 3/2021 | Weber |
| 11,141,062 B2 | 10/2021 | Geissler |
| 2002/0166760 A1 | 11/2002 | Prentiss |
| 2003/0009145 A1 | 1/2003 | Struijker-Boudier |
| 2004/0236415 A1 | 11/2004 | Thomas |
| 2005/0055014 A1 | 3/2005 | Coppeta |
| 2005/0256549 A1 | 11/2005 | Holzer |
| 2006/0020297 A1 | 1/2006 | Gerber |
| 2006/0129192 A1 | 6/2006 | Greatbatch |
| 2008/0027513 A1 | 1/2008 | Carbanaru |
| 2008/0085265 A1 | 4/2008 | Schneider |
| 2009/0259095 A1 | 10/2009 | Sieveking |
| 2010/0121256 A1 | 5/2010 | Jolly |
| 2011/0169610 A1 | 7/2011 | Geissler |
| 2012/0226265 A1 | 9/2012 | Chiao |
| 2013/0144356 A1 | 6/2013 | Horn |
| 2013/0261766 A1 | 10/2013 | Langlois |
| 2014/0121741 A1 | 5/2014 | Benett |
| 2014/0214010 A1 | 7/2014 | Kuo |
| 2014/0324138 A1 | 10/2014 | Wentz |
| 2015/0080855 A1 | 3/2015 | Kassab |
| 2015/0129664 A1 | 5/2015 | Brar |
| 2015/0372051 A1 | 12/2015 | Bower |
| 2016/0000548 A1 | 1/2016 | Aiden |
| 2016/0003229 A1 | 1/2016 | Mescher |
| 2016/0166504 A1 | 6/2016 | Jarrett |
| 2016/0250049 A1 | 9/2016 | Stalker |
| 2016/0331738 A1 | 11/2016 | Jarrett |
| 2018/0042549 A1 | 2/2018 | Ho |
| 2018/0272136 A1 | 9/2018 | Horn |
| 2018/0359850 A1 | 12/2018 | Rogers |
| 2019/0016089 A1 | 1/2019 | Bhatnagar |
| 2019/0054015 A1 | 2/2019 | Kim |
| 2019/0247306 A1 | 8/2019 | Cleek |
| 2019/0343991 A1 | 11/2019 | Andrews |
| 2019/0388500 A1 | 12/2019 | Kuzma |
| 2020/0015973 A1 | 1/2020 | Lindsey |
| 2020/0197526 A1 | 6/2020 | Brudno |
| 2020/0254266 A1 | 8/2020 | Oron |
| 2020/0268504 A1 | 8/2020 | Chitre |
| 2020/0306059 A1 | 10/2020 | Corman |
| 2020/0315488 A1 | 10/2020 | Rogers |
| 2020/0390643 A1 | 12/2020 | Forsell |
| 2020/0395168 A1 | 12/2020 | Ridler |
| 2020/0406030 A1 | 12/2020 | Mashiach |
| 2021/0077114 A1 | 3/2021 | Bonutti |
| 2021/0265328 A1 | 8/2021 | Lee |

OTHER PUBLICATIONS

Horton. "Induced Voltage and Current in Parallel Transmission Lines: Causes and Concerns", 2008, IEEE Transactions on Power Delivery, 23(4): 2339-2346.

Giordano. 'Molecular Basis of Different Outcomes for Drug-Eluting Stents that Release Sirolimus or Tacrolimus', Curr. Opin. Drug Discov. Devel., 2010; 13: 159-68.

Lee. The Newest Generation of Drug-Eluting Stents and Beyond, European Cardiology Review, 2018; 13: 54-9.

Nishida. "Biocompatibility and Durability of Teflon-Coated Platinum-Iridium Wires Implanted in the Vitreous Cavity". 2011, J. Artif. Organs, PubMed.

Gupta. "Randomized Trial of a Dry-Powder, Fibrin Sealant in Vascular Procedures". doi.org/10.1016/j.jvs.2015.05.038, PubMed.

Bhagat. "Degradable Adhesives for Surgery and Tissue Engineering", BioMacromolecules, American Chemical Society, 3009-3039, 2017.

Jeong. 'Design, Simulation and Measurement of Flexible PCB Coils for Wearable Device Wireless Power Transfer', Jeong, IEEE, 2018.

Macharia. 'Wireless Inductive Charging for Low Power Devices', 2017.

Li. 'Fully Bioabsorbable Capacitor as an Energy Storage Unit for Implantable Medical Electronics', Advanced Science, 2019.

(56)           References Cited

OTHER PUBLICATIONS

Stewart. 'Implantable Polymeric Drug Delivery Devices: Classification, Manufacture, Materials, and Clinical Applications'. MDPI, 2018; 10: 1379-1317.

Pushparaj. 'Flexible Energy Storage Devices Based on Nanocomposite Paper'. PNAS, 2007; 104: 13574-13577.

Koo. 'Wirelessly controlled, bioresorbable drug delivery device with active valves that exploit electrochemically triggered crevice corrosion'. Health and Medicine, 2020, vol. 6 No. 35.

Kwon. 'Cable-Type Flexible Lithium Ion Battery Based on Hollow Multi-Helix Electrodes'. Advanced Materials, 2012.

Grass F, Wyskovsky W. "Formation of Lumirubin During Light Therapy in Adults." Journal of Biological Sciences 4 (3):357-360 (2004).

Taranovich S. 'Achieve High Power Density with Stacked Inductor'. Aug. 25, 2021. https://www.electronicdesign.com.

Theodor M. "Subcutaneous Blood Pressure Monitoring with An Implantable Optical Sensor". Biomed Microdevices, vol. 5:811-820, 2013.

Mayo Clinic Staff. "Implantable loop recorder: A heart monitoring Device." Mayo Clinic, https://www.mayoclinic.org/tests-procedures/implantable-loop-recorder/pyc-20384986, 2022.

Knodell RG. "Effects Of Phototherapy On Hepatic Function In Human Alcoholic Cirrhosis." Gastroenterology, 70: 1112, 1976.

Ennever JF. Phototherapy For Neonatal Jaundice: Optimal Wavelengths Of Light. J Pediatr, 103: 295, 1983.

Joonkyu L. "Implantable Functional Electrical Stimulation with Inductive Power and Data Transmission System." Pub Dec. 1, 2007, doi.org/10.12701/YUJM.2007.24.2.97.

Sun Y. "Flexible Piezoelectric Energy Harvester/Sensor with High Voltage Output over Wide Temperature Range". Nano Energy, pub Jul. 2019, doi.org/10.1016/j.nanoen.2019.04.055.

Jing Fu. "Flexible Piezoelectric Energy Harvester with Extremely High Power Generation Capability by Sandwich Structure Design Strategy." Applied Math & Interfaces, 2020, DOI: 10.1021/acsami.9b21201.

Randles DA. "How many patients fulfil the surface electrocardiogram criteria for subcutaneous implantable cardioverter-defibrillator implantation?" EP Europace, vol. 16: 1015-1021, 2014.

Wiles BM. "Lead or be led: An Update On Leadless Cardiac Devices For General Physicians." Clin. Med. (Lond) 17: 33-36, 2017.

Yadav S. "Recent Developments in Forward Osmosis Membranes Using Carbon-Based Nanomaterials." ScienceDirect, Desalination 482(May 15, 2020), 114375.

Ahsan Noor Khan et al. "Radio Frequency Controlled Wireless Drug Delivery Devices", Jul. 4, 2019, Applied Physics Reviews 6, 041301, UK.

Sarah A. Stewart et al. "Implantable Polymeric Drug Delivery Devices: Classification, Manufacture, Materials, & Clinical Applications", MDPI Polymers, Aug. 11, 2018, 10(12):1379.

Sihong Wang et al. "Skin-Inspired Electronics: An Emerging Paradigm", Jan. 8, 2018, Accounts of Chemical Research, 51, pp. 1033-1045, UK.

Chi Hwan Lee et al. "Biological lipid membranes for on-demand, wireless drug delivery from thin, bioresorbable electronic implants", May 20, 2015, NPG Asia Materials, 7, e227.

Seng Han Lim et al. "3D Printed Drug Delivery and Testing Systems—a Passing Fad or the Future?", Apr. 12, 2018, Advanced Drug Delivery Reviews, 132 (2018), pp. 139-168.

Franca Nneka Alaribe et al. "Scaffolds from biomaterials: Advantages and Limitations in Bone and Tissue Engineering", May 2016, Biologia 71/4, pp. 353-366, South Africa.

Nanasaheb D. Thorat et al. "Physically Stimulated Nanotheranostics for Next Generation Cancer Therapy: Focus on Magnetic & Light Stim . . . ", Apr. 19, 2019, App.Phys.Rev. 6, 041306.

M. Goiriena-Goikoetxea et al. "Disk-Shaped Magnetic Particles for Cancer Therapy", Aug. 8, 2019, App. Phys. Rev. 7, 011306 (2020).

Amber Neely, "Zens Announces 16 Coil Liberty Qi Charger for more Flexible Wireless Charging", Aug. 23, 2019, https://appleinsider.com.

Jinwei Zhao et al, "Design, Test and Optimization of Inductive Coupled Coils for Implantable Biomed . . . ", Dec. 20, 2018, Journal of Low Power Electronics vol. 15, pp. 76-86, 2019.

Seungtaek Jeong et al. "Design, Simulation and Measurement of Flexible PCB Coils for Wearable Device Wireless Power Transfer", 2018 IEEE WPTC, Jun. 3-7, pp. 1-4, Canada.

Elly Earls, "A Breakthrough in Wireless Charging for Implants", Medical Technology, Issue 6, Mar. 2018.

Nicolynn Davis et al. "Polymeric Drug Delivery Techniques", 2015, Aldrich Materials Science Journal, Sigma-Aldrich Co. LLC.

Adam Kasinski et al. "Smart Hydrogels—Synthetic Stimuli-Responsive Antitumor Drug Release Systems", International Journal of Nanomedicine 2020: 15, pp. 4541-4572, Poland.

Saahil Sheth et al. "Predicting Drug Release from Degradable Hydrogels Using Fluorescence Correlation . . . ", Front. Bioeng. Biotechnol. Dec. 20, 2019.

Saima Amin et al. "Hydrogels as Potential Drug Delivery Systems", Sep. 18, 2009, Scientific Research and Essay vol. 3 (11), pp. 1175-1183, India.

Jianyu Li et al. "Designing Hydrogels for Controlled Drug Delivery", Nat. Rev. Mater. Dec. 2016; 1(12), USA.

Achraf Ben Amar et al. "Power Approaches for Implantable Medical Devices", Sensors 2015, (15), MDPI, 28889-28914, Aug. 30, 2015.

Sujith Sudheendran et al. "Approaches for Long Lifetime Organic Light Emitting Diodes", Advanced Science 2021, (8), 2002254.

Tomoyuki Yokota et al. "Ultraflexible Organic Photonic Skin", Apr. 15, 2016, Science Advances 2016; 2: e1501856.

Lin Edwards, "Flexible LEDs for Implanting Under the Skin", Oct. 18, 2010, https://phys.org/news/2010-10-flexible-implanting-skin.html#/google_vignette.

Jacek F. Gieras, "Electric Motors for Medical and Clinical Applications", Sep. 17, 2008, International Conference on Electrical Machines and Systems ICEMS.

Chin-Yu Lin, et al. "Bio-Compatibility and Bio-Insulation of Implantable Electrode Prosthesis Ameliorated by A-174 Silane . . . " Oct. 30, 2020, MDPI, Micromachines 2020, (11), 1064.

W. S. O'Shaughnessy et al. "Stable Biopassive Insulation Synthesized by Initiated Chemical Vapor Deposition . . . ", Feb. 28, 2007, Biomacromolecules 2007, (8), pp. 2564-2570.

Yun Li et al. "Thin Film Encapsulation for the Organic Light-Emitting Diodes Display via Atomic Layer Dep . . . ", Aug. 28, 2019, Journal of Materials Research 2020, (35), 681-700.

Qianqian Niu et al. "Natural Polymer-Based Bioabsorbable Conducting Wires for Implantable Bioelectr . . . ", Oct. 5, 2020, Journal of Materials Chemistry A, 2020, (8), 25323-25335.

Mara Johnson-Groh, "Revamped OLED Electrodes Could Cut Power Consumption", Optics & Photonic News, Optica, Jul. 1, 2021.

Changmin Keum et al. "A Substrateless, Flexible, and Water-Resistant Organic Light-Emitting Diode", Nature Communications (2020) 11:6250, Dec. 7, 2020.

Seunghwan Lee et al. "Review of Organic/Inorganic Thin Film Encapsulation by Atomic Layer Depositi . . . ", The Minerals, Metals & Materials Society 2019, 71, 197-211, Sep. 28, 2018.

Rakhi Grover et al. "New Organic Thin-Film Encapsulation for Organic Light Emitting . . . ", Journal of Encapsulation and Adsorption Sciences, 2011, 1, 23-28, Mar. 11, 2011, India.

Osaka University, "Flexible Thermoelectric Generator Module: A Silver Bullet to Fix Waste Energy Issues", Dec. 18, 2018, Phys.org, Materials Science.

"6 Kinds Small Vibration Motors", <www.nfpmotor.com/small-vibration-motors>, retrieved Jan. 2, 2022.

"Wide Range of DC Vibration Motors with off-the-shelf Sampling", <www.precisionmicrodrives.com/motors/vibration-motors> retrieved Jan. 3, 2022.

Antreas Kantaros et al. "Fabricating Lattice Structures via 3D Printing: The Case of Porous Bio-Engineered Scaffolds", Applied Mechanics, 2021, 2, 289-302, May 25, 2021.

(56) References Cited

OTHER PUBLICATIONS

Uei-Ming Jow et al. "Geometrical Design of a Scalable Overlapping Planar Spiral Coil Array to Generate a Homogenous Magnet . . . ", IEEE Trans. Magn. Dec. 21, 2012; 49(6): 2933-2945.

Vincent W. Lee et al. "Micro-LED Technologies and Applications", Information Display Magazine, 2016 vol. 32, No. 6, pp. 16-23.

Anne Corning, "Progress in MicroLED Fabrication and Quality: Closing the Commercialization Gap . . . ", Radiant Vision Systems, radiantvisionsystems.com, Sep. 7, 2021.

Xiaojie Zhou et al. "Growth, Transfer Printing and Colour Conversion Techniques Towards Full-Colour Micro-LED . . . ", Progress in Quantum Electronics, vol. 71, May 2020, 100263.

Ray-Hua Horng et al. "Fabrication and Study on Red Light Micro-LED Displays", IEEE Journal of the Electron Devices Society, vol. 6, Aug. 10, 2018.

H.W. Choi et al. "Efficient GaN-Based Micro-LED Arrays", Materials Research Society Proc. vol. 743, 2003.

David Moszkowicz et al. "Neural Supply to the Clitoris: Immunohistochemical Study with Three-Dimensional Reconstruction of Cavernous . . . ", J. Sex Med. Apr. 2011, 8(4): 1112-1122.

Mayo Clinic, "Deep Brain Stimulation", https://www.mayoclinic.org/tests-procedures/deep-brain-stimulation/about/pac-20384562.

Shoichiro Sumi et al. "Our Steps Toward Subcutaneous Transplantation of Macro-Encapsulated Islets", OBM Transplantation 2019, vol. 3, Issue 3, Jul. 24, 2019.

Tao Liu et al. "Inductance Calculation of Multilayer Circular Printed Spiral Coils", IOP Conf. Series: Journal of Physics: Conf. Series 1176 (2019) 062045, Mar. 2019.

'Uei-Ming Jow et al.' "Design and Optimization of Printed Spiral Coils for Efficient Transcutan . . . ", IEEE Transactions on Biomedical Circuits and Systems 1(3):193-202, Oct. 2007.

Sumit Pramanik et al. "Developments of Immobilized Srface Modified Piezoelectric Crystal Biosen . . . ", International Journal of Electrochemical Science 8(6):8863-8892, Jan. 2013.

S. Jo et al. "Human Body Heat Energy Harvesting Using Flexible Thermoelectric Generator for Autonomous Microsystems", Chemical and Biological Microsystems Society, 2012.

Petra S. Dittrich et al. "Lab-on-a-Chip: Microfluidics in Drug Discovery", Nature Reviews Drug Discovery, Mar. 2006, vol. 5.

Randy Horton et al. "Induced Voltage and Current in Parallel Transmission Lines: Causes and Concerns", IEEE Transactions on Power Delivery 23(4):2339-2346, Nov. 2008.

Palanisamy Mohan Kumar et al. "The Design of a Thermoelectric Generator and Its Medical Applications", MDPI, Designs 2019, 3, 22, Apr. 26, 2012.

S. Warren et al. "Feasability of Subcutaneous ECG Leads for Synchronized Timing of a Counterpulsati . . . ", Cardiovascular Engineering and Technology 3, 17-25, 2012, Nov. 4, 2011.

Hans Rutzen-Lopez et al. "Leadless Cardiac Devices-Pacemakers and Implantable Cardioverter-Defibrillators", PubMed, Curr. Treat. Options Cardiovasc. Med. Aug. 2016; 18(8):49.

Parinaz Abiri et al. "Inductively Powered Wireless Pacing via a Miniature Pacemaker and Remote Stimulation Control System", Scientific Reports 2017; 7: 6180, Jul. 21, 2017.

Chuonh Ho et al. "Foot Drop Stimulators for Foot Drop: A Review of Clinical, Cost-Effectiveness, and Guidelines", NCBI, CADTH, Nov. 21, 2018.

Daniel Martin et al. "Long-Term Results Following Electrical Stimulation of the Peroneal Nerve Using the Actigait System in . . . ", Innov. Surg. Sci. 2021; 6(1):3-9, Jan. 8, 2021.

Agnes Sturma et al. "The Long-Term Effects of an Implantable Drop Foot Stimulator on Gait in Hemiparetic Patients", PLoS One 14(4): e0214991, Apr. 17, 2019.

All Flex, "Flexible Printed Circuits", <https://www.allflexinc.com/flexible-circuits/>, retrieved Nov. 26, 2021.

Gail Baura, "Cochlear Implant", Medical Device Technologies (Second Edition), ScienceDirect, 2021.

Benedict M. Wiles et al. "Lead or be Led: an Update on Leadless Cardiac Devices for General Physicians", Clin. Med. (Lond), Feb. 2017; 17(1): 33-36.

Mike Hoskins, "Implantable Insulin Pumps are Near Extinction, But Still Alive . . . ", Diabetes Mine (Influencer), Nov. 18, 2019, healthline.com.

PC MAG, "Printed Circuit Board", <https://www.pcmag.com/encyclopedia/term/printed-circuit-board>, retrieved Nov. 29, 2021.

"Wireless Charging and Energy Harvesting to Revolutionize Medical Implants", Medical Design Briefs Magazine, Sep. 1, 2015.

K. Everaert et al. "Neuroanatomy and Neurophysiology Related to Sexual Dysfunction in Male Neurogenic Patients with Lesions to . . . ", Spinal Cord (2010) 48, 182-191, Jan. 5, 2010.

Michael A. Wirth, "Shape Analysis & Measurement", University of Guelph, Computing and Information Science Image Processing Group, 2004.

Catarina Pipino et al. "Placenta as a Reservoir of Stem Cells: an Underutilized Resource?", Nov. 25, 2012, British Medical Bulletin, vol. 105, Issue 1, Mar. 2013, pp. 43-68.

G.F. Paulus et al. "Multicenter, Phase 1, Open Prospective Trial of Gastric Electrical Stimulation for the Treatment of . . . ", Mar. 4, 2020, Obesity Surgery (2020) 30: 1952-1960.

Daniel Mark et al. "Microfluidic Lab-on-a-chip Platforms: Requirements, Characteristics and Applications", Chemical Society Reviews, Issue 3, 2010.

J.N. Mcmullin et al. "Lab-on-a-Chip Optical Detection System using Plastic Fiber Optics", Proceedings of SPIE vol. 5260, Applications of Photonic Technology 6, 2003.

Shuoliang Ding et al. "Miniaturized Implantable Power Transmission System for Biomedical Wireless . . . ", Wireless Power Transfer, Cambridge University Press, Mar. 11, 2020, pp. 1-9.

Rak-Hwan Kim et al. "Waterproof AllnGaP Optoelectronics on Stretchable Substrates with Applications in Biomedicine and R . . . ", Nature Materials vol. 9, Oct. 17, 2020, pp. 929-937.

James K. Trevathan et al. "An Injectable Neural Stimulation Electrode Made from an In-Body Curing Polymer/Metal Composite", Adv. Healthcare Mater. 2019, 1900892, Nov. 7, 2019.

Haoran Wang et al. "3D Printed Microfluidic Lab-on-a-Chip Device for Fiber-Based Dual Beam Optical Mani . . . ", Jul. 16, 2021, Scientific Reports, Nature Portfolio, (2021) 11:14584.

Mohammad A. Qasaimeh et al. "Microfluidic Probes for Use in Life Sciences and Medicine", Aug. 7, 2012, Lab on a Chip 2013, Issue 1, The Royal Society of Chemistry.

Ming-Jie Yin et al. "Optical Fiber LPG Biosensor Integrated Microfluidic Chip for Ultrasensitive GI . . . ", Apr. 28, 2016, Biomedical Optics Express, OSA, vol. 7, No. 5, May 2016.

David A. Routenberg et al. "Microfluidic Probe: a new Tool for Integrating Microfluidic Environme . . . ", Sep. 14, 2009. Lab Ship, 2010, 10, 123-127, The Royal Society of Chemistry.

Mohamad Sawan et al. "Multicoils-Based Inductive Links Dedicated to Power up Implantable Medical Devices: Modeling . . . ", Jun. 2, 2009, Biomed Microdevices (2009) 11:1059-1070.

Mahammad A. Hannan et al. "Energy Harvesting for tthe Implantable Biomedical Devices: Issues and Challenges", Jun. 20, 2014, BioMedical Engineering Online 13:79 (2014).

"Inductive Power Transmission Shielding", electronicsnotes, https://www.electronics-notes.com, retrieved Dec. 22, 2021.

Chris Burket, "EMI Suppression Shields: Understanding the Basics", Electronic Design, TechXchange: Delving Into EMI, EMC and Noise, Apr. 8, 2020.

Sukjin Kim et al. "Electromagnetic Interference Shielding Effects in Wirel . . . ", IEEE International Symposium on Electromagnetic Compatibility, 2013, pp. 773-778, Aug. 5-9, 2013.

Dibyajat Mishra et al. "Nanomagnetic Structures for Inductive Coupling and Shielding in Wireless Charging Applications", IEEE 65th ECTC, pp. 941-945, May 26-29, 2015.

Lai Ly Pon et al. "Displacement-Tolerant Printed Spiral Resonator With Capacitive Compensated-Plates for Non-Radiat . . . ", IEEE Access, vol. 7, IEEE, pp. 10037-10044, Jan. 7, 2019.

Ehsan Ashoori et al. "Design of Double Layer Printed Spiral Coils for Wirelessly . . . ", 33rd Annual International Conference of the IEEE EMBS, pp. 2882-2885, Aug. 30-Sep. 3, 2011.

Silvano Cruciani et al. "Active Shielding Design for Wireless P . . . ", IEEE Transactions on Electromagnetic Compatibility vol. 61, Issue 6, Dec. 2019, pp. 1953-1960, Oct. 10, 2019.

(56)         References Cited

OTHER PUBLICATIONS

Yi Li et al. "Textile-Based Flexible Coils for Wireless Inductive Power Transmission", Applied Sciences 2018, 8(6), 912, Jun. 1, 2018.

Wikipedia, "Flexible Electronics", web link <https://en.wikipedia.org/wiki/Flexible_electronics>, retrieved Dec. 29, 2021.

Bill Otto, Quora answer to Is it possible to transfer energy via lasers of fibre optic cable cables?, web link <https://qr.ae/pG3HhP>, Mar. 18, 2019, retrieved Dec. 28, 2021.

Jinwei Zhao et al. "Self-Powered Implantable Medical Devices: Photovoltaic Energy Harvesting Review", Advanced Healthcare Materials, vol. 9, Issue 17, 2000779, Jul. 29, 2020.

N.C. Rivron et al. "Engineering Vascularized Tissue In Vitro", European Cells and Materials vol. 15, 2008, pp. 27-40, Feb. 21, 2008.

Mihail Barboiu et al. "A Biomimetric Membrane for Desalinating Seawater on an Industrial Scale", CNRS, Nov. 9, 2020.

University of Texas At Austin, "Nanoscale Control of Desalination Membranes Could Lead to Cheaper Water Filtration", SciTech Daily, Jan. 2, 2021.

John B. Tonner et al. "Desalination and Energy Use", Encyclopedia of Energy, 2004, pp. 791-799, Jun. 17, 2004.

A.M. Corbacho et al. "Roles of Prolactin and Related Members of the Prolactin/Growth Hormon/Placent . . . ", Society for Endocrinology, vol. 173, Issue 2, pp. 219-238, May 1, 2002.

C. Ronco, "Backfiltration in Clinical Dialysis: Nature of the Phenomenon, Mechanisms and . . . ", International Journal of Artificial Organs, vol. 13, No. 1, pp. 11-21, Jan. 1, 1990.

Judah Folkman "Angiogenesis in Cancer, Vascular, Rheumatoid and other Disease", Nature Medicine, vol. 1, No. 1, pp. 27-30, Jan. 1, 1995.

Joe Miller et al. "Optical Fiber-Coupled Ocular Spectrometer for Measurement of Drug C . . . ",Jul. 23, 2010, IEEE Transactions on Biomedical Engineering, vol. 57, No. 12, Dec. 2010.

Sergiy Korposh et al. "Fibre-Optic Chemical Sensor Approaches Based on Nanoassembled . . . ", Current Developments in Optical Fiber Technology, IntechOpen, Chapter 9, Jun. 13, 2013.

Marsha A. Moses et al. "Troponin I is Present in Human Cartilage and Inhibits Angiogenesis", Proc. Natl. Acad. Sci. USA, vol. 96, pp. 2645-2650, Mar. 16, 1999.

Riaan Stopforth et al. "Experimental Study of Bullet-Proofing Capabilities of Kevlar, of Different Weights and Num . . . ", Defence Technology, 15 (2019), pp. 186-192, Aug. 8, 2018.

Alexandros Velegrakis et al. "Human Placental Growth Hormone in Normal and Abnormal Fetal Growth (Review)", Biomedical Reports, 7, 2017, pp. 115-122, May 31, 2017.

Takahiro Ito et al. "Pump-Free Microfluidic Hemofiltration Device", MDPI, Micromachines, 2021, 12, 992, Aug. 20, 2021.

ScienceDirect, "Prolactin", Web Link: <www.sciencedirect.com/topics/medicine-and-dentistry/prolactin>, Retrieved Jan. 15, 2022.

Suman Chatterjee et al. "Futuristic Medical Implants Using Bioresorbable Materials and Devices", Biosensors and Bioelectronics (2019), Jun. 29, 2019, Article No. 111489.

Satoshi Takeshita et al. "Therapeutic Angiogenesis", Journal of Clinical Investigation, vol. 93, Issue 2, Feb. 1994, pp. 662-670, Sep. 28, 1993.

Sebastian Anthony, "Graphene Body Armor: Twice the Stopping Power of Kevlar, at a Fraction of the Weight", extremetech.com, Dec. 1, 2014.

Paul Ratner, "This Ultra-Thin Material Can Stop Bullets by Hardening Like a Diamond", BigThink, Hard Science, Dec. 31, 2017.

D. T. Lincoln et al. "Growth Hormone in Vascular Pathology: Neovascularization and Expression of Receptors is Associate . . . ", Anticancer Res. Nov.-Dec. 2007;27(6B) pp. 4201-4218.

Naoya To et al. "Water-Permeable Dialysis Membranes for Multilayered Microdialysis System", Frontiers in Bioengineering and Biotechnology, 3:70, Jun. 2, 2015.

Qiuya Zhang et al. "Highly Flexible Monolayered Porous Membrane with Superhydrophilicity-Hydrophilicity for Unidirectio . . . ", ACS Nano, 2020, 14, 6, pp. 7287-7296, Jun. 2, 2020.

Joseph Feher, "Osmosis and Osmotic Pressure", Academic Press, Quantitative Human Physiology (second edition), Chapter 2.7, pp. 182-198, 2017.

Ding Wang et al, "All-Inorganic Flexible PiezoElectric Energy Harvester Enabled by Two-Dimensional Mica", Nano Energy 43, Nov. 16, 2017.

Yanhua Sun et al. "Flexible Piezoelectric Energy Harvester/Sensor with High Voltage Output over Wide Temperature Range", Nano Energy 61, Apr. 15, 2019.

Kent David, et al. "The effect of high-intensity focused electromagnetic procedure on visceral adipose tissue", J Cosmet Dermatol, 2021,00:1-6.

Ratner, Paul. "This ultra-thin material can stop bullets by hardening like a diamond." Dec. 31, 2017. Hard Science.

Myers, Dean. "Miniature coupled inductor coils enable wireless remote power and secure communication." Sep. 25, 2017. DesignWorldOnline.com.

Xu, Yuan et al. "Multiband printed loop mobile phone antenna for LTE/WWAN/GNSS Application." Received Nov. 12, 2015; Accepted Jan. 28, 2016. International Journal of Antennas and Propagation. vol. 2016, Article ID 1671273, 7 pages. http://dx.doi.org/10.1155/2016/1671273.

Bumiller, Mark. "Dispersing Powders in Liquid." Slide presentation 2013, Horiba. www.horiba.com/particle.

Hedieh Fallahi, et al. "Flexible microfluidics: Fundamentals, recent developments and applications." Micromachines 2019, 10, 830; doi:10.3390/mi10120830 www.mdpi.com/journal/micromachines.

Bovone Giovanni et al. "Engineering hydrogel adhesion for biomedical applications via chemical design of the function." ACS Biomater. Sci. Eng. Apr. 1, 2021, 7, 9, 4048-4076.

Yang, Jiawei. Hydrogel Adhesion. Doctoral dissertation 2018, Harvard University, Graduate School of Arts & Sciences. https://dash.harvard.edu/handle/1/42106933.

Mi-Kyung Lee. "Liposomes for Enhanced Bioavailability of Water-Insoluble Drugs: In Vivo Evidence and Recent Approaches." Pharmaceutics 2020, 12, 264; doi:10.3390/pharmaceutics12030264.

Descamps, Lucie, et al. "Magnetic polymers for magnetophoretic separation in microfluidic devices." Magnetochemistry, MDPI, 2021, 7 (7), pp. 100. 10.3390/magnetochemistry7070100. hal-03335744.

Guojun Liu, et al. "A micromixer driven by two valveless piezo-electric pumps with multi-stage mixing characteristics." Sensors and Actuators A: Physical; vol. 333, Jan. 1, 2022, 113225. https://www.sciencedirect.com/science/article/abs/pii/S0924424721006889.

Garzon, Vivian, et al. "Optical Biosensors for Therapeutic Drug Monitoring." Biosensors Nov. 11, 2019, 9, 132; doi:10.3390/bios9040132.

Rivero, Pedro, et al. "Optical Fiber Sensors Based on Polymeric Sensitive Coatings." Polymers Mar. 7, 2018, 10, 280; doi:10.3390/polym10030280.

Darestani, MT, et al. "Piezoelectric membranes for separation processes: Operating conditions and filtration performance." Jml of Membrane Science Feb. 19, 2013. http://dx.doi.org/10.1016/j.memsci.2013.02.024.

Xinfei, Fan et al. "Highly Permeable Thin-film Composite Forward Osmosis Membrane Based on Carbon Nanotube Hollow Fiber Scaffold with Electrically Enhanced Fouling Resistance." Environ. Sci. Technol., DOI: 10.1021/acs.est.7b05341 •Publication Date (Web): Jan. 2, 2018.

Giwa, Adewale, et al. "A critical review on recent polymeric and nano-enhanced membranes for reverse osmosis." RSC Adv., 2016, 6, 8134-8163. https://doi.org/10.1039/C5RA17221G.

Yadav, Sudesh, et al. "Recent developments in forward osmosis membranes using carbon-based nanomaterials." Desalination 482 (2020) 114375.

Wang, Jichao, et al. "Recent Developments and Future Challenges of Hydrogels as Draw Solutes in Forward Osmosis Process." http://dx.doi.org/10.3390/w12030692. Pub Mar. 3, 2020.

Lakhotiya, Harish, et al. "Low voltage non-gassing electro-osmotic pump with zeta potential tuned aluminosilicatefrits and organic dye electrodes." https://pubs.rsc.org/en/content/articlelanding/2014/ra/c4ra04058a/unauth.

(56) References Cited

OTHER PUBLICATIONS

Snyder, Jessica, et al. "High-performance, low-voltage electroosmotic pumps with molecularly thin silicon nano- membranes." PNAS | Nov. 12, 2013 | vol. 110 | No. 46 | 18425-18430. http://www.pnas.org/lookup/suppl/doi:10.1073/pnas.1308109110/-/DCSupplemental.

Li, Li et al. "Research on Forward Osmosis Membrane Technology Still Needs Improvement in Water Recovery and Wastewater Treatment." Water 2020, 12, 107; doi: 10.3390/w12010107. http://dx.doi.org/10.3390/w12010107.

Ennteck (webpage. "Nano filtration and reverse osmosis / Membrane technology." https://www.lenntech.com/nanofiltration-and-rosmosis.htm.

You, Shijie, et al. "Forward Osmosis with a Novel Thin-Film Inorganic Membrane." Environ. Sci. Technol. 2013, 47, 8733-8742. dx.doi.org/10.1021/es401555x.

Al-Lashi, RS, et al. "Ultrasonic wave propagation in powders." IOP Conf. Series: J Phys: Conf. Series 1017 (2018) 012001.

Heikkinen, Juha, et al. "Ultrasound-assisted forward osmosis for mitigating internal concentration polarization." J. Membrane Sci. vol 528, Apr. 15, 2017, pp. 147-154. https://doi.org/10.1016/j.memsci.2017.01.035.

Qasim, Muhammad, et al. Ultrasound-Assisted Forward Osmosis Desalination Using Inorganic Draw Solutes. Ultrasonics Sonochemistry. https://doi.org/10.1016/j.ultsonch.2019.104810.

Gao, Meng, et al. "Development of a Multi-Stage Electroosmotic Flow Pump Using Liquid Metal Electrodes." Micromachines 2016, 7, 165; doi:10.3390/mi7090165.

Theeuwes, F; Yum Si. "Principles of the design and operaton of generic osmotic pumps for the delivery of semisolid or liquid drug formulations." Reprint from Annals of Biomedical Engineering, vol. 4, No. 4, Dec. 1976, Academic Press, Inc. pp. 343-353.

Johnson, Dean; Borkholder, David. "Towards an implantable, low flow micropump that uses no power in the Blocked-Flow state." Micromachines 2016,7,99 ;doi: 10.3390/mi7060099.

Lee Dong Gun et al. "Design of Piezoelectric-hydraulic pump with active valves." J. Intelligent Material Systems and Structures.

Bubmann, Agnes Beate, et al. "Piezoelectric titanium based microfluidic pump and valves for implantable medical applications." Sensors & Actuators A 323 (2021) 112649.

Cobo, Angelica, et al. "A Wireless Implantable Micropump for Chronic Drug Infusion Against Cancer." Sens Actuators A Phys., Mar. 1, 2016;239:18-25. doi: 10.1016/j.sna.2016.01.001.

"Novel String-Shaped Subcutaneous ICD Proves Effective in Patients." May 16, 2017. https://www.dicardiology.com/content/novel-string-shaped-subcutaneous-icd-proves-effective-patients.

Neuzil Petr, MD. "First-In-Man Feasibility Study of Subcutaneous Defibrillation Utilizing an Integrated Flexible String Shaped Defibrillator." Heart Rhythm 2017. C-LBCT03-01.

Caicedo, Diego, et al. Why Should Growth Hormone (GH) Be Considered a Promising Therapeutic Agent for Arteriogenesis? Insights from the GHAS Trial. Cells 2020, 9, 807; doi: 10.3390/cells9040807.

Shamsodin, Mozhgan, et al. "Preparation and characterization of PES-xerogel nanocomposite ultra-filtration membrane." Cellulose. Aug. 12, 2018. https://doi.org/10.1007/s10570-018-1971-4(0123456789().,-volV()0123456789().,-volV).

Yi Li, et al. Data for the figures in smart textile based flexible coils for wireless inductive power transmission. Jan. 2015. Applied Sciences.

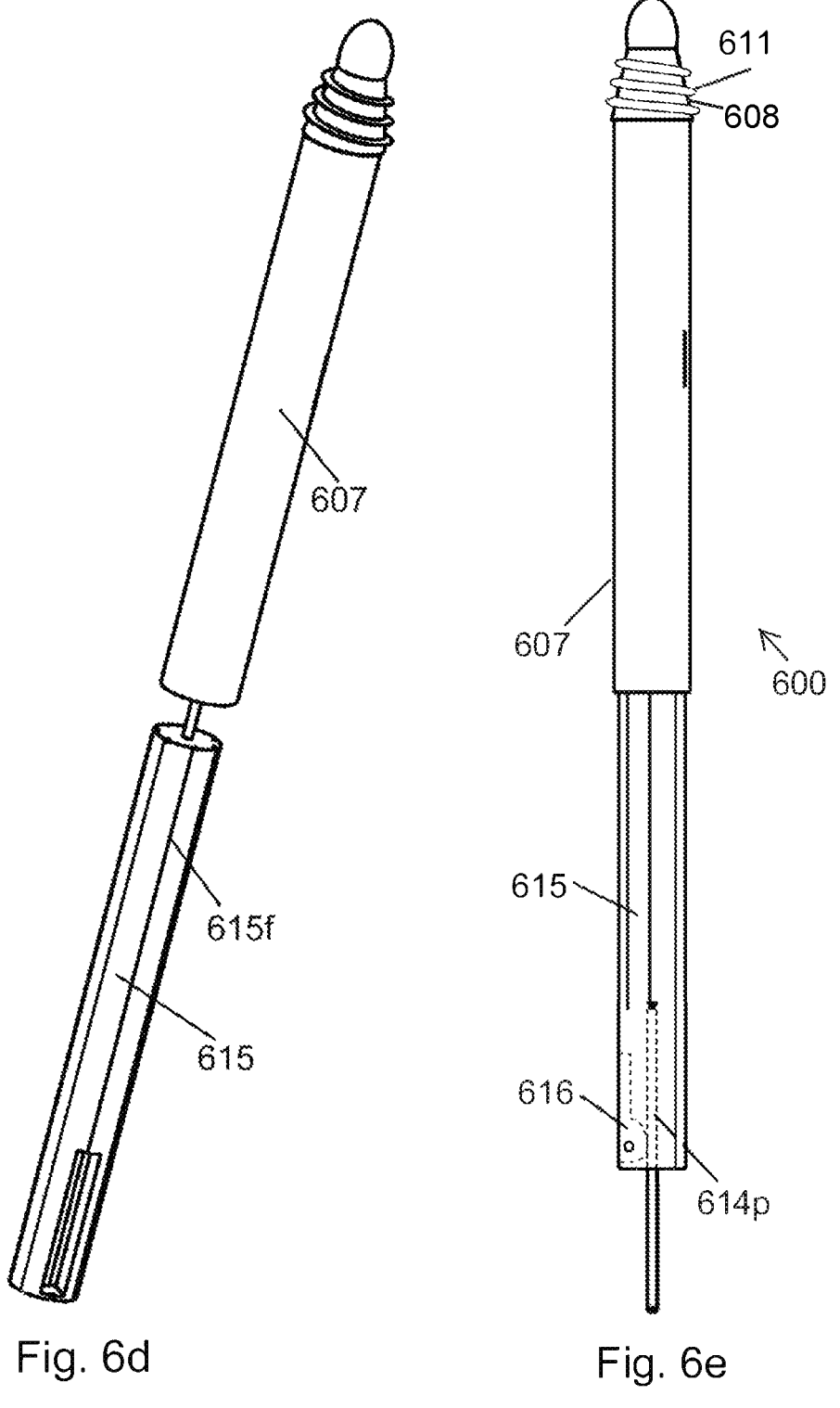
Fig. 6d                                Fig. 6e

911

912

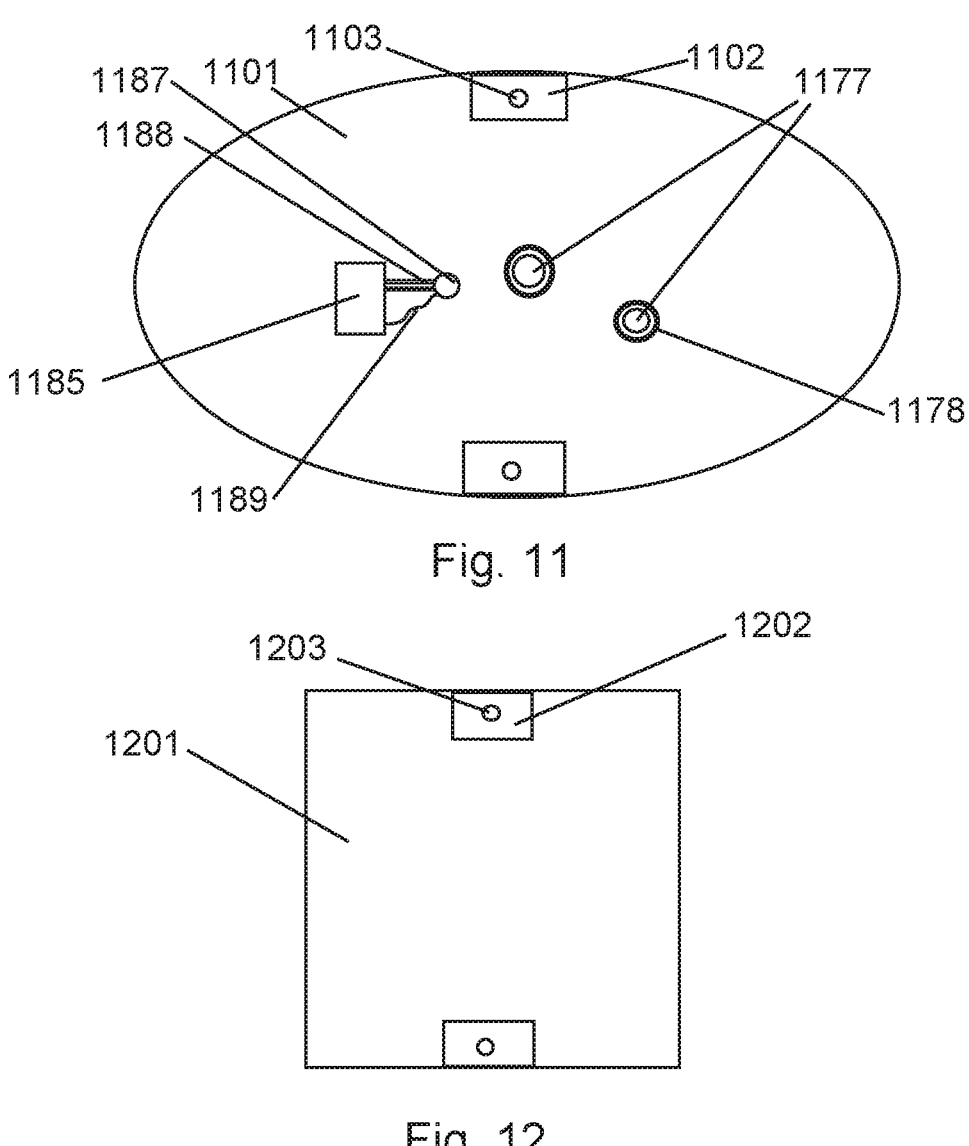
Fig. 11
Fig. 12
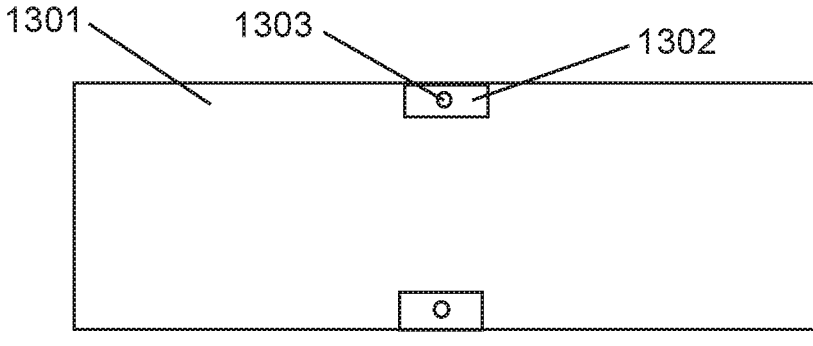
Fig. 13

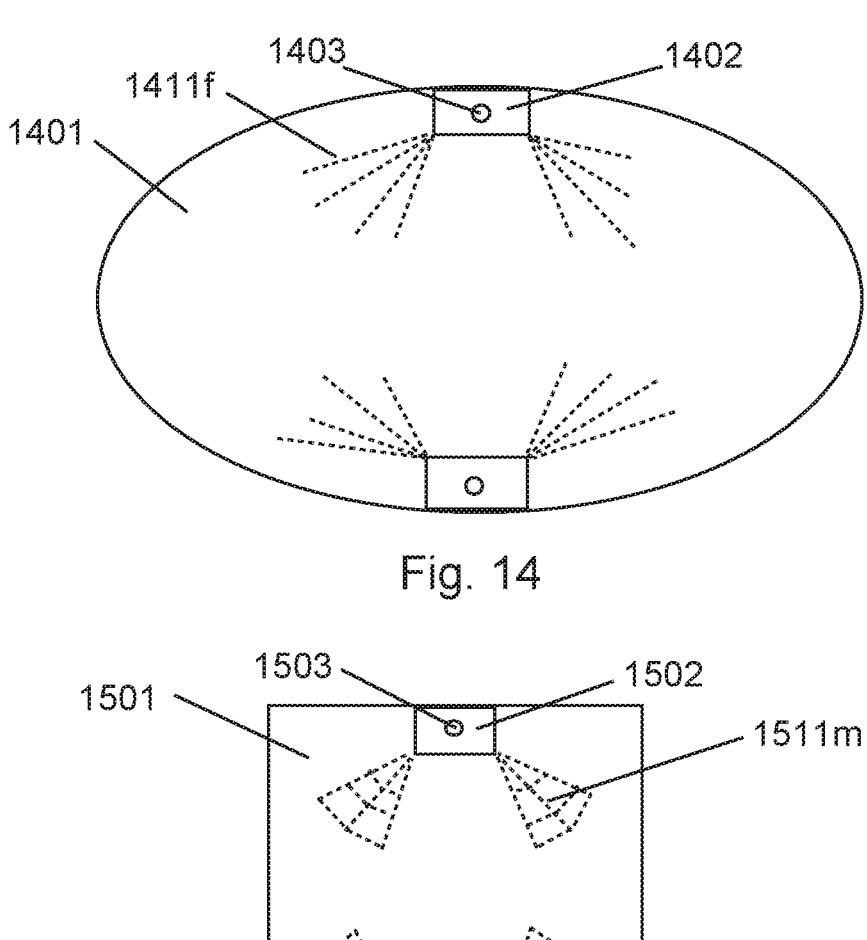
Fig. 14
Fig. 15
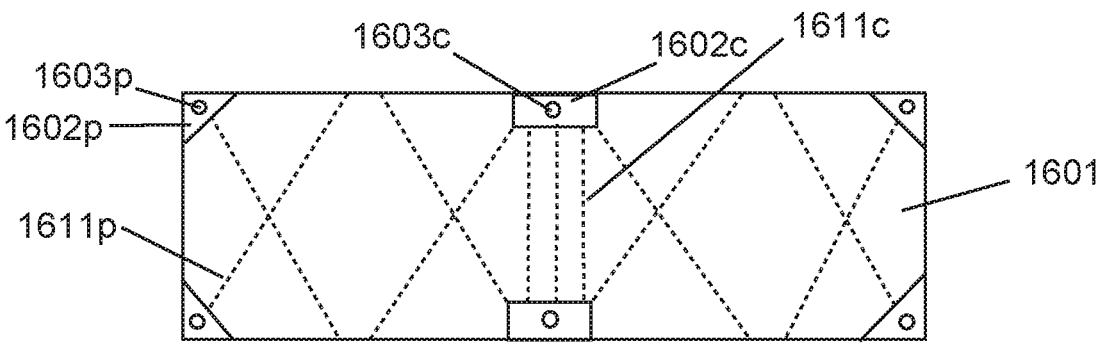
Fig. 16

1811

1808

1814

1812

1816

1815

1807

1801

1803

1822

1824b

1824

1825

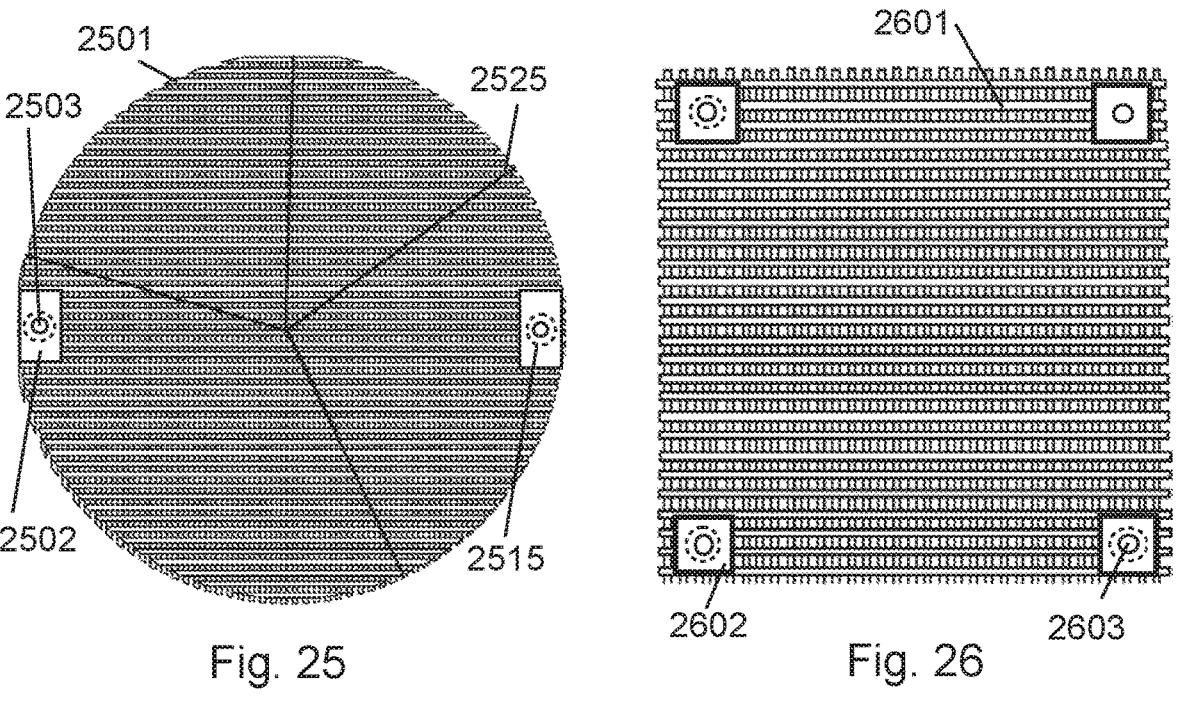
Fig. 25
Fig. 26
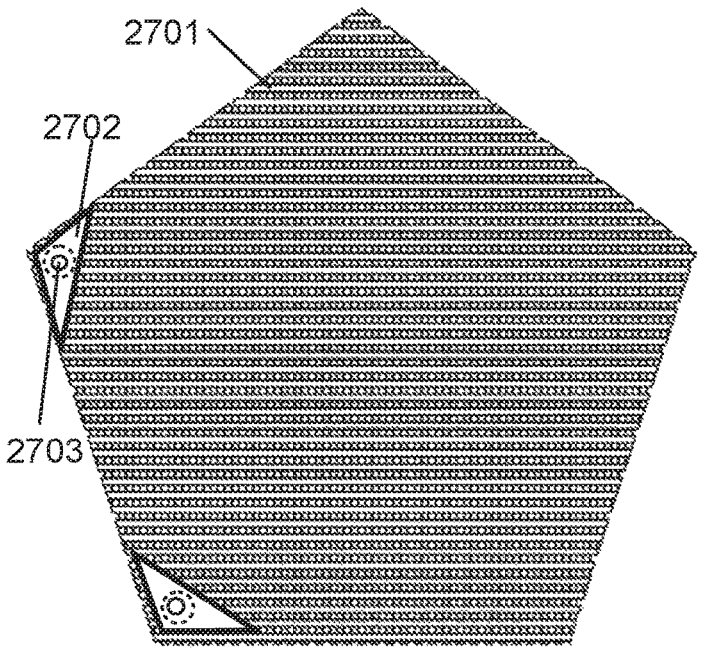
Fig. 27
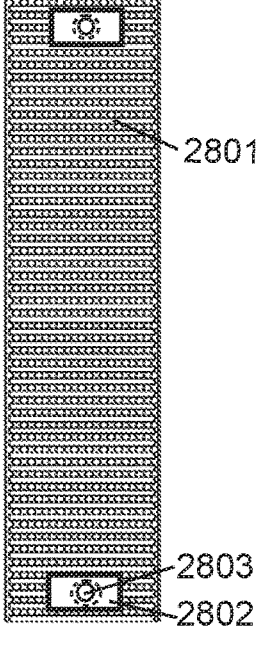
Fig. 28

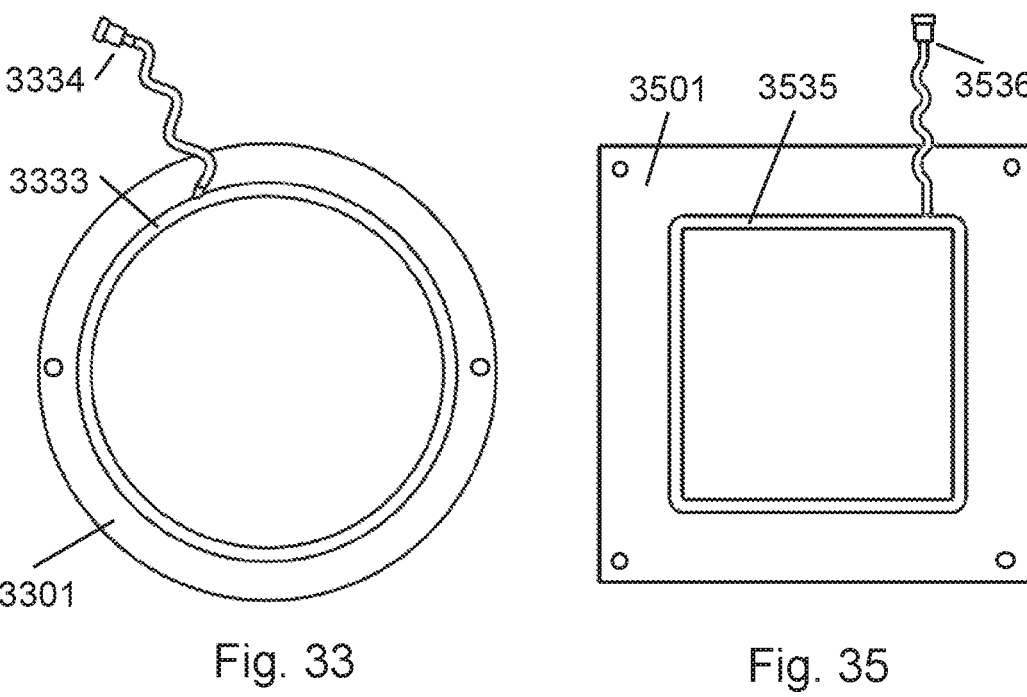
Fig. 33
Fig. 35
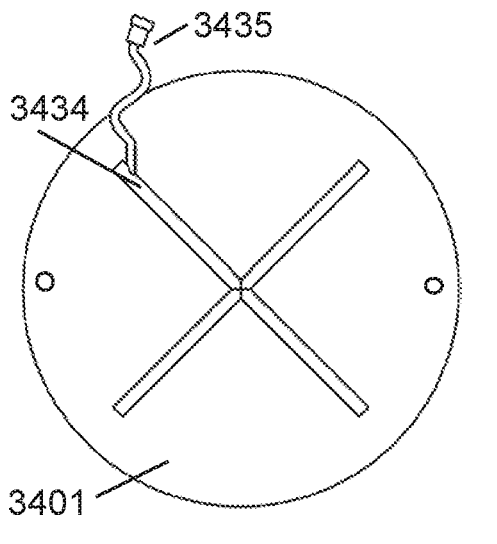
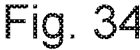
Fig. 34
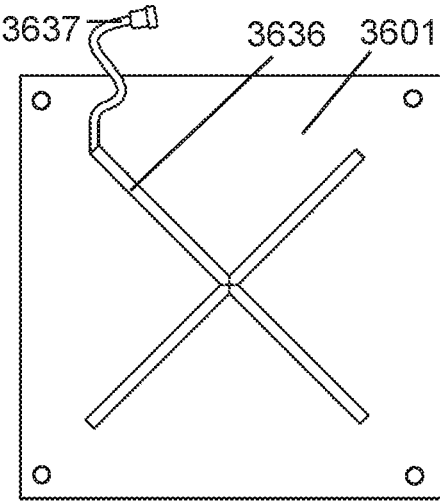
Fig. 36

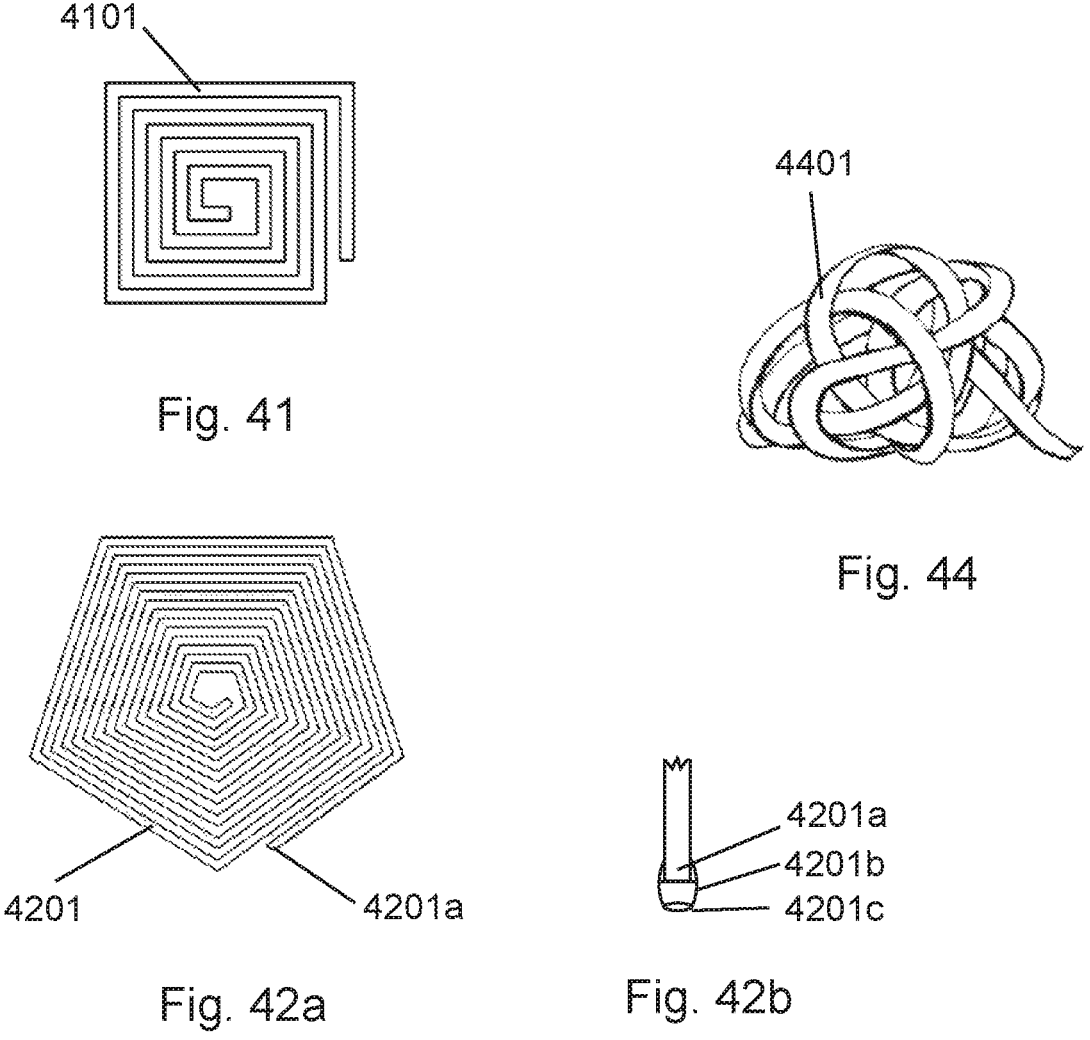
4101
Fig. 41
4401
Fig. 44
4201    4201a
4201a
4201b
4201c
Fig. 42a          Fig. 42b
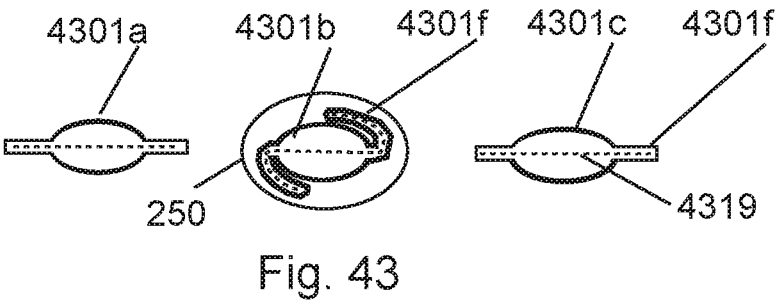
4301a          4301b          4301f          4301c          4301f
250          4319
Fig. 43

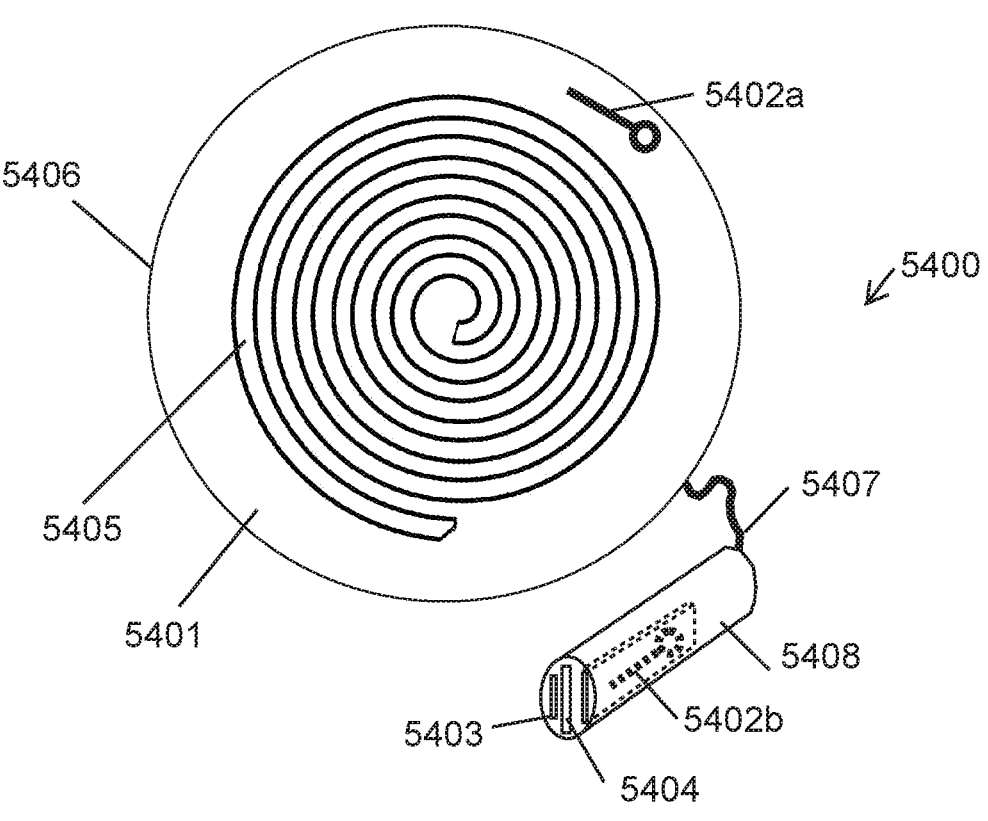
Fig. 54a
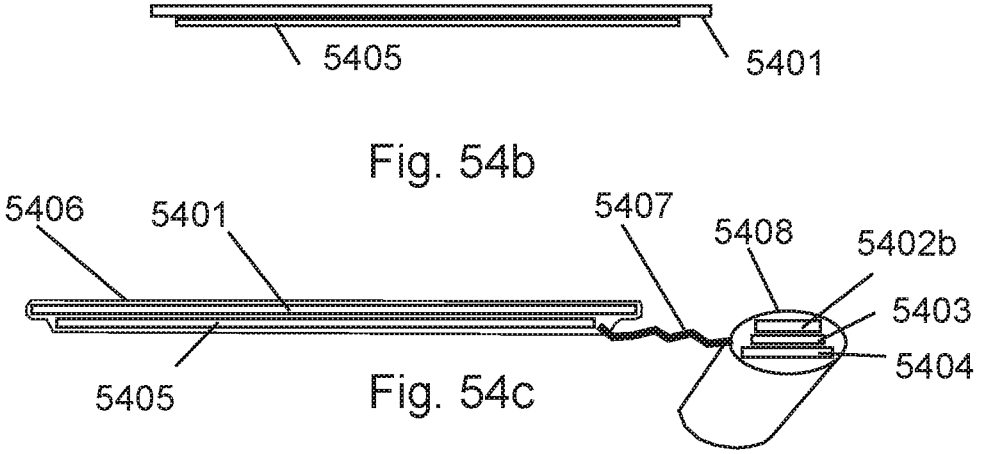
Fig. 54b
Fig. 54c 5501     5505R     5504         5505L     5503

5501              5501f 5501    5501o   5501b    5501

6300

6310c

6333v

6310b

6331

6310a 6332     6301     6301p 6331p     6331p 6331b     6331b

6331h

6331o 6331c     6331d 6331f     6331t
6331a 6331o     6301
6331b 6301     6331b     6301     6331r 6400
6401   6405R   6407   6425   6403   6424   6404
6423
6499   6411   6410     6405L   6414   6412
Fig. 64a
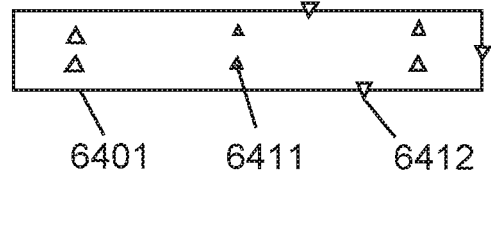
6401    6411    6412
Fig. 64b
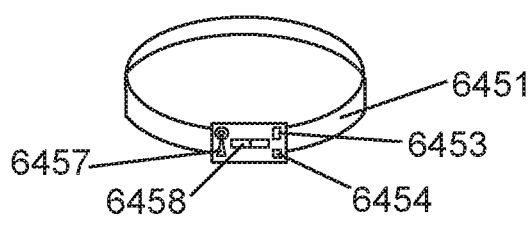
6451
6453
6457
6458   6454
Fig. 64c

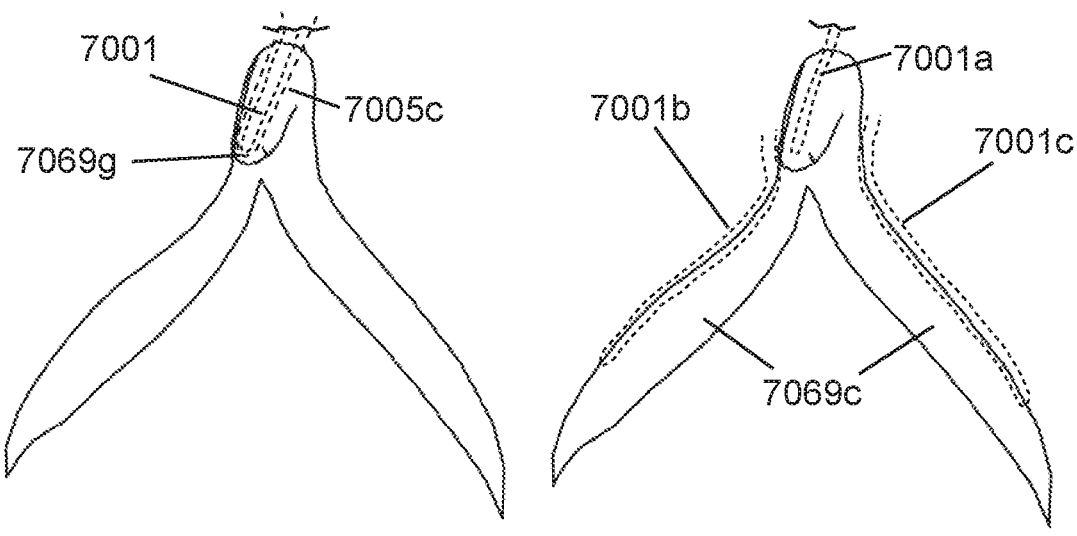
Fig. 70d                    Fig. 70e
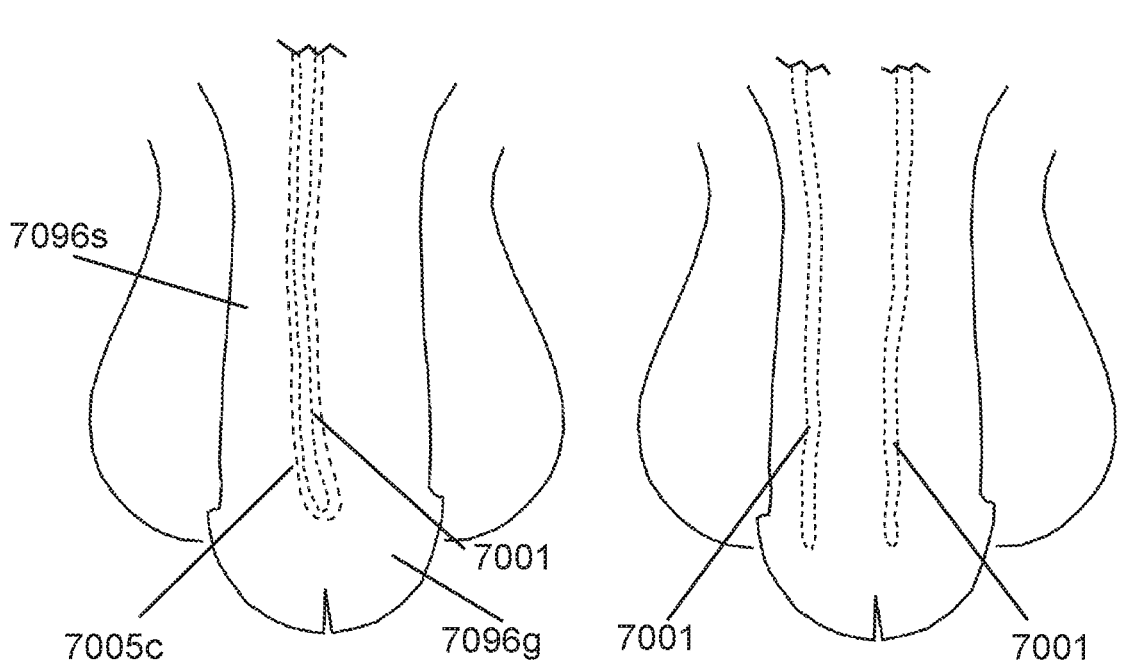
Fig. 70f                    Fig. 70g

1

COMPRESSIBLE, MINIMALLY INVASIVE IMPLANTS AND RELATED SYSTEMS AND METHODS

CROSS-REFERENCE TO RELATED APPLICATIONS

This application claims the benefit under 35 U.S.C. § 119(e) of U.S. Provisional Patent Application No. 63/295,068 filed on Dec. 30, 2021 and titled "Apparatus, Systems, And Methods For Minimally Invasive Implants And Implantation In Tissue". The aforementioned application is incorporated herein by reference in its entirety.

SUMMARY

Disclosed herein are various examples of implants, such as compressible implants, that are configured for delivery through preferably minimally invasive entrance incisions into implant pockets, along with related systems and methods. More specific examples of implants, systems, and methods for delivery of implants within subcutaneous implant pockets are disclosed below in connection with the following numbered paragraphs.

EXAMPLES

Examples of implants, systems, and methods for delivery of implants within subcutaneous implant pockets are disclosed below in connection with the following numbered paragraphs.

1. A compressible implant configured for positioning within an implant pocket, comprising:
   an implant comprising a flexible material, wherein the implant is reconfigurable in two configurations, the two configurations comprising:
   a first, compressed configuration, wherein the implant is configured to be delivered through a minimally invasive entrance incision while in the compressed configuration; and
   a second, uncompressed configuration, wherein the implant is configured to be reconfigured from the compressed configuration to the uncompressed configuration while being positioned within an implant pocket formed within a patient such that the implant can be maintained in the uncompressed configuration within the implant pocket in a functional state following implantation.

2. The compressible implant of example 1, wherein the implant comprises a footprint having an area in the uncompressed configuration, wherein the footprint comprises a maximal footprint dimension, wherein the implant comprises a maximal thickness measured in a direction at least substantially perpendicular to the footprint and wherein the implant is configured such that the maximal thickness is no greater than about 25% of the maximal footprint dimension.

3. The compressible implant of example 1, wherein the implant is configured to be delivered through a very minimally invasive entrance incision while in the compressed configuration.

4. The compressible implant of example 3, wherein the implant is configured to be delivered through an ultra minimally invasive entrance incision while in the compressed configuration.

5. The compressible implant of example 1, wherein the implant comprises a drug-delivery implant.

6. The compressible implant of example 5, wherein the implant comprises at least one of a pH sensitive, a thermosensitive, a glucose sensitive, a bioresponsive, a magnetic-sensitive, and a smart hydrogel.

7. The compressible implant of example 5, wherein the implant comprises a biodegradable binder and a resorbable anchor.

8. The compressible implant of example 5, wherein the implant comprises at least one of a small molecule and a biologic configured for delivery therefrom.

9. The compressible implant of example 1, wherein the implant comprises at least one hole configured to engage an instrument to facilitate implantation of the implant.

10. The compressible implant of example 9, further comprising an x-ray detectable marker positioned adjacent to the at least one hole.

11. The compressible implant of example 9, further comprising a protruding tab, wherein the at least one hole is formed in the protruding tab.

12. The compressible implant of example 9, further comprising at least one structural reinforcement region, wherein the at least one structural reinforcement region is positioned about the at least one hole.

13. The compressible implant of example 12, wherein the at least structural reinforcement region is positioned adjacent to a peripheral edge of the implant without protruding from the implant.

14. The compressible implant of example 1, wherein the implant comprises a polymeric matrix, and wherein the polymeric matrix comprises pores configured to release agents therefrom.

15. The compressible implant of example 1, wherein the implant comprises one or more laminates.

16. The compressible implant of example 15, wherein the implant comprises a bladder, and wherein the bladder is formed between two adjacent laminates of the one or more laminates.

17. The compressible implant of example 15, further comprising a plurality of pores formed in the one or more laminates, wherein the plurality of pores is configured to deliver drugs from the implant therethrough.

18. The compressible implant of example 17, wherein the pores comprise gates, and wherein the gates comprise at least one of electrically actuatable membranes and thermally actuatable lipid membranes.

19. The compressible implant of example 1, wherein the implant comprises a plurality of target binding materials positioned along one or more edges of the implant.

20. The compressible implant of example 1, wherein the implant comprises a footprint area of at least 50 square cm.

21. The compressible implant of example 1, wherein the implant is at least one of configured to deliver drugs within the implant pocket and comprises one or more electrical components.

22. The compressible implant of example 21, wherein the implant comprises a footprint area of at least 100 square cm.

23. The compressible implant of example 1, wherein the implant comprises a fan-shaped implant.

24. The compressible implant of example 23, wherein the fan-shaped implant is configured to accordion fold in its compressed configuration.

25. The compressible implant of example 1, wherein the implant comprises a rectangular shape in its uncompressed configuration.

26. The compressible implant of example 1, further comprising intersecting strands of materials.

27. The compressible implant of example 26, wherein the intersecting strands are formed into a mesh.

28. The compressible implant of example 27, wherein the mesh comprises a protective mesh configured to provide physical protection to a user at a location of the compressible implant within the implant pocket.

29. The compressible implant of example 28, wherein the protective mesh comprises Kevlar or graphene.

30. The compressible implant of example 28, further comprising a biocompatible plastic coating.

31. The compressible implant of example 30, further comprising an antimicrobial agent incorporated into the biocompatible plastic coating.

32. The compressible implant of example 31, wherein the antimicrobial agent is configured to be released upon impact with a penetrating object.

33. The compressible implant of example 28, wherein the implant comprises at least one peripheral fold configured to aid in mitigating a penetrating wound.

34. The compressible implant of example 28, further comprising a zone of overlap secured by a binding element.

35. The compressible implant of example 28, further comprising at least one of an inductance coil, a PCB, a sensor, and an antenna.

36. A system comprising the compressible implant of example 28, further comprising a second compressible implant configured to be positioned within the implant pocket in an overlapping configuration with the compressible implant to effectively create a larger implant.

37. The compressible implant of example 27, wherein the fibrous mesh comprises a plurality of macro-holes configured to allow for vascularization across the implant through the plurality of macro-holes.

38. The compressible implant of example 27, wherein the fibrous mesh comprises a bioabsorbable polymer.

39. The compressible implant of example 27, wherein the fibrous mesh comprises a plurality of layers.

40. The compressible implant of example 39, wherein at least one of the plurality of layers comprises a pH-sensitive layer.

41. The compressible implant of example 1, further comprising a superstructure configured to bias the implant towards the uncompressed configuration.

42. The compressible implant of example 41, wherein the superstructure is configured to automatically rigidify upon encountering body fluids.

43. The compressible implant of example 41, wherein the superstructure is further configured to deliver at least one of a drug and biologics therefrom.

44. The compressible implant of example 41, wherein the superstructure comprises opposing cross-members defining a plus shape.

45. The compressible implant of example 41, wherein the superstructure comprises a shape that at least substantially matches a shape of the implant in its uncompressed configuration.

46. The compressible implant of example 45, wherein the superstructure comprises at least one of a circular shape and a polygonal shape, and wherein the superstructure is inset from the outer perimeter of the implant in its uncompressed configuration.

47. The compressible implant of example 41, further comprising an injection port fluidly coupled with the superstructure, wherein the injection port is configured for at least one of inflating the superstructure and delivering a therapeutic agent into the superstructure for ultimate release into a patient.

48. The compressible implant of example 41, wherein the superstructure is inflatable.

49. The compressible implant of example 41, wherein the superstructure comprises a therapeutic agent contained therein.

50. The compressible implant of example 49, further comprising a micro-pump configured to selectively pump the therapeutic agent from the superstructure.

51. The compressible implant of example 1, further comprising an inductance coil configured to wirelessly generate electrical energy.

52. The compressible implant of example 51, further comprising at least one of an LED, a battery, and a drug delivery gate, wherein the inductance coil is electrically coupled to the at least one of an LED, a battery, and a drug delivery gate to provide electrical energy to power the at least one of an LED, a battery, and a drug delivery gate.

53. The compressible implant of example 51, further comprising a plurality of inductance coils.

54. The compressible implant of example 53, wherein the plurality of inductance coils comprises an array of micro-coils configured for use as an inductive link receiver.

55. The compressible implant of example 53, wherein the plurality of inductance coils comprises a stacked plurality of inductance coils.

56. The compressible implant of example 51, further comprising a voltage sensor.

57. The compressible implant of example 56, wherein the voltage sensor is configured to allow a user to maximize charging voltage by providing at least one of an audible, visual, and tactile feedback to the user during wireless charging.

58. The compressible implant of example 1, wherein the implant comprises a stent-like mesh comprising a polymer for binding drugs thereto.

59. The compressible implant of example 58, further comprising a layered structure comprising a hydrophobic layer sandwiched between two hydrophilic layers and a core comprising a hydrophobic therapeutic agent.

60. The compressible implant of example 1, further comprising a coating.

61. The compressible implant of example 60, wherein the coating comprises a bioactive coating.

62. The compressible implant of example 61, wherein the bioactive coating comprises at least one of an anti-inflammatory agent, a steroid, an anti-depressive agent, and a growth factor.

63. The compressible implant of example 60, wherein the coating comprises a pseudo-lubricant coating configured to reduce friction to facilitate removal of the implant through a minimally invasive incision.

64. The compressible implant of example 63, wherein the pseudo-lubricant coating comprises a PTFE coating.

65. The compressible implant of example 1, further comprising an inductance coil and a battery coupled with the inductance coil.

66. The compressible implant of example 1, further comprising a CPU.

67. The compressible implant of example 1, further comprising at least one electrical component.

68. The compressible implant of example 67, wherein the at least one electrical component comprises at least one stretchable, electrical component.

69. The compressible implant of example 68, wherein the at least one stretchable, electrical component comprises at least one of a stretchable conductor, a stretchable semiconductor, a stretchable dielectric, and a stretchable transistor.

70. The compressible implant of example 67, further comprising a biocompatible insulator configured to insulate the at least one electrical component from body fluids following implantation of the compressible implant.

71. The compressible implant of example 1, further comprising a reservoir for delivering a therapeutic agent to a patient therefrom.

72. The compressible implant of example 71, further comprising a micromechanical system for delivering the therapeutic agent from the compressible implant via the reservoir.

73. The compressible implant of example 71, further comprising a thermopneumatic micropump configured to deliver the therapeutic agent from the reservoir.

74. The compressible implant of example 71, wherein the reservoir is compressible.

75. The compressible implant of example 1, further comprising a release mechanism for selectively releasing a therapeutic agent from the compressible implant.

76. The compressible implant of example 75, wherein the release mechanism comprises a diaphragm membrane comprising a polymer matrix, wherein the polymer matrix is configured to be relatively non-porous in a first state and more porous in a second state, and wherein the polymer matrix is configured to transition from the first state to the second state in response to external stimuli.

77. The compressible implant of example 76, wherein the polymer matrix comprises a plurality of magnetic particles, and wherein the plurality of magnetic particles is configured to, upon application of a magnetic field, cause the diaphragm membrane to transition to the second state.

78. The compressible implant of example 75, wherein the release mechanism comprises one or more magnetic microdisks selectively actuatable by application of a magnetic field.

79. The compressible implant of example 75, wherein the release mechanism comprises a polymeric microsphere drug carrier comprising a biodegradable polymer configured to release the therapeutic agent over time.

80. The compressible implant of example 1, further comprising a biocompatible housing comprising a hollow core configured to store a therapeutic agent therein.

81. The compressible implant of example 80, wherein the hollow core comprises a plurality of compartments, each of the plurality of compartments containing a separate therapeutic agent.

82. The compressible implant of example 1, wherein the implant comprises an elongated strip comprising a plurality of spaced apart implant payload bays positioned thereon.

83. The compressible implant of example 82, wherein each of at least a subset of the implant payload bays comprises a biologic cell cluster.

84. The compressible implant of example 83, further comprising a mesh comprising a blood vessel growth stimulating hormone.

85. The compressible implant of example 84, wherein the blood vessel growth stimulating hormone comprises at least one of proliferin, prolactin, growth hormone, and placental lactogen.

86. The compressible implant of example 1, wherein the implant comprises a neuro stimulative implant comprising a plurality of electrodes configured to stimulate nerves within the implant pocket.

87. The compressible implant of example 86, further comprising a heartrate sensor, wherein the heartrate sensor is configured to adjust at least one of a signal strength and signal frequency to the plurality of electrodes based upon a heartrate detected by the heartrate sensor.

88. The compressible implant of example 86, wherein the plurality of electrodes is configured to fire at a preprogrammed firing pattern that changes over time.

89. The compressible implant of example 86, wherein each of at least a subset of the plurality of electrodes comprises a circumferential electrode extending along a band about a portion of the implant.

90. A system for positioning a compressible implant within an implant pocket, comprising:
    an implant configured to be reconfigurable in two configurations, the two configurations comprising:
        a first, compressed configuration, wherein the implant is configured to be delivered through a minimally invasive entrance incision while in the compressed configuration; and
        a second, uncompressed configuration, wherein the implant is configured to be reconfigured from the compressed configuration to the uncompressed configuration while being positioned within an implant pocket formed within a patient such that the implant can be maintained in the uncompressed configuration within the implant pocket following implantation; and
    an instrument comprising:
        a tip configured to extend through the minimally invasive entrance incision; and
        a shaft configured to engage the implant in the compressed configuration and deliver the implant through the minimally invasive entrance incision.

91. The system of example 90, wherein the instrument is configured to facilitate reconfiguring the implant from the compressed configuration to the uncompressed configuration after extending the implant through the minimally invasive entrance incision.

92. The system of example 90, wherein the tip comprises a dilator configured to expand a size of the minimally invasive entrance incision.

93. The system of example 92, wherein the tip comprises screw threads.

94. The system of example 90, wherein the instrument comprises means for securing the implant to the instrument.

95. The system of example 94, wherein the means for securing comprises one or more protrusions coupled to the shaft, wherein each of the one or more protrusions is configured to engage a hole formed on the implant.

96. The system of example 95, wherein the one or more protrusions comprise spherical protrusions.

97. The system of example 94, wherein the means for securing comprises a tab fastener configured to engage a tab extending from the implant.

98. The system of example 90, wherein the instrument further comprises a releasable handle.

99. The system of example 90, wherein the implant comprises an inductance coil.

100. The system of example 99, further comprising a wireless inductance coupling mechanism configured to wirelessly deliver electrical energy to the implant via the inductance coil.

101. An implant configured for positioning within an implant pocket, comprising:

an arm extending in a spiral shape from an outer terminus at a periphery of the implant to an inner terminus adjacent to a center of the implant, wherein the arm defines a plurality of adjacent bands having space between each adjacent band, and wherein the implant is configured to at least substantially maintain the spiral shape both before and after implantation within the implant pocket.

102. A system comprising the implant of example 101, and further comprising an auxiliary implant electrically coupled with the implant, wherein the auxiliary implant comprises at least one of an antenna, a CPU, a battery, and an inductance coil.

103. The implant of example 101, wherein the implant is configured to function as an inductance coil.

104. The implant of example 101, wherein the implant is configured for selective delivery of a therapeutic agent therefrom.

105. The implant of example 101, wherein the implant comprises a polymeric external laminate configured to deliver a therapeutic agent therefrom.

106. The implant of example 101, wherein the implant comprises a nanoscale agent responsive to at least one of light, magnetic fields, ultrasound, radio frequency, and x-ray radiation for release of a therapeutic agent.

107. The implant of example 101, wherein the implant comprises a plurality of selectively openable pores configured to be opened via thermoporation.

108. The implant of example 107, wherein the thermoporation is configured to be selectively induced via at least one of electricity, ultrasound, and radiation.

109. The implant of example 101, wherein the implant comprises at least one of an electrical component and a micropump.

110 The implant of example 101, wherein the implant comprises at least one of a radiographically, sonically, and electromagnetically identifiable material.

111. The implant of example 101, wherein the implant comprises a protective sheath.

112 The implant of example 111, wherein the implant comprises a protective inner sheath and a protective outer sheath, and wherein a fluid is contained between the protective inner sheath and the protective outer sheath.

113. The implant of example 101, wherein the implant comprises a temperature sensor.

114. The implant of example 113, wherein the implant comprises an inductance coil, and wherein the temperature sensor is configured to reduce or terminate charging from an external wireless inductance coil in response to the temperature sensor detecting a threshold temperature.

115. The implant of example 101, wherein the implant comprises a drug reservoir comprising a selectively openable gate.

116. The implant of example 115, wherein the gate is configured to be selectively dissolved electrochemically by application of a wirelessly induced current.

117 The implant of example 101, wherein the implant is non-compressible, and wherein the arm comprises a solid core.

118 The implant of example 101, wherein the implant comprises a superstructure.

119. The implant of example 118, wherein the superstructure is fluidly coupled with an injection port.

120. The implant of example 101, wherein the arm comprises a hollow center.

121. The implant of example 120, further comprising a guidewire positioned within the hollow center.

122. The implant of example 120, further comprising at least one of an electronic component, a battery, an inductance coil, a capacitor, a data storage element, a heating element, a heart rate sensor, and an oxygen saturation monitor positioned within the hollow center.

123. The implant of example 120, further comprising an EMI suppression element configured to protect one or more electrical elements positioned within the hollow center.

124. The implant of example 120, further comprising a microfluidic channel configured to deliver fluid from outside of the hollow center to the hollow center.

125. The implant of example 124, wherein the microfluidic channel terminates at a location corresponding to one of the spaces between adjacent bands of the arm.

126. The implant of example 101, wherein the implant defines a circular shape in plan view.

127. The implant of example 101, wherein the implant defines a polygonal shape in plan view.

128. The implant of example 101, wherein the outer arm terminus comprises a bulbous tissue passage facilitator configured to facilitate passage of the arm through the minimally invasive entrance incision and to inhibit tissue catching on the outer arm terminus during installation.

129. The implant of example 128, wherein the bulbous tissue passage facilitator further comprises a port providing access to an inner passage defined within the arm.

130. The implant of example 101, wherein the implant comprises one or more flexible flaps extending from the arm, and wherein each of the one or more flexible flaps is configured to compress against the arm during installation through the minimally invasive entrance incision and automatically decompress to extend away from the arm once within the implant pocket.

131. The implant of example 130, wherein each of the one or more flexible flaps is configured to deliver a therapeutic agent therefrom.

132. The implant of example 130, wherein each of the one or more flexible flaps is configured to provide increased surface area for wireless inductance charging.

133. The implant of example 101, wherein the implant is configured to at least one of function as an inductance coil, function as a drug eluting implant, and function as an antenna.

134. The implant of example 101, wherein the arm extends along at least two complete turns to form the spiral shape. The implant of example 101, wherein the implant has a diameter of at least about 2 cm. 135.

136. The implant of example 135, wherein the implant has a diameter of at least about 10 cm.

137. The implant of example 101, further comprising a plurality of electrodes positioned on an outer surface of the implant, wherein the arm comprises a hollow center, and wherein at least one of a battery, a CPU, a PCB, a heartrate sensor, a temperature sensor, and an antenna is positioned within the hollow center.

138. A system comprising the implant of example 101, further comprising an elongated strand configured to be positioned in an elongated, subcutaneous implant tunnel via a minimally invasive entrance incision.

139. The system of example 138, wherein the elongated strand comprises a plurality of electrodes configured to stimulate nerves.

140. The system of example 138, wherein the elongated strand comprises a cardioverter defibrillator.

141. The system of example 138, further comprising an EKG implant comprising a plurality of leads.

142. The system of example 141, wherein the plurality of leads of the EKG implant are resiliently flexible and configured to be delivered in a compressed configuration through a minimally invasive entrance incision and then automatically decompress once within an implant pocket to position the plurality of leads in a configuration targeting at least one of a particular heart configuration and a range of heart configurations.

143. The system of example 138, wherein the system further comprises an implantable motor unit system electrically coupled with the elongated strand, wherein the implantable motor unit system comprises a plurality of motor drives configured to be coupled to one another across a human joint to provide force to pivot the human joint.

144. The system of example 143, further comprising a second elongated strand configured to be positioned in an elongated, subcutaneous implant tunnel via a minimally invasive entrance incision electrically coupled with the elongated strand to allow for signals to be sent from the elongated strand to the second elongated strand and to at least one of the plurality of motor drives to accomplish selective pivoting of the human joint.

145. The system of example 144, wherein each of the plurality of motor drives is independently actuatable.

146. The system of example 144, further comprising at least one implantable sensor coupled with at least one of the plurality of motor drives.

147. The implant of example 101, further comprising a plurality of LEDs.

148. The implant of example 147, wherein each of the plurality of LEDs is positioned on an exterior surface of the arm.

149. An elongated, flexible implant, comprising:
a plurality of pods, wherein each of the plurality of pods is selectively coupleable with an adjacent pod of the plurality of pod to form a pod chain, and wherein the pod chain is configured to be positioned within an implant pocket through a minimally invasive entrance incision.

150. A system comprising the elongated, flexible implant of example 149, and further comprising a spiral implant comprising an arm extending in a spiral shape from an outer terminus at a periphery of the implant to an inner terminus adjacent to a center of the implant, wherein the arm defines a plurality of adjacent bands having space between each adjacent band, wherein the implant is configured to at least substantially maintain the spiral shape both before and after implantation within an implant pocket, and wherein the spiral implant comprises a hollow core.

151. The system of example 150, wherein the hollow core comprises at least one partition configured to separate the hollow core into separate functional regions.

152 The system of example 150, wherein the spiral implant is configured to collect body fluids from a patient once within an implant pocket.

153. The system of example 152, wherein the spiral implant is further configured to generate water from the body fluids, wherein at least one of the plurality of pods comprises a mixing pod comprising a dry medication, and wherein the mixing pod is configured to receive the water generated from the body fluids from the spiral implant to generate a liquid medication therefrom.

154. The system of example 153, wherein the mixing pod comprises a plurality of bays, wherein at least one bay of the plurality of bays comprises a storage bay for storage of a dry medication, wherein at least one bay of the plurality of bays comprises a mixing bay, and wherein the mixing bay is coupled with the storage bay and the spiral implant to allow for mixing of the dry medication with the water generated from body fluids from the spiral implant.

155. A method for implantation of a spiral implant through a minimally invasive entrance incision, the method comprising the steps of:
forming a minimally invasive entrance incision;
forming an implant pocket within a patient adjacent to the entrance incision;
inserting a terminal end of the spiral implant through the minimally invasive entrance incision, wherein the spiral implant comprises an arm extending in a spiral shape from an outer terminus at a periphery of the implant to an inner terminus adjacent to a center of the implant; and
rotating the spiral implant to advance the spiral implant through the minimally invasive entrance incision until the spiral implant is placed subcutaneously within the patient.

156. The method of example 155, wherein the step of forming an implant pocket comprises forming an implant pocket comprising an implant delivery pocket portion and an implant pocket portion, wherein the implant delivery pocket portion is configured to receive the spiral implant during implantation, and wherein the implant pocket portion is configured to receive the spiral implant indefinitely following implantation.

157. The method of example 156, wherein the implant delivery pocket portion is positioned on a first side of the minimally invasive entrance incision, and wherein the implant pocket portion is positioned on a second side of the minimally invasive entrance incision opposite the first side.

158. The method of example 156, further comprising advancing the spiral implant from a position at which the spiral implant is at least partially positioned within the implant delivery pocket portion to a position at which the spiral implant is fully positioned within the implant pocket portion.

159. The method of example 158, wherein the step of advancing the spiral implant from a position at which the spiral implant is at least partially positioned within the implant delivery pocket portion to a position at which the spiral implant is fully positioned within the implant pocket portion is performed by manipulating the spiral implant using finger pressure on the outer skin of the patient.

160. The method of example 156, wherein the implant pocket portion comprises a polygonal shape.

161. The method of example 155, wherein the spiral implant comprises a coating configured to reduce friction during installation.

162. The method of example 155, wherein the terminal end comprises the outer terminus of the spiral implant.

163. A compressible implant configured for positioning within an implant pocket, comprising:
an implant comprising a source of electromagnetic radiation wherein the implant is reconfigurable in two configurations, the two configurations comprising:
a first, compressed configuration, wherein the implant is configured to be delivered through a minimally invasive entrance incision while in the compressed configuration; and
a second, uncompressed configuration, wherein the implant is configured to be reconfigured from the compressed configuration to the uncompressed configuration while being positioned within an implant pocket formed within a patient such that the implant can be maintained in the uncompressed configuration within the implant pocket in a functional state following implantation.

164. The compressible implant of example 163, wherein the source of electromagnetic radiation comprises a light source, and wherein the implant is configured such that the light source is viewable from beneath the skin while in the implant pocket.

165. The compressible implant of example 164, wherein the light source comprises an LED.

166. The compressible implant of example 164, wherein the light source comprises at least one of a multilayer stack and an array of LED lights.

167. The compressible implant of example 166, further comprising a polydimethylsiloxane coating.

168. The compressible implant of example 163, further comprising a thin film encapsulation.

169. The compressible implant of example 163, further comprising an organic nanocomposite layer.

170. The compressible implant of example 163, further comprising a barrier layer configured to insulate the light source from the biological environment within the implant pocket.

171. The compressible implant of example 163, wherein the source of electromagnetic radiation comprises a therapeutic radiation source.

172. The compressible implant of example 163, wherein the source of electromagnetic radiation comprises an OLED panel, and wherein the compressible implant further comprises a peeling reduction layer.

173. The compressible implant of example 163, wherein the source of electromagnetic radiation comprises an OLED panel, and wherein the compressible implant further comprises a multi-layer encapsulation film.

174. The compressible implant of example 163, wherein the source of electromagnetic radiation comprises an mLED device, and wherein the compressible implant comprises a selectively illuminable internal tattoo.

175. The compressible implant of example 174, further comprising a wireless receiver, wherein the wireless receiver is configured to receive wireless signals for adjusting a light display associated with the selectively illuminable internal tattoo.

176. The compressible implant of example 163, wherein the source of electromagnetic radiation comprises a flexible mLED device comprising:
a flexible substrate;

an upper insulating film;
a lower insulating film;
a metal layer positioned between the upper insulating film and the lower insulating film; and
a plurality of mLED chips positioned on the flexible substrate.

177. The compressible implant of example 176, wherein the flexible substrate comprises a reflective layer.

178. The compressible implant of example 163, wherein the compressible implant comprises an illuminable internal tattoo, and wherein the source of electromagnetic radiation comprises an organic polymer LED.

179. The compressible implant of example 178, further comprising a protective passivation layer.

180. The compressible implant of example 163, wherein the source of electromagnetic radiation comprises an OLED, and further comprising a thin film encapsulation structure comprising alternating organic and inorganic layers.

181. The compressible implant of example 163, further comprising a biocompatible polymer, wherein the source of electromagnetic radiation comprises a mesh-like array of LEDs.

182. The compressible implant of example 163, wherein the implant is configured to be delivered through a very minimally invasive entrance incision while in the compressed configuration.

183. The compressible implant of example 182, wherein the implant is configured to be delivered through an ultra minimally invasive entrance incision while in the compressed configuration.

184. A system comprising the compressible implant of example 163, and further comprising:
an energy source; and
an inductance coil electrically coupled with the energy source to allow the energy source to be wirelessly recharged, wherein the inductance coil is configured to be inserted through a minimally invasive entrance incision.

185. The system of example 184, wherein the energy source comprises at least one of a battery and a capacitor.

186. The compressible implant of example 163, wherein the source of electromagnetic radiation comprises a light sheet.

187. The compressible implant of example 186, wherein the light sheet is configured to display images.

188. The compressible implant of example 187, further comprising an antenna configured to receive a signal for use in altering images displayed on the light sheet.

189. The compressible implant of example 163, further comprising a heartrate sensor.

190. The compressible implant of example 189, wherein the heartrate sensor is configured to change a light display generated by the source of electromagnetic radiation based upon a heartrate detected by the heartrate sensor.

191. A system for selective illumination of a compressible implant configured for positioning within an implant pocket, comprising:
an external device comprising a heartrate sensor and a wireless transmitter;
an implantable energy source;
an implantable inductance coil electrically coupled with the implantable energy source;
an implantable wireless receiver; and an implant comprising a light source electrically coupled with the implantable energy source, wherein the implant is reconfigurable in two configurations, the two configurations comprising:

a first, compressed configuration, wherein the implant is configured to be delivered through a minimally invasive entrance incision while in the compressed configuration; and a second, uncompressed configuration, wherein the implant is configured to be reconfigured from the compressed configuration to the uncompressed configuration while being positioned within an implant pocket formed within a patient such that the implant can be maintained in the uncompressed configuration within the implant pocket in a functional state following implantation.

192. The system of example 191, wherein the external device comprises at least one of a wristband, an armband, and a smartphone.

193. The system of example 191, wherein the implantable inductance coil comprises an arm extending in a spiral shape from an outer terminus at a periphery of the implantable inductance coil to an inner terminus adjacent to a center of the implantable inductance coil, wherein the arm defines a plurality of adjacent bands having space between each adjacent band, and wherein the implantable inductance coil is configured to at least substantially maintain the spiral shape both before and after implantation within an implant pocket.

194. The system of example 191, wherein the implantable energy source comprises at least one of a battery and a capacitor, and wherein the implantable energy source is part of the compressible implant.

195. The system of example 191, wherein the compressible implant is formed in the shape of a heart, and wherein the compressible implant is sized and configured to be positioned in an implant pocket adjacent to a user's heart.

196. The system of example 191, wherein the compressible implant is configured to adjust a light display of the light source according to a heartrate detected by the heartrate sensor.

197. A method for subcutaneously illuminating an ink tattoo, the method comprising the steps of:

forming a subcutaneous implant pocket from a minimally invasive entrance incision, wherein the subcutaneous implant pocket is formed below an ink tattoo;

compressing an illuminable implant to fit through the minimally invasive entrance incision;

advancing the illuminable implant into the subcutaneous implant pocket;

decompressing the illuminable implant; and illuminating the illuminable implant once decompressed and within the subcutaneous implant pocket to illuminate the ink tattoo from underneath the skin comprising the ink tattoo.

198. The method of example 197, wherein the illuminable implant comprises a light sheet comprising LED lights.

199. An implant configured to be inserted within an implant pocket via a minimally invasive entrance incision, comprising:

a bioresorbable material forming a substrate for the implant;

a plurality of RFID chips interspersed throughout the substrate, wherein the substrate is configured to be absorbed by a patient's tissue once within the implant pocket to leave the plurality of RFID chips within the implant pocket following implantation.

200. The implant of example 199, wherein the implant is compressible to allow for insertion through the minimally invasive entrance incision and selectively decompressible for positioning within the implant pocket.

201. The implant of example 199, wherein each of the plurality of RFID chips is positioned on the substrate randomly about the substrate relative to each of the remaining RFID chips of the plurality of RFID chips.

202. The implant of example 199, wherein at least a subset of the plurality of RFID chips comprises rechargeable power stores.

203. A neuro-stimulative implant configured to be positioned within an implant pocket, comprising:

a primary trunk extending along an elongated axis of the implant;

a plurality of branches extending from the primary trunk; and a plurality of neuro-stimulative electrodes positioned on at least a subset of the plurality of branches.

204. The neuro-stimulative implant of example 203, wherein each of the plurality of branches extends towards a proximal end of the implant.

205 The neuro-stimulative implant of example 203, further comprising an inductance coil configured to generate wireless electrical energy.

206. The neuro-stimulative implant of example 203, wherein the neuro-stimulative electrodes are configured to fire in a wave-like pattern.

207. The neuro-stimulative implant of example 203, further comprising a heartrate sensor, wherein the heartrate sensor is coupled with at least a subset of the plurality of neuro-stimulative electrodes such that at least one of a strength and a firing rate is configured to automatically change according to a heartrate detected by the heartrate sensor.

208. A neuro-stimulative implant configured to be positioned within an implant pocket, comprising:

an elongated strand comprising a serpentine shape comprising a plurality of repeated bends, wherein each bend extends in an opposite direction relative to its adjacent bends; and a plurality of neuro-stimulative electrodes positioned on the elongated strand, wherein at least a subset of the plurality of neuro-stimulative electrodes is positioned on a bend of the plurality of repeated bends.

209. The neuro-stimulative implant of example 208, wherein each of the plurality of repeated bends comprises a neuro-stimulative electrode.

210 The neuro-stimulative implant of example 208, wherein the elongated strand is formed into a sinusoidal shape.

211. A sensory feedback implant system, comprising:

a plurality of implants coupled with one another, wherein each of the plurality of implants is configured to be received in a corresponding, subcutaneous implant pocket via a minimally invasive entrance incision, and:

wherein at least one of the plurality of implants is configured to harvest electrical energy, wherein at least one of the plurality of implants comprises a sensory implant, and wherein at least one of the plurality of implants comprises an elongated strand configured to be positioned in an implant tunnel to electrically couple two implants of the plurality of implants.

212. The sensory feedback implant system of example 211, wherein the at least one of the plurality of implants configured to harvest electrical energy comprises an inductance coil.

213 The sensory feedback implant system of example 211, wherein the at least one of the plurality of implants configured to harvest electrical energy comprises a thermoelectric generator.

214. The sensory feedback implant system of example 211, wherein the at least one of the plurality of implants configured to harvest electrical energy comprises at least one of an electrostatic generator and a piezoelectric device configured to convert kinetic energy from movement of a user's body into electrical energy.

215. The sensory feedback implant system of example 211, wherein the at least one of the plurality of implants configured to harvest electrical energy comprises a bio-fuel cell.

216. The sensory feedback implant system of example 211, wherein at least one of the plurality of implants comprises an auxiliary implant comprising at least one of an antenna, a CPU, a battery, a capacitor, a data storage element, a heartrate sensor, and a lab-on-a-chip element.

217. The sensory feedback implant system of example 211, wherein the sensory implant comprises an acoustic implant.

218. The sensory feedback implant system of example 211, further comprising a pair of eyeglasses communicatively coupled with at least one of the plurality of implants.

219. An implantable pacemaker system, comprising:

at least one of a first inductance coil and a thermoelectric implant configured to be positioned in a first implant pocket via a minimally invasive entrance incision;

a second inductance coil configured to be positioned in a second implant pocket via a minimally invasive entrance incision;

an elongated flexible strand implant configured to be positioned within a tunnel implant pocket via a minimally invasive entrance incision and configured to electrically couple the at least one of a first inductance coil and a thermoelectric implant with the second inductance coil; and a wireless cardiac pacemaker configured to be positioned on or adjacent a patient's heart, wherein the wireless cardiac pacemaker comprises a third inductance coil configured to receive wireless energy from the at least one of a first inductance coil and a thermoelectric implant.

220. The implantable pacemaker system of example 219, further comprising an auxiliary implant configured to be electrically coupled with at least one of the first and second inductance coils, wherein the auxiliary implant comprises at least one of a battery, a capacitor, a CPU, a PCB, and an antenna.

221. The implantable pacemaker system of example 219, wherein the at least one of a first inductance coil and a thermoelectric implant comprises a thermoelectric implant, and wherein the thermoelectric implant comprises a spiral shape configured to be positioned through a minimally invasive entrance incision.

222. A subcutaneously implantable energy delivery system, comprising:

a first implantable inductance coil comprising an arm extending in a spiral shape from an outer terminus at a periphery of the implantable inductance coil to an inner terminus adjacent to a center of the implantable inductance coil, wherein the arm defines a plurality of adjacent bands having space between each adjacent band, and wherein the first implantable inductance coil is configured to at least substantially maintain the spiral shape both before and after implantation within a first implant pocket;

a second implantable inductance coil comprising an arm extending in a spiral shape from an outer terminus at a periphery of the implantable inductance coil to an inner terminus adjacent to a center of the implantable inductance coil, wherein the arm defines a plurality of adjacent bands having space between each adjacent band, and wherein the second implantable inductance coil is configured to at least substantially maintain the spiral shape both before and after implantation within a second implant pocket; and an elongated flexible strand implant configured to be positioned within a tunnel implant pocket via a minimally invasive entrance incision and configured to electrically couple the first inductance coil with the second inductance coil, wherein the second implantable inductance coil is configured to wirelessly deliver electrical energy to an implantable device.

223. The system of example 222, further comprising an auxiliary implant configured to be positioned within an implant pocket via a minimally invasive entrance incision, wherein the auxiliary implant comprises at least one of an antenna, a CPU, a battery, a capacitor, a data storage element, a heartrate sensor, and a lab-on-a-chip element.

224. The system of example 222, wherein the implantable device comprises at least one of a gastric implant, a motor nerve implant, a chemical pump implant, a brain implant, a cochlear implant, and an implantable motor unit.

225. A method for implantation of a flexible implant via a minimally invasive entrance incision, the method comprising the steps of:

forming an implant pocket through a minimally invasive entrance incision;

coupling one or more sutures to a compressible implant;

extending at least one of the one or more sutures into the implant pocket through the minimally invasive entrance incision and out through a needle puncture formed in the implant pocket;

extending the compressible implant through the minimally invasive entrance incision in a compressed configuration on an instrument; and decompressing the compressible implant while in the implant pocket by pulling on at least one of the one or more sutures.

226. The method of example 225, wherein the compressible implant comprises one or more holes, and wherein the step of coupling the one or more sutures to the compressible implant comprises securing the one or more sutures to the one or more holes.

227. The method of example 225, wherein the compressed configuration comprises a rolled configuration, and wherein the step of decompressing the compressible implant comprises unrolling the compressible implant.

BRIEF DESCRIPTION OF THE FIGURES

The written disclosure herein describes illustrative embodiments that are non-limiting and non-exhaustive. Reference is made to certain of such illustrative embodiments that are depicted in the figures, in which

FIG. 2a depicts a human torso having undergone comparative bilateral surgical procedures to form distinct types of implant pockets, one comprising an enlarged implant pocket that may be formed using a plurality of strokes of an electrosurgical device, and the other comprising an elongated implant pocket that may be formed by a single stroke of such an instrument or, as shown in the drawing, by a mechanical device such as scissors.

FIG. 4a depicts a top plan view of a circular, flexible, and compressible implant according to another embodiment.

FIG. 4b depicts a side view of the implant of FIG. 4a.

FIG. 4c depicts an enlarged side view of the implant.

FIG. 4d depicts a top perspective view of the implant.

FIG. 6d depicts a perspective view of an embodiment of a flexible tissue implant facilitating system (FTIFS).

FIG. 6e depicts a side view of the flexible tissue implant facilitating system of FIG. 6d.

FIG. 11 depicts a top plan view of an embodiment of a circular implant comprising non-protruding reinforcement regions.

FIG. 12 depicts a top plan view of an embodiment of a square implant comprising non-protruding reinforcement regions.

FIG. 13 depicts a top plan view of an embodiment of a rectangular implant comprising non-protruding reinforcement regions.

FIG. 14 depicts a top plan view of an embodiment of a circular implant comprising non-protruding reinforcement regions.

FIG. 15 depicts a top plan view of an embodiment of a square implant comprising non-protruding reinforcement regions.

FIG. 16 depicts a top plan view of an embodiment of a rectangular implant comprising non-protruding reinforcement regions.

FIG. 25 depicts a top view of an alternative embodiment of a compressible, circular, flexible, mesh implant.

FIG. 26 depicts a top view of an alternative embodiment of a compressible, rectangular, flexible, mesh implant.

FIG. 27 depicts a top view of an alternative embodiment of a compressible, polygonal, flexible, mesh implant.

FIG. 28 depicts a top view of an alternative embodiment of a compressible, rectangular, flexible, mesh implant.

FIG. 33 depicts a bottom view of a circular, flexible, and compressible implant with a hollow, fillable, circular shaped superstructure according to an embodiment.

FIG. 34 depicts a bottom view of a circular, flexible, and compressible implant with a hollow fillable '+' shaped superstructure according to an embodiment.

FIG. 35 depicts a lower view of a rectangular, flexible, and compressible implant with a hollow fillable rectangular shaped superstructure on one side according to an embodiment.

FIG. 36 depicts a lower view of a rectangular, flexible, and compressible implant with a hollow fillable '+' shaped superstructure according to an embodiment.

FIG. 41 depicts a top view of a rectangular, spiral implant.

FIG. 42a depicts a top view of a polygonal, spiral implant.

FIG. 42b depicts an enlarged view of a terminus of a spiral implant according to an embodiment.

FIG. 43 depicts an enlarged view of an oval cross section of a spiral band according to an embodiment.

FIG. 44 depicts a spaghetti-like, flexible implant.

FIG. 50 depicts a human patient having subcutaneous, compressible implants positioned in implant pockets.

FIG. 51a depicts a top plan view of an implant in its deployed/uncompressed state according to an embodiment.

FIG. 51b depicts a side view of the implant in its deployed/uncompressed state.

FIG. 51c depicts a side view of the implant in its rolled state.

FIG. 52a depicts a top plan view of an implant in its deployed/uncompressed state according to another embodiment.

FIG. 52b depicts a side view of the implant in its deployed/uncompressed state.

FIG. 52c depicts a side view of the implant in its rolled state.

FIG. 54*a* depicts another compressible implant comprising an auxiliary implant which may be electrically coupled to implant according to an embodiment.

FIG. 54*b* depicts an implant in its uncompressed configuration from the side, showing an inductance coil on one side of the implant.

FIG. 54*c* depicts a full system comprising an implant and an auxiliary implant.

Figures 55A, 55B, 55C:
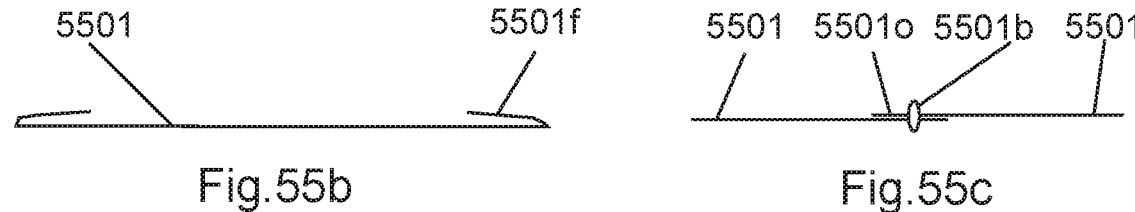
FIG. 55*a* depicts a human patient's abdomen having subcutaneous, compressible mesh implants.

FIG. 55*b* depicts a side view of a mesh implant with optional mesh implant peripheral folds.

FIG. 55*c* depicts a side view of a mesh implant with optional zone of overlap.

Figures 56A, 56B:
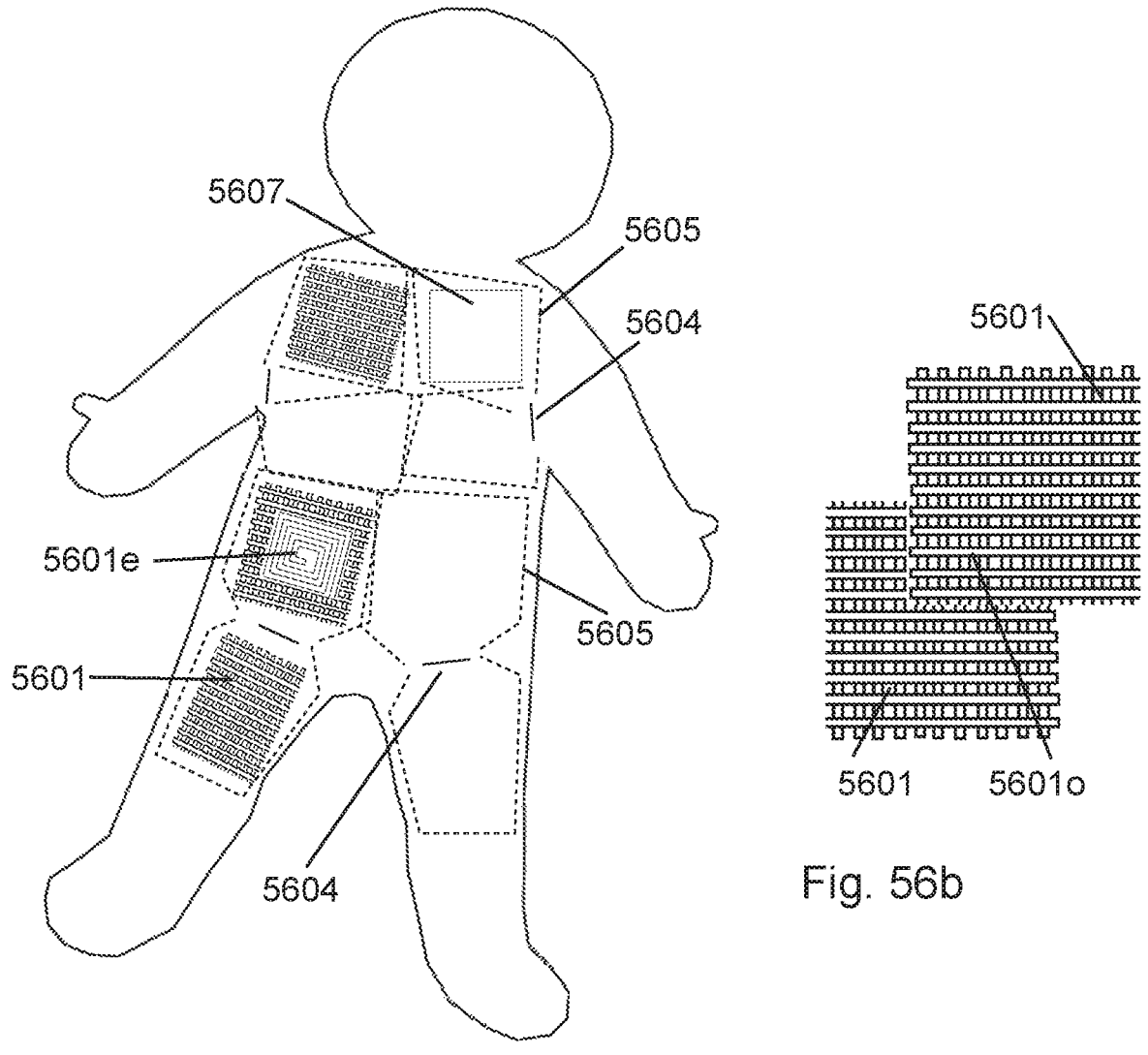

FIG. 56*a* depicts a soldier who having multiple subcutaneous, compressible mesh implants, positioned in implant pockets.

FIG. 56*b* depicts two implants that are positioned within a shared subcutaneous pocket and overlap with one another to an extent, as indicated by the overlapping region.

Figure 57A:
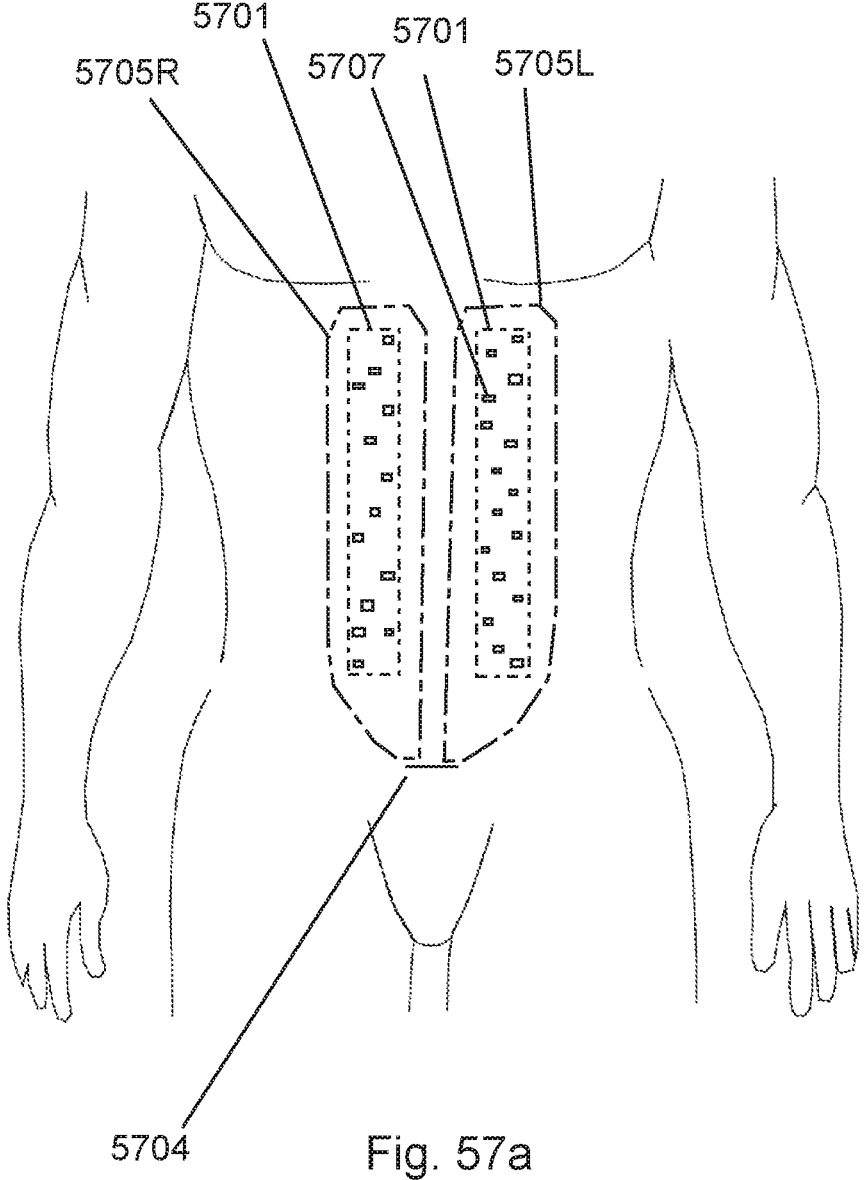

FIG. 57*a* depicts a patient's abdomen having subcutaneous, compressible implants, positioned in respective implant pockets.

Figure 57B:
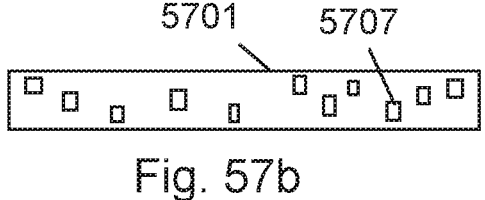

FIG. 57*b* depicts a top view of an implant containing RFID chips placed in less predictable patterns.

Figures 58A, 58B, 58C, 58D:
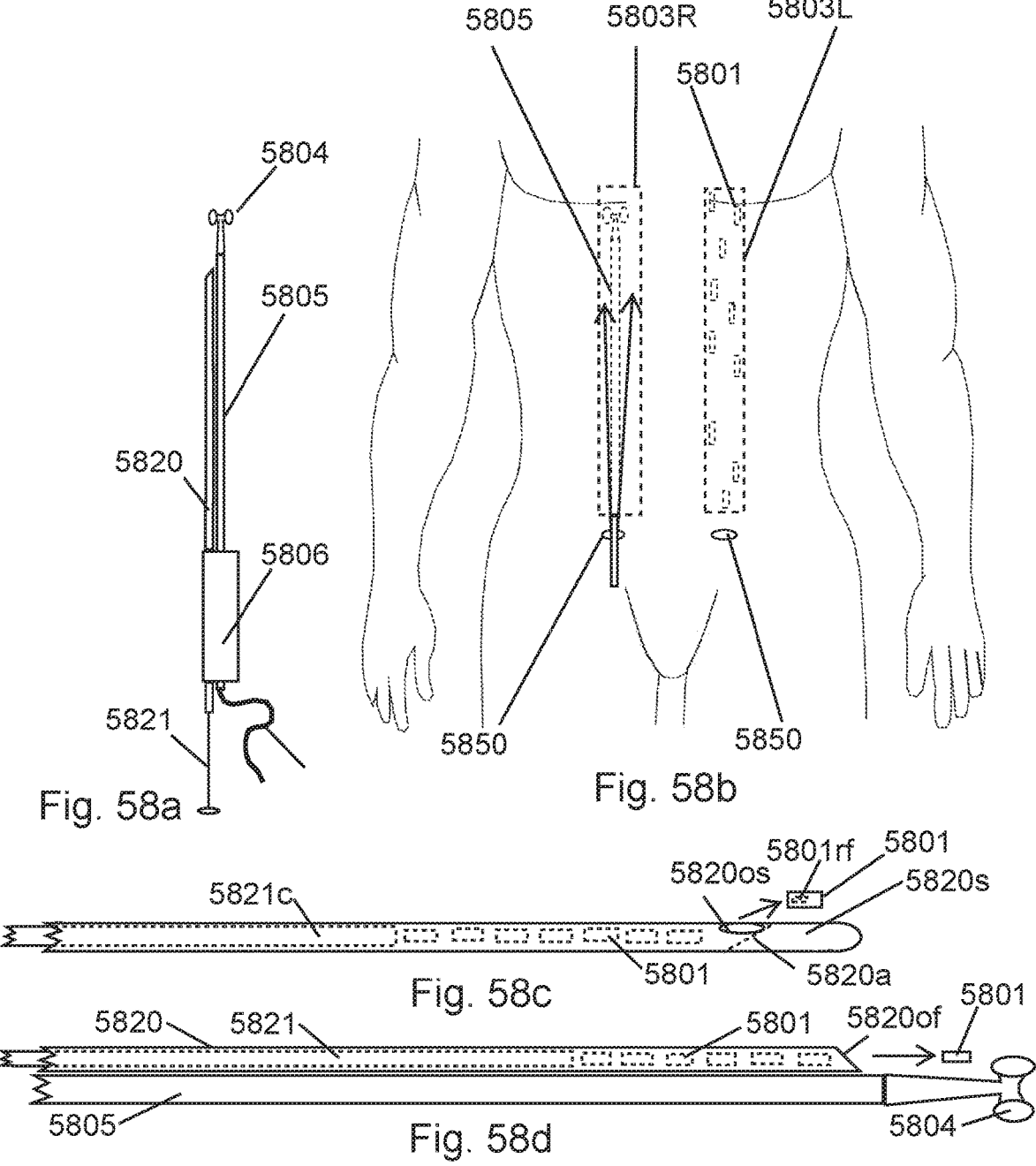

FIG. 58*a* depicts a minimally invasive electro-dissection device with a 2 bead tip according to an embodiment.

FIG. 58*b* depicts a human torso after having undergone comparative bilateral surgical procedures.

FIG. 58*c* depicts a side view of an alternative embodiment of an implant expelling cannula that is configured to expel implants from a side opening.

FIG. 58*d* depicts detailed side view of an implant expelling cannula attached to a shaft, depicting implant expelling plunger, pushing a series of the expellable implants through a frontal/distal shaft opening.

Figures 59A, 59B, 59C:
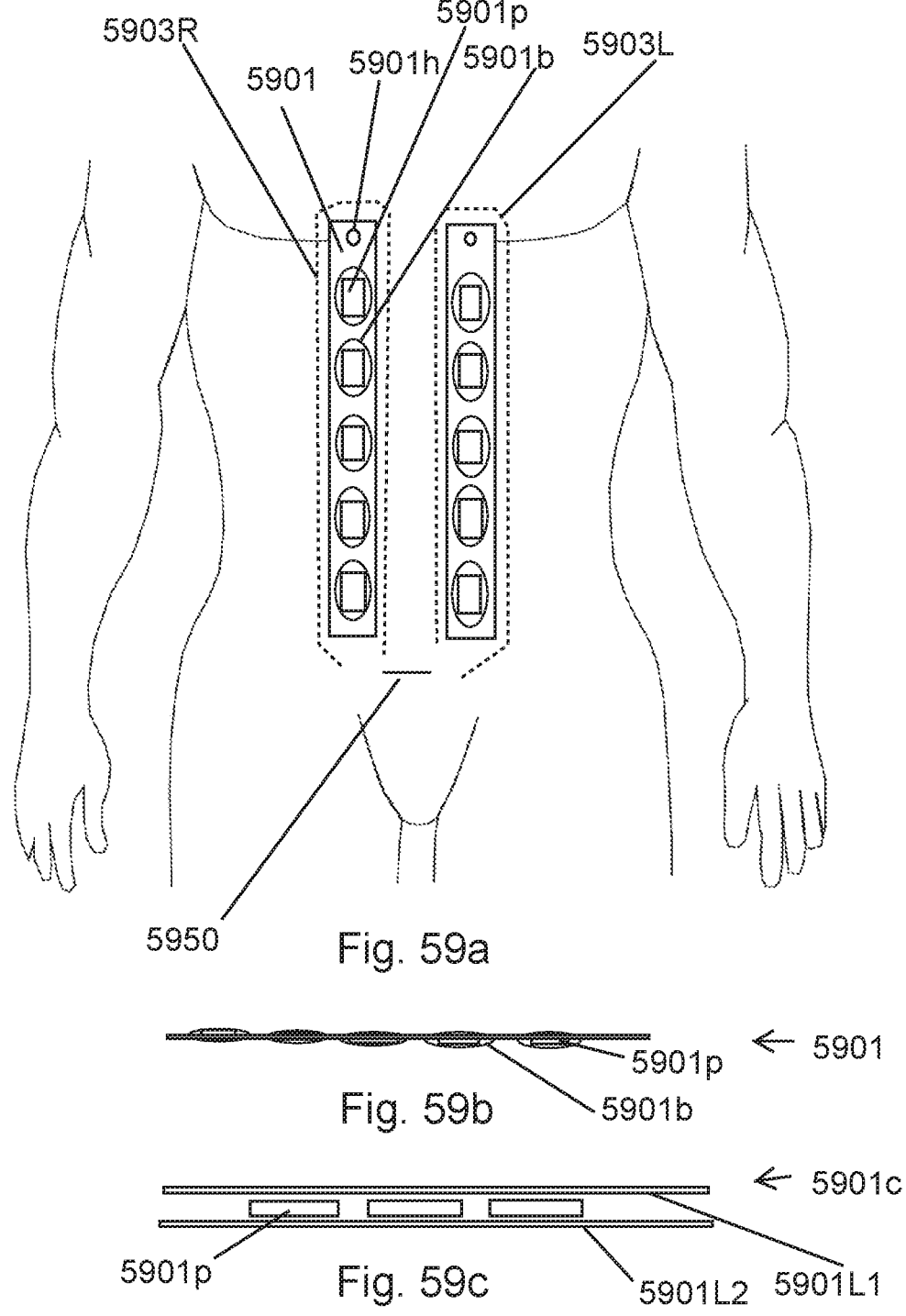

FIG. 59*a* depicts a human torso having undergone comparative bilateral surgical procedures whereupon stem cell incubator implant strips were placed in respective implant pockets.

FIG. 59*b* depicts a side view of an embodiment of a minimally invasive stem cell incubator implant strip.

FIG. 59*c* depicts a side view of an alternative embodiment of a minimally invasive stem cell incubator implant wherein payload bays are sandwiched within laminate layers.

Figures 60A, 60B, 60C, 60D:
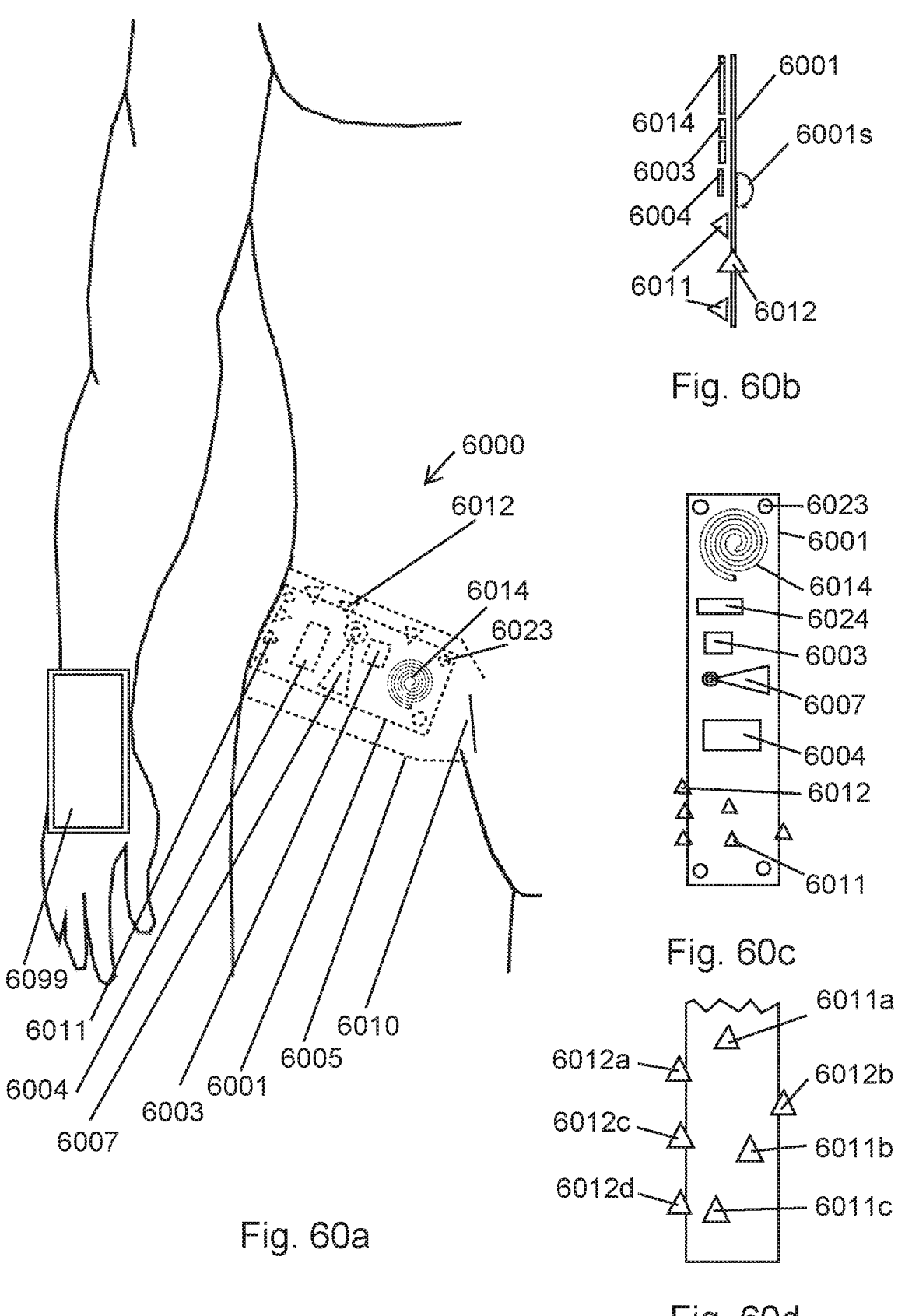

FIG. 60*a* depicts a torso of a human patient having a rectangular compressible subcutaneous electronic neuro simulative (SQENS) implant system positioned in an implant pocket made via a minimally invasive entrance incision.

FIG. 60*b* depicts a side elevation view of an implant of system illustrating how each element may be coupled to the implant according to an embodiment.

FIG. 60*c* depicts a top plan view of the implant in its deployed/uncompressed state FIG. 60*d* depicts a top plan breakaway view of the implant in its deployed/uncompressed state.

Figures 61A, 61B, 61C:
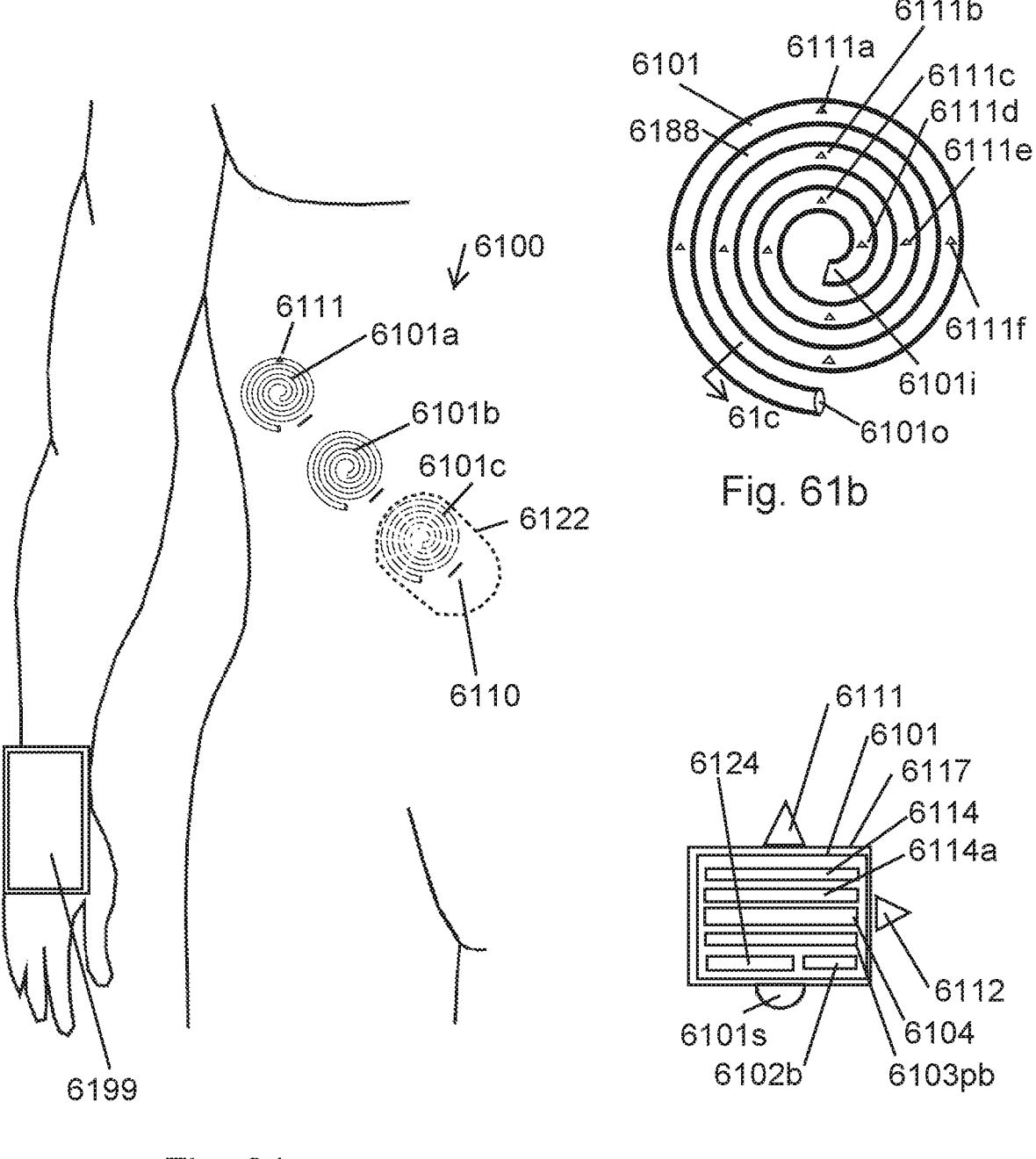

FIG. 61*a* depicts the right side of a torso of a human patient having a spiral subcutaneous electronic neuro simulative (SSENS) implant system having a plurality of implants each preferably positioned in a respective implant pocket made via a minimally invasive entrance incision.

FIG. 61*b* depicts a top view of a single 3 turn SSENS implant with an outer terminal end and electrodes dispersed along one or more sides of the faces or sides of the spiral with space between adjacent bands.

FIG. 61*c* depicts an enlarged view of a cross section of an embodiment of a spiral implant.

Figures 62A, 62B, 62C:
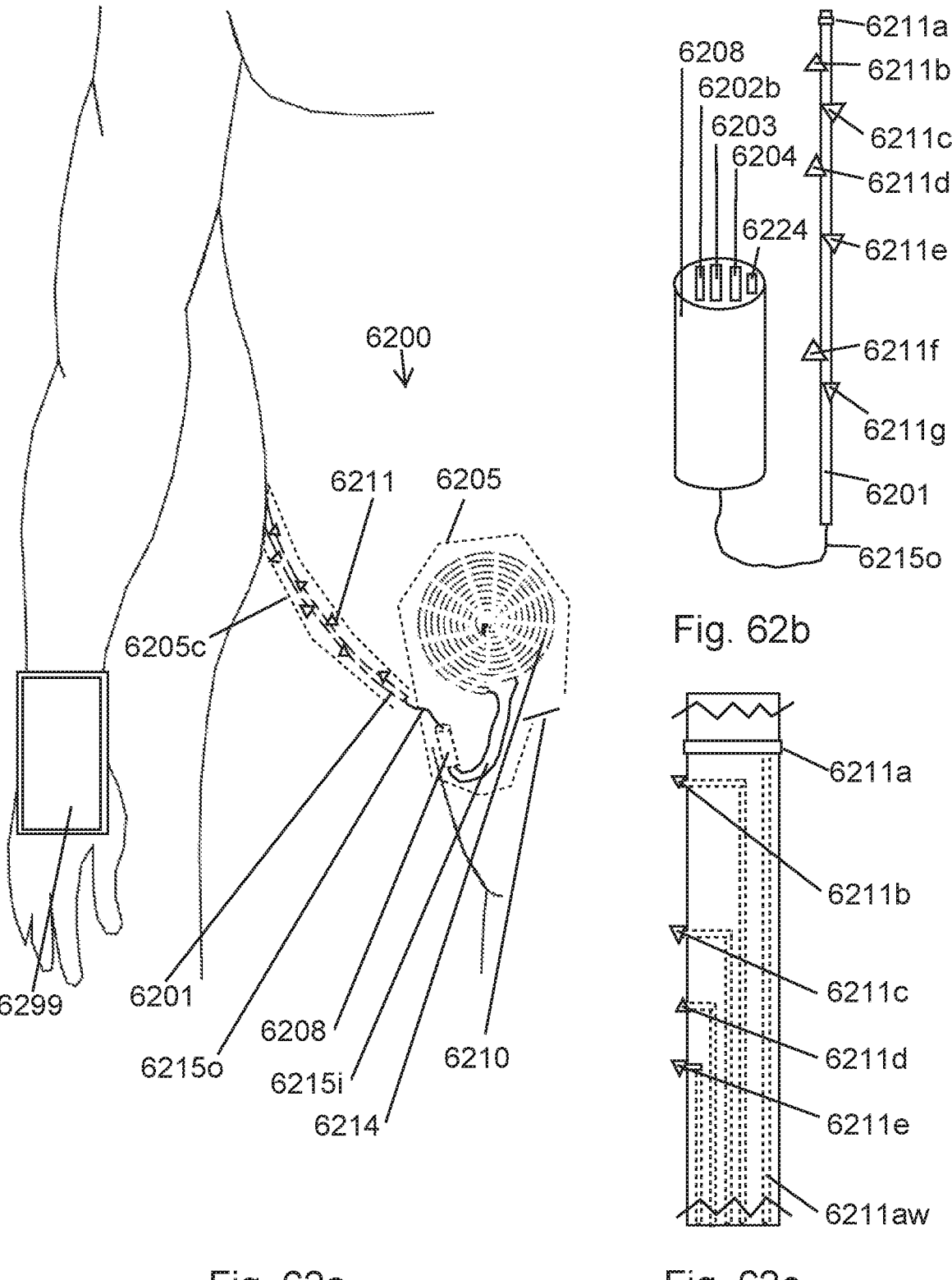

FIG. 62*a* depicts the right side of a torso of a human patient having a flexible strand/string subcutaneous electronic neuro simulative (FSQENS) implant system positioned in a respective implant pocket made via a minimally invasive entrance incision.

FIG. 62*b* depicts a side elevation view of a FSQENS flexible strand/string implant, illustrating how each of the elements may be coupled the strand FIG. 62*c* depicts an enlarged transparency view of an embodiment of a wiring scheme for various terminal electrodes along a flexible strand/string subcutaneous electronic neuro simulative (FSQENS) implant.

Figures 63A, 63B, 63C, 63D, 63E, 63F, 63G:
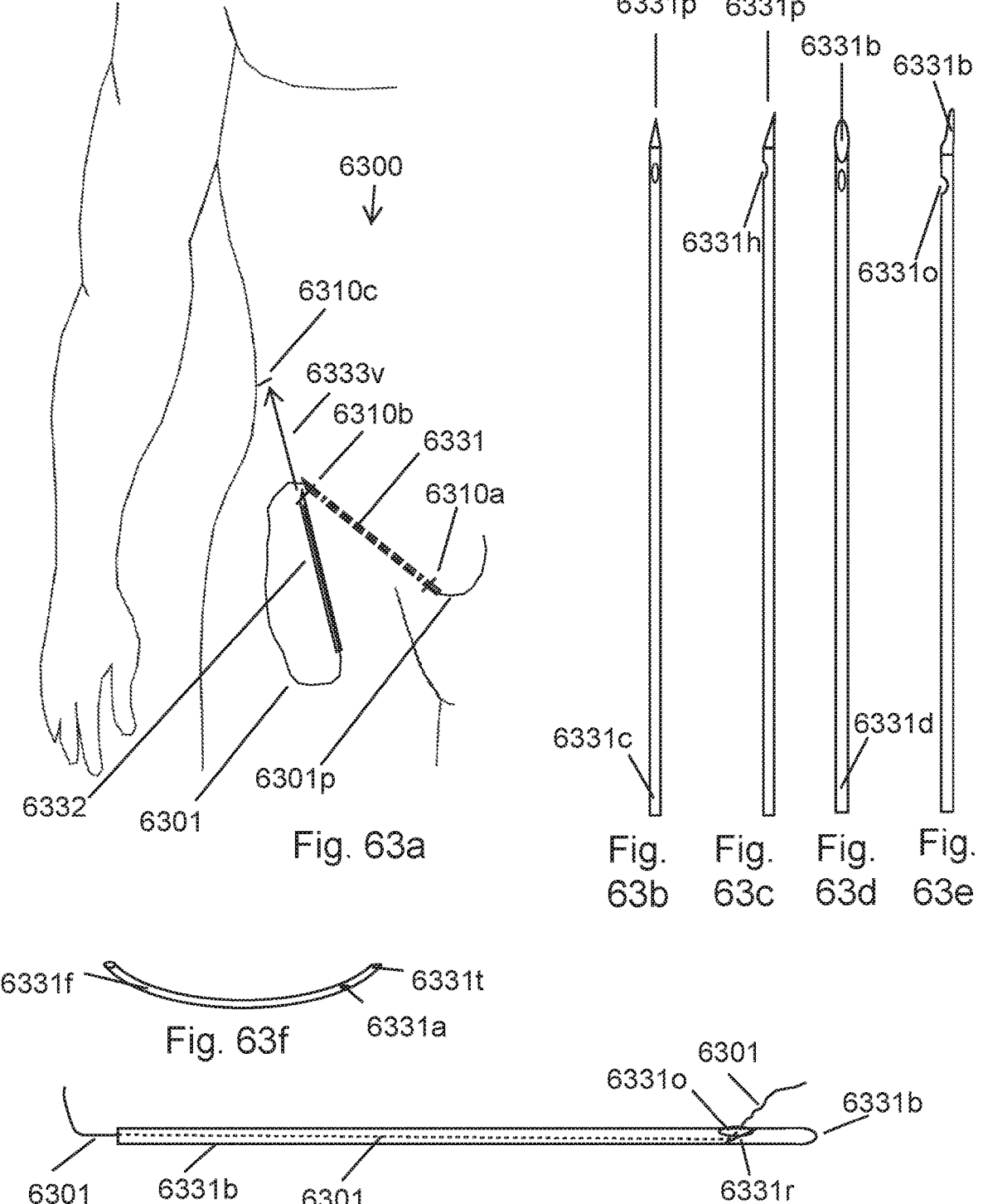

FIG. 63*a* depicts the right side of a torso of a human patient having flexible strand/string subcutaneous implants positioned in respective implant pockets made adjacent minimally invasive entrance incisions.

FIG. 63*b* depicts a top view of an upright beveled relatively sharp tipped trocar.

FIG. 63*c* depicts a top view rotated 90 degrees on its axis of the same trocar.

FIG. 63*d* depicts a top view of an upright alternative embodiment of beveled relatively blunt spatula tipped trocar.

FIG. 63*e* depicts a top view rotated 90 degrees on its axis of the same trocar.

FIG. 63*f* depicts a trocar with a curved shaft.

FIG. 63*g* depicts a side view of an alternative embodiment of an implant expelling cannula that is configured to expel an implant from a side opening rather than through the distal end of the device.

FIG. 64*a* depicts the front side of a torso of a human patient having rectangular compressible subcutaneous electronic muscle simulative (SQEMS) implant systems positioned in respective implant pockets made via a minimally invasive entrance incision.

FIG. 64*b* depicts a bottom view of an implant of the system, illustrating how each of the elements may be coupled on the implant.

FIG. 64*c* depicts a front view of an abdominal tension detecting belt that may be optionally used in conjunction with an implant according to an embodiment.

Figures 65A, 65B, 65C:
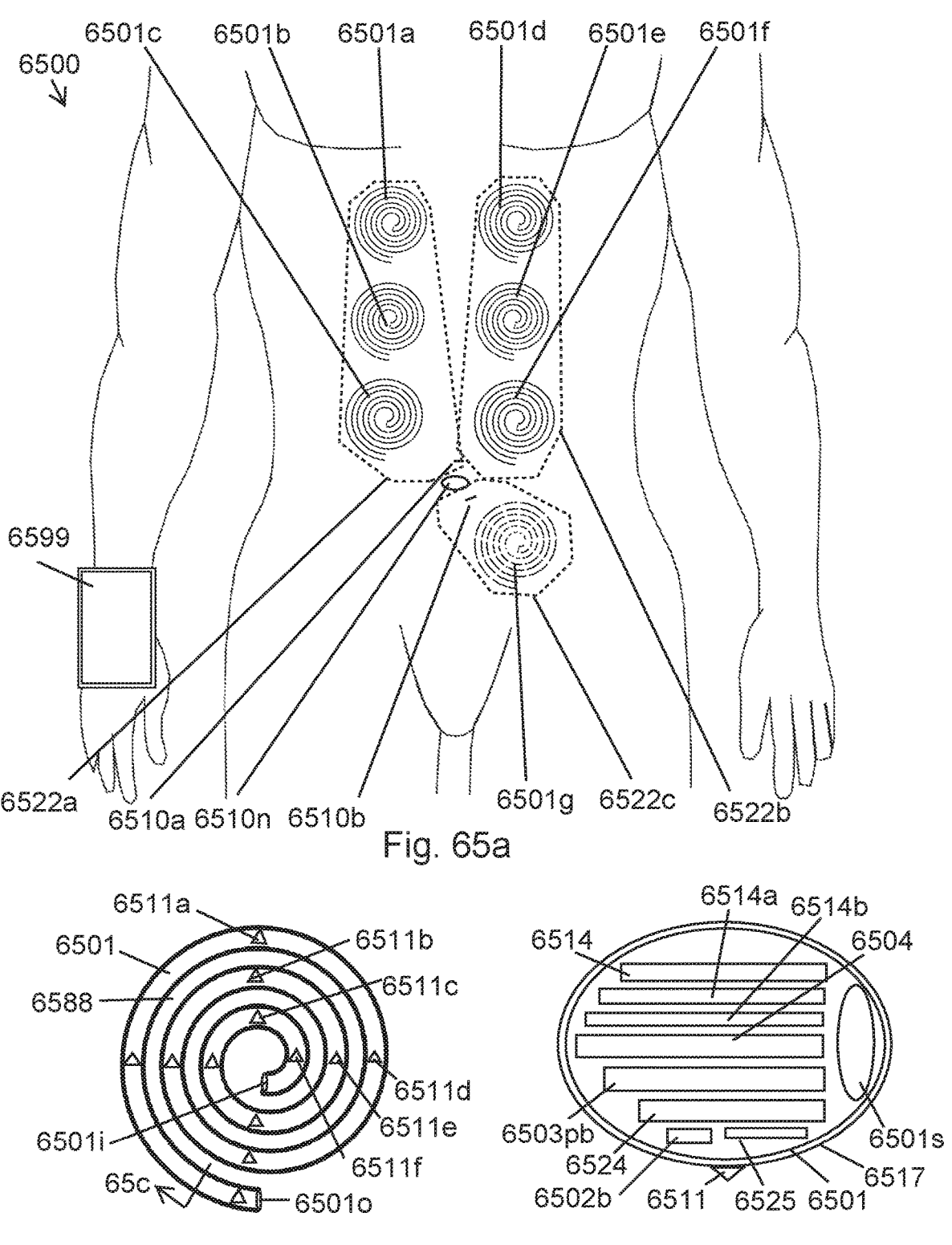

FIG. 65*a* depicts a front side of a torso of a human patient having a plurality of spiral subcutaneous electronic muscular stimulative (SSEMS) implants.

FIG. 65*b* depicts a plan view of a single 3 turn SSEMS implant.

FIG. 65*c* depicts an enlarged view of a cross section of an arm of a SSEMS implant.

Figures 66A, 66B, 66C:
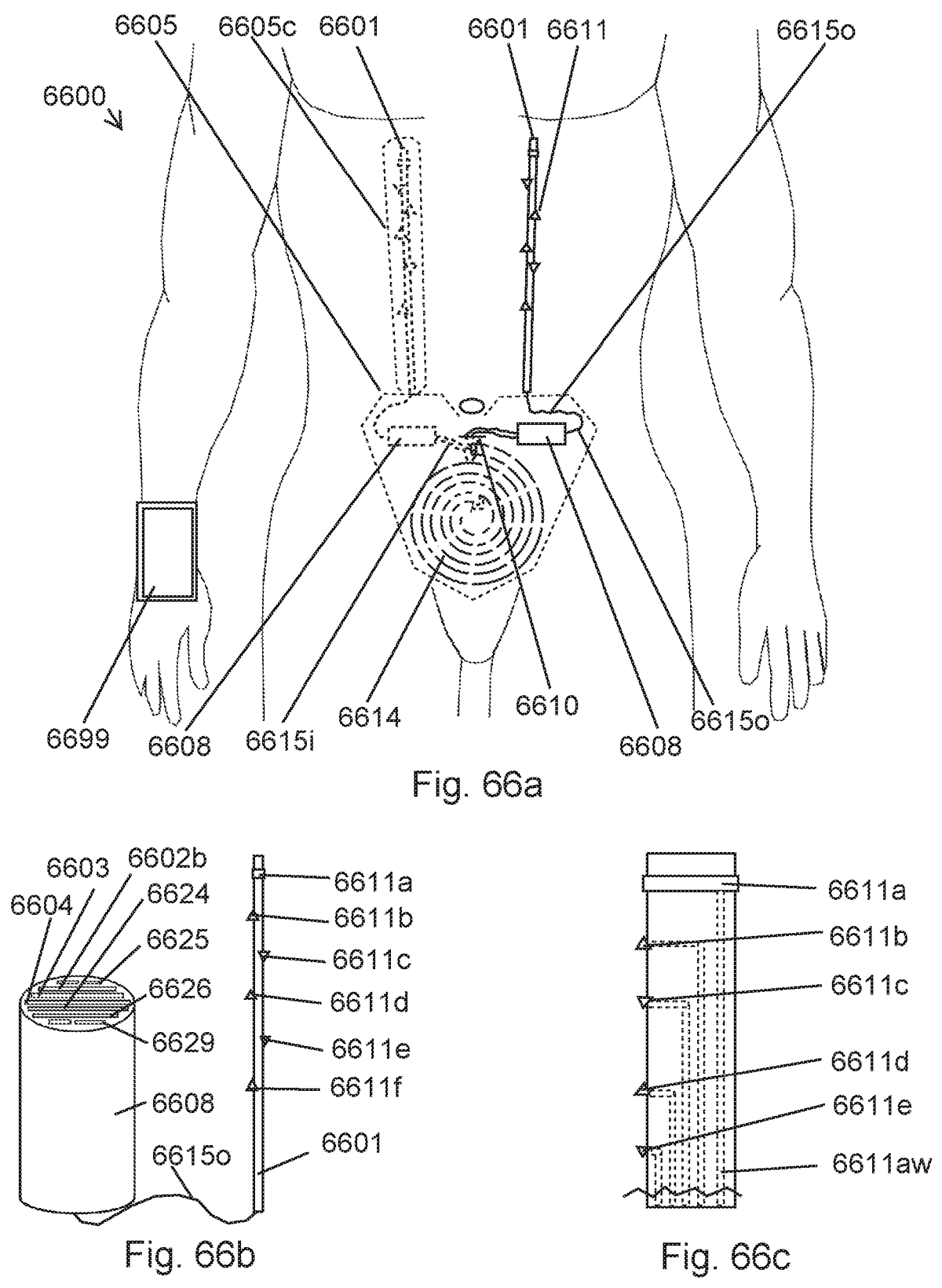

FIG. 66*a* depicts a front side of a torso of a human patient having a flexible strand/string subcutaneous electronic muscular stimulative (FSQEMS) implant.

FIG. 66*b* depicts an embodiment of an auxiliary implant that may comprise an antenna, a CPU/PCB, and a battery.

FIG. 66*c* depicts an enlarged transparency view of a wiring scheme for terminal electrodes on a FSQEMS implant.

Figures 67A, 67B, 67C, 67D, 67E, 67F, 67G, 67H, 67I, 67J, 67K, 67L, 67M, 67N, 68A, 68B, 68C, 68D, 68E, 69:
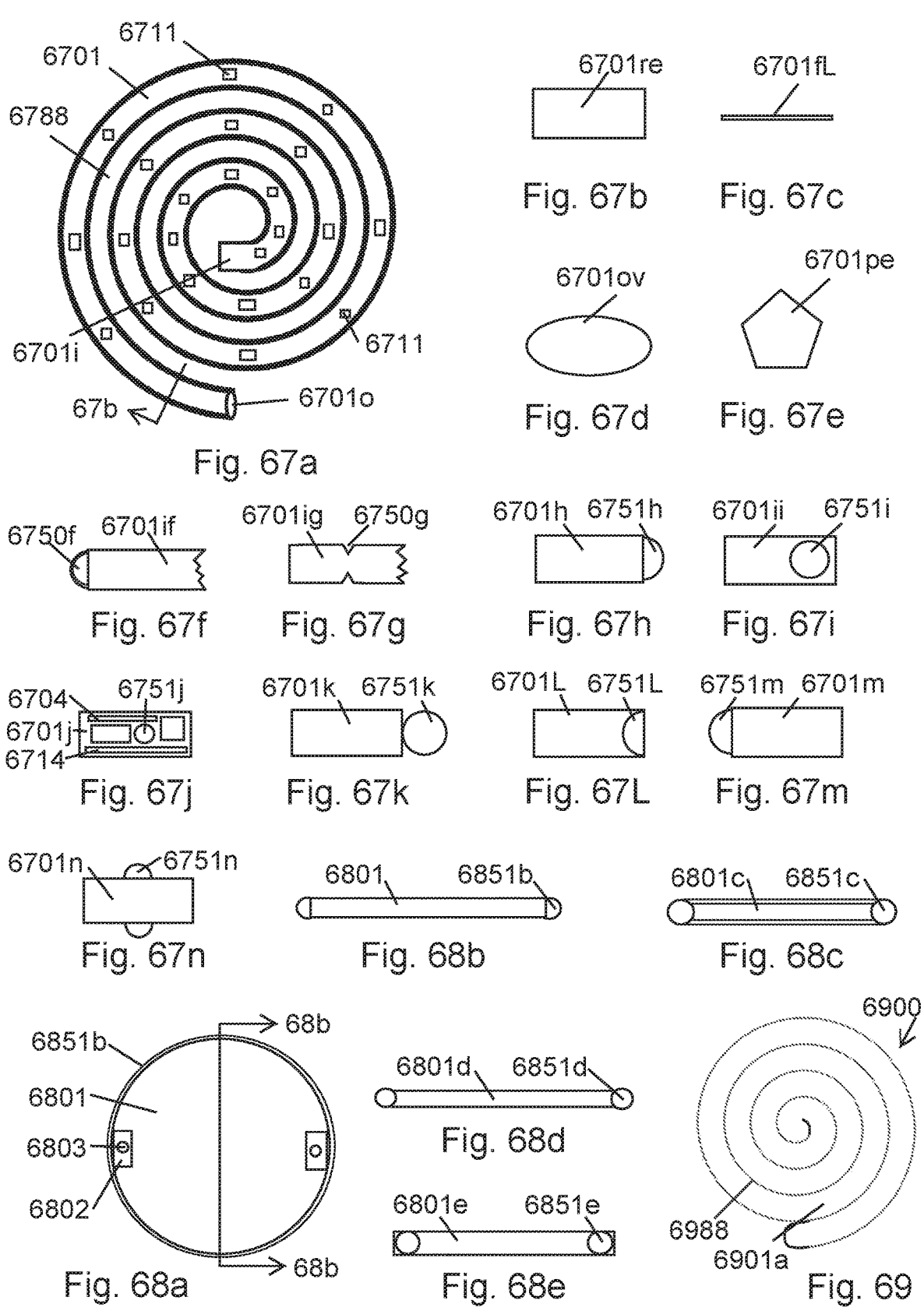

FIG. 67*a* depicts an embodiment of a spiral implant comprising a plurality of LEDs interspersed throughout the implant.

FIG. 67*b* depicts a cross sectional view spiral implant with a rectangular cross section.

FIG. 67*c* depicts a cross sectional view spiral implant with a relatively flat cross section.

FIG. 67*d* depicts a cross sectional view spiral implant with an oval-shaped cross section FIG. 67*e* depicts a cross sectional view spiral implant with a pentagonal cross section FIG. 67*f* depicts a spiral implant's inner terminus, which comprises an open loop/handle.

FIG. 67*g* depicts a spiral implant's inner terminus, which comprises a notch.

FIG. 67*h* depicts a cross sectional view of a spiral implant comprising a superstructure adhered to one side of the implant.

FIG. 67*i* depicts a cross sectional view of a spiral implant comprising a superstructure positioned within the lumen the implant.

FIG. 67*j* depicts a cross sectional view of a spiral implant comprising a superstructure positioned within the lumen the implant, sandwiched between other functional elements, such as a battery and inductance coil.

FIG. 67*k* depicts a cross-sectional view of another spiral implant comprising an externally attached superstructure on the outer side of a spiral arm.

FIG. 67L depicts a cross-sectional view of another spiral implant comprising a fully contained semicircular superstructure.

FIG. 67*m* depicts a cross-sectional view of another spiral implant comprising an externally attached superstructure on the inner side of a spiral arm.

FIG. 67*n* depicts a cross-sectional view of a spiral implant comprising a superstructure positioned on the upper and lower surfaces of the implant.

FIG. 68*a* depicts a top plan view of a compressible implant comprising a peripheral superstructure.

FIG. 68*b* depicts a cross sectional view of an embodiment of a compressible implant comprising a peripheral superstructure.

FIG. 68*c* depicts a cross sectional view of an embodiment of a compressible implant comprising a peripheral superstructure.

FIG. 68*d* depicts a cross sectional view of an embodiment of a compressible implant comprising a peripheral superstructure.

FIG. 68*e* depicts a cross sectional view of an embodiment of a compressible implant comprising a peripheral superstructure.

FIG. 69 depicts a spiral implant having little to no space between spiral arms.

Figure 70A:
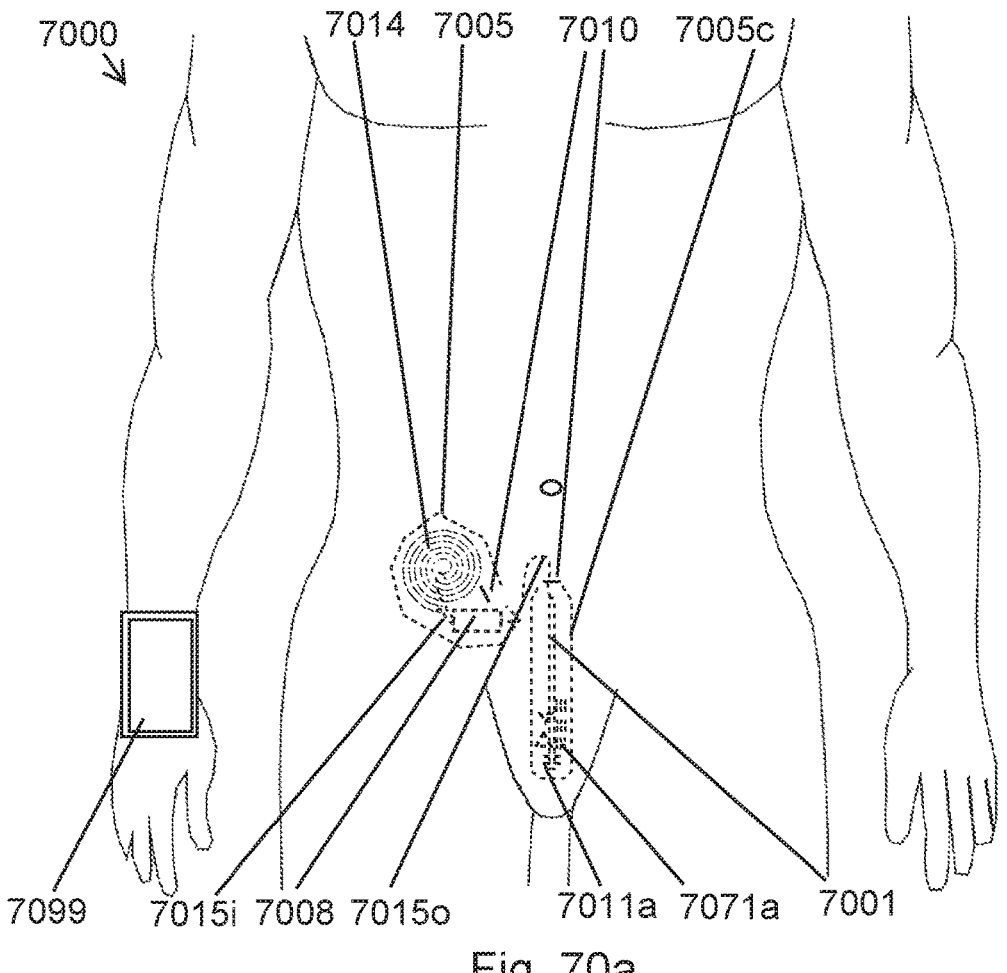

FIG. 70*a* depicts a front view of a torso of a human patient having a flexible strand/string electronic genital stimulative (FSEGS) implant system.

Figure 70B:
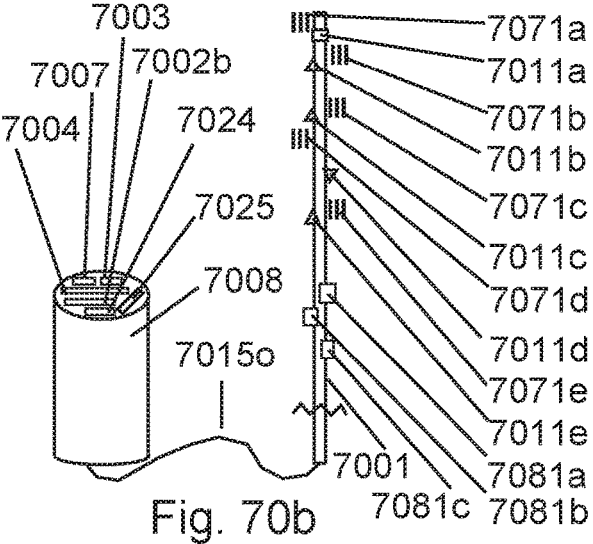

FIG. 70*b* depicts a side elevation view of a FSEGS implant and an embodiment of an auxiliary implant that may comprise an antenna, a CPU/PCB, and a battery.

Figure 70C:
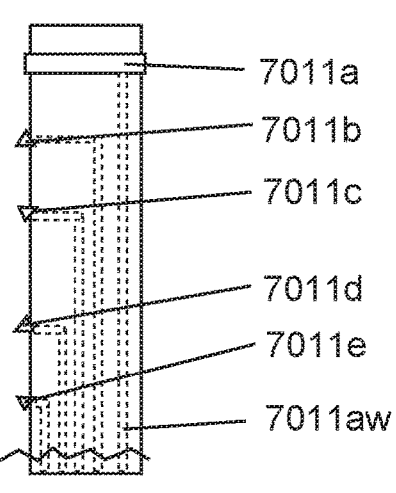

FIG. 70*c* depicts an enlarged transparency view of an embodiment of a wiring scheme for various terminal electrodes along a FSEGS implant.

FIG. 70*d* depicts a string implant extending into the glans of the clitoris.

FIG. 70*e* depicts string implants extending into the crux of the clitoris.

FIG. 70*f* depicts a FSEGS implant extending down the shaft of a penis and partially into the glans of the penis.

FIG. 70*g* depicts two implants positioned side by side within the penis.

Figures 71A, 71B, 71C:
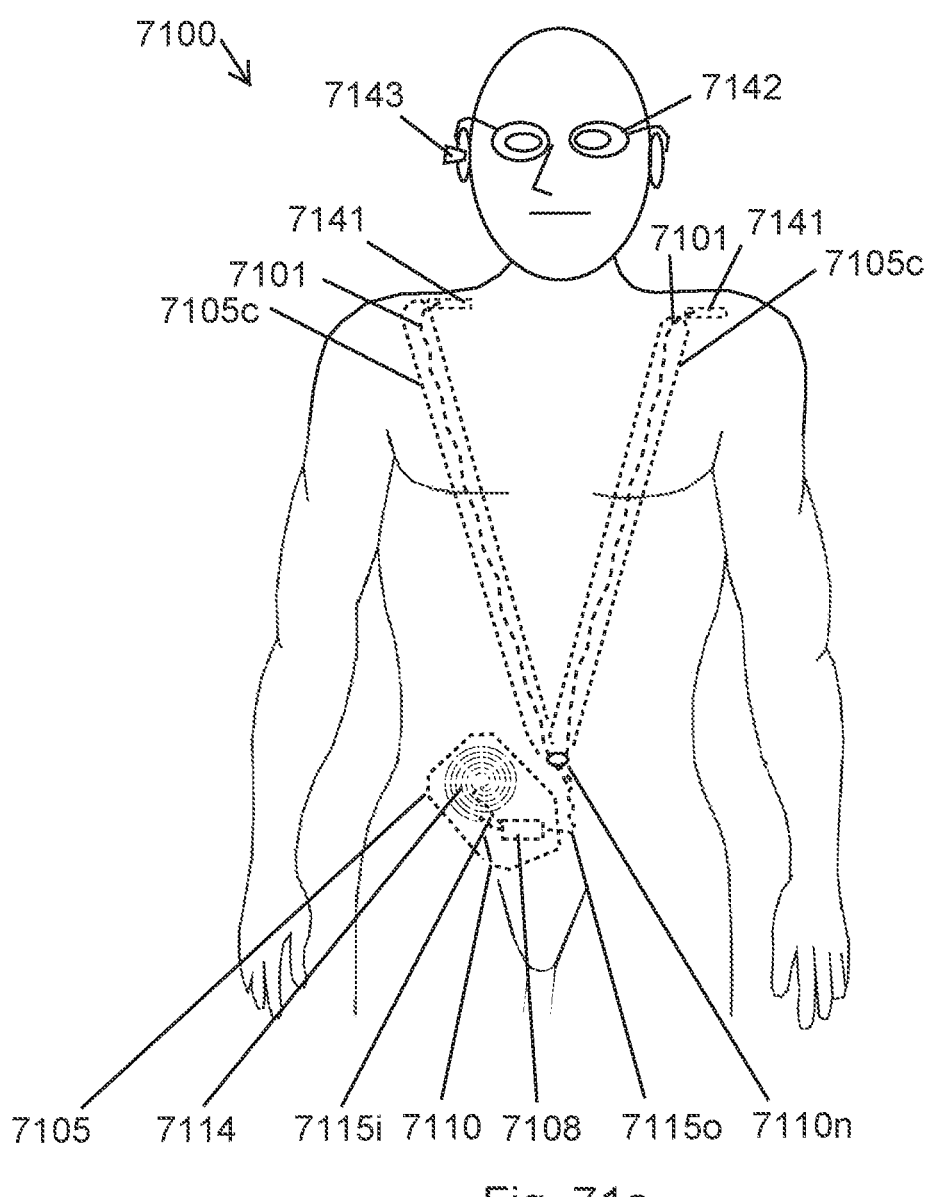

FIG. 71*a* depicts an example of a sensory-processing-feedback-system comprising a flexible strand/string electronic implant (FSEI).

FIG. 71*b* depicts a perspective view of an auxiliary implant that may comprise a battery, storage device, antenna, and a CPU/PCB.

FIG. 71*c* depicts a side perspective view of another auxiliary implant which may be positioned at the terminus of a FSEI.

Figures 72A, 72B, 72C:
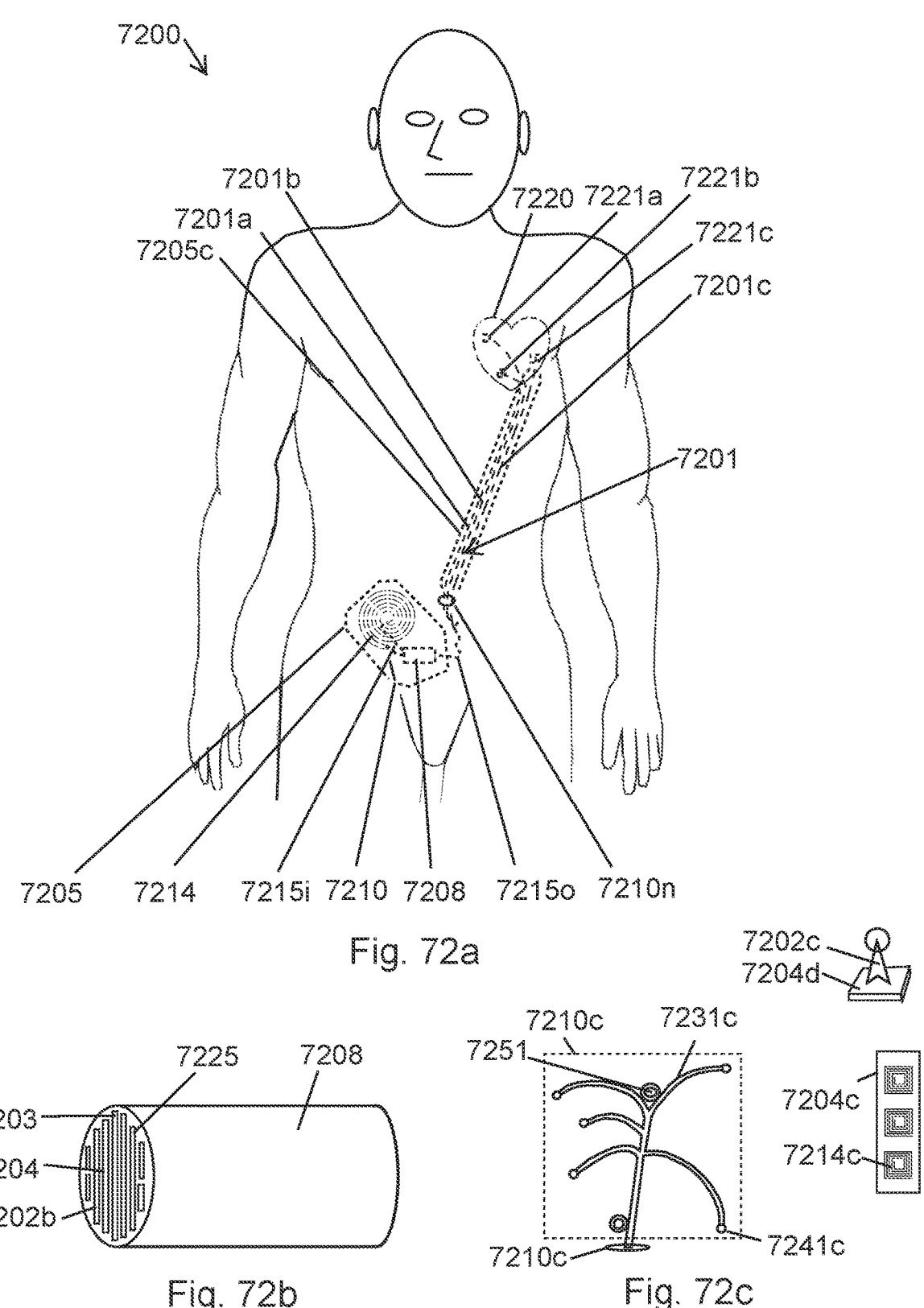

FIG. 72*a* depicts a front view of a torso having an example of a subcutaneous electrocardiogram (EKG/ECG) comprising a FSEI-EKG implant.

FIG. 72*b* depicts a perspective view of an auxiliary implant that may comprise a battery, storage device, antenna, and a CPU/PCB.

FIG. 72*c* depicts a top plan view of a Subcutaneous Electrocardiogram system that may comprise a dendritic implant.

Figures 73A, 73B, 73C:
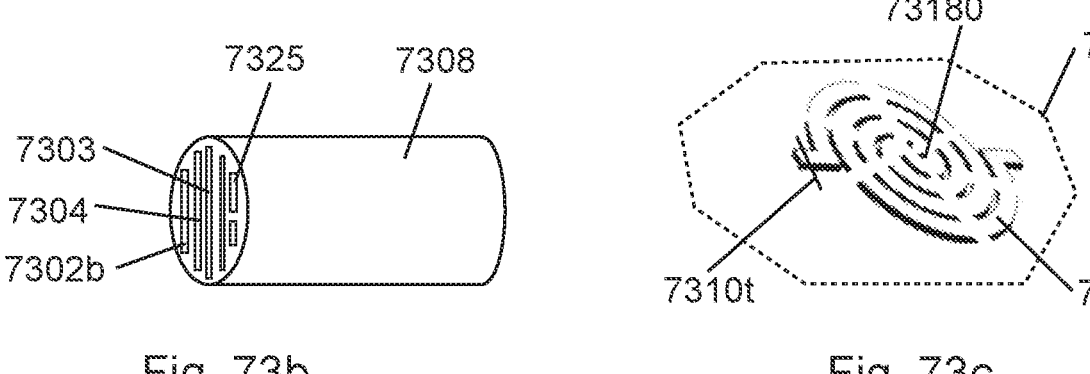

FIG. 73*a* depicts a front view of a torso having an example of a subcutaneous power delivery system comprising a FSEI.

FIG. 73*b* depicts a perspective view of an auxiliary implant that may comprise a battery, storage device, antenna, and a CPU/PCB.

FIG. 73*c* depicts a side elevation view of a powering system comprising an almost fully implanted thermoelectric implant.

Figures 74A, 74B:
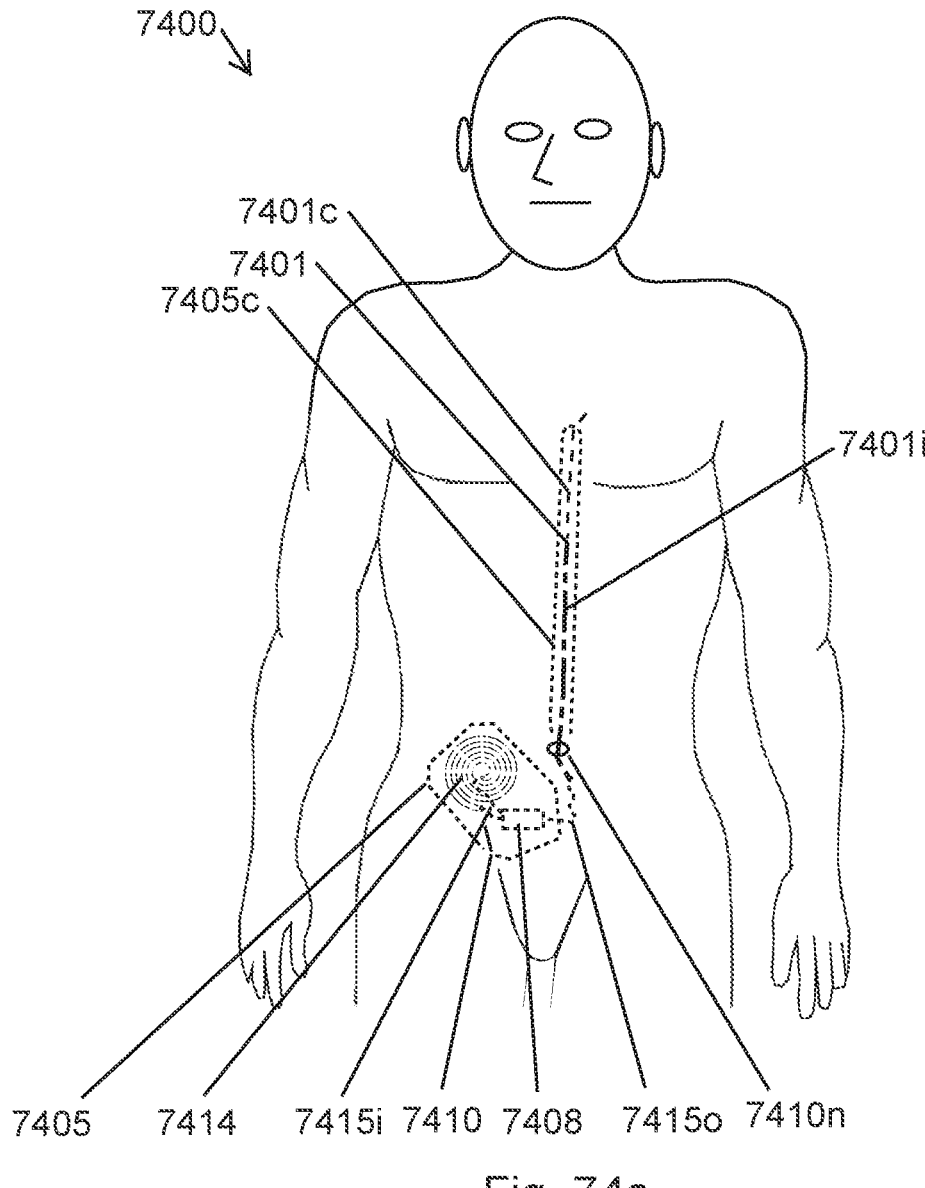

FIG. 74*a* depicts s front view of a human torso having an example of a subcutaneous power delivery system and a subcutaneous implantable cardioverter defibrillator system.

FIG. 74*b* depicts a perspective view of an auxiliary implant that may comprise a battery, storage device, antenna, and a CPU/PCB.

Figures 75A, 75B, 75C, 75D, 75E, 75F, 75G:
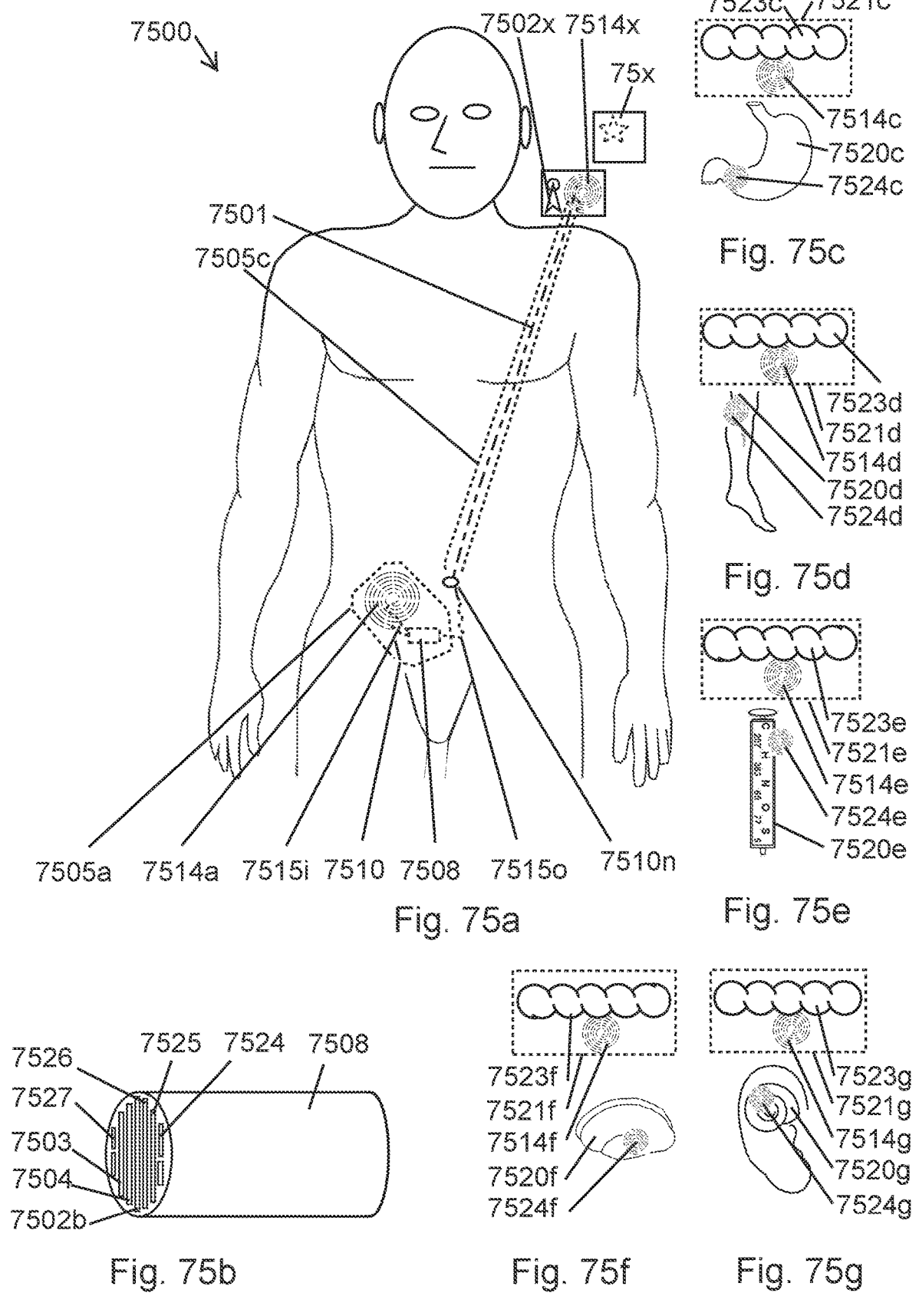

FIG. 75*a* depicts a frontal side view of a subcutaneous power delivery system comprising a FSEI to power a variety of other implanted devices.

FIG. 75*b* depicts a perspective view of an auxiliary implant that may comprise a battery, storage device, antenna, and a CPU/PCB.

FIG. 75*c* depicts a side view of a wirelessly powered gastric/stomach implant comprising an inductance coil.

FIG. 75*d* depicts a side view of a wirelessly powered foot drop/leg implant comprising an inductance coil.

FIG. 75*e* depicts a side view of a wirelessly powered drug/chemical pump implant comprising an inductance coil.

FIG. 75*f* depicts a side view of a wirelessly powered brain/nervous system implant comprising an inductance coil.

FIG. 75*g* depicts a side view of a wirelessly powered ear/internal-stimulator implant comprising an inductance coil.

Figures 76A, 76B:
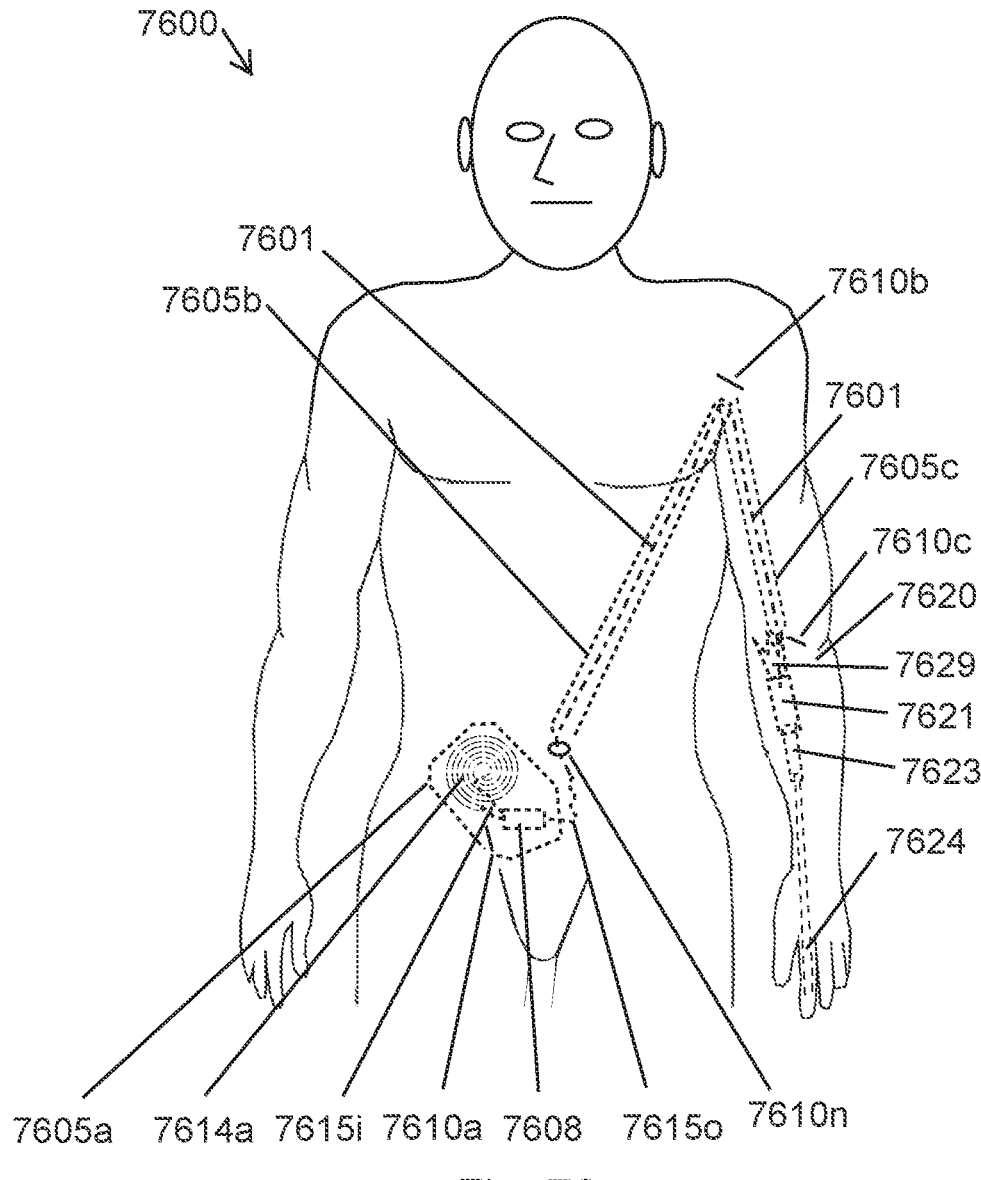

FIG. 76*a* depicts frontal side view of an example of a Subcutaneous Power Delivery System comprising FSEI providing power to implantable motor units.

FIG. 76*b* depicts a perspective view of an auxiliary implant that may comprise a battery, storage device, antenna, and a CPU/PCB.

Figures 77, 78A, 78B, 79A, 79B, 79C:
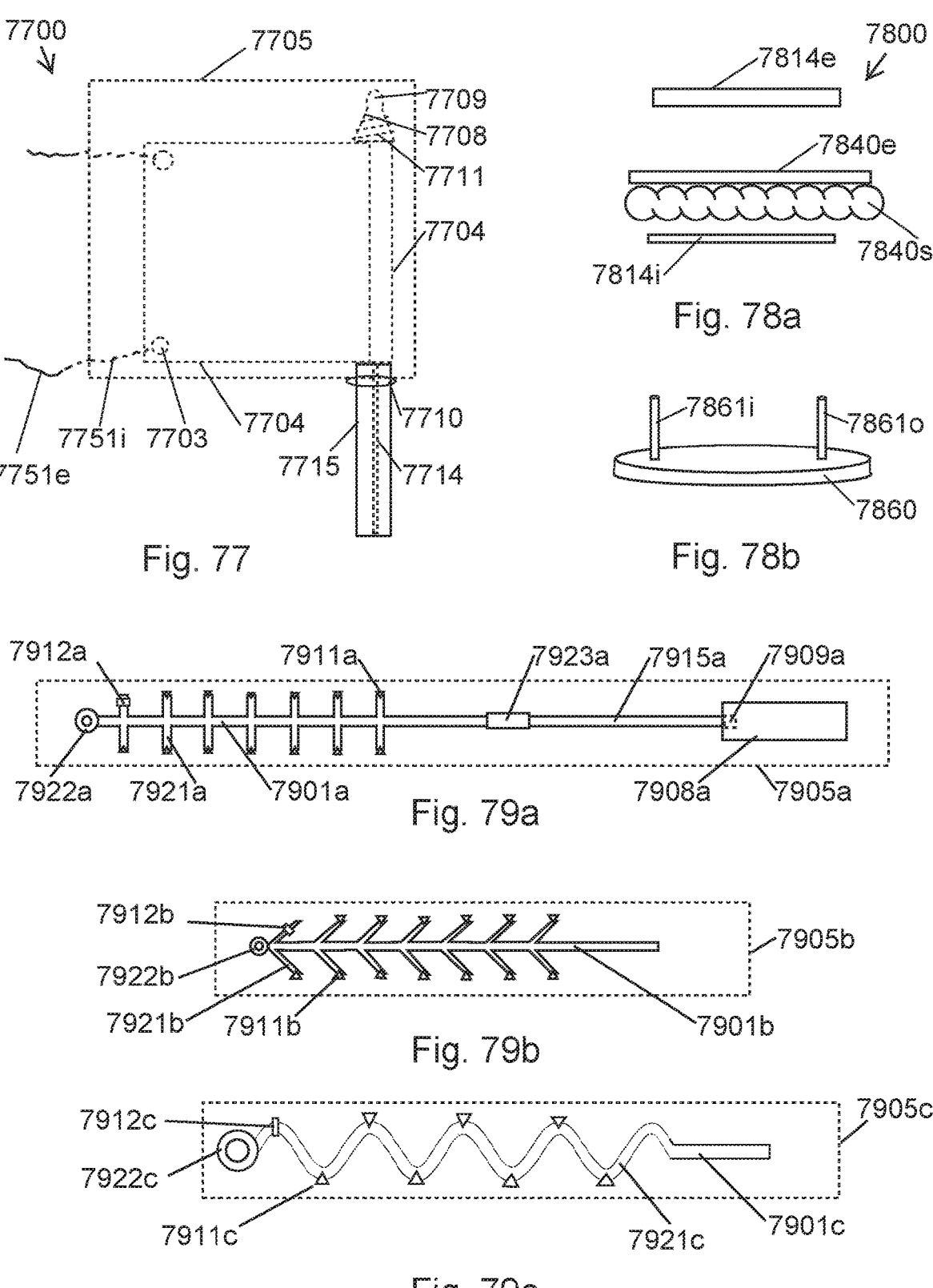

FIG. 77 depicts a top plan partially transparent view of a flexible implant facilitating system (FTIFS).

FIG. 78*a* depicts a cross sectional side view of a wireless charging system.

FIG. 78*b* depicts a perspective view of a bladder used to cool a wireless charging system.

FIG. 79*a* depicts a top plan view of a branched/dendritic flexible subcutaneous electronic neuro stimulative implant.

FIG. 79*b* depicts a top plan view of a branched/dendritic flexible subcutaneous electronic neuro stimulative implant according to another embodiment.

FIG. 79*c* depicts a top plan view of a serpentine/sinuous flexible subcutaneous electronic neuro stimulative implant.

Figures 80A, 80B, 80C, 80D:
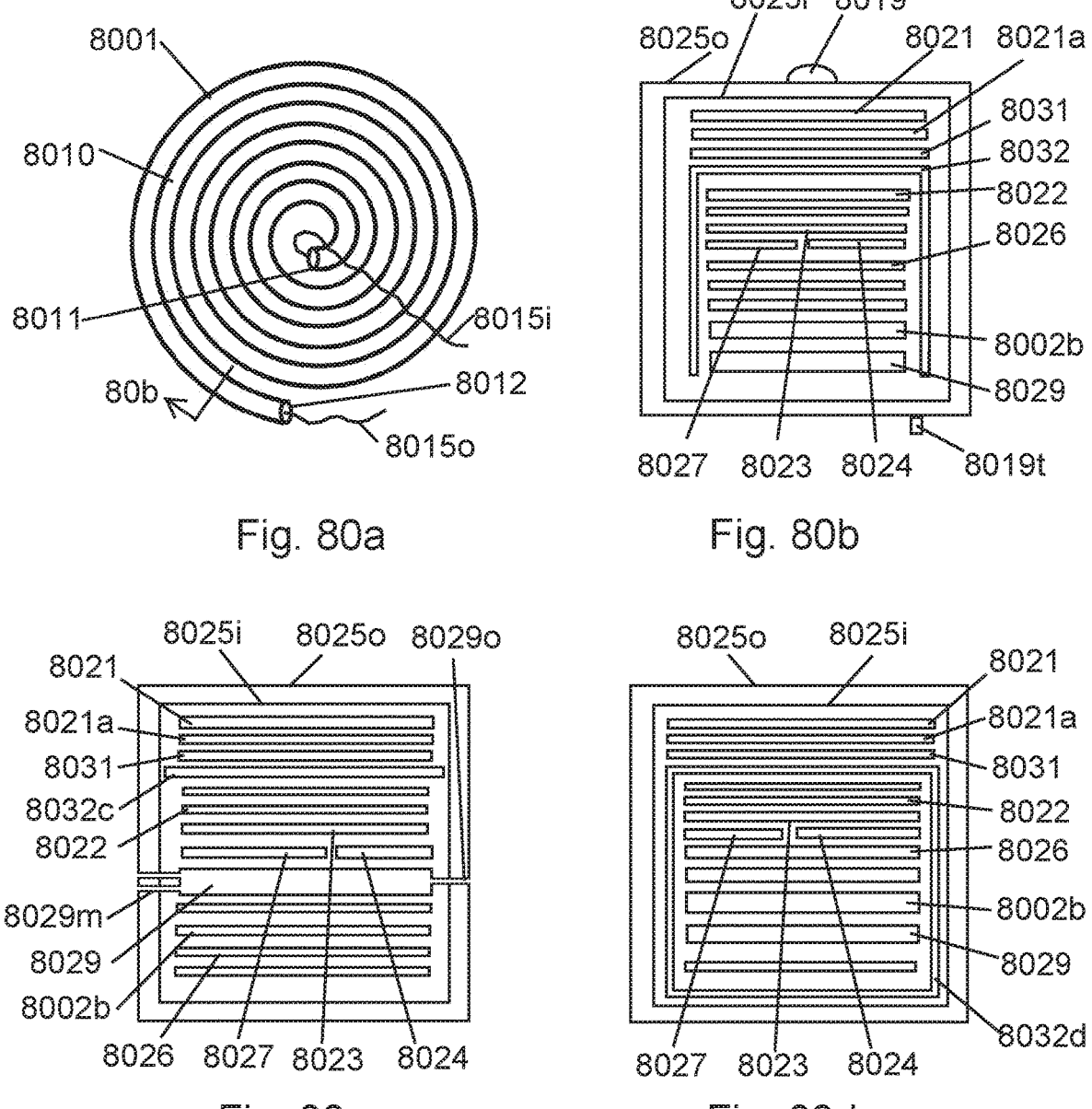

FIG. 80*a* depicts a top view of a circular, spiral implant.

FIG. 80*b* depicts a cross-sectional view of a spiral implant.

FIG. 80*c* depicts a cross sectional view of a spiral implant according to other embodiments.

FIG. 80*d* depicts a cross-sectional view of a spiral implant according to still other embodiments.

Figures 81A, 81B, 81C, 81D, 81E, 81F, 81G, 81H:
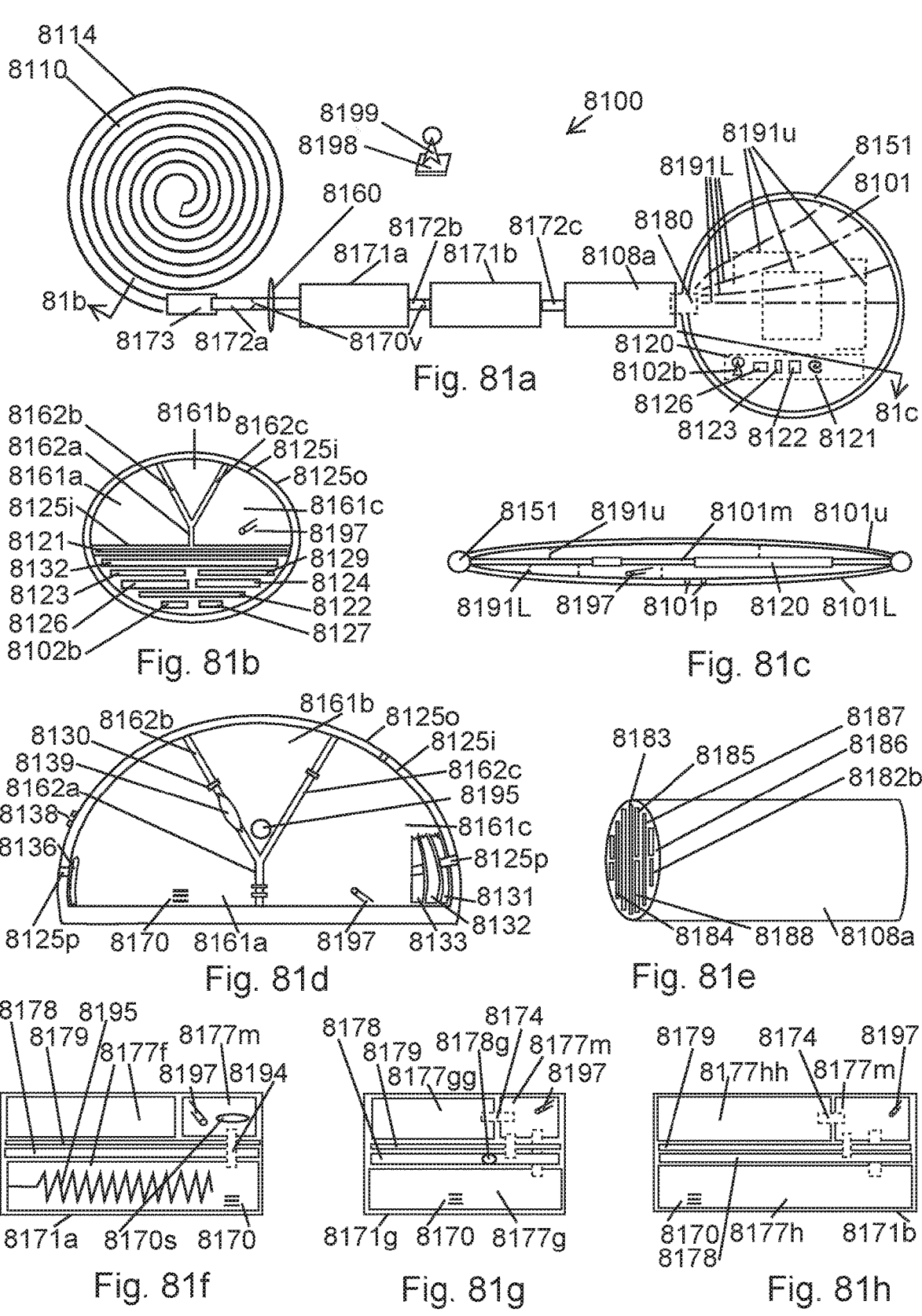

FIG. 81*a* depicts a top plan view of a composite system comprising a minimally invasive implant for prolonged/controlled drug/chemical delivery.

FIG. 81*b* depicts a cross-sectional view of a spiral implant of the system of FIG. 81*a*.

FIG. 81*c* depicts a cross-sectional view of a bladder-like compressible implant of the system of FIG. 81*a*.

FIG. 81*d* depicts an enlarged cross-sectional view of an upper portion of a spiral implant according to some embodiments.

FIG. 81*e* depicts a perspective view of an auxiliary implant of the system of FIG. 81*a*.

FIG. 81*f* depicts an enlarged view of a powder mixing/distributing segmentation pod of the system of FIG. 81*a*.

FIG. 81*g* depicts an enlarged view of a gas bubble delivery segmentation pod of the system of FIG. 81*a*.

FIG. 81*h* depicts an enlarged view of a liquid mixing/distributing segmentation pod of the system of FIG. 81*a*.

DETAILED DESCRIPTION

Figures 1A, 1B, 1C, 2B:
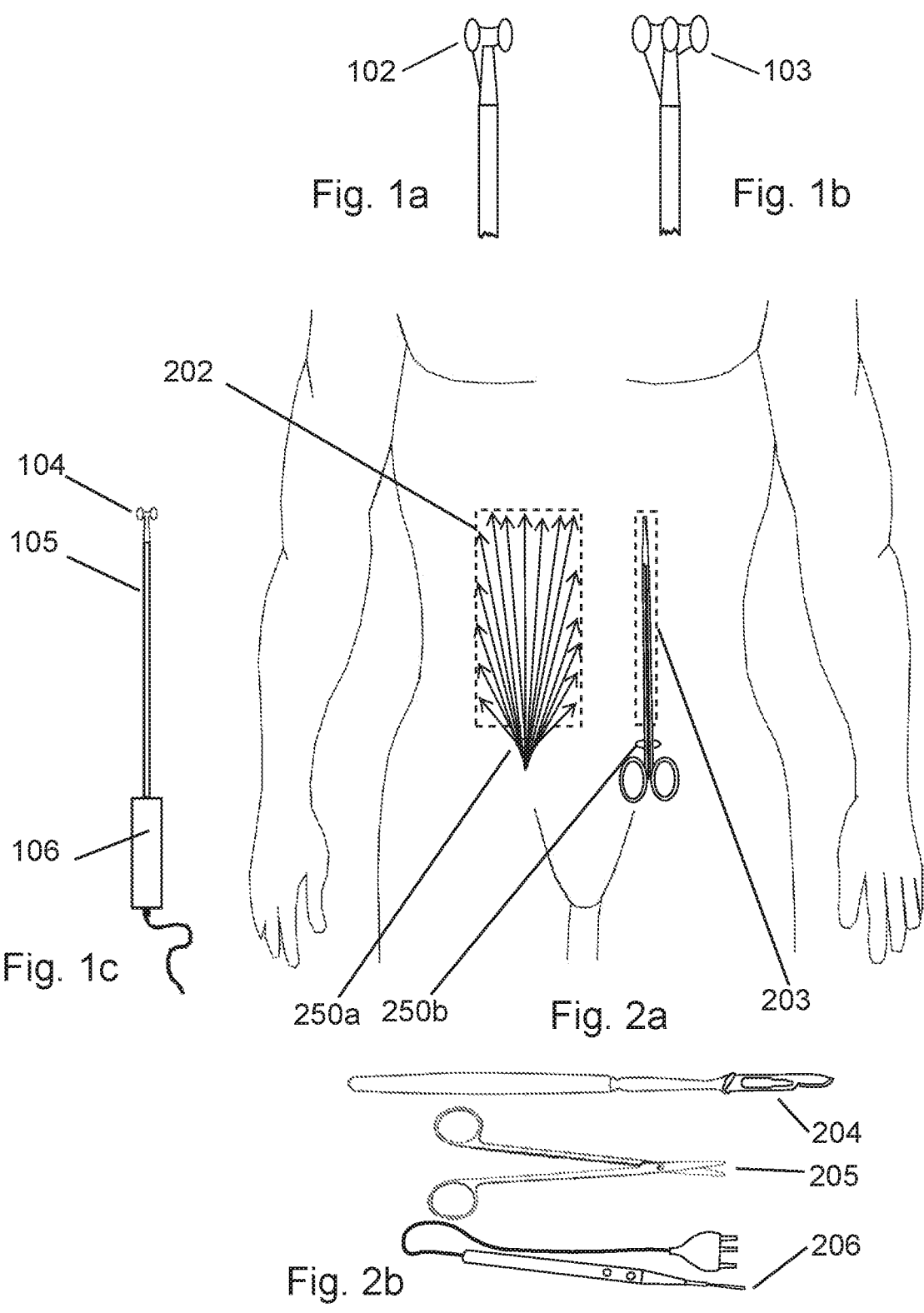
FIG. 1a depicts a top plan view of the distal portion of a minimally invasive electro-dissection device with a 2-bead tip.
FIG. 1b depicts a top plan view of a minimally invasive electro-dissection device with a tip having 2 beads and a bead-like structure therebetween.
FIG. 1c depicts a minimally invasive electro-dissection device with a 2 beaded tip protruding from a shaft with a handle.
FIG. 2b depicts traditional surgical blunt scissors, elongated scalpel, and electrosurgery pencil.

FIG. 1*a* depicts a top plan view of the distal portion of a minimally invasive electro-dissection device with a 2 bead tip having two beads protruding distally from a shaft. Tip 102 comprises a beaded structure that may be positioned at the distal end of a shaft.

FIG. 1*b* depicts a top plan view of a minimally invasive electro-dissection device with a tip having two beads and a bead-like structure therebetween. Tip 103 comprises a beaded structure that may also be positioned at the distal end of a shaft.

FIG. 1*c* depicts a minimally invasive electro-dissection device with a 2 beaded tip 104 protruding distally from a shaft 105 with handle 106 at the proximal end. Some such and similar devices may be found in U.S. Pat. No. 10,603, 101 titled "Apparatus, Systems and Methods for Minimally Invasive Dissection of Tissues"; U.S. Pat. No. 10,952,786 titled "Apparatus, Systems and Methods for Minimally Invasive Dissection of Tissues", and continuations in part thereof.

FIG. 2*a* depicts a human torso after having undergone comparative bilateral surgical procedures. On the patient's right side (the left side of the figure), a lysing tip, such as a lysing tip having beads and adjacent recesses for delivery of energy therefrom (for example in FIG. 1*c*), was used to form an implant pocket 202, with one or more dimensions substantially greater than that of the entrance incision 250*a* (about 5 mm, for example) used to begin to create the pocket. The outward arrows depict the initial forward paths of the dissection device radiating away from the entrance incision 250*a*; the device shown may also be configured to dissect in a rearward direction. However, for space considerations rearward arrows are not shown in the schematic. On the patient's left side (the right side of the figure), an elongated blunt tipped Metzenbaum surgical dissection scissors 205 is shown extended to its fullest length until the finger rings are adjacent to entrance incision 250*b*. Notice the dissection pocket 203 is limited in size due to the inability to spread the scissors caused by the diminutive entrance incision size. Thus, even if 250*b* were expanded to 1.5 cm (triple the size of 250*a*, and not desired by most patients), then scissors with overall combined shank widths of 8 mm would only allow a scissor blade tip spread at a distance of 15 cm from the finger rings in the order of less than a few millimeters in the depicted scenario. This minimal scissor blade tip spread would be very inefficient surgically for dissection and likely impractical resulting in diminutive pockets let alone the prospect of distant bleeding that is practically difficult and time consuming to stop. Also shown are other elongated, typical surgical devices.

FIG. 2*b* depicts traditional surgical blunt scissors 205, an elongated scalpel 204, and an electrosurgery pencil 206. It is noteworthy that elongated scalpel 204 and electrosurgical pencil 206 each which would typically encounter dissection limitations and timeliness impracticalities. Dissecting large areas in the subcutaneous tissue with simultaneous electro-coagulation/electro-cutting may be attempted with such instruments as ultrasound and/or radio frequency-capable insulated endoscopic scissors and/or clamping instruments (some of which may also use ultrasound). However, such scissors present a much greater energized surface area and even though their blade tips may be blunt, when electrified and being used blindly to dissect large areas rapidly may unwantedly cut through to the outside skin due to lack of precise control with such instruments; presenting a larger forward-facing energized surface area may risk damaging critical nerves and creating a more irregular dissection plane, thus increasing risks and complications. Using progressive clamping and unclamping of endoscopic clamping instruments to dissect large areas of the subcutaneous (as if a surgeon were working in the peritoneal cavity) may be very time-consuming, tedious, and may leave a highly irregular dissection area, which in itself would provide a greater surface area for complications and risks, including, but not limited to infection, hematomas, seromas, and excess fibrosis. Using energized or non-energized single-point-probe devices such as ultrasound or laser-powered liposuction cannulas and the like rarely completely cut the fibrous septae, which course vertically through the subcutaneous fat, thus leaving a Swiss cheese-like appearance in the subcutaneous, which would not practically permit sizeable implant placement. Even if the aforementioned instruments were to be using in a fanning fashion, as described in FIG. 2*a*, with the accompaniment of an endoscope to observe bleeding or plane placement, the procedure may have time inefficiencies as well as the requirement for having two instruments occupy a minimally invasive entrance incision, thus possibly doubling the required entrance incision and/or increasing the trauma to the entrance incision due to a multiplicity of instruments constantly rubbing against the entrance incision in both forward and rearward directions. Thus, endoscopic scissors and/or clamping instruments may be used to create minimally invasive body cavity (for example peritoneal, pleural) implant pockets practically; however their use to create subcutaneous minimally invasive implant pockets may be problematic or impractical in a significant portion of pockets, for example, exceeding 10 sqcm.

Figures 3A, 3B, 3C:
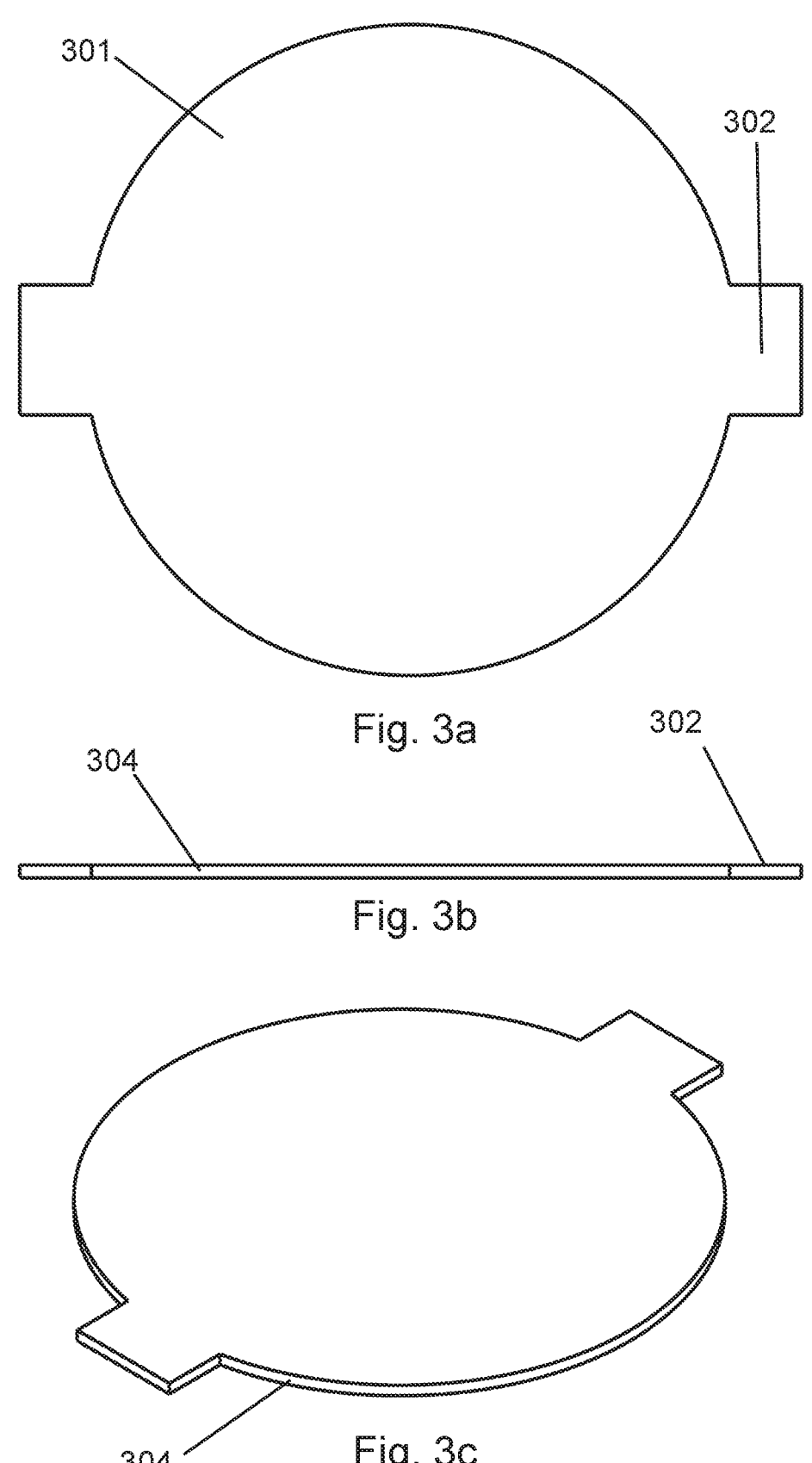
FIG. 3a depicts a top plan view of a circular, flexible, and compressible implant.
FIG. 3b depicts a side view of implant.
FIG. 3c depicts a top perspective view of implant.

FIG. 3*a* depicts a top view of a circular, flexible, and compressible implant 301. Implant 301 is compressible by being rollable and/or foldable (for possible subcutaneous placement). Implant 301 is shown in FIG. 3*a* in its unrolled or otherwise uncompressed/native state. Implant 301 may comprise, in some embodiments, a flexible solid or semi-solid material, such as a hydrogel, plastic, metal, organic polymer, biopolymer or the like. Other embodiments may comprise nanomers or even rigid solids (such as glasses, quartz, etc.), which, when fragmented in to small enough pieces and encapsulated in flexible material, may be functional for the procedures described herein. Drugs, vitamins, or other chemicals, including biologics, may also be bound or dissolved or exist in a portion or all of the structure of implant 301 by methods including but not limited to 3D printing. Different regions and/or portions of the structure may have different medications or chemicals printed or otherwise designed into them, some perhaps in the shape of a pie-chart if multiple materials are envisioned, for eventual delivery into a patient.

Implant 301 may comprise one or more protruding tabs 302 that may aid in placement into a minimally invasive entrance incision. FIG. 3b is a side view of the implant 301 depicting edge 304 and tab 302. FIG. 3c is a top perspective view of the implant 301. Implant 301 may be deployed in a compressed state, such as a rolled state, and then unrolled or otherwise decompressed once inserted through the entrance incision and positioned within the implant pocket, as will be discussed. Various embodiments disclosed herein, including but not limited to implant 301, may specifically be configured to lack any sharp edges and/or points, which may be useful to preclude, or at least inhibit, tissue irritation and/or damage, such as inflammation, which may be triggered by sharp edges, points, and the like.

In various preferred embodiments, including implant 301, the implant may be not only compressible and decompressible, but may be configured to be expanded to a flat or relatively flat shape following decompression. Breast or tissue expander implants may differ in that they may have a non-flat and/or much thicker shape in its non-footprint dimension.

Implant 301 may comprise one or more of the following or related materials: highly aqueous pH sensitive hydrogels may include those of copolymers of PMMA (polymethacrylate) and PHEMA (polyhydroxyethyl methyl acrylate), swelling in neutral or high pH, without swelling in low pH. Highly aqueous thermosensitive hydrogels may include those of poly-organophosphazene with alpha-amino omega-methylpolyethylene glycol, which may deliver drugs such as human growth hormone. Highly aqueous glucose sensitive hydrogels may include cross-linked polymers of polyethyleneglycol and methylacryluc acid, which may deliver drugs such as insulin when glucose concentrations rise. Nanohydrogels may be formed from natural polysaccharides like dextran, pullulan, or other cholesterol-containing polysaccharides, which may be used for controlled release of proteins like lysozyme, albumin, and immunoglobin. Hydrogels may be composed of polysaccharides that are functionalized with methacrylate and aldehyde groups to create a network from which chondrocyte cells may be released. Drugs such as pilocarpine and timolol may be infused in hydrogels such as xyloglucan. Microgels may also be used to deliver macromolecules, such as phagosomes, into the cytoplasms of antigen-presenting cells and mold themselves to the pattern of membrane of the tissue for cartilage repair. The aforementioned information and other drugs and hydrogels may be found in 'Hydrogels as Potential Drug Delivery Systems', Amin, Scientific Research and Essay, Vol. 3 (11), 1175-1183, 2009, which is hereby incorporated in its entirety by reference.

Hydrogels may be fabricated from synthetic polymers, such as PVA, poly(hydroxyl alkyl methacrylate), and biopolymers, such as alginate, collagen, and chitosan. Such hydrogels may be used to deliver drugs, such as recombinant human granulocyte-macrophage colony-stimulating factor (rhGMC-SF), to treat burns, for example. Hydrogels that contain hydrophobic domains may include synthetic polymers, such as poly(N-isopropylacrylamide) (PNIPAm), which may be used to deliver hydrophobic drugs, such as doxorubicin. Degradable hydrogels may include families of biodegradable PED hydrogels that may release proteins or drugs thanks to slowly hydrolyzing ester bonds. Covalent linkages between therapeutic cargo and hydrogel (such as amide bonds that have been used to conjugate TGF-Beta1 to PEG hydrogels) polymer may also, or alternatively, be used to increase stability. The aforementioned information and other combinations of drugs and hydrogels may be found in 'Designing Hydrogels for Controlled Drug Delivery', Li, Nat Rev Mater, 2016, which is hereby incorporated in its entirety by reference.

Hydrogels sensitive to pH may also be used for certain applications, which hydrogels may include, for example, poly(acrylic acid), and may be used to deliver drugs such as 2-Methoxyestradiol to, for example, tumor sites. Thermoresponsive hydrogels may also be used for various applications, and therefore may be incorporated into one or more of the implants disclosed herein. Examples of such hydrogels include poly(N-isopropylacrylamide) (PNIPAm), which may be used to deliver intravenous docetaxel (DTX). Photosensitive hydrogels may also be used in connection with one or more of the implants disclosed herein, and which may include, for example, those of [Mn(CO)3(qbt)(4-vpy)] (CF3SO3)(qbt-2-(quinolyl)benzothiazole) photoCORM, covalently bonded through 4-vinylpyridyne (4-vpy) to a 2-hydroxyethyl methacrylate polymer chain (HEMA) used to deliver carbon monoxide (CO) as an antiproliferative measure. Hydrogels sensitive to magnetic fields may also be used for certain embodiments and implementations, and which may include SPION-containing hydrogels synthesized from polymers with PEGMMA backbones crosslinked by poly(ethylene glycol) dimethacrylate (PEGDMA), coupling drug eluting and hyperthermic treatments. Bioresponsive hydrogels may be synthesized from PEG and MMP-sensitive cross-linking agents, resulting in a biodegradable system responsive to proteins such as metalloproteinase (MMP). Smart hydrogels may be used, some of which may be made to respond to numerous external stimuli to combine various methods of treatment. The aforementioned and other smart hydrogels and deliverable drugs may be found in 'Smart Hydrogels-Synthetic Stimuli-Responsive Antitumor Drug Release Systems', Kasinski, International Journal of Nanomedicine, 2020, which is hereby incorporated in its entirety by reference.

In some embodiments, biodegradable, hydrophilic hydrogels may comprise dispersed lipophilic particles with low water solubility. Such lipophilic particles may comprise, for example, hydrophobic therapeutic agents. Additional details regarding the disclosed hydrogel drug delivery system may be found in U.S. Pat. No. 10,226,417, titled "Drug Delivery Systems and Applications", which is hereby incorporated in its entirety by reference.

In some embodiments, polymeric hydrogels may be implanted for delivery of therapeutic agents (such as, for example, Insulin, Diclofenac, et al.). Such hydrogels may comprise, for example, covalently-crosslinked hydrogels, providing controlled release of therapeutic agents. Aqueous polymeric precursors may be combined ex vivo in flowable viscosities with a therapeutic agent before being injected. In some instances, the hydrogel may be designed to adhere to certain tissues, crosslink in place, and/or to degrade into biocompatible products. Such hydrogel systems may be created using biocompatible precursors (which may include, for example, vinyl caprolactam, acrylate-capped polyethylene glycol, et al) and/or may contain high proportions of water. In a preferred embodiment, the implanted hydrogel may be soft, hydrophilic, configured to conform to spaces without hard edges, and/or to degrade into biocompatible products. Some hydrogels for drug delivery may include, for example, succinimidyl succinate, succinimidyl glutarate and the like. Additional information may be found in U.S. Pat. No. 10,251,954 titled "Hydrogel Polymeric Compositions and Methods", which is hereby incorporated in its entirety by reference.

Systems for localized drug delivery may include, for example, drug eluting resorbable devices anchored to tissues and/or organs. In some embodiments, the drug eluting device may comprise a biodegradable binder and at least one resorbable anchor. Some anchor embodiments may comprise resorbable barbs, coils, or hooks. In some instances, the device may comprise, for example, a pin configuration, hook-pin configuration, chip configuration, or the like. In some embodiments, the rate of degradation may be modulated to yield longer/shorter drug delivery durations. Materials used for drug delivery may comprise, for example, polylactic-co-glycolic acid. Additional information regarding drug delivery systems that may be useful in connection with various embodiments disclosed herein may be found in U.S. Patent Application Publication No. 2015/0080855, titled "Systems, Devices, and Methods for Localized Drug Delivery", which is hereby incorporated in its entirety by reference.

Implanted drug eluting devices may comprise substances such as, for example, hydrogels and xerogels. In some instances, drug eluting hydrogels may be formed by cross-linking precursors around therapeutic agents. Precursors may be dissolved into organic solvents to create organogels, which may be formed by natural (such as, for example, polysaccharides), synthetic, or biosynthetic polymers. Synthetic organogels or hydrogels may be formed by biostable precursors, such as, for example, poly(hydroxyalkyl methacrylate) and/or polyacrylamides. Precursors may also constitute hydrophilic portions, which may comprise, for example, polyethylene oxide. Precursors may also comprise, for example, synthetic precursors, natural proteins, polysaccharides, hydrophobic/hydrophilic portions, functional groups, multi-armed precursors, dendrimers, peptides, et al. Factors such as crosslinking density of the hydrogel and molecular weight of the diffused agent may influence the rate of agent diffusion. Additional details regarding hydrogel drug delivery systems may be found in U.S. Patent Application Publication No. 2016/0166504, titled "Hydrogel Drug Delivery Implants", which is hereby incorporated in its entirety by reference.

In some embodiments, drug eluting hydrogels may be implanted so that cross-linking occurs in situ. Such hydrogel delivery systems allow for delivery of a myriad of therapeutic cargo, such as, for example, hydrophobic/hydrophilic agents. Some embodiments may comprise aqueous polymeric precursors combined in flowable viscosities with an agent and implanted into the body, where the cross-linked hydrogel forms in situ. Some embodiments may comprise hydrogels formulated to adhere to tissues, which may enhance therapeutic cargo release and stability. A preferable embodiment may comprise hydrogels that may degrade over time into biocompatible products without causing inflammation. Additional details regarding hydrogel drug delivery systems may be found in U.S. Patent Application Publication No. 2016/0331738, titled "Drug Delivery from Hydrogels", which is hereby incorporated in its entirety by reference.

Further systems for implantable drug eluting devices may comprise refillable drug-delivery devices. In some embodiments, the drug delivery device may comprise a carrier and a target recognition moiety, which may, for example, form a two-component binding pair. Drugs that may be released in this manner may include anti-cancer drugs (such as Doxorubicin), vascularization-promoting drugs, restenosis prevention drugs, and the like. In some instances, the carrier may comprise, for example, polymers, proteins, synthetic/biological hydrogels, composites, and the like. Hydrogels may comprise, for example, polyethylene glycol, collagen, alginate, polysaccharides, hyaluronic acid, et al. In some embodiments, the drug delivery system may comprise at least two drug delivery devices, which may be in the same location or in different locations within the body. In some embodiments, the target may comprise a bioorthogonal functional group and the target recognition moiety may comprise a complementary functional group, wherein both groups are capable of chemically reacting. In some embodiments, therapeutic cargo may comprise small molecules or biologics. Biologics may comprise, for example, antibodies, vaccines, gene therapy, cell therapy, and the like. Drug refills may be administered orally, intraperitoneally, intravenously, or intra-arterially. In some embodiments, the pharmaceutical composition may be attached to the target via cleavable linker, allowing the drug refill to mask the potential toxicity of the pharmaceutical composition. In certain implementations and embodiments, the pharmaceutical composition may be unmasked after delivery into the drug delivery device via cleaving the link between the pharmaceutical composition and the target. Additional details regarding such drug delivery methods may be found in U.S. Patent Application Publication No. 2020/0197526, titled "Refillable Drug Delivery Devices and Methods of Use Thereof", which is hereby incorporated in its entirety by reference.

In some embodiments, biodegradable polymer drug carriers may be used to deliver treatments for extended periods of time. Drugs that may be administered by implanted polymer drug carriers may include, for example, clonidine, which may alleviate pain caused by a plethora of sources. When implanted with a biodegradable polymer, such relief may be continued from days to months. One embodiment of a delivery system may comprise clonidine delivered by a biodegradable polymer, which may comprise, for example, poly(lactic-co-glycolide). Another embodiment may comprise, for example, clonidine hydrochloride released by poly(lactic-co-glycolide). Additional details regarding suitable methods of clonidine delivery may be found in U.S. Pat. No. 9,763,917, titled "Clondine Formulations in a Biodegradable Polymer Carrier", which is hereby incorporated in its entirety by reference.

In some embodiments, implanted hydrogels may be engineered to respond to stimuli such as, for example, temperature. In certain embodiments, such hydrogels may comprise, for example, chitosan and nucleic acids. In some instances, the hydrogel may be adjusted such that it is in a sol at room temperature and transitions into a gel once in the body. In a preferred embodiment, the weight ratio of a nucleic acid and chitosan may be from about 50:1 to about 2000:1, with DNA as the nucleic acid. In some embodiments, the nucleic acid may be DNA, RNA, or a mixture thereof. In certain instances, the DNA may include oligonucleotides, polynucleotides, and polydeoxyribonucleotides. In some embodiments, the hydrogel may comprise an additional polymer material, which may comprise, for example, hyaluronic acid, cellulose, alginate, et al. Additional details regarding hydrogel systems may be found in U.S. Patent Application Publication No. 2019/0054015, titled "Temperature Sensitive Hydrogel Composition Including Nucleic Acid and Chitosan", which is hereby incorporated in its entirety by reference.

Bioactive agent-containing gels may be used in certain applications, which may include, for example, treatment of vascular conditions. In certain embodiments, gels may be, for example, thixotropic and turbid, having high viscosity at low shear and containing bioactive agents. Therefore, under conditions of no/low blood flow, the gel may reside in the luminal space of blood vessels; the gel may be blood-soluble such that upon resumption of blood flow, the gel may dissolve. The gel may be used, in certain embodiments, to deliver bioactive agents to vascular treatment sites. Certain embodiments may comprise, for example, a cyclodextrin polymer-based composition comprising cyclodextrin, a polymer (comprising, for example, ethylene glycol units that may form a hydrogel with cyclodextrin, wherein the cyclodextrin and the polymer self-assemble to form a hydrogel), and at least one drug. Additional information regarding gel-based drug delivery systems may be found in U.S. Patent Application Publication No. 2019/0247306, titled "Articles and Methods of Treating Vascular Conditions", which is hereby incorporated in its entirety by reference.

In some embodiments, non-erodible polymeric devices may be implanted subcutaneously to administer therapeutic cargo over extended periods, ranging from months to years. In certain embodiments, cargo, such as dopamine agonist, may be released through pores in the polymeric matrix. In some instances, the polymeric device may comprise ethylene vinyl acetate (EVA), while the dopamine agonist may comprise products such as apomorphine, ropinerole, rotigotine, and the like. In certain embodiments, anti-inflammatory agents (such as antihistamine) and/or antioxidants may be contained within the polymeric matrix. Such agents may be co-administered with the dopamine agonist. Additional information regarding such agents and delivery methods may be found in U.S. Pat. No. 9,278,163, titled "Implantable Polymeric Device for Sustained Release of Dopamine Agonist", which is hereby incorporated in its entirety by reference.

In some instances, microcapsules containing therapeutic agents may be used for drug delivery. In some embodiments, the microcapsule may comprise polymers, such as, for example, polylactic acid, polyglycolic acid, and copolymers thereof. Such microcapsules may provide delayed or immediate release of therapeutic agents. In some embodiments, the microcapsules may be dispersed within a carrier such as, for example, water, a gel, and/or a nonaqueous solvent. Additional details regarding microcapsule drug delivery systems may be found in U.S. Patent Application Publication No. 2021/0077114 titled "Implantable Drug Eluting System and Method of Use", which is hereby incorporated in its entirety by reference.

Herein, Threshold Minimally Invasive Surgery in the skin, to alter or change any of the components which comprise the skin (which includes the subcutaneous fat), is to be defined as: a skin incision that measures <10% of the total perimeter or the convex perimeter of the area beneath the surface of the skin that is to be or has been altered by the proposed/completed surgery. Thus if a 10×10 cm rectangular area (=40 cm perimeter) is undermined within the subcutaneous area any incision below 4 cm would be considered THRESHOLD minimally invasive.

Herein, Very Minimally Invasive Surgery in the skin, to alter or change any of the components which comprise the skin (which includes the subcutaneous fat), is to be defined as: a skin incision that measures <5% of the total perimeter or the convex perimeter of the area beneath the surface of the skin that is to be or has been altered by the proposed/completed surgery, which may include, for example, the size of the implant pocket and/or the size of the decompressed implant itself. Thus if a 10×10 cm rectangular area (=40 cm perimeter) is undermined within the subcutaneous area any incision below 2 cm would be considered VERY minimally invasive.

Herein, Ultra Minimally Invasive Surgery in the skin, to alter or change any of the components which comprise the skin (which includes the subcutaneous fat), is to be defined as: a skin incision that measures <3% of the total perimeter or the convex perimeter of the area beneath the surface of the skin that is to be or has been altered by the proposed/completed surgery, which, again, may include the size of the implant pocket and/or the size of the decompressed implant. Thus if a 10×10 cm rectangular area (=40 cm perimeter) is undermined within the subcutaneous area any incision below 1.2 cm would be considered ULTRA minimally invasive.

For irregular areas/perimeters (even amoeba like areas of implants) measuring the convex perimeter (perimeter of the convex hull that encloses the object) as per Wirth may be carried out for a perimeter calculation using the methods and formulas presented in Shape Analysis & Measurement, Wirth M, 2004 http://www.cyto.purdue.edu/cdroms/micro2/content/education/wirth10.pdf which is hereby incorporated herein in its entirety by reference. Another simple method may be to estimate the perimeter of an irregular area using lattice points.

Herein, Threshold Minimally Invasive Implant (placed and/or configured for placement into a layer of the skin or adjacent), is to be defined as: an implant that is configured to achieve successful implantation and, in preferred embodiments/implementations, maintain function to the expectant life of the implant, after it has been inserted in a skin incision that measures <10% of the total perimeter or the convex perimeter of the implant. For the embodiments/implementations disclosed herein, a threshold minimally invasive implant comprises an implant that is insertable in a skin incision that measures less than 10% of the total perimeter or, in the case of an implant having infolds, recessions, concavities, or the like, less than 10% of the convex perimeter, of the implant's "footprint" (i.e., as used herein, the implant's two-dimensional shape from a plan view looking down at the region of the patient's skin under which the implant is configured to lie after complete installation, including decompression for compressible implants, within a patient's implant pocket; the implant's footprint would typically extend at least roughly parallel to the patient's skin, giving leeway for the various folds and curves of the skin). An implant's "footprint area" may therefore be considered, for purposes of this disclosure, the area of the implant's "footprint" using this definition. Thus, for example, an 8×8 cm rectangular implant (from the aforementioned perspective) (=32 cm perimeter) must be able to pass through a 3.2 cm incision to meet this Threshold Minimally Invasive Implant definition.

Herein, Very Minimally Invasive Implant (placed and/or configured for placement into a layer of the skin or adjacent), is to be defined as: an implant that is configured to achieve successful implantation and, in preferred embodiments/implementations, maintains function to the expectant life of the implant, after it has been inserted in a skin incision that measures <7% of the total perimeter or the convex perimeter of the implant. For the embodiments/implementations disclosed herein, a very minimally invasive implant comprises an implant that is insertable in a skin incision that measures less than 7% of the total perimeter or, in the case of an implant having infolds, recessions, concavities, or the like, less than 7% of the convex perimeter, of the implant's "footprint" (i.e., as used herein, the implant's two-dimensional shape from a plan view looking down at the region of the patient's skin under which the implant is configured to lie after complete installation, including decompression for compressible implants, within a patient's implant pocket; the implant's footprint would typically extend at least roughly parallel to the patient's skin, giving leeway for the various folds and curves of the skin). An implant's "footprint area" may therefore be considered, for purposes of this disclosure, the area of the implant's "footprint" using this definition. Thus, for example, an 8×8 cm rectangular implant (=32 cm perimeter) must be able to pass through a 2.2 cm incision to meet this Very Minimally Invasive Implant definition.

Herein, Ultra Minimally Invasive Implant (placed and/or configured for placement into a layer of the skin or adjacent), is to be defined as: an implant that achieves successful implantation and, in preferred embodiments/implementations, maintains function to the expectant life of the implant, after it has been inserted in a skin incision that measures <5% of the total perimeter or the convex perimeter of the implant. For the embodiments/implementations disclosed herein, an ultra minimally invasive implant comprises an implant that is insertable in a skin incision that measures less than 5% of the total perimeter or, in the case of an implant having infolds, recessions, concavities, or the like, less than 5% of the convex perimeter, of the implant's "footprint" (i.e., as used herein, the implant's two-dimensional shape from a plan view looking down at the region of the patient's skin under which the implant is configured to lie after complete installation, including decompression for compressible implants, within a patient's implant pocket; the implant's footprint would typically extend at least roughly parallel to the patient's skin, giving leeway for the various folds and curves of the skin). An implant's "footprint area" may therefore be considered, for purposes of this disclosure, the area of the implant's "footprint" using this definition. Thus, for example, an 8×8 cm rectangular implant (=32 cm perimeter) must be able to pass through a 1.6 cm incision to meet this Ultra Minimally Invasive Implant definition.

Herein, successful implantation and function is to be defined as the ability to maintain the expectant conformation (no folding over on itself) and/or the ability to remain in the expectant position to the expectant life of the implant after it has been inserted into a defined size limited skin incision. Heretofore, many published designs' delicate electronics or membranes would not tolerate implantation through such size proportionate incisions with many common surgical tools and thus expectant function/lifespan may be affected.

Fillable Breast and tissue expansion implants are commonly expanded to a final thickness (3rd dimension) of >50% of their largest two-dimensional footprint dimension, such as diagonal/diameter in the case of an rectangular/circular implant footprint shape; such shapes may be akin to fillable bladders. However, during a port filling phase(s), which is/are often sequential with such implants, the non-final thicknesses may range from near to 0 to the final percentage thickness. Fillable Breast and tissue expansion implants are also usually not intended for fluid storage that may contain chemicals or drugs for later delivery.

The non-linear implant embodiments described herein may be the result of pliable, expandable laminations or area intended for fluid storage that may contain chemicals or drugs for later delivery. In preferred embodiments, the non-linear implant embodiments described herein are therefore preferably configured to be more "flat" than, for example, breast and other tissue expansion implants. More particularly, in preferred embodiments, these implants are configured to avoid expansion to a final thickness of more than 25% of their largest footprint dimension.

In the case of an inflatable implant, uncompressed should be considered to encompass the implant in its final, fully inflated configuration. It should also be understood that, whereas typical tissue implants in the prior art that are wirelessly rechargeable are relatively small and therefore consume/utilize relatively small of amounts of electrical energy, due to the unique structures and methods disclosed herein, various embodiments disclosed herein may be much larger and therefore may be able to receive, generate, and/or utilize relatively much larger amounts of electrical energy, which vastly expands the potential capabilities of implants, as disclosed throughout herein, such as providing power for light emission, powering larger motors, and other larger and/or a larger number devices that, individually or collectively, require more energy.

Figures 4A, 4B, 4C, 4D:
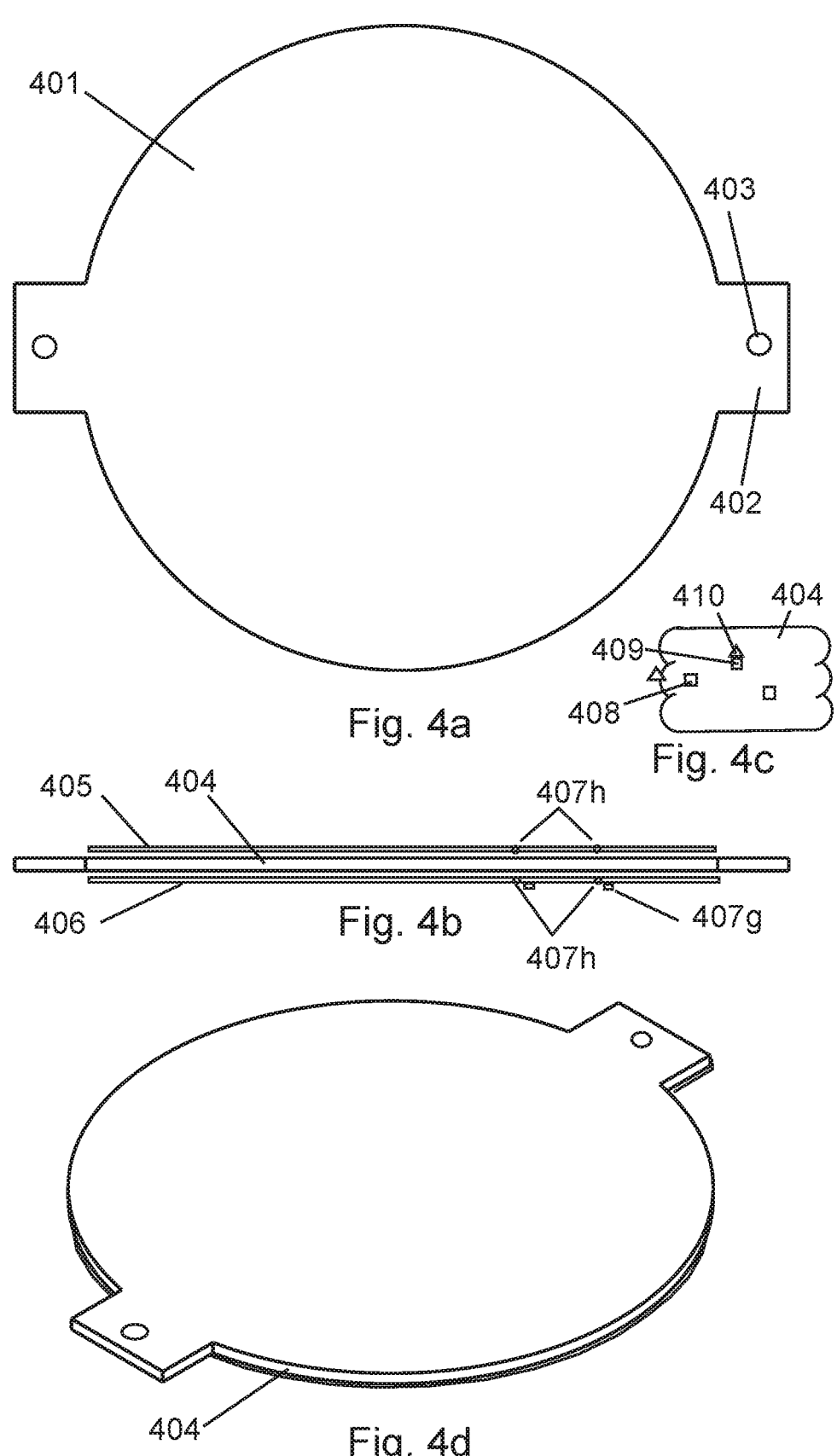

FIG. 4a depicts a top view of an alternative compressible implant 401. Implant 401 again comprises a circular, flexible, and compressible implant that may be rollable and/or foldable for possible subcutaneous placement. FIG. 4a depicts implant 401 in its unrolled or otherwise uncompressed/native state. Implant 401 may be comprised of similar materials as implant 301. Implant 401 may also comprise protruding tabs 402 that may aid in placement into a minimally invasive entrance incision. However, implant 401 may also comprise macro positioning/instrument engaging holes 403 in one or more (in some cases, all) of the protruding tabs 402 or elsewhere about its structure that may be configured to receive and/or engage an instrument, or a portion of an instrument, to facilitate placement of the implant 401 into a minimally invasive entrance incision. In some embodiments and implementations, instruments may be used that may comprise protrusions capable of dragging or pulling the material surrounding the hole, and thereby advancing implant 401, into proper position through such small entrance incisions.

FIG. 4b is a side view of implant 401, which depicts the use of optional laminates that may also comprise the implant of FIG. 4a. FIG. 4b depicts edge 404 of implant 401 with optional upper laminate 405 and lower laminate 406.

In some embodiments, laminates 405 and 406 may be sealed only at their respective outer edges to create a bladder therebetween, which may contain various fluids for eventual delivery into the patient. In some such embodiments, the structure in between the two laminates may be partially or fully removed. For example, there may be holes or other openings formed to allow fluids captured between the laminates 405/406 to pass back and forth, effectively creating a single bladder or chamber. Thus, it should be understood that one or both of the laminates 405/406 may have a surface entirely in contact with the main body of the implant 401 (despite the appearance of spaces therebetween in the figure), or there may be space adjacent to one or both laminates 405/406, which, again, may allow for containing fluids. In further contemplated embodiments, laminates may comprise ethylene vinyl alcohol co-polymers.

Laminates 405 & 406 may further comprise pores/holes/spaces 407h which may allow drugs, molecules, chemicals, and the like to exit from implant 401, preferably following implantation. Such substances may be configured to exit from the implant 401 passively by, for example, osmosis or actively by being driven, for example, indirectly by electromagnetic fields. Pores/holes/spaces 407h may be gated by structures such as gates 407g which may, for example, comprise electrically actuatable smart nanoporous membranes (as per Langer, Wireless on-Demand Drug Delivery, Nature Electronics, 2021).

Laminates 405 & 406 may comprise, in some embodiments, electroresponsive gels, such as poly(dimethyl aminopropyl acrylamide) (PDMAPAA) loaded with drugs (for example, insulin). Such gels may be configured to release the drugs and/or other chemicals/materials when stimulated by an externally applied electric field. Similarly, hydrogels prepared from chitosan-graft-polyaniline copolymer and oxidized dextran loaded with amoxicillin/ibuprofen have shown a controllable release rate set by the applied voltage. Electrically actuatable smart nanoporous membranes may also, or alternatively, be used in some embodiments, and which may be made of, for example, polypyrrole (PPy) doped with dodecylbenzenesulfonate (DBS) for pulsatile drug release. The aforementioned information and other examples of porous membranes allowing actuatable drug release that may be used in connection with one or more of the embodiments disclosed herein may be found in Wireless on-Demand Drug Delivery, Langer, Nature Electronics, 2021, which is hereby incorporated herein in its entirety by reference.

In some embodiments, thermally actuated lipid membranes may be used for on-demand drug delivery, which may be incorporated into various embodiments disclosed herein. In some instances, an inductively coupled coil may be used to deliver electrical energy to resistive heating elements. In certain embodiments, the lipid membrane may comprise, for example, dipalmitoylphosphatidylcholine, 1,2-dilauroyl-sn-glycero-3-phosphoethanolamine, dipalmitoylphosphatidylglycerol, and/or 1,2-dioleoyl-3-trimethylammonium-propane and cholesterol. The implant may comprise, in some embodiments, an array of individually addressable thermal actuators, each consisting of a receiver coil coupled to a resistor, and a layered coating of the thermally actuatable lipid membrane enclosing the drug. In a preferred embodiment, drug release may occur at a temperature above normal body temperature, but below maximum allowable temperatures, which may allow for selective actuation of drug delivery. Additional details regarding drug delivery systems may be found in "Biological Lipid Membranes for On-Demand, Wireless Drug Delivery from Thin, Bioresorbable Electronic Implants", Lee, NPG Asia Materials, 2015, 10.1038/am.2015.114, which is hereby incorporated in its entirety by reference.

FIG. 4c depicts an enlarged side view of implant 401 with target binding materials 409 binding target/subject materials 410 along the edge 404 of the implant 401, as denoted by their diagrammatic proximity. After release, target binding materials 408 may be unassociated.

FIG. 4d is a top perspective view of implant 401 also depicting the edge 404 of the implant. As previously mentioned, implant 401 may be deployed in a compressed state, such as a rolled state, and then unrolled or otherwise decompressed once inserted through the entrance incision and positioned within the implant pocket as will be discussed.

Figures 5A, 5B, 5C:
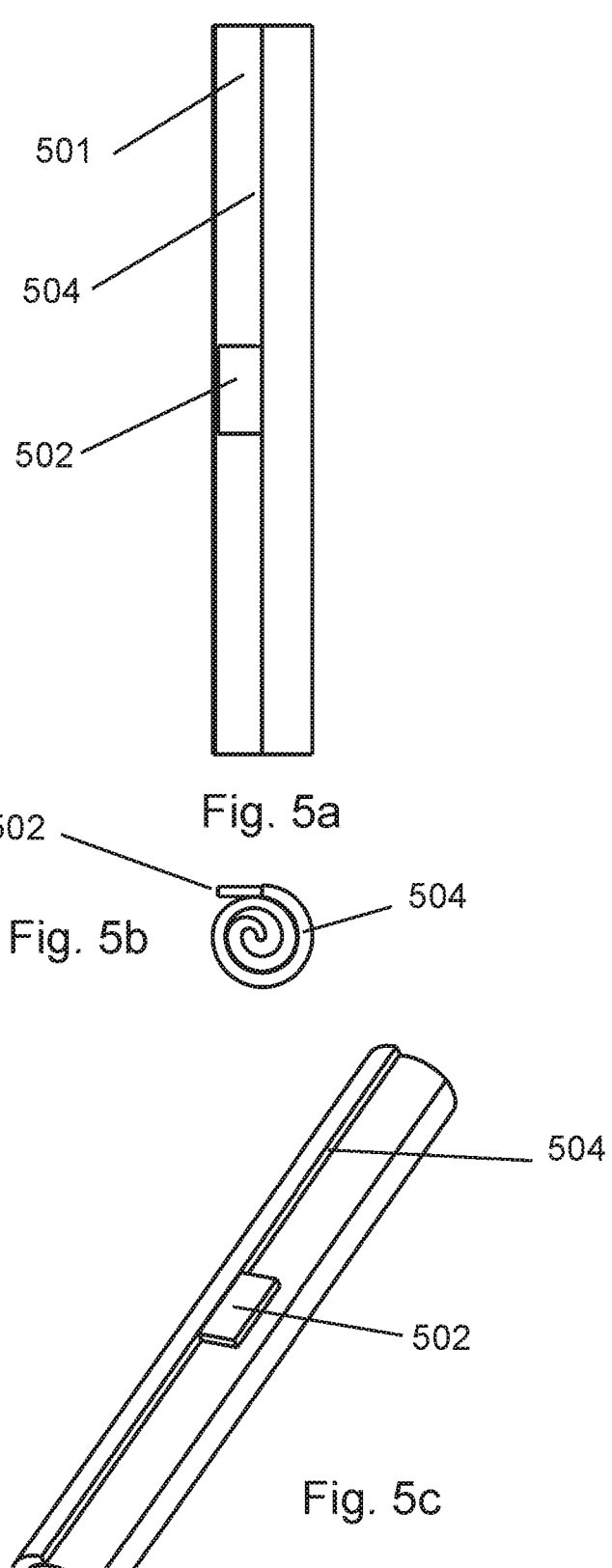
FIG. 5a depicts a side view of an implant according to another embodiment rolled into a compressed state.
FIG. 5b depicts a side view of the implant rolled into a compressed state.
FIG. 5c depicts a perspective view of the implant rolled into its compressed state.

FIG. 5a depicts a side view of an implant 501 after it has been compressed for entry through an incision. In the depicted configuration, implant 501 has been rolled into the compressed configuration shown. Implant 501 may be similar to one or more of the implants previously discussed and may therefore be made up of any of the materials previously mentioned. Implant 501 may further comprise protruding tabs 502 that may, as previously discussed, be configured to facilitate placement into a minimally invasive entrance incision with instruments to be discussed. For purposes of this disclosure, entrance incisions may be considered as forming an opening in the epidermis and dermis in order to reach the subcutaneous and/or deeper tissues.

FIG. 5b is a side view of the rolled implant 501 depicting edge 504 and tab 502. FIG. 5c is a perspective view of the implant 501 depicting edge 504 and tab 502. As demonstrated by FIGS. 5a-5c, implant 501 may be configured to allow for an implant having a large surface area, such as a rectangular-shaped implant, to be rolled in order to maximize the surface area capabilities and/or minimize the restriction of a rolled implant as it passes through the entrance incision. In some embodiments, implants comprising electronics and/or implants configured to deliver drugs may, in its respective uncompressed configuration, have a footprint area of at least 50 square cm. In some such embodiments, implants comprising electronics and/or implants configured to deliver drugs may, in its respective uncompressed configuration, have a footprint area of at least 100 square cm.

As also depicted in FIG. 5b, the implant 501 has been rolled and/or folded multiple times, the number of which may depend on the thickness and dimensions of the implant, possibly along with the desired central space following compression. Delicate electronics may not function following extremely tight rolling of certain implants, such as small yet flexible implants. Thus, the nature of the implant and the components contained thereon may also dictate the number of rolls/folds. Similarly, the size of the entrance incision may warrant tighter, or looser, folding/rolling/compression.

Figures 6A, 6B, 6C:
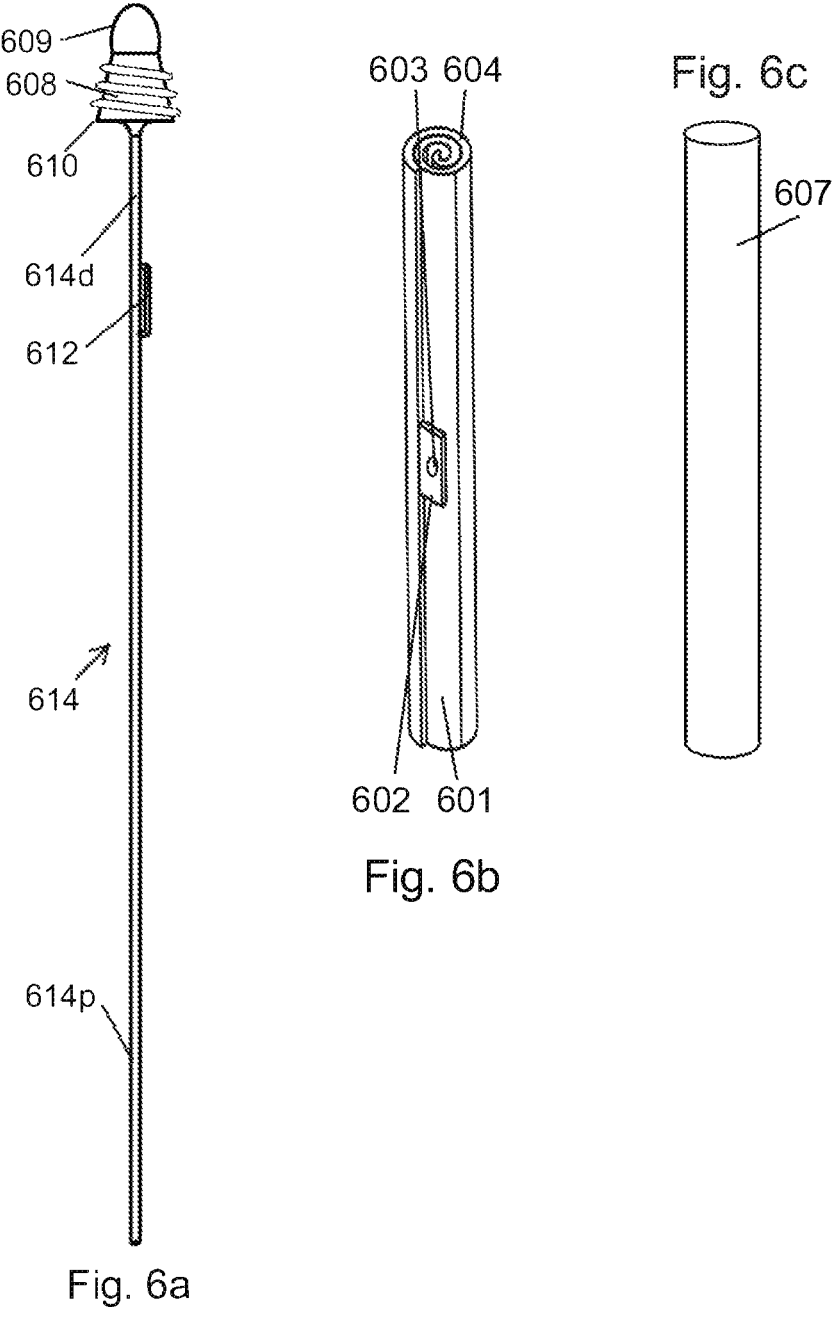
FIG. 6a depicts a side view of an instrument configured for inserting a compressible implant.
FIG. 6b depicts a perspective view of an implant rolled into a compressed state.
FIG. 6c depicts a perspective view of a sheath that may be used to protect an implant during installation.

FIGS. 6a-6e depict side views of a flexible tissue implant facilitating system (FTIFS) 600 and devices. FIG. 6a depicts an instrument (in this case a portion of a more complete instrument or a "sub-instrument") comprising a blunt introducing tip 609, a dilator 608 with widest diameter 610 and tapering to a narrower diameter at tip 609. Tip 609 is coupled to a shaft 614 having a distal portion 614d and a proximal portion 614p. In the depicted embodiment, the distal portion 614d of the shaft may comprise an implant engaging member, which in the depicted embodiment comprises a tab fastener 612. Tab fastener 612 may engage rolled implant tab 602. For example, in some embodiments and implementations, tab 602 may be inserted, either partially or fully, through the slot formed by tab fastener 612. Screw threads 611 may, in some embodiments, be oriented normal, or at least substantially normal, to the shaft axis, thus the screw threads may cut through dermis (as the entrance incision is dilated/stretched) at an angle that is close to parallel to the skin surface, thus cuts/scarification may be more difficult to notice as they are deeper than the surface mimicking the technique of subcision.

In some embodiments, a macro positioning/instrument engaging hole 603 may be formed in tab 602, which may further facilitate placement of implant 601 on the instrument. For example, in some embodiments, a surgeon may use a pair of forceps or the like, which may be inserted through the hole 603 during the procedure of coupling the implant 601 to the instrument, such as to pull the tab 602 through the slot formed by tab fastener 612. As will be described below in greater detail, in some embodiments, holes, which may be similar to hole 603, may be used to facilitate this coupling by receiving protruding members formed in the instrument, such as on the shaft of the instrument, which protruding members may extend through and engage (thus, a relatively flexible implant material and a relatively inflexible protruding member may be preferred) the material of the implant forming the hole(s).

FIG. 6b shows an implant 601 rolled up into a compressed configuration for insertion through a preferably minimally invasive entrance wound. Tab 602 is shown protruding from an edge of implant 601 that extends perpendicular to edge 604 in this configuration. Implant 601 may comprise any of the previously mentioned materials.

FIG. 6c illustrates a sheath 607 that may be used in certain embodiments and implementations. FIG. 6d shows sheath 607 after it has been coupled with the instrument with the implant 601 therein. Thus, in some implementations, sheath 607 may simply be slid over the rolled/compressed implant 601, either before or after the implant 601 has been coupled with the instrument. Sheath 607 may comprise, for example, a thin sheet of polyethylene, polyurethane, or other suitable polymer.

In FIG. 6d, the instrument is shown with sheath 607 encasing an underlying rolled implant (hidden in this view), which is in turn wrapped around the distal portion 614d of the instrument shaft, as previously mentioned. As also shown in this figure, the proximal portion 614p of this shaft may be coupled with a removable handle 615. Handle 615 may be a slidable, adjustable handle that may simply comprise a central, axial hole shaped and configured to receive the shaft therein. As also shown in the figure, handle 615 may further comprise one or more frictional features to provide for traction during use by a surgeon. In the depicted embodiment, a plurality of elongated, parallel depressions 615f are formed for this purpose (of course, these may be protruding ribs or other protruding features in alternative embodiments).

FIG. 6e shows a complete FTIF System 600. As shown in the figure, dilator 608 may comprise screw threads 611. Threads 611 may facilitate advancement of the tip 609, and the adjacent portion of the instrument and underlying implant 601, through a relatively small entrance wound. For example, a surgeon may initially advance the distal, pointed portion of tip 609 through the entrance wound. In order to stretch the wound opening to ultimately accommodate the implant 601, the surgeon may then rotate the instrument, which may cause the threads to engage the surrounding tissue and further advance the instrument (and implant 601) along the tapering section of tip 609.

FIG. 6e also shows sheath 607 fully enclosing the rolled implant (also hidden in this view). This figure also shows most of the proximal portion 614p of the shaft covered by releasable handle 615, which may be made to firmly couple, such as lock, to the shaft 614p via a lever latch 616. Lever latch 616 may have an asymmetric protuberance and asymmetric hole through which a pin may pass from the handle through the latch 616 to form a friction fit against the shaft when engaged and flush. Thus, by rotating the lever latch 616, a user may be able to lock an engagement region of the latch portion of the lever latch 616 against the shaft.

Figures 7A, 7B, 7C:
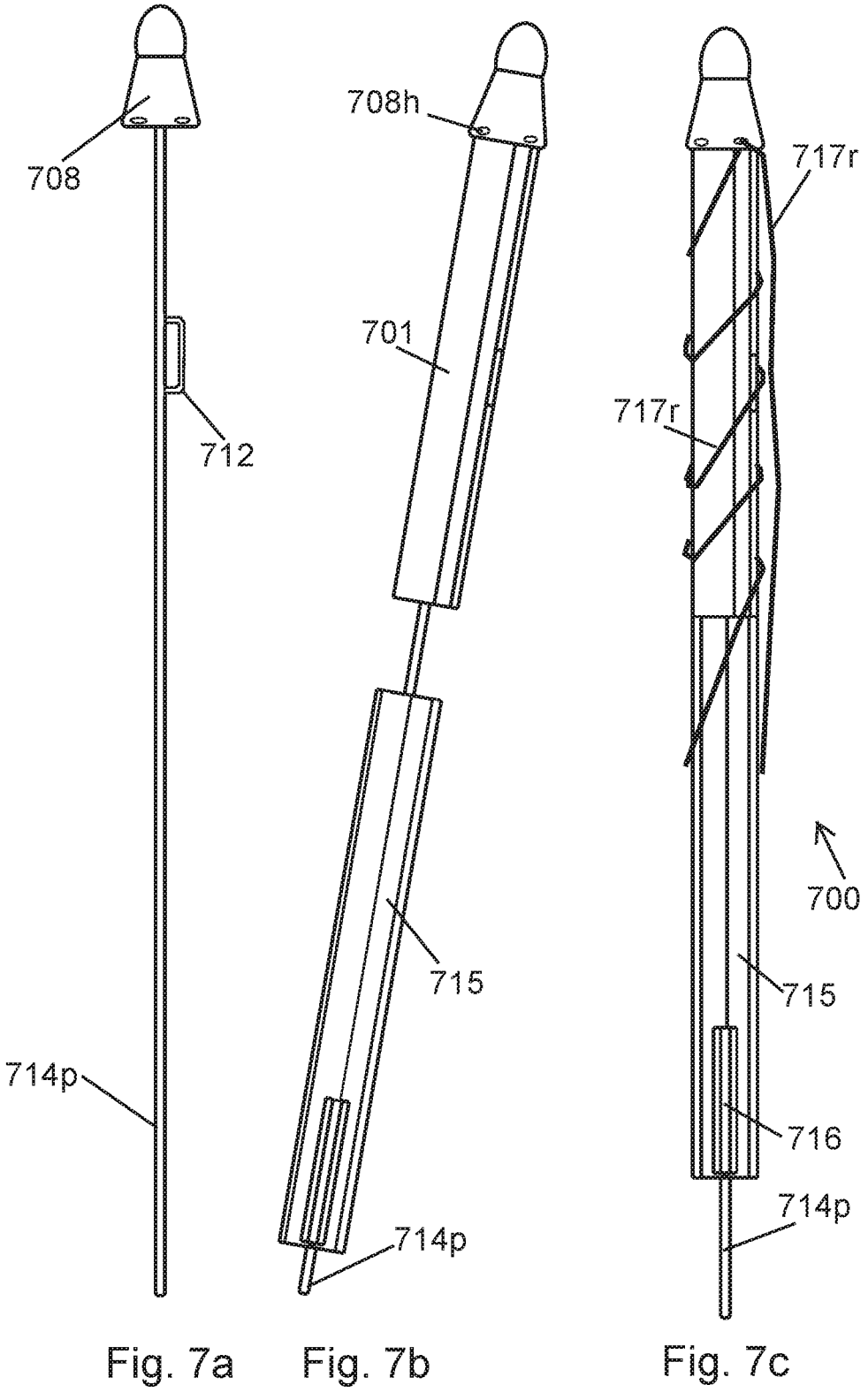
FIG. 7a depicts a side view of an instrument that may be used in connection with an FTIFS.
FIG. 7b depicts a side view of an FTIFS.
FIG. 7c depicts a side view of an FTIFS according to another embodiment.

FIGS. 7a-7c depict side views of a flexible tissue implant facilitating system (FTIFS) 700 according to other embodiments. System 700 does not use a sheath but instead uses a ribbon 717r to restrain implant 701. FIG. 7a depicts a blunt introducing tip atop dilator 708 which is attached to the shaft, comprising tab fastener 712, eventuating in proximal shaft portion 714p. FIG. 7b shows a dilator with a dilator hole 708h atop a rolled implant 701, which may be comprised of previously mentioned materials. FIG. 7c illustrates one limb of a ribbon 717r passing through a dilator hole 708h wrapped around an implant in a candy-cane fashion to secure the implant when held by the surgeon's hand against handle 715. The other limb of the ribbon 717r may be kept straight but preferably secured by the surgeon's hand until the entire implant 701 is delivered through the entrance wound successfully whereupon the wound limb of the ribbon is unwound rubbing against the entrance wound thereafter the entire ribbon can be pulled by one limb through the dilator hole. As before, lever latch 716 may be used to releasably couple handle 715 with proximal shaft portion 714p.

Figures 8A, 8B, 8C, 8D:
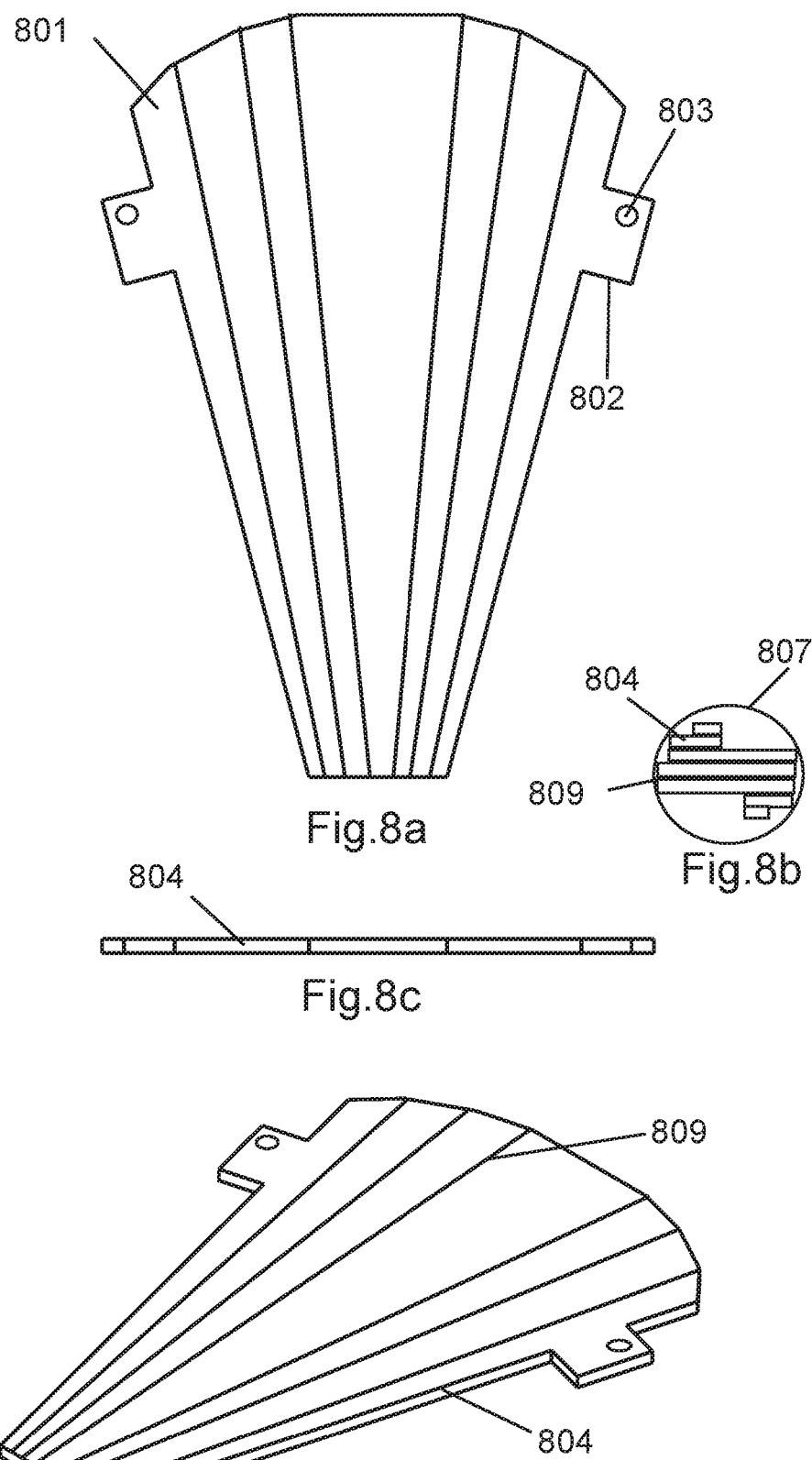
FIG. 8a depicts a top plan view of a compressible implant according to other embodiments.
FIG. 8b depicts a cross-sectional view of the implant in its folded state within a sheath
FIG. 8c depicts a side view of the implant in its uncompressed state.
FIG. 8d depicts a top perspective view of a compressible implant according to an embodiment.

FIG. 8a depicts a top view of an alternative compressible implant 801. Implant 801 may comprise a fan shaped implant that may be polygonal, flexible, and/or compressible. More particularly, implant 801 may be foldable for subcutaneous placement through a relatively small entrance wound. In some implementations, the implant may be rollable and/or rolled rather than folded, as previously discussed.

FIG. 8a depicts implant 801 in its unfolded or otherwise uncompressed/native state. Implant 801 may be made up of similar materials as implant 301. Implant 801 may also comprise one or more protruding tabs 802 that may aid in placement into a minimally invasive entrance incision. However, implant 801 may also comprise macro positioning/instrument engaging holes 803 in one or more (in some cases, all) of the protruding tabs 802 or elsewhere about its structure that may be configured to receive and/or engage an instrument, or a portion of an instrument, to facilitate placement of the implant 801 into a minimally invasive entrance incision. In some embodiments and implementations, instruments may be used that may comprise protrusions capable of dragging or pulling the material surrounding the hole, and thereby advancing implant 801, into proper position through such small entrance incisions.

FIG. 8b depicts an enlarged side view of implant 801 depicting a folded plane 804 and fold 809, encircled by implant sheath 807.

FIG. 8c is a side view of implant 801 with edge 804.

FIG. 8d is a top perspective view of implant 801 also depicting the edge 804 and fold 809 of the implant. As previously mentioned, implant 801 may be deployed in a compressed state, such as a folded state, and then unfolded or otherwise decompressed once inserted through the entrance incision and positioned within the implant pocket, as will be discussed in greater detail below.

Figure 9A:
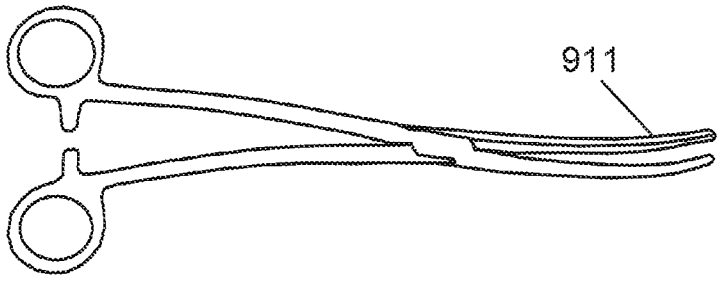
FIG. 9a depicts a surgical instrument that may be used to remove surgical instruments.
Figure 9B:
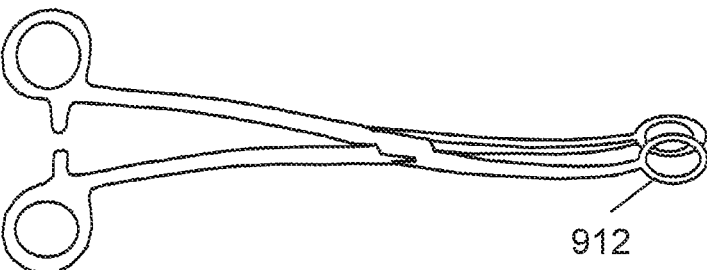
FIG. 9b depicts a surgical instrument that may be used to remove surgical instruments.

FIGS. 9a-b depict surgical tools that may aid in the removal of non-biodegradable implants. The forceps 911 in FIG. 9a may terminate in non-sharp points whereas forceps 912 in FIG. 9b may terminate in ring like shapes. Such forceps may be introduced into an entrance wound after the implant has served its usefulness or has developed a problem. An edge of the implant may be clamped and the instrument spun on its axis through the entrance wound until part or all of the implant is wound around the tool whereupon the tool and implant are pulled through the entrance wound whole (or in pieces if the surgeon has chosen to divide the implant whilst still inside the patient prior to removal).

Figures 10A, 10B, 10C, 10D, 10E:
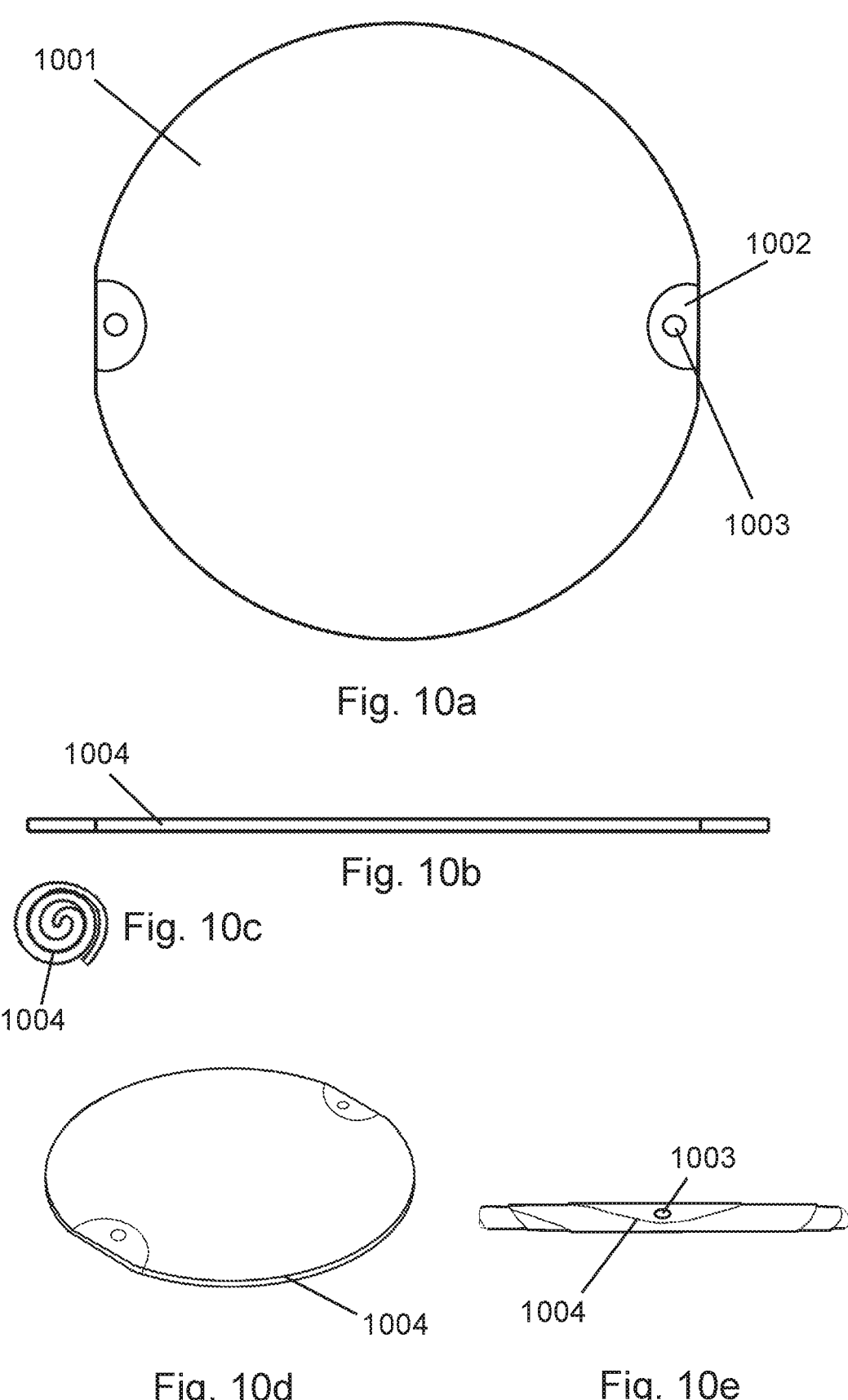
FIG. 10a depicts a top plan view of an embodiment of a compressible implant according to an embodiment.
FIG. 10b depicts a side view of the implant in its uncompressed/unrolled state.
FIG. 10c depicts an alternative side view of the implant in its compressed/rolled state.
FIG. 10d depicts a top perspective view of the implant.
FIG. 10e depicts a side view of the implant in its compressed/rolled state.

FIG. 10a depicts a top view of an alternative compressible implant 1001 according to other embodiments. Implant 1001 again comprises a circular, flexible, and compressible implant that may be foldable for subcutaneous placement. In some embodiments, the implant may be rollable and therefore may be rolled into the configuration shown in FIG. 10c. FIG. 10a depicts implant 1001 in its unrolled or otherwise uncompressed/native state. Implant 1001 may be made up of similar materials as any of the other implants disclosed herein, as previously mentioned.

Implant 1001 lacks protruding tabs that may catch on tissue near the entrance wound or occupy valuable diametric dimensions reducing the ease of which the implant may pass through a minimally invasive entrance incision. However, implant 1001 may comprise internal and/or non-protruding tabs 1002, which may otherwise be referred to herein as hole-defining and/or structural reinforcement regions. One or more of internal tabs 1002 may define one or more macro positioning/instrument engaging holes 1003. Various non-biodegradable materials such as polypropylene, poly-para-phenylene terephthalamide or polytetrafluoroethylene (PTFE) may be used to reinforce the implant and therefore may be used to form internal tabs 1002. In addition, biodegradable materials, such as polylactic acid or poliglecaprone and the like may be used. Holes 1003 may be configured to receive and/or engage an instrument, or a portion of an instrument, to facilitate placement of the implant 1001 into a minimally invasive and/or relatively (relative to the implant) small entrance incision. In some embodiments and implementations, instruments may be used that may comprise protrusions capable of dragging or pulling the material surrounding the hole, and thereby advancing implant 1001 into the proper position through such small entrance incisions. FIG. 10b depicts a side view of unrolled or uncompressed implant 1001 with edge 1004.

Implantable patch 1001 may contain drugs such as gentamicin or methotrexate, suspended in hydrogels such as PLA (polylactic acid). Also, the drugs niclosamide or IP6 (inositol phosphate) may be mixed in PCL (polycaprolactone) and/or graphene nanoplatelets in some embodiments. Biologic scaffolds may also be used, which may include drugs such as rhBMP-2 (recombinant bone morphogenetic protein-2) incorporated into PCL, PLGA (poly lactic co-glycolic acid), or Beta-TCP (tricalcium phosphate). Another example of a suitable biologic scaffold is dexamethasone, which may be embedded in Sr-MBG (strontium mesoporous bioactive glass). Bioceramics for bone generation and infections may also be used in some embodiments, and which may include VNC (vancomycin), rhBMP-2, and/or heparin, and may be embedded in materials such as brushite, unreacted alpha or beta-TCP, chitosan, and/or HPMC. VNC and ceftazidime may also be mixed into PLA cages and PLGA nanofibers. Other drugs and materials for implantable patches, stents, meshes, scaffolds, and/or bioceramics may be found in '3D Printed Drug Delivery and Testing Systems—a Passing Fad or the Future?', Lim, Advanced Drug Delivery Reviews 132 (2018) p. 139-168, 2018, which is hereby incorporated in its entirety by reference.

In some embodiments, polymers such as silicones, poly (urethane), poly(acrylates), or copolymers may be used in preparing non-biodegradable implants. Such polymers may be formed into matrices wherein the drug is homogenously dispersed, or may be formed into reservoir-type implants, which may comprise a drug core covered by a permeable membrane. In some instances, polymers such as poly(caprolactone), poly(lactic acid), or poly(lactic-co-glycolic acid) may be used to prepare biodegradable drug eluting devices. Additional details regarding suitable polymers for drug delivery may be found in 'Implantable Polymeric Drug Delivery Devices: Classification, Manufacture, Materials, and Clinical Applications', Stewart, MDPI, 2018, doi.org/10.3390/polym10121379, which is hereby incorporated in its entirety by reference.

FIG. 10c depicts a side view down the axis of a rolled or compressed implant 1001 with edge 1004.

FIG. 10d is a top perspective view of implant 1001 also depicting the edge 1004 of the implant. As previously mentioned, implant 1001 may be deployed in a compressed state, such as a rolled state, and then unfolded or otherwise decompressed once inserted through the entrance incision and positioned within the implant pocket, as will be discussed in greater detail below.

Figures 18A, 18B, 18C, 18D:
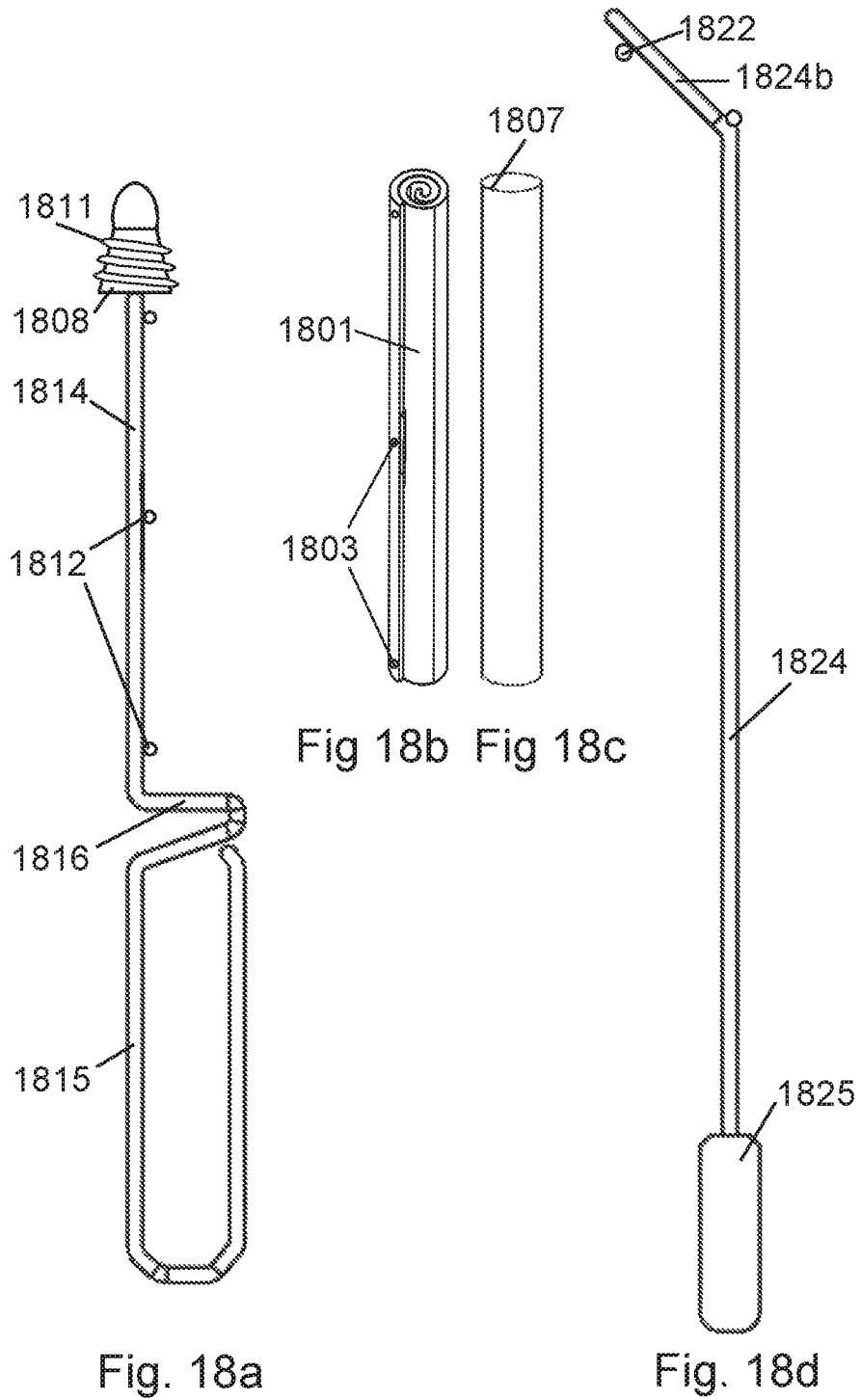
FIG. 18a depicts a side view of an alternative embodiment of a FTIFS instrument.
FIG. 18b depicts a perspective view of an implant in its rolled state, according to an embodiment.
FIG. 18c depicts a perspective view of a sheath according to an embodiment.
FIG. 18d depicts a side view of a partner instrument used to couple holes of an implant according to an embodiment.

FIG. 10e depicts another side view of implant 1001, this time viewed from the side extending along the full axis of the rolled or compressed circular implant 1001 with edge 1004 rather than looking down the axis as in FIG. 10c. Note that in implants that have fewer corners (less corner material) than a rectangular implant, such as the depicted circular implant, the ends of a rolled/folded implant may taper and/or step so that in their compressed configuration they are thicker in the center than along one or both opposing ends, as shown in FIG. 10e. In some contemplated implementations, tapered and/or stepped ends may facilitate manual insertion of the implant into a minimally invasive entrance wound by resulting in a compressed implant having one or more smaller ends to facilitate introduction through the entrance wound, especially if rotated in a direction that the implant was folded so that the implant running edge may be less prone to rub against the entrance incision whilst being rotated and pushed. Such manual insertion may be by sterile gloved fingertips. In some implementations, implant 1001 may be unfurled subcutaneously using holes 1003 and a sterile probe/instrument with protrusion 1824b as seen in FIG. 18d.

FIG. 11 depicts an alternative embodiment of an implant 1101 comprising non-protruding structural reinforcement regions 1102, each of which defines a macro positioning/instrument engaging hole 1103, which is positioned at an edge/periphery of the implant 1101, and therefore, as described above in connection with implant 1001, provides structural reinforcement to improve the structural integrity of each hole 1103. In addition, implant 1101 differs from implant 1001 in that in its uncompressed configuration it defines an oval shape rather than a circular shape. Implant 1101 further comprises a plurality of macro vascularization holes 1177 ("macro" refers to the size of the hole rather than the size of the vessels that may grow therethrough), one or more of which may comprise a reinforcement region 1178, which may be concentric with the hole(s) 1177, to provide protection and prevent or at least inhibit tearing. The use of relatively large (10-20 cm or greater in diameter or greatest dimension following implantation/decompression, as shown in FIG. 11) implants in areas such as the abdomen that derive most of their blood supply from deeper tissues, rather than tangentially from adjacent tissues, may result in a diminution of blood supply and other elements to the tissues overlying the center of the implant. If vascularization holes are present in the implant and sufficiently wide large to allow vascular ingrowth and communication with the more superficial tissues through the implant, the superficial tissues of the abdomen may experience better growth conditions and blood supply rather than only being granted blood supply from the relatively distant periphery of the implant. If the holes are under 1 mm in diameter, it may be difficult for blood vessel ingrowth to traverse from one side of the implant to the other. Therefore, one or more vascularization hole(s) 1177 exceeding 1 mm (preferably at least several mm) in diameter may be made to allow vascular ingrowth and/or vascular crossing of the implant to benefit tissues on the opposite side of the implant. The area around hole(s) 1177 may comprise a ring or other shape of reinforcement 1178 in order to maintain the integrity of the implant. In some such embodiments, an array of holes may be present in the implant, which may include dozens or even hundreds or thousands of holes, as desired. In contemplated embodiments, peripheral placement of holes may not benefit the tissues as much as centrally placed holes, as the tissues overlying the center are farther from the periphery, thus some preferred implants may comprise primarily, or exclusively in some cases, central or at least substantially centrally positioned vascularization holes. For purposes of this disclosure, a macro vascularization hole should be considered at least substantially centrally positioned if it is positioned within any point of the implant's footprint lying within about one-third of the distance from the implant footprint's mathematical centroid point and a point on the perimeter intersected by a line passing through the centroid. Some embodiments may comprise macro vascularization holes lying within a "relative center" position, which for purposes of this disclosure should be considered within any point of the implant's footprint lying within 50% of the distance from the implant footprint's mathematical centroid point and a point on the perimeter intersected by a line passing through the centroid.

In other contemplated embodiments, such holes for vascularization and biological cross communication may be present throughout the implant in desired areas. Vascularization may be more plentiful to nourish tissues distant from a blood supply in greater need. Such through/through and through holes (meaning fully penetrating the implant's thickness) may be beneficial for tissue fluid sampling in that neovascularization may not be closed end and thus pass in greater velocity and/or volume per vessel/capillary. Microfluidic channels 1188 and/or probes may allow access for Lab-on-a-chip 1185 technology within the implant or in a wired/wirelessly connected auxiliary implant to assess body fluids. Proximity of new active vessels to a protected inner wall may also be beneficial for optical sampling by fiberoptics 1189 to aid in optical analysis of body fluids passing by a through & through hole 1187

In some embodiments, microfluidic lab-on-a-chip devices may comprise dual optical fibers used for manipulation. In some instances, such devices may comprise channels for precise fiber optic alignment, a sample channel, and/or a zig-zag structure incorporated in the sample channel. In some embodiments, the fiber-optics may be used to trap different-sized microscopic particles and/or stretch cells. In certain instances, the device may be fabricated via soft lithography using Polydimethylsiloxane (PDMS). In a preferred embodiment, the fiber optic system may comprise two aligned optical fibers delivering counterpropagating laser beams, which may be used for functions such as, for example, capturing/sorting/identifying particles/cells. Additional details regarding the disclosed lab-on-a-chip devices that may be used on various implants disclosed herein may be found in "3D printed microfluidic lab-on-a-chip device for fiber-based dual beam optical manipulation", Wang, Scientific Reports, 2021, 11:14584, which is hereby incorporated by reference in its entirety by reference.

In some embodiments, microfluidic devices may be incorporated into implants, which may comprise microfluidic probes (MFP). In such MFP devices, a microfluidic stream may be applied to the sample such that the MFP uses a hydrodynamic flow confinement instead of walls to constrain a microfluidic stream. In some embodiments, such MFPs may be open microfluidic systems. Applications for such MFP devices may include, for example, control of cellular microenvironments, local processing of tissue slices, generating concentration gradients, and the like. In some embodiments, such MFPs may be fabricated in Si wafers which may be bonded to PDMS chips, which may serve as world-to-chip interfaces and/or comprise holes. Microfluidics may offer several advantages such as, for example, greater control over microenvironments. MFPs may be used in conjunction with continuous laminar perfusion for purposes such as, for example, electrophysiological studies, biomarker discovery, toxicology study, and the like. In other embodiments, MFP devices may be used for immunohistochemistry on cancerous tissue slices, which may allow for implants to be used for tissue analysis. Additional details regarding such MFP devices may be found in "Microfluidic probes for use in life sciences and medicine", Qasaimeh, The Royal Society of Chemistry 2012, DOI: 10.1039/c21c40898h, which is hereby incorporated by reference in its entirety by reference.

In some embodiments, microfluidic chips may comprise optical refractive-index (RI) sensors comprising a long-period grating (LPG) inscribed within a small-diameter single-mode fiber (SDSMF). Such devices may be fabricated via, for example, layer-by-layer self-assembly techniques, which may deposit poly(ethylenimine) and poly (acrylic acid) multilayer films the on SDSMF-LPG sensor. In certain embodiments, such SDSMF-LPG sensors may comprise a layer used for molecule sensing, such as glucose oxidase for glucose sensing. In some embodiments, the microfluidic chip may be completed by embedding the molecule sensing layer and the SDSMF-LPG into a microchannel of the chip. In some embodiments, a mixture (for example 10:1) of PDMS and crosslinker may be used for chip fabrication. In a preferred embodiment, a microchannel may comprise a spiral-shaped mixing portion, which may aid in mixing solutions homogenously before passing through sensors. Additional details regarding such biosensors may be found in "Optical fiber LPG biosensor integrated microfluidic chip for ultrasensitive glucose detection", Yin, Biomedical Optics Express, Vol. 7, No. 5, 2016, which is hereby incorporated by reference in its entirety by reference.

In some embodiments, photomultiplier tubes may be used to deliver light to and from microfluidic systems via launch-and-detect fiber probes. In some instances, such probes may be used for DNA analysis, blood cell analysis, particle counting/sorting, and the like. In some embodiments, moving particles may also be detected by LED light; however, filters may be necessary used in some embodiments to suppress background noise from the upper side of the LED spectrum. In some instances, velocities of moving microparticles may be calculated by measuring the dynamic measurements of their fluorescence. Additional details regarding such microfluidic devices may be found in "Lab-on-a-chip optical detection system using plastic fiber optics", McMullin, Applications of Photonic Technology 6, Vol. 5620, 2003, which is hereby incorporated by reference in its entirety by reference.

In some instances, microfluidic platforms may be driven by capillary, pressure, electrokinetic, and/or acoustic forces. Microfluidic platforms may offer several advantages, such as on-demand generation of liquid micro-cavities, which may enable precise manipulation of quantities of reagents down to single cells while maintaining high throughput, achieved by a favorable aspect of surface-to-volume ratio. In some instances, microfluidic platforms may be used for biotransformation (via enzymes, bacteria, eukaryotic cells, and the like), analytics (of biomolecules, proteins, nucleic acids, and the like), and/or cellular assays (to assess the effects of pharmaceutical entities). In some embodiments, microfluidic chips may displace liquid by linear actuation, pressure driven laminar flow, and the like. In some embodiments, phase transfer magnetophoresis, involving magnetic microparticles flowing through a microchannel network, may be used for DNA purification, PCR, electrophoretic separation, and the like. In some embodiments, microfluidic devices may comprise microfluidic channel circuitry with chip-integrated microvalve systems that may be used to form more complex units such as micropumps, mixers, and the like. In some instances, such chips may be fabricated with a layer of planar glass sandwiched between two layers of PDMS. Such chips may be used in applications such as, for example, protein crystallization, immunoassays, automated cell culture, and the like. In some embodiments, microfluidic devices may employ segmented flow microfluidics, which may permit the merging/splitting of droplets. In some instances, electrokinetics may be used in microfluidic operations to control electric field gradients acting on electric dipoles to have effects such as, for example, electroosmosis, electrophoresis, polarization, and the like. In some instances, electrowetting may be used to generate, transport, split, merge, and/or process microdroplets by containing droplets on a hydrophobic surface comprising arrays of addressable electrodes. In some embodiments, microfluidic devices may comprise dedicated systems for massively parallel analysis. Such arrays may comprise microarrays and/or bead-based assays in combination with picowell plates. Additional details regarding such microfluidic platforms may be found in "Microfluidic lab-on-a-chip platforms: requirements, characteristics and applications", Mark, Chemical Society Reviews, Issue 3, 2010, which is hereby incorporated by reference in its entirety by reference.

FIG. 12 depicts another alternative embodiment of an implant 1201 comprising non-protruding structural reinforcement regions 1202, each of which again defines a macro positioning/instrument engaging hole 1203 and therefore, as described above, provides structural reinforcement to improve the structural integrity of each hole 1203. In addition, implant 1201 differs from implants 1001 and 1101 in that in its uncompressed configuration it defines a square shape.

FIG. 13 depicts yet another alternative embodiment of an implant 1301 comprising non-protruding structural reinforcement regions 1302, each of which again defines a macro positioning/instrument engaging hole 1303 and therefore, as described above, provides structural reinforcement to improve the structural integrity of each hole 1303. In addition, implant 1301 differs from the previous implants in that in its uncompressed configuration it defines a rectangular but not square shape, the elongated nature of which may be preferred for certain applications.

FIG. 14 depicts still another alternative embodiment of an implant 1401, which again comprises non-protruding structural reinforcement regions 1402, each of which again defines a macro positioning/instrument engaging hole 1403 and therefore, as described above, provides structural reinforcement to improve the structural integrity of each hole 1403. In addition, however, implant 1401 comprises reinforcing fibers 1411*f* interspersed throughout the implant 1401. In some embodiments, including the depicted embodiment, these fibers 1411*f* interconnect with the structural reinforcement regions 1402. However, this need not be the case in all contemplated embodiments. These fibers 1411*f* may assist in maintaining the overall structural integrity of the implant 1401 during use, as the implant may be stretched, pulled, etc. as it is being installed. Thus, although each of FIGS. 14-16 depicts structural fibers being used in connection with structural reinforcement regions, it is contemplated that these fibers may be used without accompanying structural reinforcement regions in other embodiments.

FIG. 15 depicts a further alternative embodiment of an implant 1501, which again comprises non-protruding structural reinforcement regions 1502, each of which again defines a hole 1503 and therefore, as described above, provides structural reinforcement to improve the structural integrity of each macro positioning/instrument engaging hole 1503. In addition, however, implant 1501 comprises reinforcing fibers or other strands of a material, including a hollow material in some embodiments. However, in this embodiment, these fibers are formed into a fibrous mesh 1511*m*. In some embodiments, including the depicted embodiment, the fibers of mesh 1511*m* interconnect with the structural reinforcement regions 1502. However, this need not be the case in all contemplated embodiments. For example, various other mesh implants are disclosed herein that may simply comprise a mesh made up of intersecting strands of material that make up the implant, rather than serve as structural reinforcement for the implant. Such intersecting strands may, in some embodiments, be coated with laminates or other biocompatible materials that may allow passage of internal substances, such as drugs, therethrough to modulate their bioavailability.

FIG. 16 depicts another alternative embodiment of an implant 1601, which again comprises non-protruding structural reinforcement regions. In this embodiment, there are both peripheral structural reinforcement regions 1602*p*, which are positioned at each corner, and central structural reinforcement regions 1602*c*, which are positioned on both sides of the implant 1601 along a central region thereof. As with the previous embodiments, each of the structural reinforcement regions may again define a macro positioning/instrument engaging hole (holes 1603*p* and 1603*c*) and therefore, as described above, may provide structural reinforcement to improve the structural integrity of each hole. In addition, however, implant 1601 comprises reinforcing fibers. However, in this embodiment, these fibers are formed into separate sections, namely, a series of centrally positioned columns 1611*c* and a series of intersecting angled lines along both peripheral/lateral sections adjacent thereto, as indicated at 1611*p*.

Figures 17A, 17B, 17C:
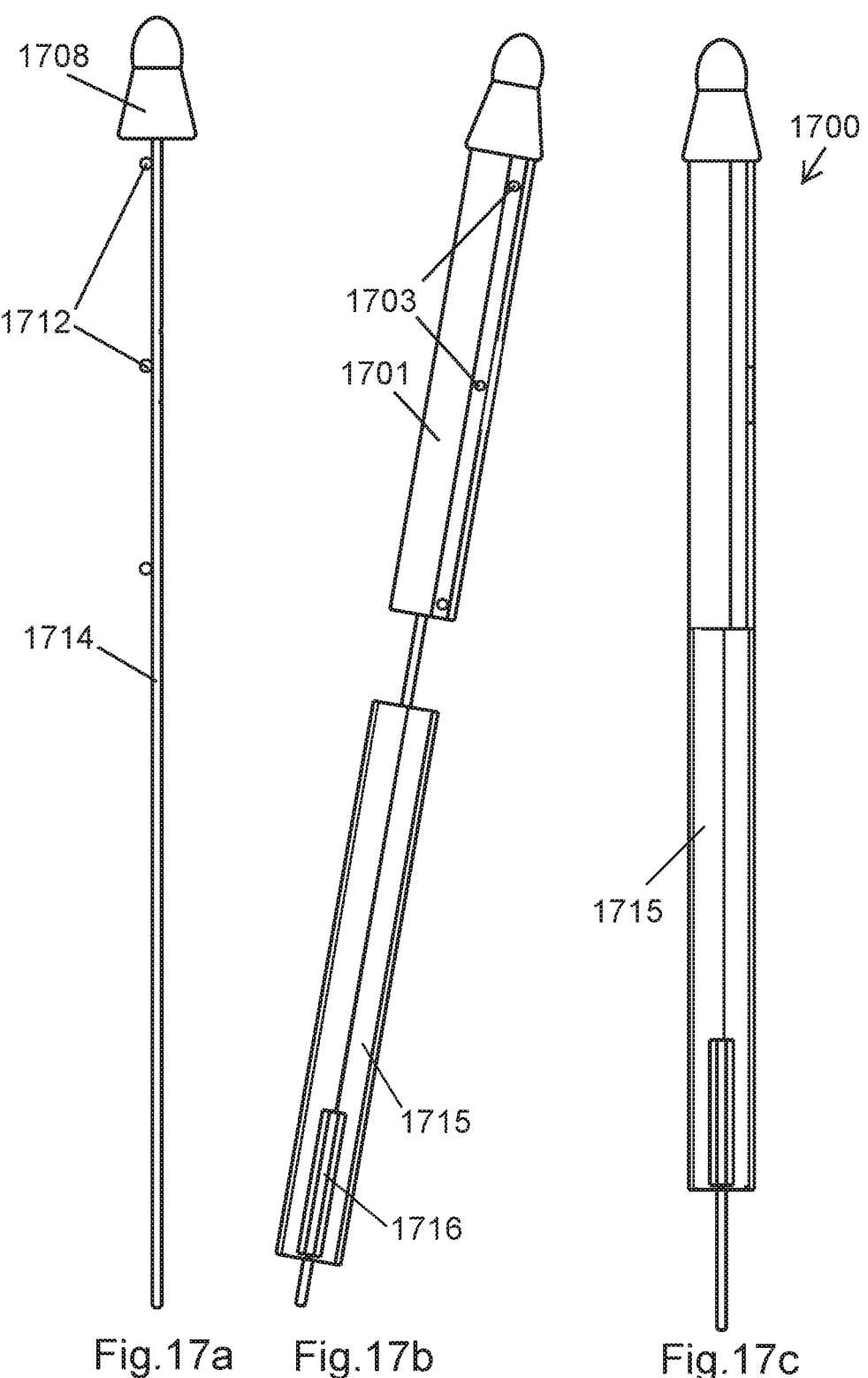
FIG. 17a depicts a side view of an embodiment of a FTIFS instrument.
FIG. 17b depicts a side view of a complete FTIFS.
FIG. 17c depicts a side view of a complete FTIFS.

FIGS. 17a-17c depict side views of a flexible tissue implant facilitating system (FTIFS) 1700 according to other embodiments. System 1700 may, in some embodiments, use a sheath (not shown in the figures) to restrain implant 1701 beneath dilator 1708. FIG. 17a depicts protrusions 1712, which may be spheres in some embodiments (including the depicted embodiment) attached to the shaft 1714. Shaft 1714 may be of varying lengths to accommodate varying dimensions of implants. In some embodiments, it may be preferable to have uniform spacing of protrusions along a shaft that may match distances between implant holes in a system, such as macro positioning/instrument engaging holes 1703. If the holes of an implant with or without reinforcement are slightly elastic, the use of spherical protrusions may give a more secure grip around the inner shaft-fixated portions of the spheres and a more definitive possibly palpable or audible release as the hole would act like a sphincter around the sphere. A size differential between the sphere and the hole may be beneficial as the surgeon can 'load' the implant onto the shaft's spheres outside the body with force and when the implant is inside the body detach by twisting or minimal force against another object introduced into the entrance wound. When flexible implant materials are used, it may therefore be useful to form the holes in the implant of smaller diameter than that of the spherical protrusions 1712 such that the protrusions 1712 stretch the hole, which snaps back to secure the implant to the instrument. Of course, a wide variety of alternative features may be used for securing the implant to the instrument, such as snaps or other reclosable fasteners, for example. In other contemplated embodiments, the holes may be larger than placement device protrusions such that the loose fitting facilitates/accelerates unhooking the placement device.

FIG. 17*b* shows handle 1715 securing the proximal or base portion of the implant 1701 with lever latch 1716, thereby releasably maintaining fixation in FIG. 17*c*.

FIGS. 18*a*-18*d* depict side views of various elements in a flexible tissue implant facilitating system (FTIFS) according to other embodiments wherein a shaft 1814 of an instrument may be bent into a handle-like shape which may reduce costs, parts and medical waste. Shaft 1814 may be bent into a ledge-like area to restrict proximal movement of implant 1801. The depicted embodiment shows sheath 1807 to restrain implant 1801 beneath dilator 1807. In other embodiments, a sheath may be optional. FIG. 18*a* depicts protrusions 1812, preferably spheres, coupled with the shaft 1814, which in turn bends into handle ledge 1816 to restrict implant movement and handle 1815 to facilitate rotational implantation. As before, shaft 1814 may be of varying lengths to accommodate varying dimensions of implants. As previously mentioned, a size differential between the sphere and the macro positioning/instrument engaging hole may be beneficial as the surgeon can 'load' the implant onto the shaft's spheres outside the body with force and when the implant is inside the body detach by twisting or applying minimal force against another object. The instrument may further comprise a dilator 1808, which may comprise threads 1811, as previously mentioned. In further contemplated embodiments, protrusions 1812 may be cylindrical with rounded tips, which may protrude, for example, between about 4 and about 8 mm from shaft 1814. Preferably, protrusions 1812 are about 1 mm smaller in diameter than the corresponding hole(s) 1803 within which they are configured to be received. In some embodiments, protrusions 1812 may extend from the distal portion of the shaft at an angle between about 20 and about 90 degrees; such protrusions 1812 may be of a smaller diameter than the holes of the implant to facilitate unhooking.

In the depicted embodiment, an additional instrument may be used, such as that shown in FIG. 18*d* with shaft 1824, which may also be introduced into the entrance wound/incision. FIG. 18*d* shows a partner instrument in the system that may couple implant holes 1803 via protrusions 1822 and/or branch 1824*b*, which extends from shaft 1824 at an angle relative to shaft 1824. Shaft 1824 is attached to handle 1825; this hooking instrument may be used in concert with that of FIG. 18*a* or separately to, for example, unwind an implant forced into the entrance wound manually as well in some implementations. Other instruments, such as endoscopy graspers and the like, may also be used as desired.

Figures 19A, 19B, 19C, 19D, 20A, 20B, 20C:
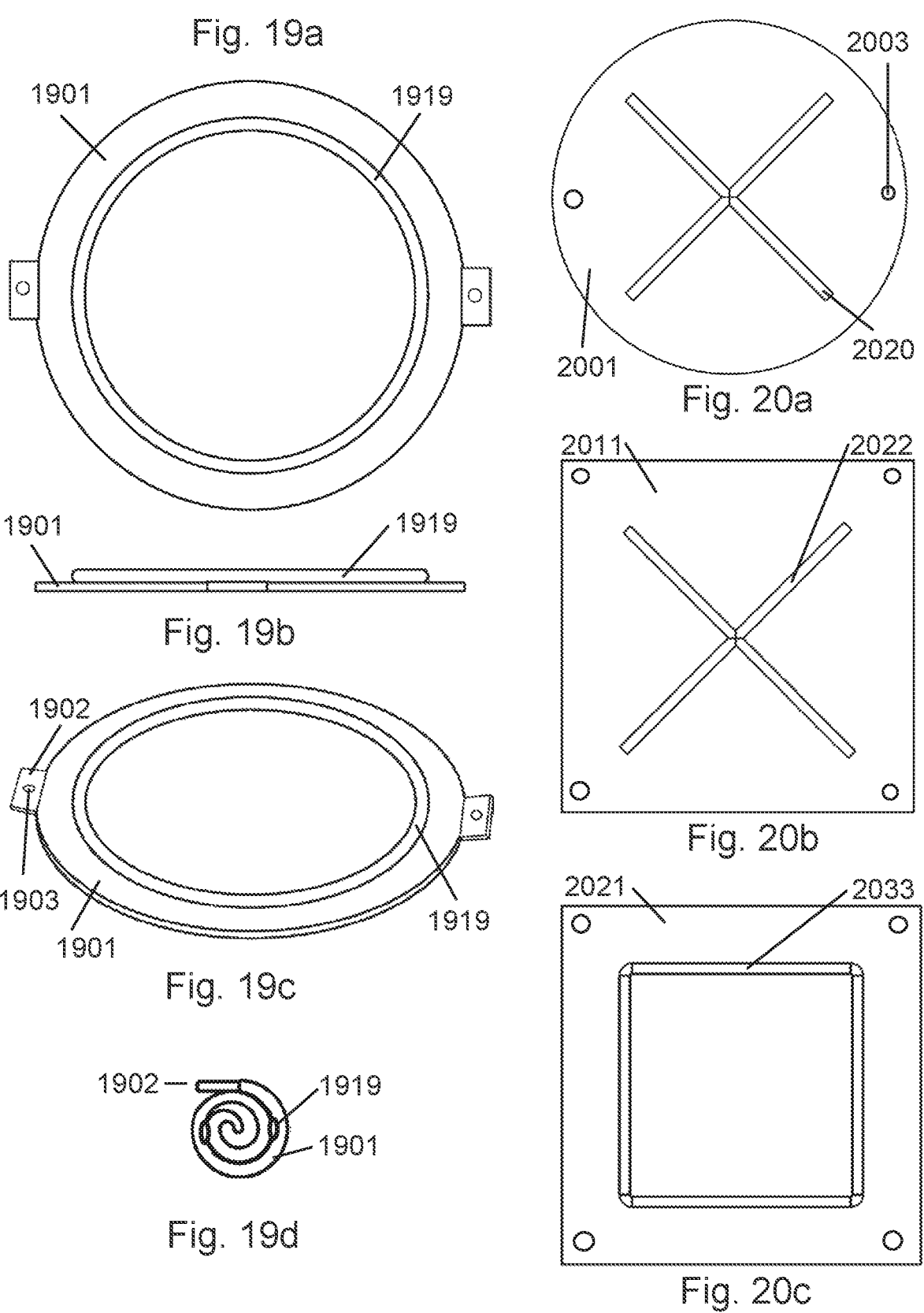
FIG. 19a depicts a bottom plan view of a circular, flexible, and compressible implant with a circular superstructure according to an embodiment.
FIG. 19b depicts a side view of a circular, flexible, and compressible implant with a circular superstructure according to an embodiment.
FIG. 19c depicts a bottom perspective view of a circular, flexible, and compressible implant with a circular superstructure according to an embodiment.
FIG. 19d depicts a side view of implant in its rolled state according to an embodiment.
FIG. 20a depicts a bottom view of a circular, flexible, and compressible implant with a '+' shaped superstructure according to an embodiment.
FIG. 20b depicts a bottom view of a rectangular, flexible, and compressible implant with a '+' shaped superstructure according to an embodiment.
FIG. 20c depicts a bottom view of a rectangular, flexible, and compressible implant also with a rectangular shaped superstructure according to an embodiment.

FIG. 19*a* depicts a bottom plan view of a circular, flexible, and compressible implant 1901 with the addition of superstructure 1919 on one or more sides. In some embodiments, superstructure 1919 is circular in overall shape and/or cross section and may be present only on one side of implant 1901, which may be directed inward in a patient when implanted. It is also contemplated, however, that in alternative embodiments, one or more such superstructures may be present on both sides of an implant.

Implant 1901 may be compressible by being rollable and/or foldable. Implant 1901 is shown in FIG. 19*a* in its unrolled or otherwise uncompressed/native state. Implant superstructure 1919 may likewise be compressible. Implant superstructure 1919 may comprise, in some embodiments, a flexible solid or semisolid material, such as a hydrogel, plastic, metal, organic polymer, biopolymer or the like. Other embodiments may comprise a polymeric external lamination or containment to retain more dissolvable materials such as hydrogels and the like. Thus, in some embodiments, superstructure 1919 may be configured to automatically rigidify upon encountering body fluids. This may allow implant 1901 to be implanted with the entire structure, including superstructure 1919, in a compressed configuration and then, upon unrolling, unfolding, or otherwise decompressing implant 1901, having superstructure 1919 provide rigidity to maintain implant 1901 in its decompressed configuration.

Drugs, vitamins, or other chemicals, including biologics, may also be bound, dissolved, or otherwise present in a portion or all of the structure of implant 1901 and/or superstructure 1919. Different regions and/or portions of the superstructure 1919 may also have different medications or chemicals printed or otherwise incorporated into them, some perhaps in the shape of a pie-chart if multiple materials are envisioned, for eventual delivery into a patient. In addition, electronics, micro-pumps, and/or printed circuit boards may be positioned on or within implant superstructure 1919 when properly protected.

FIG. 19*b* is a side view of the implant 1901 depicting implant superstructure 1919 extending above the lower/distal surface of the implant 1901.

FIG. 19*c* is a bottom perspective view of the implant 1901. Implant 1901 together with implant superstructure 1919 may be deployed in a compressed state, such as a rolled state, and then unrolled or otherwise decompressed once inserted through the entrance incision and positioned within the implant pocket, as will be discussed. Implant superstructure 1919 may be decompressed and/or shrunken on implantation if it is surrounded by a semipermeable plastic membrane annealed to implant 1901 and filled with a relatively water lacking hydrogel/xerogel or the like, for example. After implantation, fluid osmotically moving into the superstructure 1919 may provide turgor and rigidity. In some embodiments, micro-pumps, which may either be part of the implant 1901 or temporarily coupled therewith, may aid in filling the implant superstructure 1919. In addition, in some embodiments, such pump(s) may be used to drive fluids out of superstructure 1919 and/or other portions of implant 1901.

In some embodiments, semipermeable membranes may be used to allow for diffusion of water into a medical implant. In certain instances, such devices may have high water permeability, and may restrict the diffusion of other compounds. Such semipermeable membranes may comprise, for example, a separating functional layer comprising, for example, polyamide, which is formed from an aromatic polyfunctional amine and a polyfunctional acid halide. In some embodiments, the semipermeable membrane may comprise a base material layer and a porous support membrane layer in addition to the separating functional layer. Additional details regarding such semipermeable membranes may be found in U.S. Pat. No. 9,486,745, titled "Semipermeable Membrane and Manufacturing Method Therefor", which his hereby incorporated in its entirety by reference.

In some embodiments, polymeric membranes may also be used as permselective membranes. In some instances, a suitable derivative of a tri/tetracarboxylic acid may be reacted with a diamine to form a polyamic acid, which may be used to form a film, which may be imidized to form a polyamide-imide film, which may be treated to open the imide rings. Such a process may be used to form a permselective membrane. Additional details regarding such permselective membranes may be found in U.S. Pat. No. 3,835,207, titled "Method for Forming Reverse Osmosis Membranes Composed of Polyamic Acid Salts", which is hereby incorporated in its entirety by reference.

As also shown in FIG. 19c, implant 1901 may comprise one or more tabs 1902, one or more of which may comprise a macro positioning/instrument engaging hole 1903 for coupling with a suitable instrument, as previously described.

FIG. 19d is a side view of the rolled implant 1901 depicting tab 1902 and a portion of implant superstructure 1919.

FIG. 20a depicts a bottom view of a circular, flexible, and compressible implant 2001 with a '+' shaped superstructure 2020 on one side along with a pair of opposing macro positioning/instrument engaging hole s 2003. These elements may be similar to those described previously in connection with other embodiments.

FIG. 20b depicts a bottom view of a rectangular, flexible, and compressible implant 2011 also with a '+' shaped superstructure 2022, on one side and holes in each corner.

FIG. 20c depicts a bottom view of a rectangular, flexible, and compressible implant 2021 also with a rectangular shaped superstructure 2033 on one side and instrument holes in each corner. In addition to the circular and rectangular-shaped superstructures, it is contemplated that other embodiments may comprise other polygonal shapes, as desired.

Figure 21:
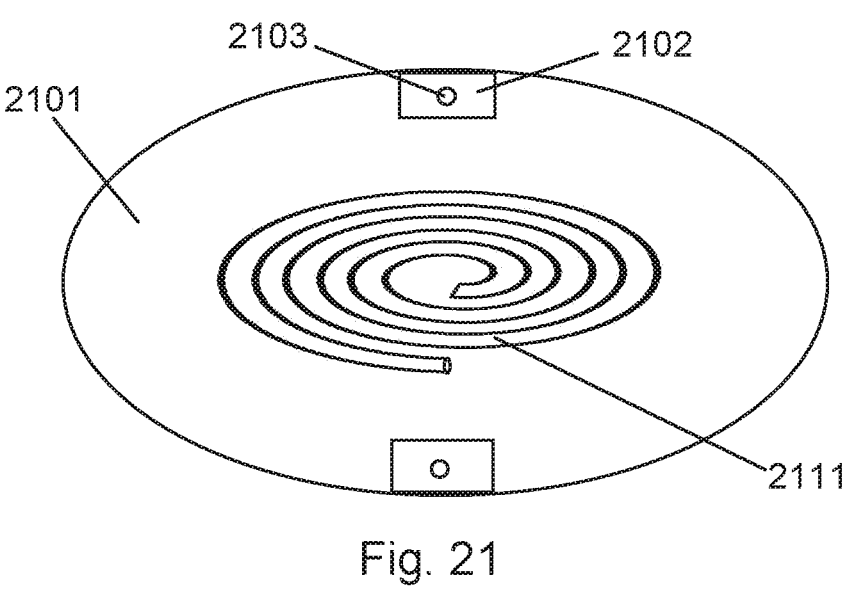
FIG. 21 depicts a top view of an alternative, oval, flexible, compressible implant, which may comprise an oval inductance coil according to an embodiment.

FIG. 21 depicts a top view of an alternative compressible implant 2101 according to other embodiments. Implant 2101 again comprises an oval, flexible, and compressible implant that may be rollable for subcutaneous placement. In some embodiments, the implant 2101 may be foldable. Implant 2101 may be made up of similar materials as any of the other implants disclosed herein, and as previously mentioned. Implant 2101 lacks protruding tabs that may catch on tissue near the entrance wound or occupy valuable diametric dimensions reducing the ease of which the implant may pass a minimally invasive entrance incision. However, as previously mentioned, macro positioning/instrument engaging hole s 2103 with surrounding optional reinforced zones 2102 may be provided, which may be configured to receive and/or engage an instrument, or a portion of an instrument, to facilitate placement of the implant 2101 into a minimally invasive and/or relatively (relative to the implant) small entrance incision.

Implant 2101 may also serve as a substrate for an inductance coil 2111, which may serve as an antenna or wireless energy charger for other elements in or about the implant. This may be useful for a variety of purposes to take in energy for various purposes. For example, coil 2111 may be used to generate wireless power for LEDs, batteries, and the like, or to generate an electric field to drive a drug delivery element or system, such as to open a gate for delivery of such a drug. Coil 2111 may also be used as an antenna to facilitate wireless communication with an electrical component of an implant. For example, signals may be received and/or sent from sensors and/or a CPU to provide instructions to and/or receive data from an internal sensor or another element of an implant.

Figure 22:
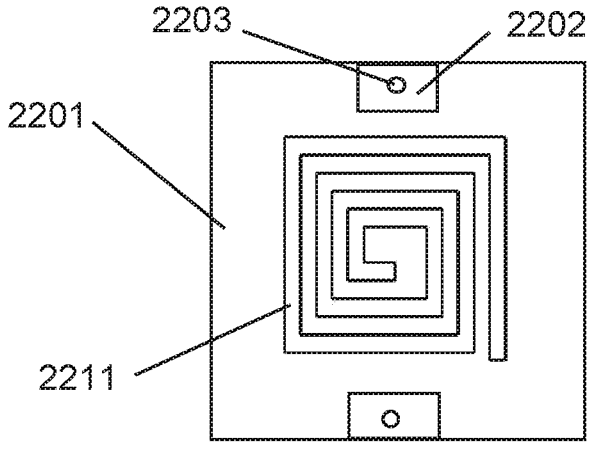
FIG. 22 depicts a top view of an alternative, rectangular, flexible, compressible implant, which may comprise a rectangular inductance coil according to an embodiment.

FIG. 22 depicts a top view of an alternative compressible implant 2201 that may be similar to the implant shown in FIG. 21, aside from the shape of the implant 2201 and that of its corresponding inductance coil 2211, both of which are rectangular-shaped. Macro positioning/instrument engaging holes 2203 with surrounding optional reinforced zones 2202 may be configured to receive and/or engage an instrument, or a portion of an instrument, to facilitate placement of the implant 2201 into a minimally invasive and/or relatively (relative to the implant) small entrance incision. Implant 2201 may also serve as a substrate for the aforementioned inductance coil 2211, although a variety of shapes of coil other than the depicted shape may be used.

In some embodiments, RF energy transmission systems may be used to transmit energy and/or data. Such devices may comprise, for example, circular radiating patches and circular ground planes printed on a circular substrate. In some embodiments, two slots, such as circular slots, may be cut away from the patch to allow for two different operating frequencies. In order to improve biocompatibility, the receiving antenna may be covered by a substrate. In a preferred embodiment, power in the receiving circuit may flow through a voltage doubler in order to be converted into DC. In some embodiments, diodes, such as Skyworks 7630 or HSMS 2850, may be used for power rectifying. In some embodiments, the rectifying circuit may fit in a surface of the same, or at least substantially the same, size as the antenna. Also, in certain instances, another circuit layer may be added to the back side of the antenna. In some embodiments, the antenna's ground plane and the circuit's ground plane may be electrically connected. Additional details regarding such transmission systems may be found in "Miniaturized Implantable Power Transmission System for Biomedical Wireless Applications", Ding, Wireless Power Transfer, Oxford University Press, 2020, pp. 1-9, which is hereby incorporated herein in its entirety by reference.

In some embodiments, an array of micro-coils may be used in an inductive link receiver. In some such embodiments, such receiving arrays may be less sensitive to lateral and/or angular misalignment effects. In certain embodiments, both sides of an inductance link may be tuned to a same resonant frequency to increase power transfer efficiency. Additional details regarding such micro-coils may be found in "Multicoils-based Inductive Links Dedicated to Power up Implantable Medical Devices: Modeling, Design, and Experimental Results", Sawan, Springer Science, Biomed Microdevices, 2009, 11:1059-1070, which is hereby incorporated herein in its entirety by reference.

In some embodiments, a plurality of implanted coils may be used to receive energy transcutaneously, simultaneously, or at least substantially simultaneously, from a plurality of external coils. In certain embodiments, such coil systems may comprise feedback systems comprising RF receivers. In some instances, the amount of power required to power an implanted circuit may be divided into a number of portions such that each coil may provide a certain fraction of the required power. In some embodiments, a second circuit may also be provided, which may comprise a control system and/or voltage control circuit for maintaining a sufficient amount of power to the second circuit. In some embodiments, first and second coils may form a plurality of coil pairs. In some instances, each receiving coil may be implanted beneath different segments of tissue at different locations around the body as desired. Additional details regarding power transmission systems that may be useful in connection with various embodiments disclosed herein may be found in U.S. Pat. No. 6,058,330, titled "Transcutaneous Energy Transfer Device", which is hereby incorporated herein in its entirety by reference.

Some embodiments and implementations may incorporate various elements as part of a system for transcutaneous power transfer and/or communication via induction. The implant in such embodiments may include one or more transmitting coils, one or more of which may be located outside of the body, such as in a charging/external device, and a receiving component, which may be located subcutaneously, preferably on the implant. In some embodiments, the transmitting and/or receiving components of the system may comprise elements and/or features configured to allow for variations in effective coil area of the inductance coils. Examples of such elements/features can be found in U.S. Pat. No. 10,080,893 titled "Varying the Effective Coil Area for an Inductive Transcutaneous Power Link", which is hereby incorporated in its entirety by reference.

Some embodiments may comprise a flux receiver and/or a flux concentrator. Flux receivers are typically used in conjunction with a receiving inductance coil. The receiving coil may, as previously mentioned, be used for communication and/or for power transfer. The implanted medical device may employ a receiving coil disposed around a flux concentrator located within the device. The flux concentrator may be used to concentrate the near-field-energy through the receiving coil, which may convert the near-field-energy into electrical energy. Examples of suitable flux receivers and concentrators that may be useful in connection with various embodiments disclosed herein can be found in U.S. Pat. No. 10,918,875 titled "Implantable Medical Device with a Flux Concentrator and a Receiving Coil Disposed about the Flux Concentrator", which is hereby incorporated in its entirety by reference.

Some embodiments may comprise other features, such as varied geometries for one or more of the inductance coils. Some such embodiments may include coils wherein the coil is larger at a first location than at a second. Other embodiments may comprise a coil wherein the first and second locations are on the same turn of the coil. Still other embodiments may comprise a coil wherein the first location is on the first turn and the second location is on the final turn. Such inductance coil pairs may be used for transcutaneous power delivery or communication with implanted medical devices. Additional details and examples of such features can be found in U.S. Patent Application Publication No. 2020/0395168 titled "Inductance Coil with Varied Geometry", which is hereby incorporated in its entirety by reference.

In some instances, voltage and current may be induced in a deenergized wire, which may run parallel to an energized wire. Such induced voltage and current may be caused by electric-field and magnetic-field induction. Additional details regarding induction in parallel wires may be found in "Induced Voltage and Current in Parallel Transmission Lines: Causes and Concerns", Horton, 2008, IEEE Transactions on Power Delivery, 23 (4): 2339-2346, which is hereby incorporated herein in its entirety by reference.

Figure 23:
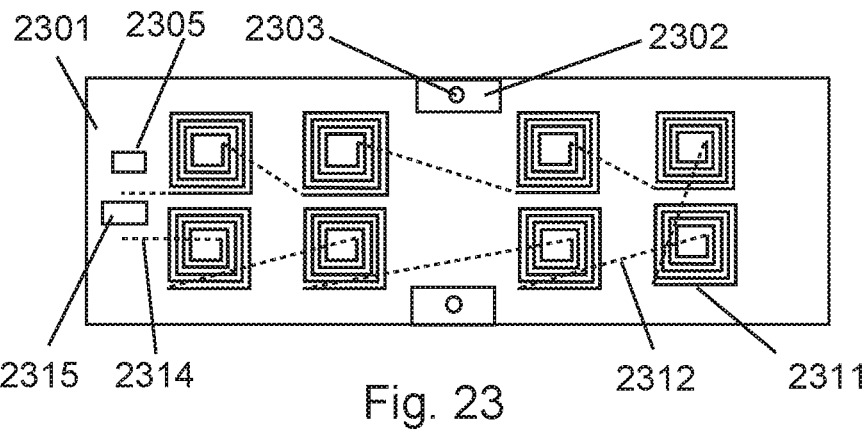
FIG. 23 depicts a top view of an alternative compressible elongated rectangular shaped implant which may serve as a substrate for a plurality of inductance coils according to an embodiment.

FIG. 23 depicts a top view of an alternative compressible elongated rectangular shaped implant 2301. Macro positioning/instrument engaging hole s 2303 with surrounding optional reinforced zones 2302, may be configured to receive and/or engage an instrument, or a portion of an instrument, to facilitate placement of the implant 2301 into a minimally invasive and/or relatively (relative to the implant) small entrance incision. Implant 2301 may also serve as a substrate for a plurality of inductance coils 2311, which may be electrically coupled via conductive wiring 2312. Each of these coils 2311 is shown as being formed into the same rectangular shape, but any number of shapes may be used, which may be consistent throughout the implant 2301 or may differ therewithin. Inductance coils linked in series as shown in the figure may minimize the deleterious effects of transferring energy transcutaneously from an external energy source, possibly improving energy transfer efficiency. Inductance coils 2311 may terminate in wiring 2314 and/or an electrical port, which may be linked to other electrical components 2315, such as a CPU. In some embodiments, inductance coils, such as but not limited to inductance coils 2311, may be used to power various elements on the implant, such as LEDs, pumps, electrical field generators, antennae, sensors, etc.

Some embodiments may comprise a voltage sensor 2305, which may be helpful during charging once the implant 2301 is within a patient and therefore the various inductance coils 2311 in the implant may not be visible to the practitioner. By providing a voltage sensor 2305, a user may be able to move a transmitting coil of an inductive charger (either one large coil or an array of smaller coils similar to the receiving coils on the implant 2301) about the region of the patient under which the implant 2301 lies and view the voltage changes and thereby maximize the charging voltage. In embodiments having separate internal and external arrays of matching sizes, it may be beneficial to correctly align the transmitting and receiving coils. However, if the transmitting array is much larger than the receiving array, then precisely aligning the arrays may not be necessary as the inner portion of the transmitting array may exhibit homogenous magnetic field-like characteristics, therefore resulting in similar change in magnetic field across the receiving array. In either case, having a voltage sensor, which may be linked with a notifier, such as an audible alarm or a dial/scale that is externally viewable, the user may be able to maximize the efficiency of recharging a battery, which may be part of the implant 2301.

In some embodiments, a plurality of transmitting coils may be overlapped or stacked in order to overcome inefficiencies due to misalignment of the transmitting and receiving wireless charging inductance coils. Such designs may generate a homogenous magnetic field across the entire transmitting array, allowing more freedom of placement for the receiving coil(s) while retaining high efficiency. Further details regarding these features may be found in 'Geometrical Design of a Scalable Overlapping Planar Spiral Coil Array to Generate a Homogenous Magnetic Field', Jow, IEEE Trans Magn, 2012; 49:2933-2945, which is hereby incorporated in its entirety by reference.

Secondary inductance coils, which may comprise inductance coils that are, in some cases, stacked and/or layered on top of one another on the implant rather than positioned in an array as shown in FIG. 23, may also be used in some embodiments. Such secondary inductance coils may, in addition to the primary coil(s), in some embodiments be enclosed within a housing of the implanted device in order to enhance power transfer to greater depths. Such enhanced power transfer may be achieved, for example, by multiple coils that are longitudinally aligned and/or physically and electrically parallel, thereby forming a secondary loop for a power delivery system rather than having only a single loop. Such systems with two or more receiving inductance coils can double the amount of turns collecting magnetic flux. Additional details regarding such secondary inductance coils may be found in U.S. Pat. No. 7,191,007 titled "Spatially Decoupled Twin Secondary Coils for Optimizing Transcutaneous Energy Transfer (TET) Power Transfer Characteristics", which is hereby incorporated in its entirety by reference.

Figure 24A:
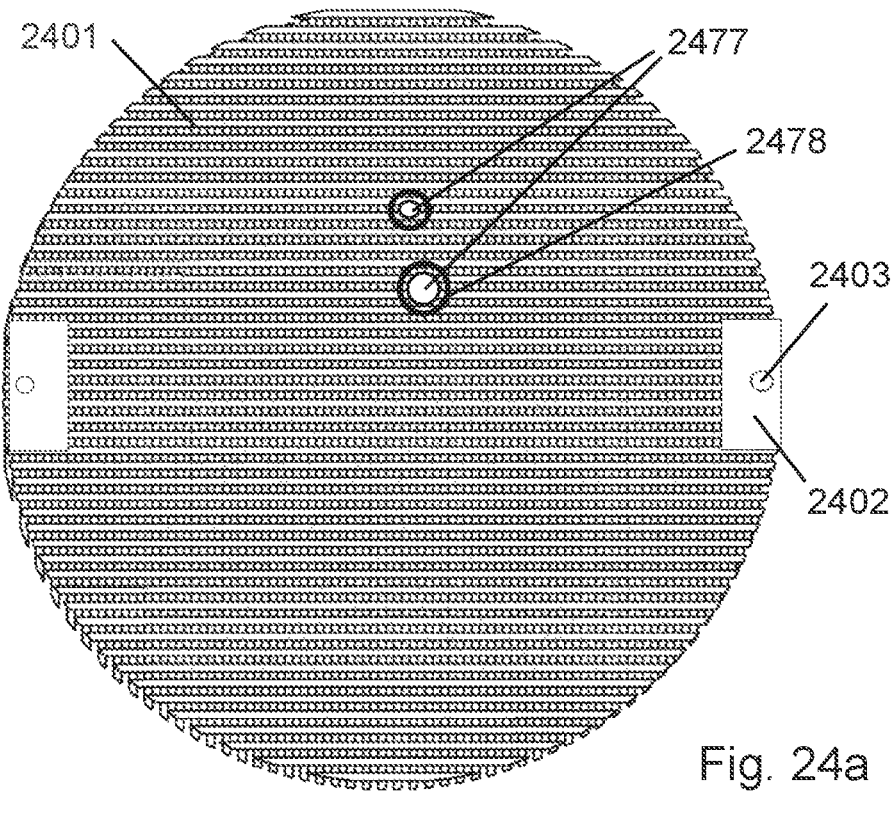
FIG. 24a depicts a top view of a circular, flexible, compressible mesh implant.

FIG. 24a depicts a top view of an alternative compressible implant 2401 according to other embodiments. Implant 2401 again comprises a circular, flexible, mesh and compressible implant that may be foldable for subcutaneous placement. In some embodiments, the implant may be rollable and therefore may be rolled into the configuration shown in FIG. 24d. FIG. 24a depicts implant 2401 in its unrolled or otherwise uncompressed/native state. Unlike the previous similar implants mentioned above, implant 2401 may be made up of a mesh lattice, which may comprise, for example, a bioresorbable or non-bioresorbable polymer. This may be more useful for delivery of drugs not requiring moisture, and may also substantially increase the available surface area of the implant. Such mesh implants may also be manufactured using an additive manufacturing process. The use of mesh implants that are sizeable may be beneficial to the overlying tissues, for example the skin of the abdomen in a 10-20 cm diameter mesh implant, because, if the mesh is sufficiently wide to allow vascular ingrowth and communication with the more superficial tissues through the implant, the superficial tissues of the abdomen may experience better growth conditions and blood supply rather than only being granted blood supply from the relatively distant periphery of the implant. If the mesh size is under 1 mm, it may be difficult for blood vessel ingrowth to traverse from one side of the mesh to the other. Therefore, one or more macro vascularization hole(s) 2477 exceeding 1 mm (preferably at least several mm) in diameter may be made even in a mesh to allow vascular ingrowth and/or vascular crossing of the implant to benefit tissues on the opposite side of the implant. The area around hole(s) 2477 may comprise a ring or other shape of reinforcement 2478 in order to maintain the integrity of the implant. Areas of reinforcement for implanted Kevlar mesh around a hole may be beneficial to prevent ballistic penetration if hole placement were to weaken a particular area. In contemplated embodiments, peripheral placement of holes may not benefit the tissues as much as centrally placed holes, as the tissues overlying the center are farther from the periphery, thus implants may comprise central holes. In other contemplated embodiments, such holes for vascularization and biological cross communication may be present throughout the implant in desired areas. In contemplated embodiments of spiral coil implants, the spacing between spiral arms may be altered in order to allow vascular ingrowth into and across those areas.

Implantable mesh 2401 may contain drugs such as gentamicin or methotrexate, suspended in hydrogels such as PLA (polylactic acid). Also, the drugs niclosamide or IP6 (inositol phosphate) may be mixed in PCL (polycaprolactone) and/or graphene nanoplatelets in some embodiments. Biologic scaffolds may also be used, which may include drugs such as rhBMP-2 (recombinant bone morphogenetic protein-2) incorporated into PCL, PLGA (poly lactic co-glycolic acid), or Beta-TCP (tricalcium phosphate). Another example of a suitable biologic scaffold is dexamethasone, which may be embedded in Sr-MBG (strontium mesoporous bioactive glass). Bioceramics for bone generation and infections may also be used in some embodiments, and which may include VNC (vancomycin), rhBMP-2, and/or heparin, and may be embedded in materials such as brushite, unreacted alpha or beta-TCP, chitosan, and/or HPMC. VNC and ceftazidime may also be mixed into PLA cages and PLGA nanofibers. Other drugs and materials for implantable patches, stents, meshes, scaffolds, and/or bioceramics may be found in '3D Printed Drug Delivery and Testing Systems—a Passing Fad or the Future?', Lim, Advanced Drug Delivery Reviews 132 (2018) p. 139-168, 2018, which is hereby incorporated in its entirety by reference.

Drugs released by drug eluting stents may also be used in some embodiments. Such drugs may include, for example, immunosuppressants such as Sirolimus and Tacrolimus. Such drugs may aid in counteracting neointimal hyperplasia. Sirolimus-eluting-stents may aid in reducing incidents of restenosis. Additional details regarding such drugs, which again may be taken from the context of stents to the implants disclosed herein, may be found in 'Molecular Basis of Different Outcomes for Drug-Eluting Stents that Release Sirolimus or Tacrolimus', Curr. Opin. Drug Discov. Devel., Giordano, 2010; 13:159-68, which is hereby incorporated in its entirety by reference.

The technology behind drug eluting stents may, in some embodiments, be repurposed for use in connection with one or more of the implants disclosed herein. For example, in some embodiments, a mesh may be formed having materials and/or structures similar to a stent. Such meshes may therefore comprise, for example, various alloys/metals, such as cobalt chromium or platinum chromium, which may allow thinner struts while retaining high radial strength, radiopacity, biocompatibility, and/or corrosion resistance. Lipophilic drugs, such as paclitaxel may be linked to the mesh without the use of a polymer in some embodiments. Further drugs that may be eluted from the mesh may include, for example, everolimus, zotarolimus, umirolimus, novolimus, amphilimus, and/or sirolimus. Polymers used to bind drugs to stent-like meshes in an implant may include, for example, vinylidene-fluoridehexafluoropropylene copolymers and/or C10-C19-polyvinylpyrrolidone polymers. Biodegradable polymer coatings may also be used, and which may comprise lactic and/or glycolic acids. Such copolymers may include, for example, polylactic (PLLA, PDLLA), polyglycolic (PGA), and/or polylactic-co-glycolic (PLGA) copolymers. The aforementioned mesh materials may, in some embodiments, be made to have smooth, macroporous, microporous, and/or nanoporous surfaces. Such mesh materials may also be filled with drugs, resulting in release through laser-drilled holes. Such materials may also be coated with biological agents such as CD34 to enhance vessel healing in certain applications. Composites such as titanium nitride oxide may also, or alternatively, be used to accelerate endothelialization. Further information regarding the aforementioned stent-like mesh materials may be found in 'The Newest Generation of Drug-Eluting Stents and Beyond', Lee, European Cardiology Review, 2018; 13:54-9, which is hereby incorporated in its entirety by reference.

Implantable devices, such as stents, may, in some embodiments, comprise cells that produce and release therapeutic agents. Such cells may be naked cells, encapsulated cells, or some mixture thereof. Such stents may comprise, for example, subcutaneous ports, catheters, and reservoirs. In some instances, the implant may be engineered using stent technology, such as providing a framework for a stent in a mesh or other form more suitable for the implants disclosed herein. Some such embodiments may therefore be configured such that therapeutic agents are released in response to changing physiological conditions. In some embodiments, the reservoir may contain, for example, cells or other therapeutic agents, and may comprise, for example, a porous polymer, such as alginate. Further embodiments may comprise reservoirs that may function as immune-barriers, shielding therapeutic cells from the body's immune system while allowing exchange of nutrients. Additional details regarding stent materials and related therapeutic systems that may be useful in connection with the implants disclosed herein may be found in U.S. Pat. No. 9,788,978, titled "Implantable Systems and Stents Containing Cells for Therapeutic Uses", which is hereby incorporated in its entirety by reference.

In some embodiments, stent-like meshes may be configured to release therapeutic cargo. In certain embodiments, such implants may therefore comprise at least one first hydrophilic polymeric material incorporating particles comprising an outer layer of a second hydrophilic material, an inner layer comprising a first hydrophobic material, and a core comprising a hydrophobic therapeutic agent. In some such embodiments, the first and second hydrophilic materials may be the same. In some instances, the hydrophilic material may comprise polymers such as, for example, polyvinyl alcohol (PVA), and/or poly(L-lactide). In some other embodiments, the device may comprise at least one first polymeric hydrophobic material incorporating particles comprising an outer layer of a second hydrophobic material, an inner layer comprising a first hydrophilic material, and a core comprising a hydrophilic therapeutic agent. In some embodiments, the first and second hydrophobic materials may be the same. In some instances, the hydrophobic polymeric material may comprise, for example, copolymers of styrene and isobutylene, polyanhydrides, and/or the like. Additional details regarding drug eluting stents, which, again, may be used to create various drug-eluting implants suitable for placement in the implant pockets disclosed herein, may be found in U.S. Pat. No. 8,119,153, titled "Stents with Drug Eluting Coatings", which is hereby incorporated in its entirety by reference.

In some embodiments, implanted mesh devices may comprise multiple layers, some of which may be sensitive to stimuli such as, for example, pH. In an embodiment, such a device may comprise: a primary coextensive structural layer that may be non-degradable; at least one interior coextensive pH sensitive layer; at least one exterior coextensive pH sensitive layer. In some instances, pH triggers may cause changes, such as, for example, water solubility and/or degradation, in properties of the pH sensitive layers. Additional details regarding such mesh devices may be found in U.S. Patent Application Publication No. 2019/0343991, titled "Multi-Layered Device", which is hereby incorporated in its entirety by reference.

In some embodiments, implanted meshes may comprise tubular members having a plurality of openings. In some instances, such devices may also comprise at least on elongated polymer strand used for delivery of therapeutic agents. Additional details regarding such mesh devices may be found in U.S. Patent Application Publication No. 2004/0236415, titled "Medical Devices Having Drug Releasing Polymer Reservoirs", which is hereby incorporated in its entirety by reference.

In some embodiments, implanted mesh devices may comprise demineralized bone fibers mechanically entangled into a biodegradable or permanent mesh. The mesh may further comprise materials such as, for example, PLGA, degradable/non-degradable polymers, PTFE, and the like. Additional details regarding these additional mesh devices may be found in U.S. Pat. No. 10,813,763, titled "Implantable Mesh", which is hereby incorporated in its entirety by reference.

In some embodiments, implantable meshes may be coated with biodegradable agents. In some embodiments, such agents may facilitate implanting of the mesh. In some instances, biodegradable polymer coatings may comprise, for example, temporary stiffening agents, biologically active agents, and/or drugs. Additional details regarding such mesh implants may be found in U.S. Pat. No. 10,765,500, titled "Temporarily Stiffened Mesh Prostheses", which is hereby incorporated in its entirety by reference.

In some embodiments, implanted meshes may comprise coatings that may contain bioactive materials which may be eluted. In certain instances, sol-gel technology may be used to apply said coatings. Such bioactive coatings may comprise, for example, anti-inflammatory agents, anti-depressive agents, growth factor, and the like. In some instances, various bioactive agents may be combined, and/or the bioactive portions may comprise two or more layers, each with adjustable bioactive materials. Additional details regarding such coatings and mesh implants may be found in U.S. Pat. No. 10,285,968, titled "Drug Eluting Expandable Devices", which is hereby incorporated in its entirety by reference.

In some embodiments, implanted mesh devices may comprise bioabsorbable polymers. Such bioabsorbable polymers may comprise, for example, polyhydroxyalkanoate, poly-L-lactic acid, polyanhydride, and the like. Additional details regarding such polymers may be found in U.S. Pat. No. 9,980,800, titled "Bioabsorbable Mesh for Surgical Implants", which is hereby incorporated in its entirety by reference.

In some embodiments, implanted devices may be coated with rotational spun materials that may be used to deliver therapeutic agents. In some instances, drugs such as, for example, rapamycin, paclitaxel, heparin, and the like may be delivered in this manner. In certain embodiments, the rotational spun coating may comprise, for example, PTFE, Kevlar, polyethylene, chitosan, chitin, and the like. In certain instances, the released therapeutic agent may be associated with the rotational spun coating by methods of bonding such as, for example, covalent and/or ionic bonding. Additional details regarding such materials and coating methods may be found in U.S. Pat. No. 9,198,999, titled "Drug-Eluting Rotational Spun Coating and Methods of Use", which is hereby incorporated in its entirety by reference.

In some embodiments, implanted meshes may be used in conjunction with stimulation devices. Such stimulation devices may comprise, for example, electrical neurostimulators. In some embodiments, such meshes may comprise incorporated electrically conductive elements. Such electrically conductive elements may be used to electrically conduct the modulated waveform emanating from the neurostimulator. Additional details regarding such neurostimulation devices may be found in U.S. Pat. No. 8,751,003, titled "Conductive Mesh for Neurostimulation", which is hereby incorporated in its entirety by reference.

In some embodiments, polymeric porous films may be used to elute bioactive agents. In some instances, factors such as, for example, the polymer's composition, concentration, initial molecular weight, surfactant, homogenization rate, and the like may be used to alter the release profile of therapeutic cargo. In certain embodiments, the porous film may comprise polymers such as, for example, PDLGA. Additional information regarding porous films may be found in U.S. Pat. No. 8,697,117, titled "Drug-Eluting Films", which is hereby incorporated in its entirety by reference.

In some embodiments, meshes may be coated in biodegradable polymers and formed into pouches for implantable devices, such as, for example, cardiac rhythm management devices. Such mesh pouches may be used to inhibit bacterial growth, provide pain relief, inhibit scarring/fibrosis, permit tissue ingrowth, and the like. In some instances, the biodegradable polymer coating may comprise polymers such as, for example, polylactic acid, polyglycolic acid, polyethylene oxide, and the like. Additional details regarding such mesh pouches may be found in U.S. Pat. No. 8,591,531, titled "Mesh Pouches for Implantable Medical Devices", which is hereby incorporated in its entirety by reference.

In some embodiments, flexible mesh implants may be adapted for repairing a tissue or a muscle wall defect. In such mesh implants, mesh 'arms' extending outwards from a primary region may be folded/bent over and fixed (via, for example, glue or welding) to the primary region. In certain embodiments, the preformed mesh may have a flat, two-dimensional shape, which may be manipulated into a configuration comprising a three-dimensional shape via folding/bending. Additional details regarding such mesh implant may be found in U.S. Pat. No. 10,357,350, titled "Surgical Implant", which is hereby incorporated in its entirety by reference.

In some embodiments, implanted mesh devices may be used to repair the pelvic floor. Such meshes may comprise implanted supportive slings adapted to anchor into patient tissue. In some instances, applications may include, for example, hernia, vaginal prolapse, and the like. Additional details regarding such mesh implants may be found in U.S. Pat. No. 10,251,738, titled "Pelvic Floor Repair System", which is hereby incorporated in its entirety by reference.

In some embodiments, implanted devices may comprise three-dimensional reticulated mesh structures. In some instances, the layer-built components of said structures may comprise, for example, Ti-6Al-4V or Co-26Cr-6Mo-0.2C powders. In certain embodiments, the three-dimensional structure may comprise, for example, a porous coating, a sintered mesh array, and the like. In some instances, the structure may be configured to release therapeutic agents, such as, for example, cellular growth factors. Additional details regarding such structures may be found in U.S. Pat. No. 8,828,311, titled "Reticulated Mesh Arrays and Dissimilar Array Monoliths by Additive Layered Manufacturing Using Electron and Laser Beam Melting", which is hereby incorporated in its entirety by reference.

In some embodiments, implants may comprise fenestrated hollow shells with biologic cores. In some instances, designs may improve interface with surrounding tissue, aiding in processes such as, for example, fixation to the surrounding tissue. In certain embodiments, such devices may be used for functions such as, for example, gene therapy, tissue engineering, and growth factors. Additional details regarding such shells and related processes may be found in U.S. Patent Application Publication No. 2020/0015973, titled "Tissue Integration Design for Seamless Implant Fixation", which is hereby incorporated in its entirety by reference.

Figure 24B:
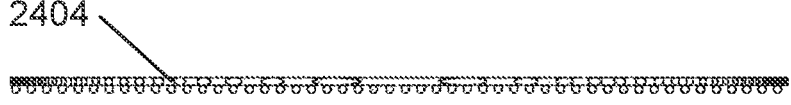
FIG. 24b depicts a side view of a circular, flexible, compressible mesh implant.
Figure 24C:
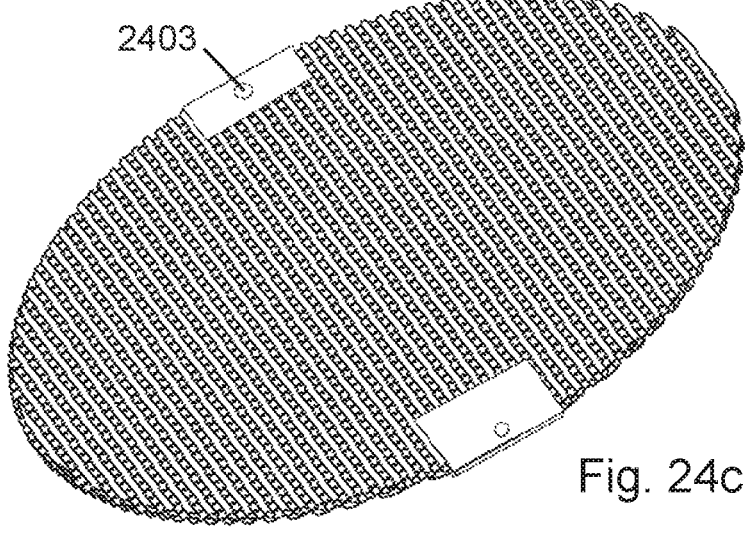
FIG. 24c depicts a top perspective view of a circular, flexible, compressible mesh implant.
Figure 24D:
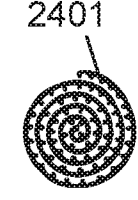
FIG. 24d depicts a side view of a rolled/compressed implant.

Implant 2401 lacks protruding tabs that may catch on tissue near the entrance wound or occupy valuable diametric dimensions reducing the ease of which the implant may pass a minimally invasive entrance incision. However, implant 2401 may comprise internal and/or non-protruding tabs 2402, which may otherwise be referred to herein as hole-defining and/or structural reinforcement regions. One or more of internal tabs 2402 may define one or more macro positioning/instrument engaging holes 2403. FIG. 24b depicts a side view of unrolled or uncompressed implant 2401 with edge 2404. FIG. 24c is a top perspective view of implant 2401 also depicting hole 2403. Mesh implants may be 3D printed and subject to lamination such as previously discussed for other implants. FIG. 24d depicts a side view of a rolled or compressed implant 2401.

It is possible that implants may draw unwanted scarring or immune-responses from the recipient. In contemplated embodiments, meshes, implant envelopes, and the like may be impregnated with fibrosis and/or other immune inhibiting drugs may be used to treat scarification/keloids including steroids. For example, triamcinolone acetonide (TAC), 5-fluorouracil (5-FU), bleomycin (BLM), and verapamil (VER) may be used in some such embodiments and implementations. Some such drugs may have anti-inflammatory and antimitotic mechanisms thus inhibiting growth of fibroblasts and reducing endothelial budding and synthesis of procollagen and glycosaminoglycan. Such medications may be bound, sometimes releasably, to enveloping elements or to attached biodegradable elements such as polylactic acid, poliglecaprone and the like for slow release.

FIG. 25 depicts a top view of an alternative compressible implant 2501 according to other embodiments. Implant 2501 again comprises a circular, flexible, mesh and compressible implant that may be foldable for subcutaneous placement. Implant 2501 may be made up of similar materials as any of the other implants disclosed herein, as previously mentioned. However in light of 3D printing of various medicines and other deposition methods, implant 2501 may be partitioned via sectors 2525 into various zones containing various concentrations of various medicines and chemicals as may be needed. Macro positioning/instrument engaging holes 2503 optionally surrounded by reinforcement zones 2502 may be beneficial for placement.

Holes 2503 may be also optionally surrounded by a detectable marker 2515, which may be beneficial for determining placement or affixing the implant until the body's natural tissue response restrains the implant. The marker may comprise a denser material buried within (dashed lines shown here) the areas around the hole(s) 2503. In some embodiments, marker 2515 may comprise a metal to allow for detection by way of, for example, an x-ray. Other dense materials useful as a marker may be biodegradable or bioabsorbable, such as calcium bound in a polymer and the like. Other dense materials for use in markers 2515 may comprise nonbioabsorbables, such as certain polymers and the like. Other contemplated embodiments may merely rely on a difference in density, including an interface between densities, to allow detection. Knowing the location of a hole without direct visualization, a surgeon may then affix the implant into proper position via a transcutaneous suture that may later be removed once fixation is deemed satisfactory. Having holes and/or markers located at certain known zones on an implant may facilitate proper subsurface orientation and/or unfolding. In some embodiments, the marker(s) 2515 may comprise a peripheral target for use in detecting the implant and/or marker and/or for use in identifying a suitable location for a point of attachment, such as a suture. In some embodiments, sectors 2525 may be defined simply by virtue of the application of distinct drugs or other substances on them. Alternatively, however, it is contemplated that some embodiments may comprise sectors defined by physical barriers, which may, for example, prevent drugs from mixing with one another.

FIG. 26 depicts a top view of an alternative compressible implant 2601 according to other embodiments. Implant 2601 comprises a rectangular, flexible, mesh and compressible implant that may be foldable/rollable for subcutaneous placement. Implant 2601 may comprise macro positioning/instrument engaging holes 2603 optionally surrounded by reinforcement zones 2602 may be beneficial for placement, each of which is placed in a respective corner region of the implant 2601.

FIG. 27 depicts a top view of an alternative compressible implant 2701 according to other embodiments. Implant 2701 comprises a polygonal, flexible, mesh and compressible implant that may be foldable/rollable for subcutaneous placement. Implant 2701 may comprise macro positioning/instrument engaging holes 2703 optionally surrounded by reinforcement zones 2702 may be beneficial for placement. Reinforcement zones 2702 and their corresponding holes 2703 are shown at just two of the corners of the polygonal implant 2701, but may be present at each of the corners, or elsewhere (such as between the corners) in alternative embodiments.

FIG. 28 depicts a top view of an alternative compressible implant 2801 according to other embodiments. Implant 2801 comprises a rectangular, elongated, flexible, mesh and compressible implant that may be foldable for subcutaneous placement. Implant 2801 may comprise macro positioning/instrument engaging holes 2803 optionally surrounded by reinforcement zones 2802 may be beneficial for placement. A single reinforcement zone 2802 and corresponding hole 2803 is shown at each opposing end of the elongated dimension of the implant 2801.

Figure 29:
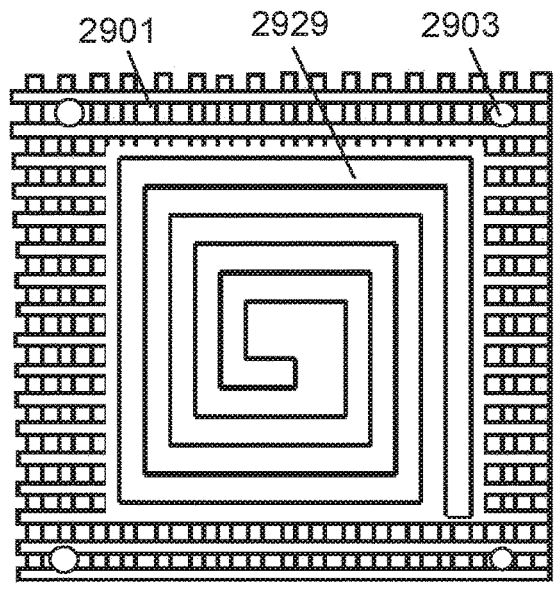
FIG. 29 depicts a top view of a mesh implant that may comprise openings and an inductance coil according to an embodiment.

FIG. 29 depicts a top view of another implant 2901 that is similar to implant 2201 except it is made from a mesh material and comprises openings (as in macro positioning/instrument engaging holes) 2903 formed within the mesh without providing reinforcement regions. It is contemplated that these regions may not be needed for some embodiments, depending upon the material used for the implant. In addition, a large inductive coil 2929 is positioned within the implant 2901.

In some embodiments, one or more of the implants may comprise a biocompatible coating, such as, for example, PTFE. In some instances, PTFE coatings may be used to facilitate removal of the implant as a pseudo-lubricant. Additional details regarding PTFE coatings may be found in "Biocompatibility and Durability of Teflon-Coated Platinum-Iridium Wires Implanted in the Vitreous Cavity", Nishida, 2011, J. Artif. Organs, PubMed, which is hereby incorporated herein in its entirety by reference.

In some instances, Fibrin may be used as a sealant/adhesive in some implants. Additional details regarding Fibrin and its possible uses in various implants may be found in "Randomized Trial of a Dry-Powder, Fibrin Sealant in Vascular Procedures", Gupta, doi.org/10.1016/j.jvs.2015.05.038, PubMed, which is hereby incorporated herein in its entirety by reference.

In some embodiments, glues and/or adhesives may be used such as, for example, hemostats, sealants, and the like, which may be used with various implants for various purposes, including for rigidifying a superstructure, for example. In a preferred embodiment, an adhesive may have strong wet adhesion, high stability, rapid curing/crosslinking, low toxicity, and/or biodegradability. In some instances, fibrin glues may be used, which may contain antifibrinolytic agents, such as epsilon amino caproic acid. In certain embodiments, crosslinks may be formed between the adhesive glycoproteins with collagen and/or other proteins. Fibrin composition may be modulated to control degradation time. In some embodiments, gelatin-resorcinol-formaldehyde/glutaraldehyde (GRFG) may be used as glue. In basic conditions, the resorcin-formaldehyde may form a cross-linked polymer. Clinical use in human patients may be limited by carcinogenic properties of aldehydes, however, veterinary/animal use may be possible due to shorter lifespans, making for less carcinogenic expression. In some embodiments, gelatin-resorcin-based adhesives may be crosslinked with water-soluble carbodiimide or genipin instead of formaldehyde glutaraldehyde. In some instances, proteinoids (such as RGDKANE) may be used to improve cross-linking and/or bonding strength. In certain select embodiments, cyanoacrylate glue may be used for adhesive purposes. In some instances, the alkyl sidechains may be replaced with alkoxy chains to improve the elasticity of the glue. Clinical use in human patients may be limited by toxic properties of cyanoacrylates, however, veterinary/animal use may be possible. In some embodiments, adhesives may comprise, for example, polysaccharide, polypeptides, and/or polymeric adhesives. Groups such as, for example, amine, hydroxyl, and carboxylic acid may adhere to amine groups on tissues via covalent interaction. In a preferred embodiment, an adhesive may comprise a gelatin due to its biodegradability and biocompatibility. In some instances, hydrogels may be used as adhesives by, for example, cross-linking aldehyde functionalized alginate with amine-functionalized gelatin via, for example, Schiff base reactions. Some embodiments of adhesives may comprise, for example, vinylated proteins and/or polysaccharides, which may adhere to tissues upon photo-irradiation. In some instances, adhesives may also, or alternatively, be configured for localized drug delivery. In some embodiments, adhesives may be functionalized with phenolic and/or thiol groups to promote tissue interaction. Certain embodiments of tissue adhesives may employ techniques such as laser welding, layer-by-layer assembly, and/or temperature-dependent hardening. In other embodiments, adhesives may comprise Poly(ethyleneglycol) (PEG)-based hydrogels. To render PEG biodegradable, it may be modified with degradable functionalities or be copolymerized with degradable polymers. PEG may also be combined, in some instances, with polysaccharides and/or protein-based adhesives. Some medical adhesives may also be biomimetic. Such biomimetic tissue adhesives may comprise, for example, mussel-inspired adhesives, gecko-inspired adhesives, sandcastle worm-inspired tissue adhesives, barnacle mimetic adhesives, caddisfly-inspired adhesives; et al. Additional details regarding potentially useful medical adhesives may be found in "Degradable Adhesives for Surgery and Tissue Engineering", Bhagat, BioMacromolecules, American Chemical Society, 3009-3039, 2017, which is hereby incorporated herein in its entirety by reference.

Preferred methods and systems for wireless power transfer into the body will avoid unwanted heating and potential health concerns. Thus, some embodiments and implementations may include the use of multiple flexible coils to avoid performance loss through heating of the skin. They may also, in some embodiments and implementations, include software to optimize power delivery to avoid unwanted tissue heating. Additional details that may be useful in this regard for various embodiments disclosed herein may be found in 'A Breakthrough in Wireless Charging for Implants', Earls, Medical Technology, Issue 6, 2018, which is hereby incorporated in its entirety by reference.

Implantable inductance coil designs may include those attached to flexible PCBs. To avoid any potential health risks due to alternating magnetic fields from the Tx (transmitting coil), ferrite materials may be used on the top and bottom of WPT (wireless power transfer) coils. The aforementioned information and further details may be found in 'Design, Simulation and Measurement of Flexible PCB Coils for Wearable Device Wireless Power Transfer', Jeong, IEEE, 2018, which is hereby incorporated in its entirety by reference.

Designs for various implantable Near-Field Inductive Coupling inductance coils may optimize the tradeoff between coil quality factors and coupling coefficient, to tailor specific coils for various needs and high efficiency. An example of such an optimized design along with methods for optimizing the design for inductance charging coils and devices may be found in 'Design, Test and Optimization of Inductive Coupled Coils for Implantable Biomedical Devices', Zhao, Journal of Low Power Electronics, Vol. 15, 76-86, 2019, which is hereby incorporated in its entirety by reference.

Figure 30:
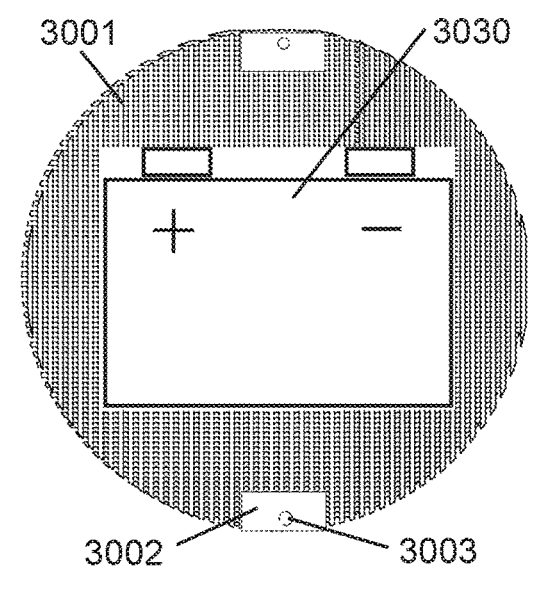
FIG. 30 depicts a top view of a mesh implant which may comprise reinforcement regions, holes, and/or batteries according to an embodiment.

FIG. 30 depicts a top view of still another implant 3001, which again may comprise various reinforcement regions 3002 and/or macro positioning/instrument engaging holes 3003 for facilitating coupling with a suitable instrument as desired. In addition, implant 3001 comprises a battery 3030, which may be useful for providing energy for actuation of a drug delivery mechanism/system. Battery 3030 may also be configured to receive energy from an inductance coil (not shown) or the like, as desired, and as discussed in greater detail above.

In some instances, a thin battery may be positioned inside an inductance coil. The device may be implanted in the body; the battery may be used to power medical devices, and the coil may be used to wirelessly charge the battery. Additional information may be found in U.S. Pat. No. 8,798,752, titled "Removable Implantable Battery Positioned Inside Implant Coil", which is hereby incorporated in its entirety by reference.

In some embodiments, implantable micro-generators may comprise mechanisms for harnessing and converting mechanical energy from natural body movement into electrical energy. In certain embodiments, the general construction of the micro-generator may resemble that of a winding mechanism for a mechanical watch. Such generators may comprise, for example, a rotating mass with an offset center of mass. Natural movement of the body may cause the rotating mass to rotate. The generator may convert this rotational kinetic energy of the spinning mass into electrical energy for use by one or more implants. In some instances, such micro-generators may be used to charge capacitors or implantable batteries. The micro-generator may also be used to power pacemakers, defibrillators, and the like. Additional details regarding generators for harnessing the energy of natural body movements, which may allow for generation of energy for implants without use of inductance coils and/or batteries (although batteries may still be useful to store such energy) may be found in U.S. Patent Application Publication No. 2005/0256549, titled "Micro-Generator Implant", which is hereby incorporated in its entirety by reference.

In some embodiments, power supplies may be implanted subcutaneously. In some instances, the power supply may comprise of one or more thin photovoltaic cells contained in a case formed by lamination of plastic layers. The layers may be thin and translucent in the area covering the cell so that the power supply may be flexible. The power supply may be used to power a variety of different implanted devices. Additional details regarding such power supplies may be found in U.S. Pat. No. 6,961,619, titled "Subcutaneous Implantable Power Supply", which is hereby incorporated in its entirety by reference.

In some embodiments, medical devices may contain rechargeable lithium-ion batteries. In some instances, the battery may comprise a positive electrode including a current collector and first and second active materials. The battery may also comprise negative electrode with a current collector, a third active material, and lithium in electrical contact with the current collector of the negative electrode. In some embodiments, the device may be used to provide therapeutic treatment to patients. Additional details regarding such batteries and related devices and methods may be found in U.S. Pat. No. 7,642,013, titled "Medical Device Having Lithium-Ion Battery", which is hereby incorporated in its entirety by reference.

In some embodiments, implanted batteries may be biodegradable. Upon undergoing electrochemical oxidation, the anode (comprising an inner and outer surface) material may result in a non-toxic product; upon undergoing electrochemical reduction, the cathode (comprising an inner and outer surface) material may result in a non-toxic product. In a preferred embodiment, the cathode should present larger standard reduction potential than the anode. In some instances, the inner surface of the cathode may be separated from the inner surface of the anode by a permeable membrane in direct fluid contact with the body's aqueous environment. In certain embodiments, one or more biodegradable coatings may be disposed over the outer surface of the cathode and a portion of the outer surface of the anode. Additional details regarding such degradable batteries may be found in U.S. Pat. No. 9,362,571, titled "Degradable Implantable Battery", which is hereby incorporated in its entirety by reference.

In some embodiments, micro batteries may be biocompatible, self-recharging, and/or biofueled. In some instances, the micro battery may comprise bio-membranes to diffuse bio-fluids across an anode and a cathode. In certain embodiments, bio-membranes may comprise compartments for chemical storage and bio-fuel storage. Biofluids to power the battery may include, for example, glucose. In certain instances, bio-membranes may be configured to allow diffusion of a bio-fluid across an anode and a cathode to generate electron flow to charge the battery or to provide a constant power supply. Additional details regarding suitable micro batteries may be found in U.S. Pat. No. 10,340,546, titled "Self-Rechargeable Bio-fueling Micro Battery with a Glucose Burning Chamber", which is hereby incorporated in its entirety by reference.

In some embodiments, high-powered batteries may be implanted for medical use. In some instances, the battery may comprise an input, output, numerous battery modules, each module comprising numerous low voltage battery cells in permanent parallel arrangements. In certain embodiments, a switch may be used so that the battery modules may be charged in parallel (for low charging voltage), and/or so that the battery modules may discharge in series (for high output voltage). In some instances, the power source may also be used to power implantable defibrillators as an alternative to high voltage capacitors. Additional details regarding such battery systems may be found in U.S. Patent Application Publication No. 2006/0129192, titled "High-Energy Battery Power Source for Implantable Medical Use", which is hereby incorporated in its entirety by reference.

In other embodiments, high power implantable batteries may comprise a first high-rate electrochemical cell and a second high-rate electrochemical cell, which may be connected in parallel to a low power control circuit and in series to a high power output circuit. Implanted medical devices incorporating such batteries may include, for example, hermetic enclosures and circuits and resistive loads for power control. Additional details regarding such batteries may be found in U.S. Pat. No. 7,209,784, titled "High Power Implantable Battery with Improved Safety and Method of Manufacture", which is hereby incorporated in its entirety by reference.

Components of the external transmitting component of a Wireless Inductance Coupling Mechanism (WICM), which may be used in various embodiments to provide power to the implant, may include a power supply, an oscillator, and a transmitter coil. Components of the receiving component of the WICM may include the receiver coil, power rectifier, and power stabilizer, resulting in an efficient and stable voltage to power a device or charge a battery. The oscillator may generate a high oscillating current, in order to have a strong alternating magnetic field generated by the transmitting coil. The rectifier may serve to rectify the high frequency voltage into a pulsating DC signal. A capacitor may be used as a filter to smooth the ripple DC current emanating from the rectifier. Further capacitors may be wired as decoupling capacitors, which may be configured for filtering high frequency noise at the output (the battery being charged). Voltage regulators may also be used, which may keep the voltage stable so circuits may have a constant charging voltage. Regarding coil design, flat spiral coils have higher efficiency with longer distance of transmission, and may therefore be preferable for certain implants. Additional details regarding such inductance coupled wireless charging may be found in 'Wireless Inductive Charging for Low Power Devices', Macharia, 2017, which is incorporated herein in its entirety by reference.

Figure 31:
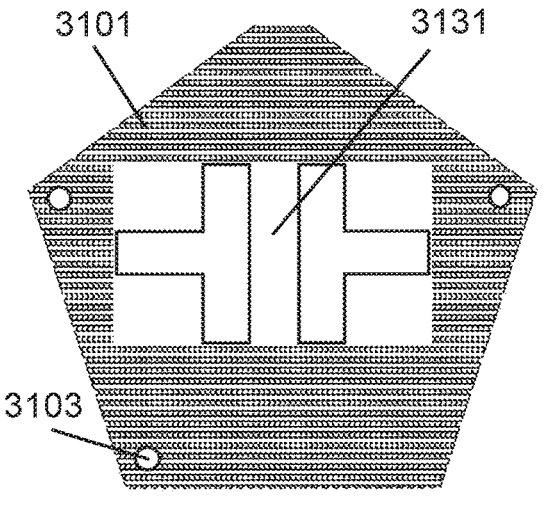
FIG. 31 depicts a top view of a mesh implant which may comprise reinforcement regions, holes, and/or capacitors according to an embodiment.

FIG. 31 depicts a top view of still another implant 3101 that is similar to implant 3001 except it has a capacitor 3131 and defines a different shape (a pentagon). Macro positioning/instrument engaging holes 3103 may again be provided.

Biodegradable capacitors may also be used in certain embodiments, in which capacitors may be attached to an implantable pad. Such implantable pads may comprise, for example, those with a symmetrical stacked structure of one or more of the following: PLA supporting substrate, PLA nanopillar arrays, zinc oxide nanoporous layers, and PVA/PBS hydrogel layers. The aforementioned information and further information may be found in 'Fully Bioabsorbable Capacitor as an Energy Storage Unit for Implantable Medical Electronics', Li, Advanced Science, 2019, which is incorporated herein in its entirety by reference.

Figure 32:
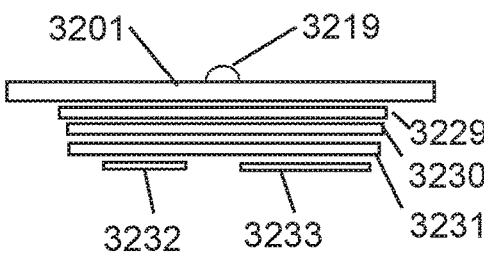
FIG. 32 depicts a side view of an implant, which shows how various elements may be stacked or otherwise applied to a single implant according to an embodiment.

FIG. 32 depicts a side view of an implant 3201, which shows how various elements may be stacked or otherwise applied to a single implant. Thus, an inductance coil 3229 is shown coupled to the implant 3201, along with a battery 3230, which may be used to receive and store energy from the inductance coil 3229 and may therefore be electrically coupled with inductance coil 3229. A capacitor 3231 may also be present in the assembly, along with various other electrical components as needed, such as a CPU 3232 and/or adjunctive circuitry 3233, which may, for example, provide protection to CPU 3232 and superstructure 3219.

In some embodiments, implantable medical devices may include rechargeable lithium-ion batteries. In some instances, such batteries may comprise titanium anodes and circuitry for battery charging and protection. Additional details may be found in U.S. Pat. No. 7,295,878, titled "Implantable Devices Using Rechargeable Zero-Volt Technology Lithium-Ion Batteries", which is hereby incorporated in its entirety by reference.

In a preferred embodiment, skin-inspired electronics may be capable of stretching, self-healing, and/or biodegrading. In some instances, such devices may comprise stretchable conductors (such as poly(3,4-ethyl-enedioxythiophene) polystyrene sulfonate (PEDOT:PSS)), stretchable semiconductors (such as poly(3-hexylthiophene) copolymerized with amorphous polyethylene), stretchable dielectrics (such as PDMS), stretchable sensors and displays, and stretchable transistors. In some instances, material designs may be based on intermolecular interactions such as, for example, hydrogen bonding, metal-ligand coordination, pi-pi interactions, and/or electronic interactions. In some embodiments, self-healing matrices may be coupled with conducting fillers. Biodegradable materials that may be used in electronics may comprise, for example, silk, cellulose, gelatin, PLGA, and the like. Additional details regarding such electronic devices may be found in "Skin-Inspired Electronics: An Emerging Paradigm", Wang, Accounts of Chemical Research, 2018:51; 1033-1045, which is hereby incorporated in its entirety by reference.

In order to protect the electronic components and circuitry from bodily fluids, implant 3201 may be insulated by biocompatible insulators, which may include polyimide and parylene-C. Additional details regarding such implantable insulators may be found in 'Bio-Compatibility and Bio-Insulation of Implantable Electrode Prosthesis Ameliorated by A-174 Silane Primed Parylene-C Deposited Embedment', Lin, Micromachines, 2020, which is incorporated herein in its entirety by reference.

Further methods for insulating implant 3201 may comprise polymeric materials, such as poly(V3D3) (poly(trivinyltrimethylcyclotrisiloxane), which may be used as a permanent electrical insulator. Such polymeric materials may be deposited onto surfaces via methods such as initiated chemical vapor deposition. Additional details regarding poly (V3D3) may be found in 'Stable Biopassive Insulation Synthesized by Initiated Chemical Vapor Deposition of Poly(1,3,5-trivinyltrimethylcyclotrisiloxane)', O'Shaughnessy, Biomacromolecules, 2007; 8:2564-2570, which is hereby incorporated in its entirety by reference.

For a permanent electrical implant, non-biodegradable insulators may be preferred. Non-biodegradable polymers such as silicones, poly(urethanes), poly(acrylates), or copolymers such as poly(ethyelene vinyl acetate) may be used as non-biodegradable electrical insulators for implantable electronics. Additional details regarding such insulating polymers may be found in 'Implantable Polymeric Drug Delivery Devices: Classification, Manufacture, Materials, and Clinical Applications', Stewart, MDPI, 2018; 10:1379-1317, which is hereby incorporated in its entirety by reference.

To power implant 3201, ultrathin batteries or capacitors may be used. Such designs may include flexible batteries attached to an implantable pad formed by nanoporous cellulose paper embedded with aligned carbon nanotube electrodes and electrolytes functioning as a cathode and a thin Li-metal layer as anode with Al on both sides of the battery acting as current collectors. Flexible capacitors attached to implantable pads may include those formed by two layers of nanoporous cellulose paper embedded with aligned carbon nanotube electrodes with an electrolyte layer in between the cellulose paper layers. The aforementioned information and further schematics may be found in 'Flexible Energy Storage Devices Based on Nanocomposite Paper', Pushparaj, PNAS, 2007; 104:13574-13577, which is hereby incorporated in its entirety by reference.

Rechargeable lithium cells may be used in certain embodiments, which may, for example, include being used to charge/power other implants (in addition to the implant within the implant pocket itself, or as an alternative to that implant). For example, lithium cells or other similar batteries may be used to power implanted battery powered devices, such as automatic implantable cardioverters/defibrillators. Implanted devices may further comprise sensors and/or controllers to monitor the charging state of the battery and/or accelerate the charging process, which may occur via, for example, magnetic induction. Further details regarding such cells may be found in U.S. Pat. No. 5,411,537 titled "Rechargeable Biomedical Battery Powered Devices with Recharging and Control System Therefor", which is hereby incorporated in its entirety by reference.

In some embodiments, cardioverter-defibrillators may be implanted subcutaneously. In some instances, such devices may comprise, for example, a hermetically sealed housing with one or more subcutaneous sensing and cardioversion-defibrillation delivery leads. As another alternative embodiment, two hermetically sealed housings may be connected by a power/signal cable. In some embodiments, the housings may be configured to match various rib structures. Additional details regarding implantable cardioverter-defibrillating devices may be found in U.S. Pat. No. 7,684,864, titled "Subcutaneous Cardioverter-Defibrillator", which is hereby incorporated in its entirety by reference.

FIG. 33 depicts a bottom view of a circular, flexible, and compressible implant 3301 with the addition of hollow, fillable, circular shaped superstructure 3333 on one side. In some embodiments, superstructure 3333 is circular in overall shape and cross section and may be present only on one side of implant 3301, which may be directed inward in a patient when implanted. Implant 3301 may be compressible by being rollable and/or foldable. Implant 3301 is shown in FIG. 33 in its unrolled or otherwise uncompressed/native state. Implant superstructure 3333 is likewise compressible. Implant superstructure 3333 may be hollow on the inside and/or may have an outer layer comprising, in some embodiments, a flexible plastic, organic polymer, biopolymer, or the like. Other embodiments may comprise a polymeric external lamination or containment to retain more dissolvable materials, such as hydrogels and the like. Drugs, vitamins, or other chemicals, including biologics, may also be bound, dissolved, or otherwise present in a portion or all of the structure of implant superstructure 3333 or elsewhere on implant 3301. Different regions and/or portions of the superstructure may also have different medications or chemicals printed or otherwise designed into them. In addition, electronics, micro-pumps, and/or printed circuit boards may be positioned in or on implant superstructure 3333 when properly protected. Injection port and/or tubing 3334 may also be used to allow a surgeon or other user to inject fluids for inflating superstructure 3333 and/or for injecting drugs. Port 3334 may extend above the patient's skin or, alternatively, may be positioned below the patient's skin to allow for subcutaneous injection of such drugs and/or other fluids. In some embodiments, port 3334 may have radiographically, sonically, or electromagnetically identifiable material positioned therein to allow injection needle filling of the superstructure, for example, with medications such as for chemotherapy.

Hydrogels may be used to fill superstructure 3333 in some embodiments. Common hydrogels used for drug delivery may include polyethylene glycol (PEG), which is inherently non-biodegradable. In order to make non-biodegradable hydrogels degradable, various degradable and reactive groups may be added to hydrogels such as PEG to make them biodegradable. Hydrogel chain lengths and multifunctionalities may also be used to modulate degradation. Degradable hydrogels may also be used for drug delivery while offering the additional benefit of not requiring surgery for removal after the drug has been delivered. Additional details regarding such drug release characteristics and models may be found in 'Predicting Drug Release from Degradable Hydrogels Using Fluorescence Correlation Spectroscopy and Mathematical Modeling', Sheth, Bioengineering and Biotechnology, 2019, doi.org/10.3389/fbioe.2019.00410, which is hereby incorporated in its entirety by reference. In some embodiments the hydrogel may lack water and thus be a more compact relatively dry, xerogel which may absorb water through a selectively permeable membrane or other means to become a hydrogel.

FIG. 34 depicts a lower view of a circular, flexible, and compressible implant 3401 with the addition of hollow fillable '+' shaped superstructure 3434 on one side. In some embodiments, superstructure 3434 may be circular in cross section following inflation. Injection port and tubing 3435 may also be used, which may be in fluid communication with superstructure 3434, as described above.

Micromechanical systems (MEMS) may be used in some embodiments in order to provide control of release kinetics to the patient or physician. Such MEMS may comprise micropumps, microprobes, cantilevers, microneedles, shape memory alloys, and/or microchips. Microchips may provide complex release patterns while providing data telemetry. Microchips may be categorized into solid state silicon chips or resorbable polymeric chips. Microchips may comprise drug delivering components such as reservoir arrays, batteries, microcontrollers, processing units, and/or antennae. Titanium coatings may be used in one or more biocompatible layers for microchips. Reservoirs may be made to be individually addressable or may use processes, such as electrothermal activation, to melt the caps off of the reservoirs to selectively deliver drugs from the implant. RF systems may be used to transfer power to the chip, which rectifies the power into a DC voltage. Pumps used to infuse drugs in connection with various embodiments disclosed herein may comprise, for example, infusion pumps, peristaltic pumps, osmotic pumps, and positive displacement pumps. Power may be provided via RF technology. Microvalves may be incorporated into the design of the implant and/or superstructure and be selectively actuated to control routing of drug formulations. Such microvalves may, for example, comprise thermoresponsive materials, such as hydrogels or other materials, such as paryelene, ionic polymer metal composites, and/or piezoelectric materials. Spiral coils or multilayer coils may be used to receive RF power. Thermopneumatic micropumps may transfer heat generated from RF transmission to the pump chamber, resulting in drug flow.

In some embodiments, drug eluting capsules may comprise a reservoir and a split ring reservoir. When the external radio frequency (RF) matches the resonant frequency of the split ring reservoir, heat may be generated to melt the lid of the capsule to release the drug. Microbots may also be used to deliver drugs. Microbots may be controlled or powered by external RF signals or external magnetic fields to propel themselves through blood vessels. Furthermore, microbots may hold their own power source or use the external RF or magnetic field for power or drug release. Nanoparticles may also be used for drug delivery or therapy. When exposed to external radio waves, nanoparticles (such as those composed of Gold) may generate heat for thermal ablation of cancerous cells, which may allow for various implants disclosed herein to be used for cancer treatments. The surfaces of nanoparticles may also be coated with antibodies (such as cancer specific antibodies), proteins, peptides, or even sugar residues to improve internalization within the target cells. Cristalline silicon, quantum dots, and platinum nanoparticles have shown high heat generation when exposed to RF radiations. Nanoparticles may be infused with sponge-like microspouters for precise repeated drug delivery. Such reversibly deforming magnetic sponges may comprise, for example, polydimethylsiloxane elastomers and ferromagnetic carbonyl iron microparticles. Additional details, including devices and methods for implantable wireless power transfer devices that may be used in various embodiments disclosed herein may be found in 'Radio Frequency Controlled Wireless Drug Delivery Devices', Khan, Applied Physics Reviews 6, 2019 (041301), which is hereby incorporated in its entirety by reference.

In some instances, pharmaceutical agents may be delivered by implanted actuating drug delivery devices. Some embodiments may comprise, for example, a compressible dispensing chamber situated in a first compartment, a reciprocating plunger for dispensing doses, a compressible drug reservoir chamber situated in a second compartment, a one-way valve between the dispensing and the reservoir chambers, and/or a compressible filler fluid chamber in communication with the first two compartments. Various other elements, such as a control board, motor driver, microprocessor, and/or battery may also be provided. In certain embodiments, the device may be refillable. Additional details regarding such drug delivery systems may be found in U.S. Patent Application Publication No. 2014/0214010, titled "Drug Delivery Device with Compressible Fluid Chambers", which is hereby incorporated in its entirety by reference. Certain embodiments of suitable drug delivery systems may comprise, for example, devices comprising dual-drug configurations that may dispense each drug independently. In such embodiments, the first and second drug chambers may have a one-way valve into compartments containing pistons and second compartments comprising followers in flow communication with said pistons. Additional details regarding such drug delivery systems may be found in U.S. Pat. No. 9,381,299, titled "Implantable Drug Delivery Devices", which is hereby incorporated in its entirety by reference.

In certain instances, pumps may be implanted subcutaneously to deliver drugs to specific target sites via implanted catheters. Types of subcutaneously implanted pumps may include, for example, osmotic pumps, vapor pressure pumps, electrolytic pumps, piezoelectric pumps, electrochemical pumps, effervescent pumps, and the like. In certain embodiments, drug delivery pumps may be implanted subcutaneously to release drugs into the myocardial tissue via catheters. Additional details regarding such pumps and drug delivery methods may be found in U.S. Patent Application Publication No. 2003/0009145, titled "Delivery of Drugs from Sustained Release Devices Implanted in Myocardial Tissue or in the Pericardial Space", which is hereby incorporated in its entirety by reference.

Certain embodiments of implantable drug delivering devices may comprise, for example, numerous reservoirs located within a substrate, rupturable reservoir caps, and/or means for accelerating the release of the reservoir contents. Means for enhancing release of reservoir contents may include, for example, shape memory materials, propellants to create expanding products, flexible membranes, methods for enhancing diffusion, or the like. In some embodiments, the reservoir caps may be selectively disintegrated via methods such as, for example, electric current, thermal ablation, oxidation, or the like. Additional details regarding such drug delivery systems may be found in U.S. Patent Application Publication No. 2005/0055014, titled "Methods for Accelerated Release of Material from a Reservoir Device", which is hereby incorporated in its entirety by reference.

In some embodiments, implantable drug delivery apparatuses may comprise, for example, drug supply reservoirs that may supply drugs into a delivery channel and actuators for delivering said drugs. The drug reservoir may be coupled, in certain embodiments, to the delivery channel via one or more drug supply valves. In some instances, the drug delivery channel(s) may be used to deliver drugs to various parts of the body. A first actuator may be used to drive the drug through the delivery channel and out of the outlet with a controlled degree of dilution with a carrier fluid. In certain embodiments, a second actuator may be used to cause drug flow in the delivery channel. In some instances, the drug reservoir may be pressurized. Additional details regarding such drug delivery systems may be found in U.S. Pat. No. 8,876,795, titled "Drug Delivery Apparatus", which is hereby incorporated in its entirety by reference.

In some instances, implanted drug delivery systems may comprise hollow members that may define at least one lumen for facilitating recirculating flow of a therapeutic fluid through the lumen and/or a pump to control the flow rate of the therapeutic fluid. In some embodiments, the therapeutic fluid may comprise a bodily fluid and a drug. In certain instances, recirculating fluid may be used to fill depleted volume within the device once the drug is dispensed. A preferable embodiment may comprise a device enabling recirculating drug delivery using a cannula interface to a targeted internal cavity of a patient. In some embodiments, the interface member may be configured to draw bodily fluid from the location where the drug is being delivered. Such systems may aid in, for example, reducing net infusion rates without having to reduce the pump's flow rate. Additional details regarding such drug delivery methods may be found in U.S. Pat. No. 7,867,193, titled "Drug Delivery Apparatus", which is hereby incorporated in its entirety by reference.

In certain embodiments, drugs may be delivered by implanted microminiature infusion devices. Such devices may comprise, for example, a reservoir for therapeutic fluid, a driver, and/or one or more electrodes which may be used to deliver therapeutic electrical stimulation. In some instances, the driver may comprise a pump, such as, for example, a diaphragmatic, negative pressure or peristaltic pump. In some embodiments, the driver may be actuated by electromagnetic means. Additional details regarding such drug infusion devices may be found in U.S. Pat. No. 7,776,029, titled "Microminiature Infusion Pump", which is hereby incorporated in its entirety by reference.

In some embodiments, implanted drug delivery devices may comprise release mechanisms which may selectively release therapeutic agents in response to external stimuli. In some instances, such devices may comprise release mechanisms sealingly engaged with a reservoir to release cargo. In some embodiments, the release mechanism may comprise a diaphragm membrane comprising a polymer matrix, which may be non-porous in a first state; however, in response to external stimuli, the matrix may transition to a second, substantially porous, or at least more porous, state. In certain instances, the polymer matrix may comprise, for example, a plurality of magnetic particles, which upon application of a magnetic field, may cause the diaphragm to transition to the second state. In some embodiments, the membrane may be composed of electrospun nanofibers comprising magnetic particles. In some instances, the device may comprise a rotating membrane. In some such embodiments, the rotating membrane may be affixed to a non-moveable membrane in such a way that the non-moveable membrane is between the rotating membrane and reservoir and/or may define at least one hole or pore. The rotatable membrane may be rotated such that when holes in the rotating and non-moveable membranes align, therapeutic agents may be released. In some embodiments, the release mechanism may comprise micro channels connecting the reservoir to pores in the membrane. In certain embodiments, such micro channels may comprise valves allowing or restricting fluid flow. Additional information regarding such drug delivery devices may be found in U.S. Patent Application Publication No. 2012/0226265, titled "Remotely Controlled Drug Delivery Systems", which is hereby incorporated in its entirety by reference.

In some instances, devices may be used to regulate microfluidic flow. Such devices may comprise, for example, substrates defining fluid-conducting chambers, a flexible membrane sealing the chamber, such that the flexible membrane may be moved between two positions, one allowing more fluid flow than the other, and a method (such as, for example, electromagnetic mechanisms) disposed on the substrate to shift the membrane between positions. Additional details regarding such flow regulators may be found in U.S. Patent Application Publication No. 2016/0003229, titled "Electromagnetically-Actuated Microfluidic Flow Regulators and Related Applications", which is hereby incorporated in its entirety by reference.

In some embodiments, implantable devices may be configured for zero-order drug release kinetics. Such devices may comprise, for example, a housing formed from biocompatible materials. Said housing may comprise a hollow core with passages connecting the core to the exterior space, drugs loaded through a first end, and/or a biocompatible seal on the housing's first end. In some embodiments, the device may comprise multiple compartments, enabling individual release rates of therapeutic agents. The device may be used to deliver agents such as, for example, drugs, proteins, genetic materials, et al. In some instances, the device may be biodegradable. Additional details regarding such drug delivery devices may be found in U.S. Patent Application Publication No. 2018/0042549, titled "Methods for Making Controlled Delivery Devices Having Zero Order Kinetics", which is hereby incorporated in its entirety by reference.

FIG. 35 depicts a lower view of a rectangular, flexible, and compressible implant 3501 with the addition of hollow fillable rectangular shaped superstructure 3535 on one side. In some embodiments, superstructure 3535 may be circular in cross section following inflation. Injection port and tubing 3536 may also be used, and may be in fluid communication with superstructure 3535.

Superstructure 3535 may, in some embodiments, contain magnetic microdisks. Magnetic fields may be used to control micro magnetic disks in order to damage target cell integrity, deliver drugs, generate heat, and/or separate tumor/cancer cells for early detection. Various types of magnetic disks may include, for example, in-plane synthetic antiferromagnetic (SAF) disks, perpendicular SAF disks, and vortex disks. In-plane disks may have two ferromagnetic layers separated via nonmagnetic spacer with magnetic moments in-plane in opposite directions. Perpendicular disks may have two ferromagnetic layers separated via nonmagnetic spacer with magnetic moments out-of-plane pointing in opposite directions. Magnetic disks may use mechanical force (from torque via external magnetic field) to induce apoptosis in target cells. Vortex disks may be comprised of Ni80Fe20 and be capped with two gold layers (to insulate the body from adverse effects). Such disks may be functionalized with antibodies matching antigens on the membranes of targets cells to induce apoptosis via torque and mechanical force. Magnetic disks may also be endocytosed by target cells and accumulated into lysosomes, which may be ruptured by the disks' torque. Magnetic disks may also be used for drug and gene delivery. Polymers such as thiolated chitosan may be assembled onto the surface of the disks. Mechanical torque and force may then be used to permeabilize the target cell membrane while simultaneously delivering therapeutic material. Magnetic disks may also be used for magnetic hyperthermia, the major heating mechanism being hysteresis loss. Various additional details and further information that may be useful in connection with the implants disclosed herein may be found in "Disk-Shaped Magnetic Particles for Cancer Therapy", Munoz, Applied Physics Review 7, 2020 (011306), which is hereby incorporated in its entirety by reference.

FIG. 36 depicts a lower view of a rectangular, flexible, and compressible implant 3601 with the addition of hollow fillable '+' shaped superstructure 3636 on one side. In some embodiments, superstructure 3636 may be circular in cross section following inflation. Injection port and tubing 3637 may also be used, and which may be in fluid communication with superstructure 3636.

Drug delivery systems according to various embodiments disclosed herein may include microparticles (which may include biodegradable polymers, natural polymers), nanoparticles (which may include biodegradable polymers, natural polymers), micelles (which may include amphiphilic block copolymers), drug conjugates (which may include hydrophilic polymers, dendrimers), hydrogels and implants (which may include hydrophilic polymers, biodegradable polymers, natural polymers), or the like. Nanomaterials for drug delivery and theranostics may include, for example, gold nanoparticles, silver nanoparticles, iron oxide nanoparticles, carbon nanotubes, fluorescent nanodiamonds, silica nanobeads, or the like. Polymeric micelle nanoparticles may be created from the self-assembly of amphiphilic block copolymers. Methods for loading micelles with drugs may include, for example, solvent evaporation, co-solvent evaporation, dialysis, flash nanoprecipitation, and the like. Diblock copolymers used for micelles may include Poly(L-lactide-block-acrylic acid) and triblock copolymers may include Polylactide-block-poly(ethyleneglycol)-block-polylactide. Polymeric microsphere drug carriers may be used to protect unstable drugs pre- and post-administration. Microspheres may be used to release drugs over time and prolong therapeutic effect. Microspheres may be comprised of biodegradable polymers, such as poly(lactide-co-glycolide) (PLGA). The surfaces of nanoparticles may be modified polyethylene glycol to prolong in-vivo lifetime. Polymers used in connection with various embodiments disclosed herein may also be configured for resistance to immunological response due to their lack of surface identifying proteins. Microgels and nanogels may also be used in some embodiments to encapsulate water-soluble, small molecule APIs that would otherwise be difficult to encapsulate using traditional biodegradable polymeric particles. Polymeric nanoparticles may be prepared via methods such as nanoprecipitation. Liposomes may also be used as drug delivery devices due to their excellent biocompatibility while nanoparticles possess excellent stability and drug carrying capacity. Lipid-polymer hybrid nanoparticles (LPNs) may be used to combine the advantageous properties of liposomes and nanoparticles. Polymers that may be used in the cores of LPNs may include PLGA, while lipids such as phosphatidylcholine may be used in the shell of the LPN, along with poly(ethylene glycol) (PEG) lipid conjugates. In some embodiments, LPNs may also be engineered to be stimuli responsive, responding to stimuli such as pH by using pH sensitive lipid coatings (such as lipid-succinate-mPEG). LPNs may be particularly useful to deliver drugs such as docetaxel, paclitaxel, curcumin, and doxorubicin. Polysaccharides such as chitosan may be used as drug delivering molecules and/or may be formulated into drug delivering nanoparticles (by mechanisms such as covalent crosslinking, ionic crosslinking, polyelectrolyte complexation, and self-assembly of hydrophobically modified polysaccharides, depending on desired structural characteristics). Such natural polymers may form bioadhesions which are advantageous as carriers because they can prolong residence time, and therefore increase the absorbance of loaded drugs. Depending on desired nanoparticle or nanomicelle characteristics, natural polymers may be modified prior to use with various implants disclosed herein. One such example may be chitosan: amphiphilic chitosan may be formed by grafting hydrophobic groups onto the amine functional groups. Furthermore, the hydrophobic cores of certain micelle carrier systems can improve drug solubility and stability by acting as reservoirs for water-insoluble drugs. Amphiphilic natural polymer-based micelles (such as those based on chitosan) may be used to encapsulate drugs such as ibuprofen and amphiphilic adriamycin for ultimate delivery in one or more of the implants disclosed herein. Natural polymer-based micelles may even encapsulate certain proteins, peptides, and nucleic acids. Stimuli-responsive materials may also be used to selectively deliver drugs as needed, which materials may include thermo- and/or pH-sensitive materials (thermal- and pH-sensitive materials are the most prevalent due to the different thermal and pH conditions in various areas of the body). Thermosensitive polymers may ideally exhibit transition temperatures close to physiological temperatures. Stimuli-responsive polymers may be formulated into stimuli responsive micelles to deliver drugs such as doxorubicin to cancer cells. The structures of such polymers may also be modified to coat liposomes. Hydrogels may also, in some embodiments, be coupled with nanometer-sized shape-changing structures to release drugs. Swelling and de-swelling can cause mechanical deformations that can be used to enable actuation in some embodiments. Self-folding drug delivery systems (DDS), such as theragrippers (DDS that have digits that may open and close in response to external stimuli), may be used for chemomechanical controlled drug release. Drugs such as mesalamine and doxorubicin may be loaded into such theragrippers. Hydrogels used for drug delivery may be functionalized with a variety of groups such as methoxy, hydroxyl, maleimide, thiol, and azide moieties. Hydrogels may also be used to create biomatrices that may encapsulate various cell types such as fibroblasts. Further drug/therapeutic cargo-delivery media that may be useful in connection with various embodiments may include collagen, poly(2-oxazoline), polyoxazolines, dendritic polyester scaffolds, raft polymer carriers, and/or linear branched polyethylenimines. Further details regarding drug and therapeutic cargo delivery techniques that may be useful for various embodiments may be found in 'Polymeric Drug Delivery Techniques Translating Polymer Science for Drug Delivery', Aldrich Materials Science (2015), which is hereby incorporated in its entirety by reference.

Figures 37A, 37B, 37C, 37D, 38, 39, 40:
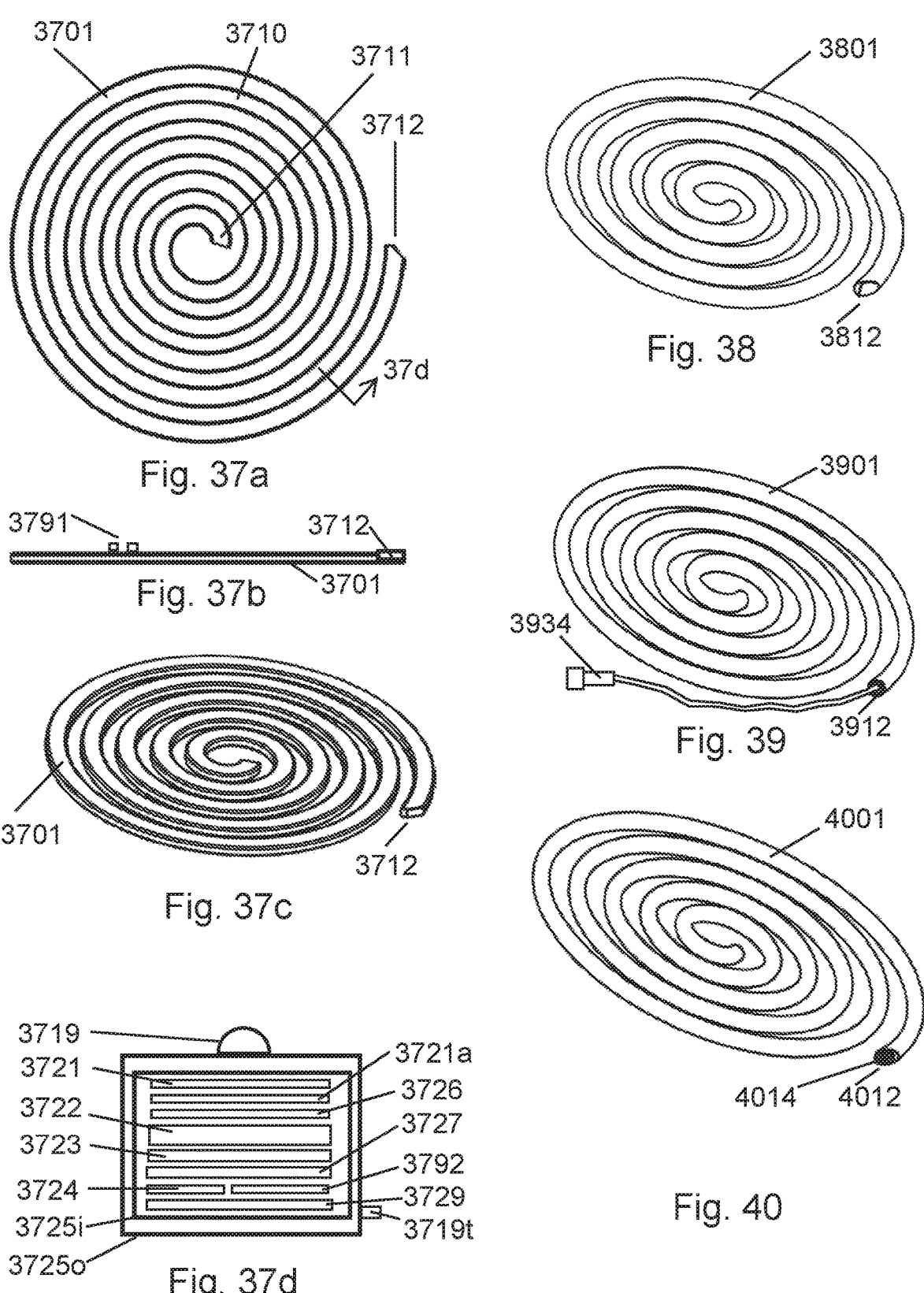
FIG. 37a depicts a top view of a circular, spiral implant.
FIG. 37b depicts a side view of the circular, spiral implant.
FIG. 37c depicts a top perspective view of the circular, spiral implant.
FIG. 37d depicts an enlarged cross-sectional view of an embodiment of circular, spiral implant.
FIG. 38 depicts a perspective view of a circular, spiral implant with a circular solid cross section according to an embodiment.
FIG. 39 depicts a perspective view of another circular, spiral implant with a circular hollow cross section according to an embodiment.
FIG. 40 depicts a perspective view of another circular, spiral implant with a circular cross section comprising an internal guidewire according to an embodiment.

FIG. 37a depicts a top view of a circular, spiral implant 3701 with outer arm band terminus 3712 and inner arm band terminus 3711 and space 3710 between the bands. In the depicted embodiment, space 3710 is similar in size as the corresponding width of each adjacent arm/band, a pair of which defines the size of the space 3710. In some embodiments, space 3710 may therefore be the same, or at least substantially the same, as this aforementioned arm/band width. Of course, in other embodiments, space 3710 may be less (or more) than this arm/band width. In fact, in some embodiments, space 3710 may, in a resting configuration of implant 3701, be zero or close to zero (see FIG. 69, for example). However, in such embodiments, preferably the arms are sufficiently flexible and separable to allow for temporary separation of the arms to create sufficient space to facilitate installation using, for example, one of the techniques described herein through a minimally invasive entrance incision. Irrespective of whether there is permanent space between the adjacent bands/arm regions of a spiral implant or whether the implant is sufficiently flexible to temporarily create such space to allow for this installation, however, it should be understood that, as used herein, the term "space"—or the phrase "space in between adjacent bands" of a spiral implant-should be considered to require the ability to utilize this space to insert the spiral implant through an entrance incision (preferably a minimally invasive entrance incision) with just one arm/band extending through the entrance incision at any given moment during an installation procedure (as opposed to the entire implant). Thus, it should be understood that the use of the aforementioned "space" in this context, whether permanent or temporary, should be considered to exclude any devices that have structures that preclude use of this space for this purpose, such as, for example, spiral-shaped inductance coils having a substrate, such as a plate or other element, connecting each of the various bands of the coil together, which, again, would preclude installation in the aforementioned manner despite the possible presence of "space" in some sense between the bands of the coil.

It should be understood that some embodiments comprising a spiral/coil shape, or an at least substantially spiral shape, may extend in a vertical direction (perpendicular to the space between adjacent bands referenced above) and may therefore, for example, form a cone shape. Thus, there may be "space" between each adjacent band in the same plane or, in some embodiments, there may be space between each adjacent band in a vertical direction such that the entire coil does not reside in the same plane, either instead of or in addition to the lateral "space" mentioned above.

In some embodiments, spiral implant 3701 may be circular in overall shape and rectangular in cross section. As described below, however, various other shapes may be used in alternative embodiments. Spiral implant 3701 may be rigid or, if preferred, more flexible. In some embodiments, the spiral implant 3701 may be compressible by being rollable and/or foldable. In some embodiments, spiral implant 3701 may comprise a metal, ceramic, cermet, glass, flexible plastic, organic polymer, biopolymer, or the like. Other embodiments may comprise a polymeric external lamination or containment to retain more dissolvable materials such as hydrogels and the like. Drugs, vitamins, or other chemicals, including biologics, may also be bound, dissolved, or otherwise present in a portion or all of the structure of spiral implant 3701 and/or elements contained therein.

Spiral implant 3701 may, in some embodiments, comprise pores 3791, for example, nanoscale agents responsive to stimuli. Such nanoscale agents may respond to stimuli such as light, magnetic fields, ultrasound, radio frequency, and x-ray, which may allow for selective actuation from outside of the user/patient's body. Magnetic fields may be used for magnetoporation and magnetic field drug targeting. Electric current or voltage may be used for electroporation and iontophoresis. Ultrasound may be used for sonodynamic therapy and sonoporation. Pulsed light may be used for optoporation and drug release. Temperatures may be influenced for thermoporation and hyperthermia. Such temperature changes may be induced for example, by electricity (via, for example, a thin-film resistor), by ultrasound, or by radiation, such as microwave or infrared radiation. Hyperthermia may be induced via magnetic particles or near infra-red light coupled with gold nanorods. Various hybrids of magnetic nanoparticles may be used to eradicate tumors such as breast, liver, colon, and more, via magnetic fluid hyperthermia. Various light-triggered functions could be implemented in a nanodevice, such as light-induced cancer nanotheranostics, which normally respond to UV, visible, and near infra-red light. Photosensitizers responsive to UV, visible, or NIR light may include inorganic or organic photosensitizers, such as, for example zinc phthalocyanine, zinc oxide, quantum dots, and the like. NIR light can trigger nanoparticles, such as gold nanorods, polypyrrole, and others for photothermal therapy. Due to the low penetration depth of light, optical fibers inserted through surgery or endoscopy may aid in delivering light deeper into the body. Further information regarding such possible nanoscale agents and related materials and devices may be found in 'Physically stimulated nanotheranostics for next generation cancer therapy: focus on magnetic and light stimulations', Thorat, Applied Physics Reviews 6, 2019 (041306), which is hereby incorporated in its entirety by reference.

Different regions and/or portions of spiral implant 3701 may also have different medications or chemicals printed or otherwise designed into them. In addition, electronics, micro-pumps, and/or printed circuit boards may be present in the spiral implant 3701 when properly protected. Radiographically, sonically, and/or electromagnetically identifiable material may also be present in implant 3701 to aid in locating and/or manipulating the implant. Spiral implants may be inserted by rotating/winding the implant into a minimally invasive entrance wound, as will be discussed and depicted later in greater detail. Spiral implants may also lend themselves to carrying electronics, such as inductance coils, thin film batteries, printed circuit boards as well as chemicals, medicines, and/or biopolymers.

In some embodiments, spiral implants, such as implant 3701, may measure at least 2 cm in diameter (measured along the implant's footprint from one outer edge of an outer band to the opposite outer edge of the outer band). In some such embodiments, spiral implants may measure at least 5 cm in diameter, and in some cases may measure at least 10 cm in diameter, or in some such embodiments at least 20 cm in diameter.

FIG. 37*b* is a side view of the implant 3701 also depicting outer arm band terminus 3712, which, as discussed below, may comprise an opening to allow for access to the interior of implant 3701 or may be solid.

FIG. 37*c* is a top perspective view of the implant 3701 also depicting outer arm band terminus 3712.

FIG. 37*d* depicts a cross-sectional view of spiral implant 3701 taken from FIG. 37*a* along the line and arrow depicted therein. The cross-sectional view of spiral implant 3701 depicts superstructure 3719 positioned on the upper surface of the implant. Of course, in alternative embodiments, the superstructure 3719 may be positioned on any other side and/or portion of the implant. Spiral implant 3701 may also comprise temperature sensor 3719*t*, which may protrude from another location on implant 3701. The depicted embodiment also comprises various layers/elements, including a metallic inductance coil 3721, battery 3722 (thin film in this embodiment), printed circuit board 3723, one or more additional inductance coils 3721*a*, capacitor 3726, data storage 3727, lab-on-a-chip 3729, antenna 3792, ancillary electronics 3724, such as a heating element, thin film resistors, etc., and polymeric protective inner sheath 3725*i*, which may be positioned adjacent to protective outer sheath 3725O. As also shown in this figure, a hollow space may be created between inner and outer sheaths 3725I/3725O, which may be used to contain a fluid and/or gel, for example, which may serve as a protective sheath/seal, a superstructure, and/or a location for drug containment and/or delivery. In some embodiments, microfluidic channels (not shown) may bring patient serum/blood/tissue fluid located outside of the protected encasement/wrapper in contact with lab-on-a-chip for analysis(es). In further contemplated embodiments, temperature sensors may be placed in many locations on the inside and/or outside of spiral implant 3701 or any of the other implants disclosed herein. Temperature sensors located on the outside may, in some embodiments, be configured to send temperature data to a CPU, which may be programmed with a set temperature threshold such as, for example, 45° C., to possibly shut down or reduce external wireless inductance coil charging to protect delicate adjacent tissue. Once external temperatures return to a preset safe threshold, for example 42° C., wireless charging may recommence. Temperature sensors placed internally in the spirals may have preset thresholds to alter the charging parameters to protect one or more of the aforementioned internal elements of the spiral coil 3701. Some contemplated embodiments may comprise multiple internal antennas.

Silk nanoribbons (SNR), konjac glucomannan (KGM), and chromium or aurum may be used to prepare biodegradable wires for use in some embodiments. A vacuum filtration process may be used to combine SNR and KGM into a thin film. Chromium or Aurum may be evaporated onto the composite film as electrodes. Further details regarding such processes may be found in 'Natural Polymer-Based Bioabsorbable Conducting Wires for Implantable Bioelectronic Devices', Niu, Journal of Materials Chemistry A, 2020, DOI: 10.1039/d0ta09701b which is hereby incorporated in its entirety by reference.

Implantable wireless drug eluting devices may, in some embodiments, employ a wirelessly induced current to electrochemically accelerate the dissolution of a metal gate sealing a drug reservoir, leading to drug release. For example, polybutanedithiol 1,3,5-triallyl-1,3,5-triazine-2, 4,6 (1H,3H,5H)-trione penteonic anhydride (PBTPA) may be used as a substrate and reservoir for the drug in question. Current may be delivered to the device via inductive wireless charging for immediate actuation or, alternatively, the energy may be stored in a capacitor for subsequent actuation at a desired time. Electrodes of Mg may comprise the gates in some embodiments. The harvester may generate an overpotential bias, which leads to accelerated electrochemical corrosion of the Mg electrodes via Faradic reaction enabled by the surrounding biofluid. Given the irreversible nature of the reaction, the device may only be of single use in some embodiments. Additional details regarding such possible applications may be found in 'Wirelessly controlled, bioresorbable drug delivery device with active valves that exploit electrochemically triggered crevice corrosion', Koo, Health and Medicine, 2020, Vol. 6 No. 35, which is hereby incorporated in its entirety by reference.

In some embodiments, additional elements, such as electronic elements, may be coupled to the coil to make the coil more useful as a standalone implant, or an implant configured to standalone as a power supply to another, secondary implant. In some such embodiments, use of a unitary coil, as shown in FIG. 80a, may eliminate the need for an auxiliary implant altogether. In contemplated embodiments, a unitary coil may therefore be coupled with other implants, such as implants to which the unitary coil is providing energy, without the use of an auxiliary implant to aid the unitary coil in doing so. It is also contemplated, however, that some coil embodiments may have some, but not all, of the components that may be provided on an auxiliary implant, and may therefore be considered a "hybrid" coil implant.

FIG. 38 depicts a perspective view of a circular, spiral implant 3801 with circular cross section and a solid (as opposed to hollow) center terminating in outer arm band terminus 3812.

FIG. 39 depicts a perspective view of another circular, spiral implant 3901 with circular cross section. However, unlike spiral implant 3801, spiral implant 3901 comprises a hollow center terminating in outer arm band terminus 3912. Injection port and/or tubing 3934 may also be used to allow a surgeon or other user to inject fluids for inflating a superstructure hidden within implant 3901 and/or for injecting drugs. Port 3934 may extend above the patient's skin or, alternatively, may be positioned below the patient's skin to allow for subcutaneous injection of such drugs and/or other fluids. In some embodiments, port 3934 may have radiographically, sonically, or electromagnetically identifiable material positioned therein to allow injection needle filling of the superstructure, for example, with medications, such as for chemotherapy. FIG. 40 depicts a perspective view of still another circular, spiral implant 4001 with circular cross section. In this embodiment, the center of implant 4001 is hollow again and terminates in outer arm band terminus 4012. However, unlike spiral implant 3901, spiral implant 4001 comprises an internal guidewire 4014 for rigidity to facilitate implantation or the like. In alternative embodiments, such as likely smaller spiral implants, guidewire 4014 may be removable, which may allow for retraction and introduction of other elements and/or materials, such as gels, drugs, electronics, etc.

FIG. 41 depicts a top view of a rectangular, spiral implant 4101 which may be both rectangular in shape in plan view, as shown in the figure, and in some embodiments, may also be rectangular in cross section. Alternatively, the cross-sectional shape may be circular, oval, or other suitable shapes in other embodiments including but not limited to geometric or 3 dimensional. In some embodiments, additional elements, such as electronic elements, may be coupled to the coil to make the coil more useful as a standalone implant, or an implant configured to standalone as a power supply to another, secondary implant. In some such embodiments, use of a unitary coil, as shown in FIG. 80a, may eliminate the need for an auxiliary implant altogether. In contemplated embodiments, a unitary coil may therefore be coupled with other implants, such as implants to which the unitary coil is providing energy, without the use of an auxiliary implant to aid the unitary coil in doing so. It is also contemplated, however, that some coil embodiments may have some, but not all, of the components that may be provided on an auxiliary implant, and may therefore be considered a "hybrid" coil implant.

FIG. 42a depicts a top view of a pentagonal/polygonal, spiral implant 4201, which may be rectangular in cross section with outer arm band terminus 4201a. In further contemplated embodiments, the cross section may be a non-rectangular shape. As should be apparent from considering the shape of this implant, it is contemplated that spiral implants may be formed into any shape as desired, preferably in a manner that allows for winding/rotation of the implant into a minimally invasive entrance incision one band/arm at a time, as discussed herein. As shown in FIG. 69, as the space between adjacent arms approaches zero, the possibilities for shapes either formed by spiral arms or cut into a spiral are virtually limitless.

FIG. 42b depicts an enlarged top view of outer arm band terminus 4201a with a bulbous reduced catching tissue passage facilitator 4201b with opening/port 4201c which may be configured to accommodate electronic coupling and/or fluid delivery/extraction. For example, tissue passage facilitator 4201b may comprise a smooth cap and/or bulb configured to both facilitate passage of the terminus 4201a through the entrance wound and to provide a smoother tip to prevent terminus 4201a from catching on tissue as the implant 4201 is rotated and advanced into the body/pocket. Port 4201c may comprise an electrical port electrically coupled to another element of the implant or an accessory device, implant, and/or element of a system, such as the auxiliary implant 5408 shown in FIG. 54a, which will be discussed in greater detail below.

FIG. 43 is an enlarged view of an oval cross section of a spiral band 4301b located between spiral band 4301a and spiral band 4301c. Spiral band 4301b is shown passing through and being compressed by an entrance wound 250. In this embodiment, the implant comprises flaps 4301f, which may be flexible and partially or fully fold/wrap around spiral band 4301b, which may allow the flaps to bend, fold, compress, or otherwise fit into the minimally invasive entrance wound 250 with a lower profile and unfold/decompress once inside the body, as shown in the other two arms/bands 4301a and 4301c. In the configuration shown in FIG. 43, band 4301a is inside the patient, as it has already passed through the entrance wound 250, whereas band 4301c has yet to pass through the entrance wound 250 and is therefore wholly outside of the patient. The procedure by which this implant is inserted into the patient will be described below in greater detail.

In some embodiments, the flaps 4301f may allow a flexible inductance coil 4319 to be positioned not only within the central portion of spiral band 4301b but also may extend within the flaps 4301f themselves. Flaps 4301f can unfold like the solar panels on a satellite once in the body to present a greater surface area for various purposes. For example, when an inductance coil 4319 is positioned, either partially or wholly, therein, this may provide increased surface area for an inductive charger. Increased surface area may also be beneficial for medicine/drug release in alternative embodiments. Thus, for example, in some embodiments, flaps 4301f may be fluidly coupled with the center/main body of the spiral implant and may be configured to recoil/unfold to the configurations of the inner and outer bands of the implant, 4301a and 4301c, respectively, by virtue of the fluid pressure contained therein.

FIG. 44 depicts an implant 4401 in which the bands are rectangular in cross section resembling linguine, and which may be spaghetti-like following implantation, such as similar to the configuration shown in FIG. 44. In alternative embodiments, the cross-sectional shape may instead be circular more like spaghetti or other shapes as desired. Once implanted spaghetti-like implants may be relatively planar/flattened (x,y dimensions much greater than thickness z dimension) and/or take on a 'tertiary' 3-dimensional shape (wherein x,y,z dimensions are within less than one order of magnitude of each other) for example if placed in the peritoneal cavity. In some embodiments, such an implant may be used to fill subcutaneous, muscular, and/or other outwardly visible defects from trauma or cancer and/or be multifunctional by carrying monitoring electronics for a cancer recurrence or anti-cancer therapy. In some embodiments, such shapes may be useful when implanted into anatomical locations such as the thoracic cavity or abdomen, for example, in or around the omental areas.

Figure 45A:
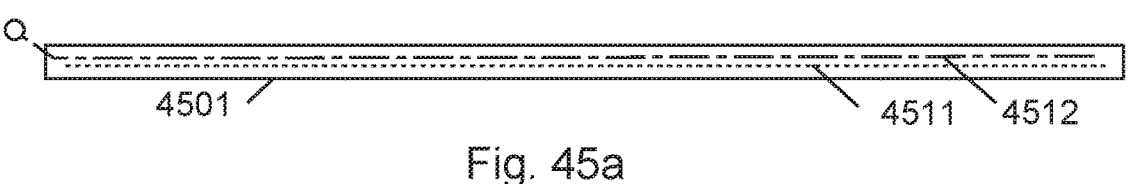
FIG. 45a depicts a side view of a portion of an embodiment of a flexible, spaghetti-like implant, which may contain electronics.

FIG. 45a is a side view of a portion of a flexible implant 4501, which, in turn, may contain electronics 4511, and which may, again, be spaghetti-like during and/or after implantation if desired. Electronics 4511 may comprise inductance coils, batteries, printed circuit boards, thin film resistive heaters, and the like. In some embodiments, the implant 4501 may resemble a tapeworm. Optional guide wire 4512, shown here as extending in a straight line, may facilitate implantation and/or be removable from implant 4501. Optional guide wire 4512 may comprise, for example, a metal or other material configured for placement within the implant, such as, for example, a naturally conformed stainless, spring steel coil may be used to introduce a soft, highly flexible implant into a tissue pocket and, upon removal, leave the implant in a desired coil shape imparted by the shape of the guide wire. In some embodiments, a shape memory material may be used to form guide wire 4512, such as a shape-memory alloy or shape-memory polymer. This may allow for implants of a wide variety of shapes, such as elongate implants, to be inserted through a minimally-invasive entrance wound, and resume any shape within the body, or remain in an elongated configuration, as desired.

To power such spaghetti-like implants, flexible, cable-like batteries may be used in some embodiments. Flexible implantable battery designs may include, for example, cable-type lithium ion batteries. Such batteries may comprise several Cu anode strands (coated with Ni—Sn) in a hollow helical shape, using a modified PET separator membrane wound around with an Al coil, surrounded by a LiCoO2 tubular cathode, the entirety of which may be insulated. The aforementioned information and further schematic may be found in 'Cable-Type Flexible Lithium Ion Battery Based on Hollow Multi-Helix Electrodes', Kwon, Advanced Materials, 2012, which is hereby incorporated in its entirety by reference.

Figure 45B:
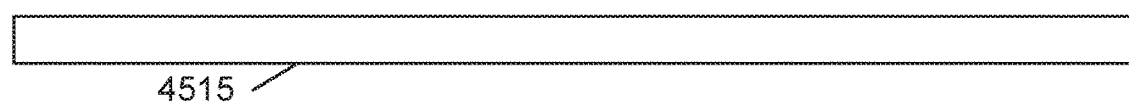
FIG. 45b depicts a side view of a rigid hollow cannula/trocar, which may facilitate implanting of spaghetti-like implants according to an embodiment.

FIG. 45b is a side view of a rigid hollow cannula/trocar 4515, which may facilitate subcutaneous, intraperitoneal, or intrathoracic implantation of a flexible spaghetti-like implant. In other implementations, the cannula/trocar may have some degree of flexibility or see use in other organ systems/cavities.

Figure 45C:
FIG. 45c depicts a side view of a plunger that may be used to drive a spaghetti-like implant through a cannula/trocar.

FIG. 45c is a side view of a plunger 4520 that may be used to drive an implant, such as a flexible and/or spaghetti-like implant through a rigid hollow cannula/trocar into its target resting site. The plunger system may have plunger piston 4525 to drive the implant through the cannula when a force is applied by a surgeon to plunger top 4530.

Figure 46A:
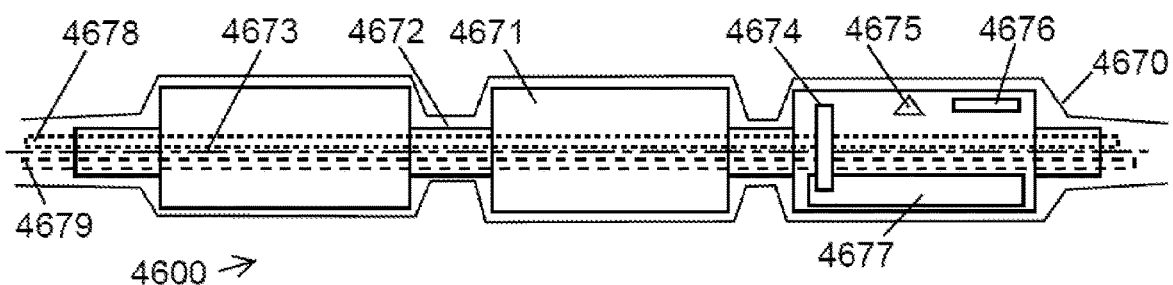
FIG. 46 depicts a side view of a flexible/spaghetti-like implant system according to an embodiment.

FIG. 46a is a side view of a flexible and/or spaghetti-like implant system 4600 which may be somewhat reminiscent of a segmented tapeworm. Implant system 4600 may comprise enlarged segmentation pod 4671 with connecting segments 4672, which may comprise tubes, for example, through which may pass various elements as desired, such as flexible electronics 4673, including, for example, inductance coils, wiring, printed circuit boards, fiber-optics, and the like. The segmentation pods 4671 may, in some embodiments, be removable and addable to allow the implant to be modular and/or customizable. One or more of the segmentation pods 4671 may, for example, comprise/contain one or more micro-pumps/motors 4674, Printed Circuit Board 4675, sensors 4676, fluidic tubing 4678, fluidic tubing 4679, which may be configured to deliver fluids in the opposite direction of tubing 4678, and/or storage bays 4677, which may house drugs, fluids, powders, etc. In further contemplated embodiments, a wrapper 4670 may be placed overlying the exterior of pods 4671 and/or outside of connection segments 4672, which may facilitate sliding the implant into an incision and past tissues and/or may provide protection and/or a fluid seal to protect the components of the various pods 4671. In some embodiments, wrapper 4670 may comprise a shrink wrap or may otherwise be adherent to one or more of the pods 4671, in which case the wrapper 4670 may pinch/extend into the space overlying one or more of segments 4672 between the pods. Although wrapper 4670 is shown open at both ends, which is intended to convey the notion that any number of additional pods 4671 may be added to the implant at either end, it should be understood that it would typically be closed before implantation.

Figure 46B:
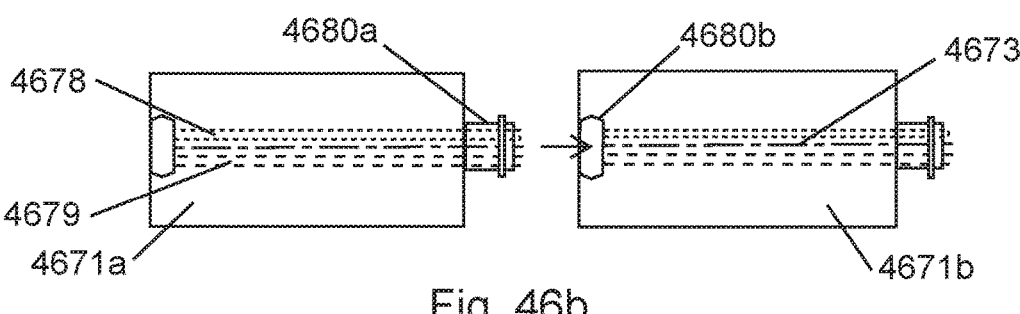

FIG. 46b depicts an embodiment that facilitates the aforementioned modularity. More particularly, a first pod 4671a is shown being coupled with a second pod 4671b using a releasable male connector 4680a configured to fit within a female connector 4680b. In this manner, pods can be obtained/added to the assembly as needed. For example, a pharmacist may add drugs to a pod specifically tailored for a particular patient and then the pod may be snapped or otherwise coupled to the chain by coupling it with an adjacent pod. It should also be understood that pods may be selectively coupleable with any of the other implants and/or implant components disclosed herein. For example, an implantable inductance coil may be configured with a connector configured to couple to a pod to allow for selective addition of a power source. The reference to spaghetti is to indicate that what may start as an organized implant, such as an implant wound around a spool, once inserted into the body may assume a relatively random appearance, similar to that of a long spaghetti noodle dropped at random. Areas where spaghetti-like implants may be helpful may include, for example, intra-abdominal, intra-thoracic, or other body cavities, where an assumption of filling a natural void/crevasse with conformable materials is possible. In a subcutaneous layer, it is possible that a spaghetti-like implant may be useful in an area where tissue is missing from previous trauma or a natural space of a breast, scrotum, or axilla.

Figure 47C:
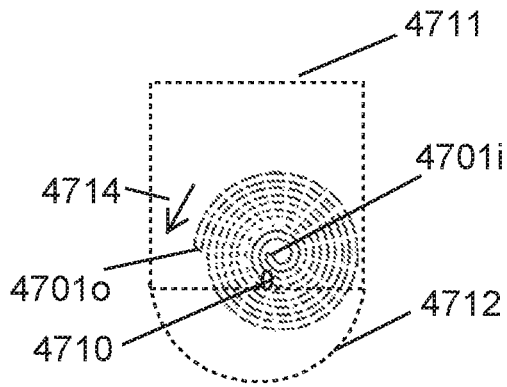
FIG. 47c depicts an implant pocket and delivery pocket, with a spiral implant having undergone several turns through an incision for implanting.
Figure 47A:
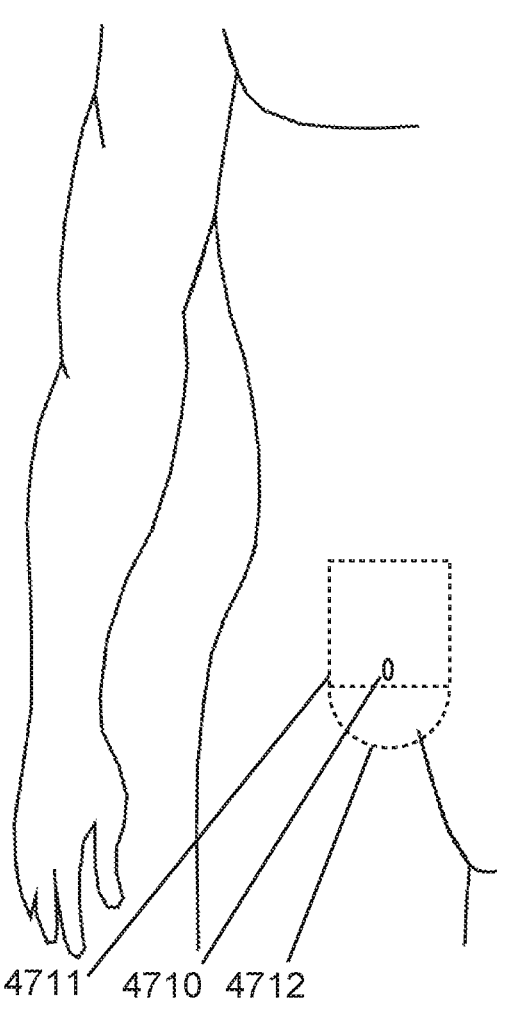
FIG. 47a depicts an implant pocket, implant delivery pocket, and entrance incision.

FIGS. 47a-e depict a method for placing the outer portion/terminus 47010 of a spiral implant into a subcutaneous implant pocket comprised of two pocket portions outlined in dashed lines in FIG. 47a, namely, an implant pocket portion 4711, which may be similar to the pockets previously described, and an implant delivery pocket portion 4712, which is formed below the minimally invasive entrance incision 4710 and opposite the minimally invasive entrance incision relative to the implant pocket portion 4711 in these figures. As described in greater detail below, implant delivery pocket portion 4711, which is semicircular in the depicted embodiment, due to the shape of the implant 4701, but may be formed of other shapes in alternative methods, is a temporary pocket that is only used during implantation of implant 4701. By contrast, implant pocket portion 4711 is configured to fully and, in some cases permanently, receive the full implant 4701.

FIG. 47a depicts the right side of a human torso in which a epidermal/dermal entrance incision 4710 has been made, typically with a scalpel, to create a relatively minimal entrance wound into the subcutaneous/fatty layer below in the inguinal/hypogastric area to create an implant pocket via minimally invasive dissection instrument, such as shown in FIGS. 1 and 2. In some implementations, the pocket location is anywhere on the body that a dissection can practically be made in non-bony, non-cartilaginous tissues.

Figure 47D:
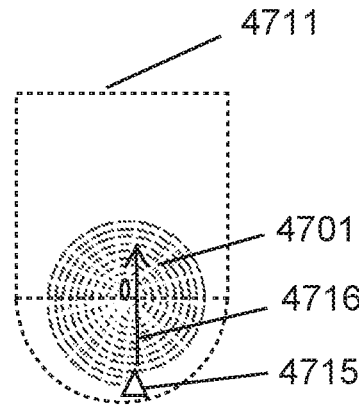
FIG. 47d depicts an implant pocket and delivery pocket, with a spiral implant implanted through incision.
Figure 47B:
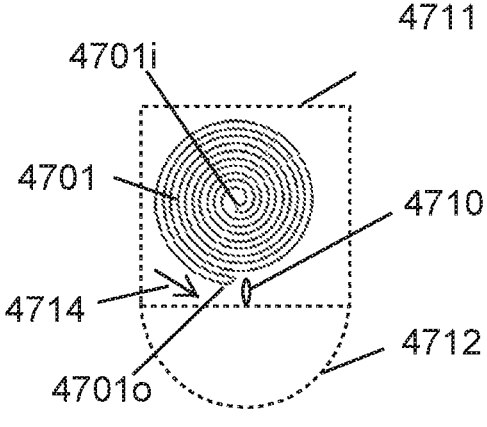
FIG. 47b depicts an implant pocket and delivery pocket, with a spiral implant on the surface of the skin.

FIG. 47b depicts the dashed outline of a implant delivery pocket portion 4712 and a connected polygonal implant pocket 4711 (which may be shaped otherwise in other embodiments) in the subcutaneous layer with minimally invasive entrance wound 4710 lying roughly in-between their intersection/abutment. A spiral implant 4701 is resting pre-placement, as shown in FIG. 47b, on the outside of the skin in which it may eventually be placed almost directly below. Once the spiral implant 4701 is picked up by the surgeon, preferably with sterile technique, the outer portion 47010 of spiral implant 4701 is made to fit through entrance wound 4710 in a rotating direction 4714.

Wires/wiring elements may be coupled to inner coil terminus 4701i and/or outer coil terminus 47010, which may be left in place as the coil is rotated or otherwise positioned within an implant pocket, such as implant pocket 4711. These wires/elements, which are preferably durable and flexible, may remain passing through incision 4710 and, if sufficiently flexible and dynamically connected may rotate with the coil as it turns and is repositioned from outside of the body to within an implant pocket through a minimally invasive entrance incision, as discussed throughout this disclosure.

FIG. 47c depicts the dashed outline of an implant delivery pocket portion 4712 and a connected implant pocket portion 4711 in the subcutaneous layer with minimally invasive entrance wound 4710. Spiral implant 4701 has been rotated several turns now in the direction of arrow 4714 adjacent the outer end/portion of the implant 47010 and thus much of the implant 4701 is depicted in dashed lines indicating that this portion is in the subcutaneous layer below the outer dermal layers of the skin. It is to be noted that the inner terminal end 4701i of the coil and the adjacent portion of the implant 4701 is the region now left for the surgeon to advance and twist as it lies external to entrance wound 4710. Also, much of the implant 4701 has, at the point of the procedure depicted in FIG. 47c, migrated away from the implant pocket portion 4712 and into the implant delivery pocket portion 4711 by virtue of rotational insertion and the shape. Thus, it should be apparent that, if the external terminus 47010 is inserted first, as the implant 4701 is advanced into the body, the implant 4701 will naturally move towards the implant pocket portion 4711.

Figure 47E:
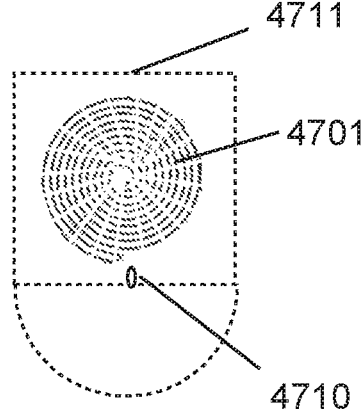
FIG. 47e depicts a spiral implant completely implanted and situated in an implant pocket.
Figures 48A, 48B, 48C, 48D, 48E, 48F, 48G, 48H, 48I, 48J, 48K, 48L:
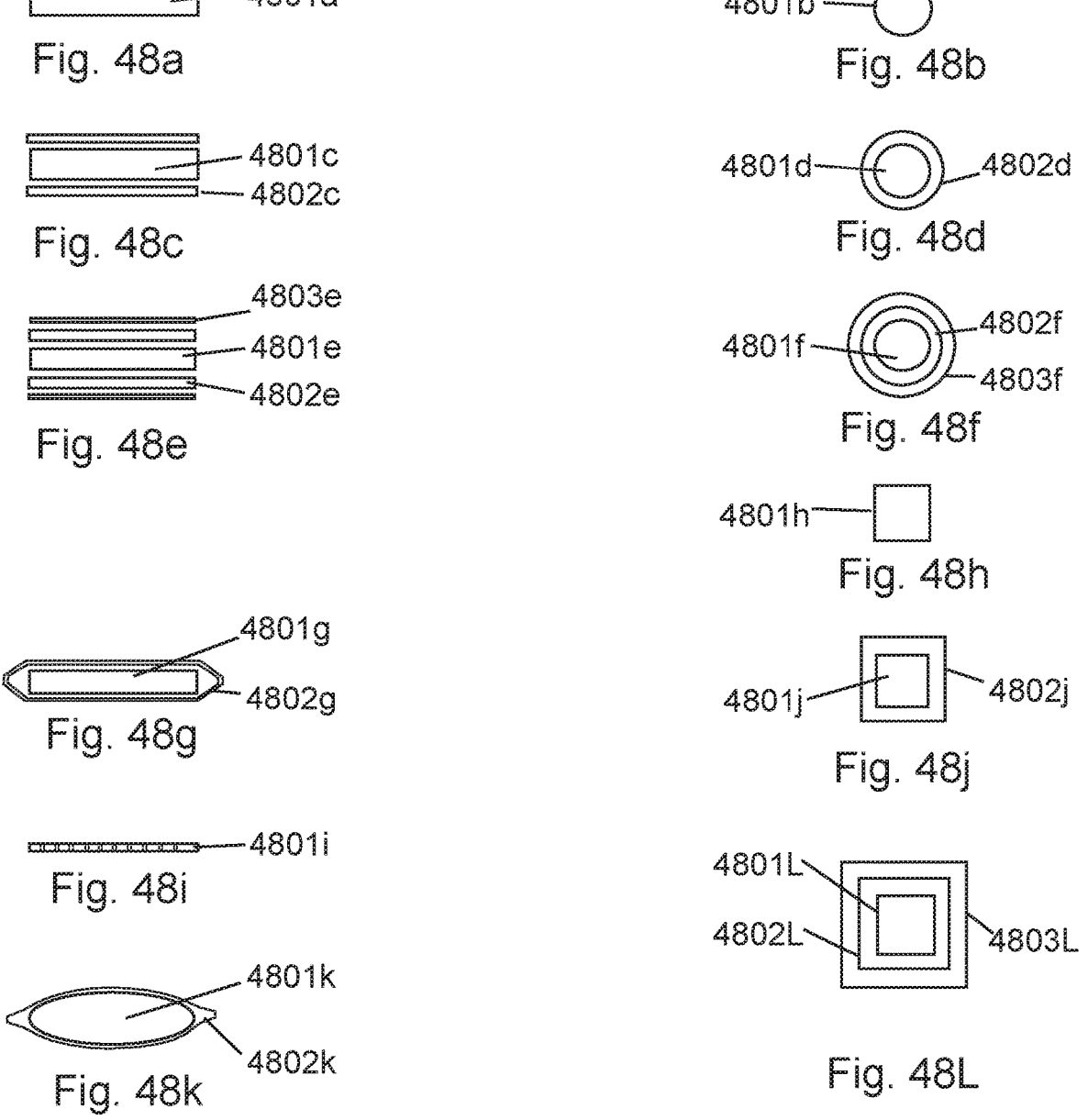
FIG. 48a depicts a flat implant viewed from the side.
FIG. 48b depicts a circular cross-section of an implant.
FIG. 48c depicts a cross-sectional view of an implant comprising an encasement.
FIG. 48d depicts a circular cross-section of an implant comprising an encasement.
FIG. 48e depicts a cross-sectional view of an implant comprising an encasement of multiple layers.
FIG. 48f depicts a circular cross-section of an implant comprising an encasement of multiple layers.
FIG. 48g depicts a cross-sectional view of a fully encased implant.
FIG. 48h depicts a rectangular cross-section of an implant.
FIG. 48i depicts a cross-sectional view of a flattened implant comprising an internal mesh.
FIG. 48j depicts a rectangular cross-section of a fully encased implant.
FIG. 48k depicts an oval-shaped cross-section of a fully encased implant.
FIG. 48l depicts a cross-section of an implant comprising a full encasement of multiple layers

FIG. 47d depicts a subsequent stage of the process at which point the implant 4701 has been fully inserted below the patient/user's skin in the subcutaneous layer. Spiral implant 4701 is now depicted by completely dashed lines and is thus appreciated to be entirely hidden from view below the surface of the skin. The implant 4701 has likely migrated as far as it may go into the implant delivery pocket portion 4712 by virtue of rotational insertion and the shape. The surgeon may then advance the implant 4701 into the implant pocket portion 4711, as shown in FIG. 47e. In some implementations, this may be done via finger pressure on the outer skin by palpation and finger pressure, preferably using the feel of the edge implant 4701 at location 4715 in the direction of the arrow 4716 in FIG. 47d. By pressing the surgeon's finger against the edge of the implant 4701 and pushing in the direction of arrow 4716, akin to kneading dough, the surgeon can migrate the implant 4701 away from the entrance incision more toward and into the implant pocket portion 4711. In some contemplated implementations an instrument or suture may be used to place/move the implant.

FIG. 47e depicts implant 4701 wholly within implant pocket portion 4711 in the subcutaneous layer. The entrance wound may now be sewn shut unless there are more ancillary parts to connect or deliver through the entrance wound, such as a wire, tube, or the like, which may be used to connect the implant with a source of energy, access to drugs, or the like.

In alternative implementations for placing a spiral implant into a subcutaneous implant pocket, the inner portion/terminus 4701i may instead be inserted/passed through the minimally invasive entrance incision 4710 before the outer portion/terminus 47010 and rotated/spun in the direction of the inner portion/terminus 4701i into pocket 4711 with little or none of the implant requiring semicircular implant pocket 4712 for placement, especially if implant 4701 is flexible. Thus there may be no need for semicircular implant pocket 4712 if this alternative method is used. A possible disadvantage of placing a spiral implant where the inner portion/terminus 4701i may be inserted/pass first is that the inner terminus, which moves the least during implantation rotation (as it is the center of a circle) will pass farther into the implant pocket toward the end of the procedure, thus making placement of a fixation suture via the inner terminus 4701i a bit more difficult.

Faraday's law states that the EMF induced by a change in magnetic flux depends on the change in flux A, time $\Delta t$, and number of turns of coils. Thus the number of turns shown in the diagram and/or the apparent spacing may not be representative of the optimal choices for a given use.

FIGS. 48a-48L depict various alternative embodiments of respective spiral implants 4801a-4801L having various alternative configurations. Implant 4801a comprises a flat implant viewed from the side. Implant 4801b comprises a spiral circular implant viewed in cross-section, which may comprise, for example, one band of a spiral implant. Implant 4801c comprises an encasement 4802c, which may comprise one or more layers. Implant 4801d also comprises an encasement/outer layer 4802d. Implant 4801e comprises multiple laminates/layers, namely an inner layer 4802e and an outer layer 4803e. Similarly, implant 4801f comprises an inner encasement 4802f and an outer encasement 4803f. Implant 4801g comprises a flat implant having a full encasement 4802g. Implant 4801h comprises a rectangular-shaped implant in cross-section (again, this may be but one arm/branch of a spiral implant in some embodiments). Implant 4801i comprises a flattened implant comprising an internal mesh. Implant 4801j comprises a full encasement 4802j. Implant 4801k comprises a cross-sectionally oval-shaped bladder-like implant having a corresponding oval-shaped encasement 4802k. Implant 4801L comprises two encasements, namely, an inner encasement 4802L and an outer encasement 4803L. In some contemplated embodiments, part or all of an implant or encasement may be bioabsorbable/biodegradable. However, in other contemplated embodiments, part or all of an implant may not be bioabsorbable/biodegradable; in some of those contemplated embodiments, all or part of the implant may be coated with polytetrafluoroethylene (PTFE) or other inert/biocompatible substances/elements. A coating with such a material and/or the like may make surgical extraction through a relatively small entrance wound more feasible, especially for instruments such as those shown in FIGS. 9a-b. In some contemplated embodiments of spiral/coil and/or mesh type implants, such a coating may be beneficial to facilitate removal and/or minimize tissue interaction.

Figure 49:
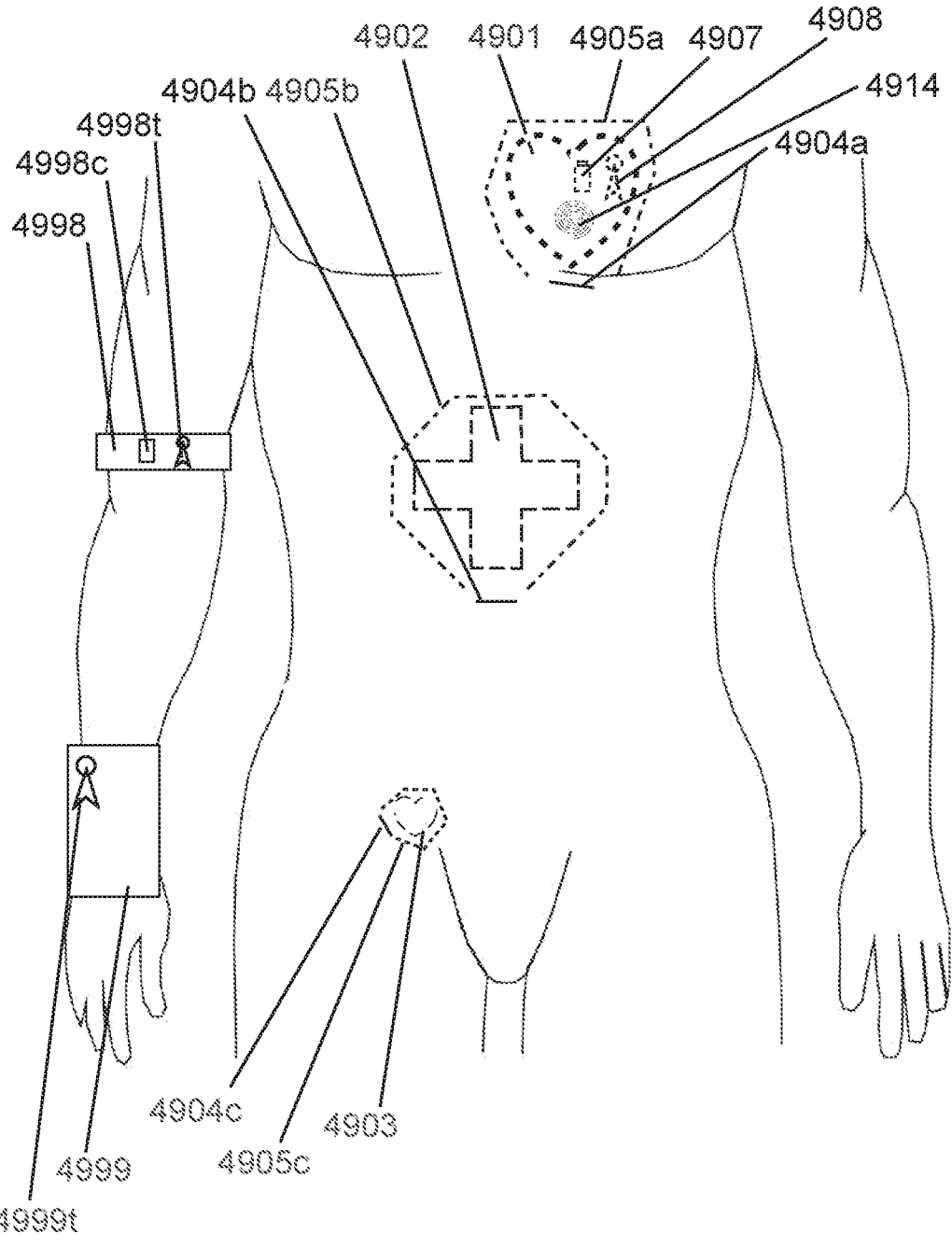
FIG. 49 depicts a human torso having undergone surgery using a lysing tip to form implant pockets which may contain subcutaneous light sources.

FIG. 49 depicts a human patient after having undergone a surgical procedure using a lysing tip, such as a lysing tip having beads and adjacent recesses for delivery of energy therefrom, to form one or more implant pockets, each having one or more dimensions substantially greater than those of the incision 4904*a*/4904*b*/4904*c* used to create the respective pocket 4905*a*/4905*b*/4905*c*. Each of the implant pockets 4905*a*/4905*b*/4905*c* has a respective implant 4901/4902/ 4903 contained therein. In the depicted example, each of the implant pockets 4905*a*/4905*b*/4905*c* contains a respective implant 4901/4902/4903 comprising a subcutaneous tattoo.

Each of the subcutaneous tattoos 4901/4902/4903 shown in FIG. 49 is an illuminated tattoo comprising light sources, such as LEDs, mLEDs, or OLEDs. Thus, implant 4901 comprises a heart-shaped LED subcutaneous tattoo implant, which is positioned within an implant pocket 4905*a* formed in the chest area above the patient's heart organ. Implant 4902 comprises a cross-shaped LED subcutaneous tattoo implant, which is positioned within an implant pocket 4905*b* formed in a central region of the patient's abdomen. Implant 4903 comprises a miniature heart-shaped LED subcutaneous tattoo implant, which is positioned within yet another implant pocket 4905*c* formed adjacent to the patient's groin region.

An external device, such as a smartphone or an external wearable device, such as a watch or other armband 4998, in some embodiments, may be used to detect the heartrate of the patient. Armband 4998 may therefore comprise a heartrate sensor 4998*c* and a wireless transmitter or transceiver 4998*t*, which may allow for sending of signals containing the heartrate to a smartphone 4999 via transceiver 4999*t* and/or to an internal receiver or transceiver that may be part of one or more implants, or auxiliary implants. In this manner, a user may be able to link an internal tattoo, such as implant 4901, with the user's heartrate such that the illumination provided by the implant 4901 matches up with the user's heartbeat. To accomplish this feature, one or more other implants or implant components may be provided, such as an inductance coil 4914 and/or an energy storage source, such as a battery 4907 or supercapacitor, which may be positioned on the implant 4901 or in a connected auxiliary implant. A wireless receiver or transceiver 4908 may be positioned on one or more of the implants, such as implant 4901, and may be configured to receive signals from the heartrate sensor 4998*c*, either directly from the armband 4998 or indirectly through smartphone 4999, which may be programmed to allow a user to, for example, change the colors, patterns, etc. of the illumination provided by the implant 4901, along with, or as an alternative to, linking the pattern to the wearer/user's heartrate.

In some embodiments, thin film encapsulation may be used to encapsulate OLED devices. Methods to perform thin film encapsulation may include, for example, atomic layer deposition (ALD). In some embodiments, Al2O3 may be used as an atomic layer deposed barrier layer. In some instances, O3-based Al2O3 may be used as it may exhibit better barrier properties than H2O-based Al2O3. It may be preferred to use O3 as an ALD reactor, but H2O may be used in some instances. In other embodiments, nanolaminates such as, for example, Al2O3/TiO2, may be prepared by ALD. In some embodiments, barrier structures may comprise hybrid materials with embedded polymers in a laminated structure to combine high barrier properties with high flexibility. Some embodiments may comprise an Al2O3/ HfO2 nanolaminate barrier with an inserted layer of SiNx to help alleviate barrier stress. In some embodiments, OLED devices may benefit from additional heat sink systems. In some such embodiments, ultrathin heat conducting films with high flexibility, ductility, and/or transparency may therefore be used to encapsulate OLED devices. Such barrier layers may simply comprise Ag or Al2O3/Ag/Al2O3 structures to improve anti-reflection effect. In a certain embodiment, a barrier layer may comprise an Al2O3/Ag/Al2O3/ S—H nanocomposite/Al2O3 structure. An organic nanocomposite layer may be inserted to improve flexibility. Additional details regarding such encapsulation methods and materials may be found in "Thin Film Encapsulation for the Organic Light-Emitting Diodes Display via Atomic Layer Deposition", Li, Journal of Materials Research, 2019, DOI: 10.1557/jmr.2019.331, which is hereby incorporated herein in its entirety by reference.

In some embodiments, LED devices may be used for light-emitting sutures, implanted sheets (i.e. LED tattoos), optical sensors, catheters, phototherapy, and the like. In some instances, contacts, interconnections, and/or structural bridges may be printed onto a temporary substrate, which may comprise, for example, PMMA, before being transferred to and integrated on elastomeric sheets, which may comprise, for example, poly(dimethylsiloxane) (PDMS). PDMS may be preferred as it is a soft, elastomeric, biocompatible material. In a preferred embodiment, arrays of mLEDs may be connected by serpentine-shaped ribbons which may serve as electrical interconnects or structural bridges. Such serpentine structures may absorb some or most of the applied strain. In some embodiments, LED devices may comprise multilayer stacks or LED arrays to overcome possibly low LED density within a single array. Integration of numerous arrays may be accomplished with PDMS coatings, which may serve as interlayer dielectrics, encapsulants, and/or adhesives. Such PDMS coatings may, in some embodiments, be as thin as 300 micrometers thick, resulting in four-layer LED system with a thickness of up to ~1.3 mm. In some embodiments, LED devices may be connected in series to allow full control over the entire array. In some instances, an mLED array may be placed on a thin sheet of polyethylene terephthalate film coated with an adhesive epoxy layer, and encapsulated on both sides with PDMS. Thin ceramic-insulated gold wires may be used to connect metal pads around the edges of the array to external power sources. Additional details regarding suitable LED devices may be found in "Waterproof AlInGaP Optoelectronics on Stretchable Substrates with Applications in Biomedicine and Robotics", Kim, Nature Meterials, 2010, DOI: 10.1038/NMAT2879, which is hereby incorporated herein in its entirety by reference.

In some embodiments, stretchable LED arrays may be used in fluid composition sensors, proximity sensors, and/or light emitting sutures. In some embodiments, such LED devices may comprise waterproof protecting elements, thereby permitting interaction of the device with biological environments. In some embodiments, such devices may comprise flexible and/or stretchable electronic circuits, which may comprise inorganic semiconductor elements, controllers in electrical communication with said circuit, and/or a flexible substrate, which may comprise materials such as PDMS, and/or an encapsulation barrier layer which may comprise an elastomer material. In a certain embodiment, the LED device may comprise a suture, which may comprise biocompatible, bioinert materials, or a combination thereof. In certain embodiments, the suture may be bioresorbable, comprising materials such as, for example, PLA, PLGA, and the like. In some instances, such materials may comprise, for example, polyglycolic acid, polylactic acid, polypropylene, polyester, nylon, and the like. In some embodiments, the device may comprise a barrier layer having a microstructured external surface providing a plurality of features, such as, for example, channels, pores, openings, and the like, exposed to the biological environment. In some embodiments, such features may be patterned using replica molding and/or nano-imprint lithography techniques. In some embodiments, the implanted LED device may be used to provide phototherapy to a target tissue. In some embodiments, the device may be in electrical communication with a controller which may, for example, provide a current/voltage to the circuit. In some embodiments, electrical interconnects with the controller may be used, which may comprise wire bonded interconnects, ribbon cables, lithographically patterned conductors, and the like. In some embodiments, LED arrays may comprise, for example, AlInGaP LEDs, GaN LEDs, stacked inorganic LEDs, inorganic LEDs, and the like. In some embodiments, each LED may be individually addressable. In some embodiments, LED arrays may be stacked, in which a stacked LED element may emit green, red, and/or blue light. In some embodiments, the LED array may generate electromagnetic radiation, which may be used for tissue actuation, detection, and/or transmission through a plasmonic crystal or the like. In some instances, the LED array layers may be configured in a laterally offset position such that the LEDs in each layer do not reside on top of each other. In some embodiments, the device may employ an island bridge structure, in which bridges connecting device islands may be wavy, buckled, serpentine, and/or meandering. In certain embodiments, the LED device may be in optical communication with a plasmonic crystal, which may be used to transmit or receive/electromagnetic radiation. Additional details regarding such structures and materials for LEDs may be found in U.S. Patent Application Publication No. 2018/0359850, titled "Waterproof Stretchable Optoelectronics", which is hereby incorporated herein in its entirety by reference.

In some embodiments, flexible and/or stretchable electronic displays may be implanted in the body. Such implantable electronics may comprise, for example, a flexible and/or stretchable substrate, a stretchable and/or flexible circuit supported by the substrate, a barrier layer encapsulating at least a portion of the circuit, and/or substrate. In some embodiments, the flexible/stretchable substrate may comprise polymers, rubber/silicone materials, biocompatible/bioinert materials, gas-permeable elastomeric sheets, and the like. In certain embodiments, the circuit may comprise any combination of, for example, electrodes, transistors, inducers, LEDs, LED arrays, capacitors, sensors, actuators, inductors, controllers, and the like. Other embodiments may comprise circuits comprising nanoribbons, micromembranes, and/or nanomembranes, which may comprise, for example, metallic structures, crystalline structures, or any hybrid thereof. In some instances, the circuit may comprise island and bridge structures. In some embodiments, the barrier layer may comprise, for example, polymers (organic/inorganic), elastomers, biopolymers, biocompatible/bioinert materials, and the like. Some examples of barrier compositions may include, for example, acrylate polymers, siloxane polymers, cyanoacrylates, and the like. The barrier layer may be used, in some embodiments, for functions such as, for example, electronic, thermal, and/or optical insulation from the biological environment. Such implanted electronics may also comprise a multilayer geometry. For example, the substrate, circuit, and barrier layer may comprise stacked layers, potentially with intermediate layers. In some embodiments, the barrier may be structured to comprise optically transmissive/opaque regions, and/or regions permeable to select molecules. In other embodiments, the barrier may comprise, for example, multilayer structures and/or nano/microstructured features. In certain embodiments, actuating elements may include, for example, electrode elements, electromagnetic radiation-emitting elements, LEDs, lasers, and the like. Additional details regarding such electronic devices may be found in U.S. Patent Application Publication No. 2020/0315488, titled "Flexible and Stretchable Electronic Systems for Epidermal Electronics", which is hereby incorporated in its entirety by reference.

In some instances, implanted devices may be configured to use light or other electromagnetic radiation for therapeutic purposes. Such implanted devices may comprise, for example, an antenna, circuitry, supercapacitors, light sources (which may be assembled into an array), and/or fiber optic light guides (to guide light to the target tissue). In certain embodiments, the device may receive energy via transcutaneous wireless transmission from an external coil, which may charge a supercapacitor, which may, in turn, provide power to the light sources. In a preferred embodiment, the device may use light to target light-sensitive proteins, triggering a change within the targeted tissue. In certain embodiments, the device may be remotely powered and/or employ wireless communication. In some instances, the device may be controlled via onboard computer or external data telemetry. In some embodiments, the light sources may comprise, for example, LEDs or lasers. Additional details regarding such light therapy devices and methods may be found in U.S. Patent Application Publication No. 2014/0324138, titled "Wirelessly-Powered Illumination of Biological Tissue", which is hereby incorporated in its entirety by reference.

A peeling reduction layer may be used in some embodiments, for example, to reduce potential peeling of an OLED panel. The OLED device may comprise, for example, a substrate (comprising opening and non-opening regions), OLEDs disposed on the substrate, a bank layer on a non-opening region, and a peeling reduction layer having a reverse-tapered shape disposed in the non-opening area. Additional details regarding OLED devices with peeling reduction layers may be found in U.S. Pat. No. 9,570,524, titled "Flexible Organic Light Emitting Diode Display Panel", which is hereby incorporated in its entirety by reference.

In some embodiments, LEDs may comprise a layered stack, which may comprise, for example, a p-type layer, an n-type layer, and a p/n junction therebetween. In certain instances, a p-electrode may be disposed on a first side of the substrate in contact with the p-type layer on an exposed surface and an n-electrode on a first side of the substrate in contact with a surface of an n+ sub-layer of the n-type layer. Additional details regarding such LEDs may be found in U.S. Pat. No. 8,502,192 titled "LED with Uniform Current Spreading and Method of Fabrication", which is hereby incorporated in its entirety by reference.

In some embodiments, LED chips may comprise a plurality of sub-LEDs mounted on a submount. In some instances, sub-LEDs may be serially interconnected such that the voltage necessary to drive the sub-LEDs depends on the number of sub-LEDs and the junction voltage of the sub-LEDs. Additional details regarding such LED devices may be found in U.S. Pat. No. 8,530,921, titled "High Voltage Low Current Surface Emitting LED", which is hereby incorporated in its entirety by reference.

Some embodiments may comprise implanted LED devices configured for cell stimulation. In some instances, gene transfer (via methods such as, for example, a virus) may be used to induce expression of photosensitive biomolecular proteins. Such proteins may comprise, for example, photosensitive proteins that bind to target cells. In other embodiments, the device may be used to stimulate electrically-excitable cells, such as, for example, neurons. Additional details regarding such devices may be found in U.S. Patent Application Publication No. 2008/0085265, titled "System for Optical Stimulation of Target Cells", which is hereby incorporated in its entirety by reference.

In some instances, LED devices may be used to stimulate target cells along an elongated light-delivery passageway. Such devices, in some embodiments, may be used to deliver light to light-responsive proteins adjacent to activated light sources along the elongated light-delivery structure. Such cells may comprise, for example, neurons, which may be genetically altered to express proteins such as, for example, ChR2, rendering the neurons responsive to light. Additional details regarding such light-stimulation devices and techniques may be found in U.S. Pat. No. 10,426,970, titled "Implantable Optical Stimulators", which is hereby incorporated in its entirety by reference.

In some embodiments, LED devices may be flexible. Such devices may comprise, for example, a flexible LED module in which LEDs are disposed in an array on a flexible circuit board, a protective sheet covering the LEDs, a heat conduction sheet under the flexible LED module, and/or a heat radiation sheet under the heat conduction sheet. Additional details regarding such flexible LED devices may be found in U.S. Pat. No. 10,107,488, titled "Flexible LED Substrate Device", which is hereby incorporated in its entirety by reference.

In some embodiments, OLED displays may be flexible. Such devices may comprise, for example, multi-layer encapsulation films with a metal layer on or within a bending portion of the film. Such multi-layer encapsulation films may include, for example, at least a first inorganic layer, an organic layer, and a second inorganic layer. The metal layer may be formed and placed such that it reduces the stress generated and prevents cracks from forming within the encapsulation film due to bending. Additional details regarding such flexible OLED devices may be found in U.S. Pat. No. 10,326,109, titled "Flexible Organic Light Emitting Diode Display Device", which is hereby incorporated in its entirety by reference.

In some embodiments, organic LEDs may be used as part of and/or in connection with various implants disclosed herein. Such LEDs may be implemented into circuits by linking the anode to the positive terminal side of a battery preferably contained on the implant and linking the cathode of the OLED to the negative battery terminal side. In circuits with OLEDs, current limiting resistors may be useful as well, as too much current can cause burn-out. Other OLED properties worthy of consideration may include forward voltage drop, maximum recommended current, and luminosity.

Micro LED (mLED) devices may be used in some embodiments, such as embodiments involving illuminated internal tattoos. Such devices may comprise, for example, two-dimensional arrays of parallel-addressed InGaN blue micro-LEDs. InGaN or GaN LEDs may offer new approaches to allow more light to be released from LEDs by increasing surface area via etching of microdisks. LED wafers may be grown of sapphire substrates while employing GaN buffer layers, Si-doped GaN layers, InGaN/GaN multi-quantum wells for emission. SiO2 layers may be used as insulation layers before Ti or Al are used for the n-contact and Ni or Au are used for the p-contact. Sloped sidewalls may be employed to allow individual elements to be easily interconnected in parallel via metallization. Although LEDs, mLEDs, or the like may be preferred, any light sources, including incandescent light sources, may be used in various embodiments. Further details regarding GaN-based mLEDs may be found in 'Efficient GaN-based Micro-LED Arrays', Choi, 2003, Mat. Res. Soc. Symp. Proc. Vol. 743, Materials Research Society, which is hereby incorporated in its entirety by reference.

Microdisplays (mD) may be comprise, in some embodiments, GaN-based mLEDs of green and blue with transparent epitaxial and insulating sapphire substrates. Red mLEDs may comprise, for example, AlGaInP, which may be grown on opaque and/or conductive GaAs substrates. AlGaInP epilayers may also be used for certain applications, in which epilayers may, for example, be bound to double polished sapphire substrates via, for example, wafer-bonding followed by removal of the absorbing GaAs substrate. In order to improve performance of red mLEDs, the epilayer of the mLEDs may be transferred to a sapphire substrate via wafer bonding in some embodiments and implementations. Luminescence of such mLEDs may be dependent on current; as distance from the p-contact increases, resistance increases, leading to a decrease in brightness. Thus, the amount of current delivered to the mLEDs may be adjusted by the user, such as via a wireless communication technology, such as Bluetooth®, to allow the user to adjust the lighting and/or display of the underlying implant. Further details regarding mLEDs and microdisplays that may be useful in connection with one of more of the embodiments disclosed herein, such as AlGaInP-based red mLEDs, may be found in 'Fabrication and Study on Red Light Micro-LED Displays, Horng, 2018, IEEE 2168-6734 (c), which is hereby incorporated in its entirety by reference.

mLED displays may, in some embodiments, be based on inorganic GaN-based LEDs. mLED displays may offer advantages such as high resolution, high brightness, flexibility, durability/reliability, low power consumption, and fast response time. The growth technique, transfer printing technique, and/or color conversion technique may be used to yield a full-color mLED display, which may comprise and/or be part of various implants disclosed herein. mLEDs may include, for example, nanowire LEDs, multicolor quantum well (QW) mLEDs, and nanoring LEDs. QW mLEDs may be integrated with complementary metal-oxide-semiconductors (CMOS) for certain uses. Transfer printing techniques for assembly and processing of mLED displays may include, for example, the pick-and-place process (which may utilize polydimethylsiloxane stamps (PDMS)), laser selective-release, electrostatic pick-up transfer, electromagnetic pick-up transfer, and/or fluidic transfer. Color conversion may be achieved via one or more of the following methods: using UV mLED arrays to excite organic fluorescent materials; and combining quantum dots and inkjet printing technique with UV mLED arrays. Color conversion may be achieved with materials such as colloidal CdSe/ZnS nanocrystals combined with self-aligned curing methods to limit the material to the top of designated UV mLEDs. Donor substrates for mLEDs may include Si, SiC, sapphire substrates, and others. To form a top-emission mLED, epitaxial growth of mLED may be performed on the substrate by, for example, metal-organic chemical vapor deposition (MOCVD). In some embodiments, the epitaxial structure may consist of a doped GaN buffer layer, a n-GaN layer, an InGaN/GaN multiple QW region, and a p-GaN layer. An indium tin oxide (ITO) film, which may be formed via electron beam evaporation of magnetron supporting, may be fabricated on the surface of the p-GaN layer. The epitaxial wafer may then be mesa-etched by, for example, inductively coupled plasma and thermally annealed to form a p-type ohmic contact of p-GaN. Plasma-enhanced chemical vapor deposition may be used to deposit a SiO2 passivation layer for certain embodiments. Sputtering may be used to deposit a Ti/Au layer on the ITO layer to form a p-pad. Substrate removal may be useful in connection with full-color displays. Removal methods may include, for example, the laser lift-off technique (which only works with UV-transparent substrates, such as sapphire substrates), and the chemical substrate removal method (which may only be viable with Si substrate). Nanostructure pixels for full-color mLED displays may be precisely fabricated through high-resolution photolithography. Selective-area growth techniques (SAG) may allow precise control over the growth of InGaN/GaN nanowires. Nanowire (ensemble InGaN/GaN or single) diameter may be increased to yield color emissions shifting from blue to red. Core-shell nanowires composed of, for example, lateral and longitudinal QWs may have color modulation due to changes in bias voltages, shifting from red to blue as voltage increases. Again, this introduces the possibility of modulating the voltage of the LEDs/display to selectively adjust one or more aspects and/or parameters of the implant. Nanoring LED fabrication via monolithic epitaxial growth may also be used to yield full-color mLED displays. Color conversion may be utilized in some embodiments to change the colors of monochrome mLEDs. Red and green lights may be obtained by exciting red and green quantum dots or phosphors with blue/UV mLEDs. AJ printing methods for color conversion may be coupled with photoresist molds to reduce optical crosstalk and improve color purity. Geometric color converters may also be employed to improve contrast and purity of mLED colors. The liquid-capillary force transferring technique may be used in the process of color conversion. Further details regarding mLED technology and mLED displays that may be useful in connection with one or more of the implants disclosed herein may be found in 'Growth, Transfer Printing and Colour Conversion Techniques Towards Full-Colour Micro-LED Display', Zhou, 2020, JPQE, 100263, which is hereby incorporated in its entirety by reference.

mLEDs may also employ color filters in some embodiments to change the color of monochromatic mLEDs to encompass the RGB spectrum. Furthermore, mLED displays may utilize flexible substrates to allow for flexible displays, which may be particularly useful due to the nature of the implants disclosed herein in preferred embodiments. Variations in luminance may occur and thus require correction to yield uniform brightness across the display. Further details surrounding such mLED displays may be found in 'Progress in MicroLED Fabrication and Quality: Closing the Commercialization Gap', Corning, 2021, Radiant Vision Systems, radiantvisionsystems.com/blog/progress-microled-fabrication-and-quality-closing-commercialization-gap, which is hereby incorporated in its entirety by reference.

mLED arrays may constitute direct-view mLED displays or mLED microdisplays. Direct-view mLED displays may, for example, comprise mLEDs fabricated with small pixel pitches, separated into individual dice, and transferred to an active-matrix backplane using methods such as the pick-and-place technique. The larger expansion may allow for high luminescence displays. The large unoccupied space between individual LEDs may allow for interconnection electronics and larger current distribution for passive-matrix display development and integration and also permits active-matrix approaches for large-areas. Resulting large (3-70 in) direct-view mLED displays may show improved luminescence coupled with improved color gamut. Secondary substrates for direct-view mLED displays may include glass or flexible substrates. Active-matrix formats may be formulated by transferring mLEDs to secondary substrates with, for example, indium gallium zinc oxide and/or low-temperature polysilicon transistors. mLED microdisplays may use semiconductor integration to combine small pixel-pitch mLEDs with transistor back plates, which may be integrated with optical systems. Due to the small pixel-pitch for micro displays, the scaling of mLEDs may benefit from full integration at the wafer-fabrication level, resulting in active-matrix schemes as passive-matrix schemes may be unable to achieve brightness or resolution for displays under 2 in. Methods for semiconductor integration may include pixel-to-transistor bonding, chip-level mLED pixel-to-CMOS-transistor bonding, LED epitaxial transfer to silicon CMOS, and/or integration with thin-film transistors. Micro-tube technology may aid in the bonding process in chip-level bonding. Transistors may be fabricated from polycrystalline silicon to yield a high-performance low-temperature transistor from which necessary circuits may be formed. Colors may be generated via, for example, one or more of the following methods: combining three mLED microdisplays; integration of phosphor materials; and stacking of red, green, and blue epitaxial layers. Parabolic mLED structure may be used for light collimation and light extraction (analogous to InfiniLED®'s mLED technology). Further information on mLED displays may be found in 'Micro-LED Technologies and Applications', Lee, Frontline Technology, 2016, which is hereby incorporated in its entirety by reference.

In some embodiments, micro LED (mLED) displays for use in implants may be assembled using micro-printing technology. In some instances, mLED devices may be prepared on a native substrate and be printed onto a display substrate, which may be, for example, flexible and/or transparent. Such methods may allow for the formation of mLEDs under conditions that may not be suitable for the display substrate. Certain embodiments may comprise display substrates comprising, for example, plastic, polymers, resins, sapphire, and the like. Some embodiments may comprise displays with sparsely distributed mLEDs and/or integrated functions such as embedded memory, micro-sensors (such as light sensors), power harvesting devices, antennae, and the like. In some instances, additional mLEDs of different colors, such as yellow, cyan, or slightly different RGB emitters, may be used to broaden the color gamut. Additional details regarding such displays may be found in U.S. Patent Application Publication No. 2015/0372051, titled "Micro Assembled LED Displays and Lighting Elements", which is hereby incorporated in its entirety by reference.

Processes such as bonding and laser lift off may be used to transfer mLEDs from the working substrate onto the carrier substrate, which may, for example comprise flexible and/or biocompatible materials. It may be preferable for certain applications that the carrier substrate comprises at least two layers, which may include a carrier layer and flexible polymer layers. Such a carrier substrate may allow singulated LED structures to be embedded within a flexible environment, which may be particularly useful for some of the implants disclosed herein. Certain embodiments may comprise, for example, GaN-based mLED matrices on flexible substrates, suitable for implanting within the body. Additional details regarding such methodologies and systems may be found in U.S. Pat. No. 10,276,631, titled "Method for Producing a Micro-LED Martix, Micro-LED Matrix and Use of a Micro-LED Matrix", which is hereby incorporated in its entirety by reference.

Certain embodiments of flexible mLED devices may comprise, for example, a flexible substrate, upper insulating film, lower insulating film, a thin metal layer between the upper and lower insulating films, a plurality of mLED chips arrayed on the top surface of the flexible substrate, and/or a light-transmitting resin on the top surface of the flexible substrate to cover the top and side surfaces of the mLED chips. In some embodiments, the flexible substrate may comprise a reflective layer, such as a white reflective layer, which may be in contact with the light-transmitting resin. Further details regarding such mLED displays may be found in U.S. Patent Application Publication No. 2021/0265328, titled "Flexible Lighting Device and Display Panel Using Micro LED Chips", which is hereby incorporated in its entirety by reference.

In some instances, mLED devices may include, for example, those in which CMOS (complementary metal-oxide-semiconductor) cells may be arranged in a mLED driving substrate backplane and a mLED panel which may be flip-chip bonded onto the driving substrate. In certain embodiments of the mLED panel, mLED pixels may be electrically connected with the CMOS cells, in which mLED pixels may be formed by etching a first surface of an emission structure along a pixel region, and separators may be formed on a second surface in between locations of mLED pixels. Additional information regarding such mLED displays may be found in U.S. Pat. No. 10,636,349, titled "Micro LED Display Device and Method of Fabricating the Same", which is hereby incorporated in its entirety by reference.

Reflective pixels in or beneath a display viewing area may be used in certain embodiments such as, for example, a reflective display with a mLED front light. Some embodiments may include a display comprising a layer of reflective pixels beneath a viewing area, and a layer, which may be, for example, a transparent layer, which may be positioned on or over the reflective display viewing area. In some instances, the layer (transparent in this example) may comprise a plurality of mLEDs oriented to emit light toward the reflective display viewing area, a plurality of conductors electrically connected to the mLEDs, and/or a controller for mLED function. Additional details regarding such reflective displays may be found in U.S. Pat. No. 10,133,426, titled "Display with Micro-LED Front Light", which is hereby incorporated in its entirety by reference.

In some instances, mLED devices may comprise a receiving substrate and a mLED. In certain embodiments, the mLED may constitute first and second semiconductor layers, a current controlling layer, reflective layers, and/or one or more electrodes. The first and second type semiconductors may be joined. The current controlling layer may be joined with the semiconductor layers, and may comprise at least one opening therein. The reflective layer may be electrically coupled with the first type semiconductor layer. The first electrode may be positioned on the receiving-substrate layer-facing side of the reflective layer, acting as an adhesive bonding system with the receiving substrate. Additional details regarding such mLED devices may be found in U.S. Pat. No. 10,297,719, titled "Micro-Light Emitting Diode (Micro-LED) Device", which is hereby incorporated in its entirety by reference.

Some embodiments of mLED devices may constitute mLEDs comprising, for example, a micro p-n diode and a metallization layer between the p-n diode and a bonding layer. In some instances, a conformal dielectric barrier may span the sidewalls of the p-n diode. In some embodiments, the bottom surface of the p-n diode may be wider than the top surface of the p-n diode, which may be accomplished by, for example, providing tapered sidewalls. In other embodiments, the top surface of the p-n diode may be wider than the bottom surface of the p-n diode, or of the same width as the bottom layer. In other embodiments, the bottom surface of the p-n diode may be wider than the top surface of the metallization layer. Once formed, the mLED structure and arrays may be transferred from a native substrate to a receiving substrate. In certain embodiments, the receiving substrate may comprise, for example, a lighting substrate, a substrate with devices such as transistors or integrated circuits, and/or substrates with metal redistribution lines. Additional details regarding such mLED devices may be found in U.S. Pat. No. 10,297,712, titled "Micro LED Display", which is hereby incorporated in its entirety by reference.

The subcutaneous tattoos 4901/4902/4903 shown in FIG. 49 may also comprise organic LED devices in some embodiments, such as organic Polymer LEDs (PLEDs), which may be as thin as 3 micrometers or less. Such PLEDs may be manufactured, for example, on ultrathin parylene films while using transparent electrodes from indium tin oxide (ITO). A protective passivation layer (which may comprise of 5 alternating layers of SiON and Parylene) may be inserted into the display film to improve durability and half-life of the PLED. The aforementioned PLED system may, in some embodiments and implementations, be used in conjunction with organic photodetectors (OPD) to yield ultrathin sensors, such as reflective pulse oximeters. Such organic optical devices may also be made flexible and stretchable by using rubber substrates and laminating in prestretched acrylic tape-silicone rubber sheets. Further information regarding such PLEDs may be found in 'Ultraflexible Organic Photonic Skin', Yokota, 2016, advantages.sciencemag.org, which is hereby incorporated in its entirety by reference.

Organic LEDs are often extremely sensitive to water vapor and oxygen exposure. Thin Film Encapsulation (TFE) methods may therefore be employed for encapsulating implantable OLED devices into a biocompatible implant. In order to minimize risk of damaging the OLEDs, films may need to be applied at lower temperatures, which may lead to defects. Multilayer films with alternating stacks may be used if desired such that defects in each individual layer do not span the whole thickness of the encapsulation. One layer of the alternating stack in some cases may be composed of TPD (TPD-N, N'-diphenyl-N, N'-bis-3-methylphenyl [1,1'-biphenyl]-4,4'-diamine, while another layer may be composed of a synthesized material XP (2.2.6. 5,5'-(4,4'-(2,6-di-tert-butylanthracene-9,10-diyl)bis(4,1-phenylene)) bis(2-(4-hexylphenyl)-1,3,4-oxadiazole). Vacuum thermal deposition may be used in some embodiments to form the alternating stack for encapsulation. Further details may be found in 'New Organic Thin-Film Encapsulation for Organic Light Emitting Diodes', Grover, Scientific Research, 2011; 1:23-28, which is hereby incorporated in its entirety by reference.

Some implantable LEDs may comprise biocompatible polymers, such as poly(dimethylsiloxane) (PDMS), to create a mesh-like array of LEDs. Polymers such as PDMS may make the array flexible and/or stretchable. Further information regarding such implantable LEDs may be found in 'Flexible LEDs For Implanting Under the Skin', Edwards, 2010, which is hereby incorporated in its entirety by reference.

Additional embodiments may involve and/or comprise encapsulation materials for OLED devices to prevent damage from external sources. In some embodiments, thin film barriers may be ideal, as thin film barriers provide the OLED with flexible capabilities. Such barriers may include, for example, alternating layers of Al2O3 and polymerized hexane. On top of such thin film barriers, biocompatible layers may be placed to protect the receiving organism. Further information regarding encapsulation for OLED devices may be found in 'Review of Organic/Inorganic Thin Film Encapsulation by Atomic Layer Deposition for a Flexible OLED Display', Lee, The Minerals, Metals, and Materials Society, 2018, which is hereby incorporated in its entirety by reference.

OLED devices may also be fabricated in such a way that they do not require being attached to a substrate. Some such OLEDs may be sandwiched between 2 hybrid TFE (thin film encapsulation) layers (one composed of Al2O3/ZrO2 nano-laminates and the other Parylene-C). Such substrateless encapsulation may make the OLED flexible and water-resistant. Further information on substrateless OLED devices may be found in 'A Substrateless, Flexible, and Water-Resistant Organic Light Emitting Diode', Keum, Nature Communications, 2020; 11:6250, which is hereby incorporated in its entirety by reference.

Each of the implant pockets may be formed and sized to specifically accommodate a particular implant. Thus, the implant pocket 4905b containing the cross is largest to accommodate the largest of the depicted tattoo implants and the implant pocket 4905c containing the miniature heart is smallest to accommodate the smallest of the depicted tattoo implants. However, each of the implant pockets, along with each of the respective implants 4901/4902/4903, is substantially larger than the incision made in order to form the pocket. More particularly, each incision has a length that is substantially smaller than the "width" or largest dimension of the implant pocket parallel to the incision.

In preferred embodiments and implementations, the length of each incision 4904a/4904b/4904c may be between about 5 mm and about 25 mm. In some such embodiments and implementations, the length of the incision 4904a/4904b/4904c may be between about 12 mm and about 18 mm. Thus, the procedures described herein can all be considered minimally invasive and should lead to little scarring. However, the size of the implant and implant pocket can be much larger, due to the techniques and inventive structures and features described herein.

For example, in some embodiments and implementations, the size of the implant pocket may therefore have a maximum dimension that is more than three times the length of the entrance incision. In some such embodiments and implementations, the size of the implant pocket may therefore have a maximum dimension that is more than four times the length of the entrance incision. In some such embodiments and implementations, the size of the implant pocket may therefore have a maximum dimension that is more than five times the length of the entrance incision.

In some embodiments and implementations, the size of the implant pocket may have a maximum dimension in a direction parallel, or at least substantially parallel, to a direction of the incision, that is more than three, four, or five times the length of the entrance incision.

In some embodiments and implementations, the implant pocket may have a minimum dimension of at least three, four, or five times the length of the entrance incision.

In some embodiments, the implant itself may be configured to be substantially reduced in size to allow for insertion through the entrance incision and then expanded once past the entrance incision and is within the implant pocket. This reduction and expansion in size may be accomplished, for example, by compressing, rolling, and/or folding the implant, as previously discussed.

In some preferred embodiments and implementations, the maximal dimension of the uncompressed implant—in height, width, and/or any measurable dimension—after implantation may be at least four times the maximal, cross-sectional dimension of the implant in its compressed/deployment configuration. In some such embodiments and implementations, the maximal dimension of the uncompressed implant—in height, width, and/or any measurable dimension—after implantation may be at least seven times the maximal, cross-sectional dimension of the implant in its compressed/deployment configuration. In some such embodiments and implementations, the maximal dimension of the uncompressed implant—in height, width, and/or any measurable dimension—after implantation may be at least ten times the maximal, cross-sectional dimension of the implant in its compressed/deployment configuration.

In some embodiments and implementations, the implant in its deployed or uncompressed (uncompressed should be considered to encompass any implant in a state prior to its having been rolled, folded, or otherwise compressed or after it has been unrolled, unfolded, or otherwise decompressed; in the case of an inflatable implant, uncompressed should be considered to encompass the implant in its final, fully inflated configuration) configuration has a minimum cross-sectional dimension that is more than three, four, or five times the minimum cross-sectional dimension of the implant in its compressed or delivery configuration so that it can be inserted through the aforementioned, minimally invasive entrance incision.

In some embodiments and implementations, the subcutaneous tattoo implants may be programmable and/or wirelessly rechargeable. For example, a user may be able to change the color of the light emitted by the LEDs, turn them on or off, and/or make them flash, possibly in a desired pattern of flashing. In addition, as discussed in greater detail below, the implants may comprise induction coils and/or circuits to allow for wireless recharging.

Figures 50, 51A, 51B, 52A, 52B:
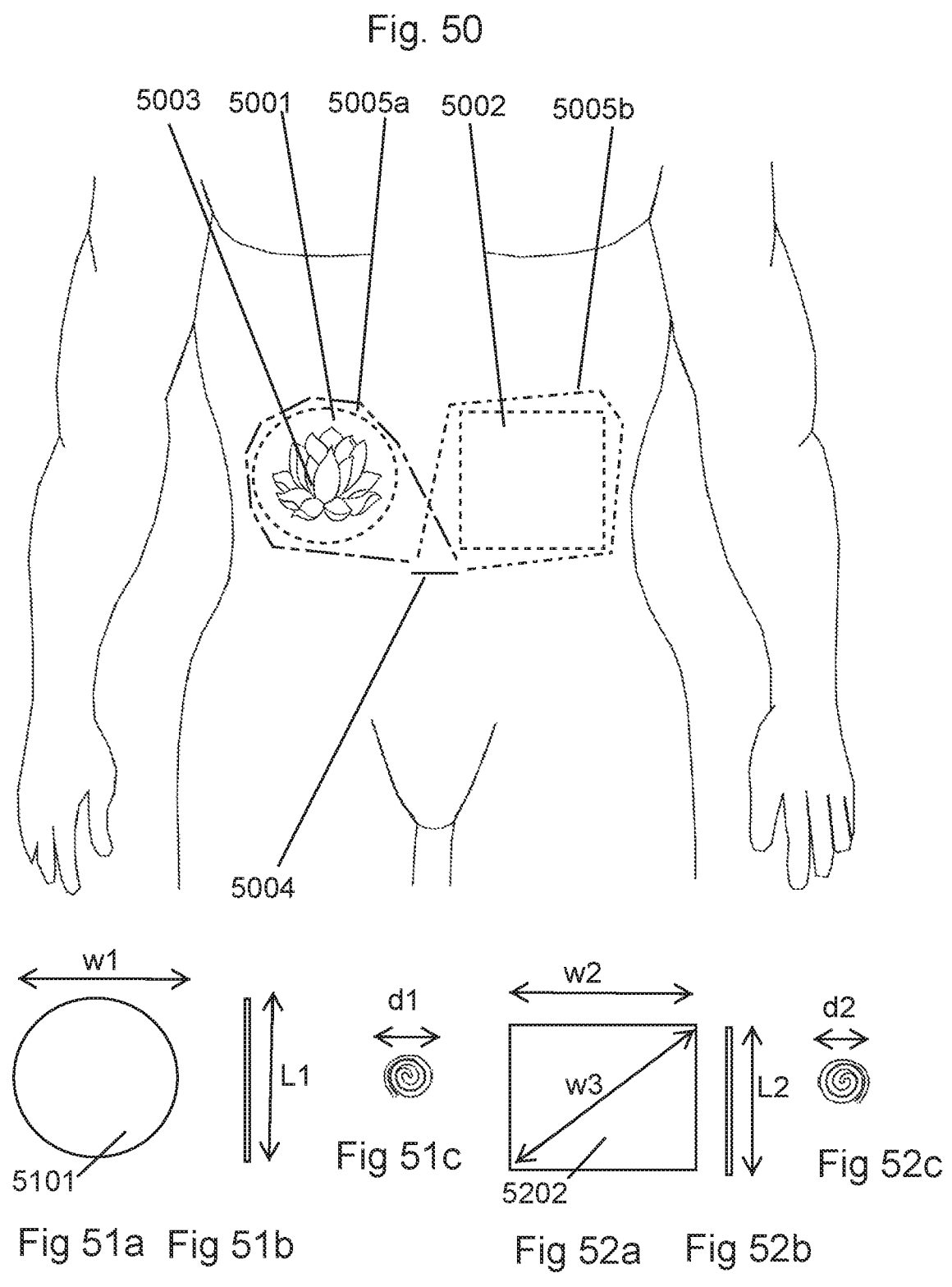

FIG. 50 depicts another human patient having other subcutaneous, compressible implants positioned in respective implant pockets. More particularly, a light sheet 5001 is positioned within an implant pocket 5005a behind a traditional, ink tattoo 5003. This may allow a user to selectively illuminate a tattoo. Light sheet 5001 may, in some embodiments, comprise a flexible, compressible sheet comprising light sources, such as LEDs, mLEDs, or OLEDs. Again, implant pocket 5005a is much "larger" (as described previously) than the entrance incision 5004 used to allow a lysing tip to enter the subcutaneous region of the body and to create the implant pocket 5005a. Similarly, light sheet 5001 is, in its deployed and/or uncompressed state, much "larger" than it is in its compressed state and much larger than the length of the entrance incision 5004.

Another subcutaneous, compressible implant is shown at 5002. Implant 5002 may comprise a screen, such as an LED screen, that may be used to display an image or video, for example. Again, implant 5002 is positioned within an implant pocket 5005b, as previously described, and may be deployed in a compressed state, such as a rolled state, and then unrolled or otherwise decompressed once inserted through the entrance incision and positioned within the implant pocket. In the depicted embodiment, due to the nature of the lysing tip and the techniques involved in creating the implant pocket, the same entrance incision 5004 may be used to create both implant pockets 5005*a*/5005*b*. Indeed, as shown in FIG. 50, implant pocket 5005*a* may be formed by extending a tissue dissector towards the left from incision 5004 and implant pocket 5005*b* may be formed by extending the tissue dissector towards the right from incision 5004, in both cases preferably with a back and forth motion that progressively widens the respective pocket.

FIG. 51*a* depicts a plan view of the implant 5101 in its deployed/uncompressed state. FIG. 51*b* depicts a side view of implant 5101 in its deployed/uncompressed state. FIG. 51*c* depicts a side view of implant 5101 in its compressed state, which, as previously mentioned, is the state within which implant 5101 may be inserted through an entrance incision. In the depicted embodiment, compressing implant 5101 comprises rolling implant 5101, as shown in FIG. 51*c*.

The distance w1 shown in FIG. 51*a* is the width or diameter of the implant. Similarly, the distance L1 is the length of the implant. In the case of a circular implant, distances W1 and L1 are the same. However, this may not be the case in, for example, a rectangular implant. Distance d1 is the cross-sectional diameter of the implant following compression (rolling in the case of the depicted embodiment) to prepare for insertion into a patient. Although d1 is a diameter in the case of a rolled implant forming a circular shape in cross section, this need not be the case in all contemplated embodiments. Thus, it should be understood that, for example, in the case of implants that are folded, d1 may be a corner to corner diagonal distance. D1 should therefore be considered the maximal cross-sectional dimension of the implant in its compressed configuration (and therefore the dimension that must be minimized in order to minimize the size of the entrance wound.

FIG. 52*a* depicts a plan view of the implant 5202 in its deployed/uncompressed state. FIG. 52*b* depicts a side view of implant 5202 in its deployed/uncompressed state. FIG. 52*c* depicts a side view of implant 5202 in its compressed state, which, as previously mentioned, is the state within which implant 5202 may be inserted through an entrance incision. As with implant 5201, implant 5202 is rolled in its compressed state. However, as discussed elsewhere in this disclosure, alternative embodiments are contemplated in which implants may be compressed in other ways, such as by folding them, deflating them, or the like.

Similar distances are shown in FIGS. 52*a*-52*c*. Thus, distance w2 is the width of rectangular-shaped implant 5202 prior to compression and w3 is the maximal distance of the implant in this configuration from this view. Similarly, L2 is the length of the implant, which may differ from w2 for non-square, rectangular implants, and d2 is the maximal cross-sectional dimension in the compressed configuration.

Figures 53A, 53B, 53C:
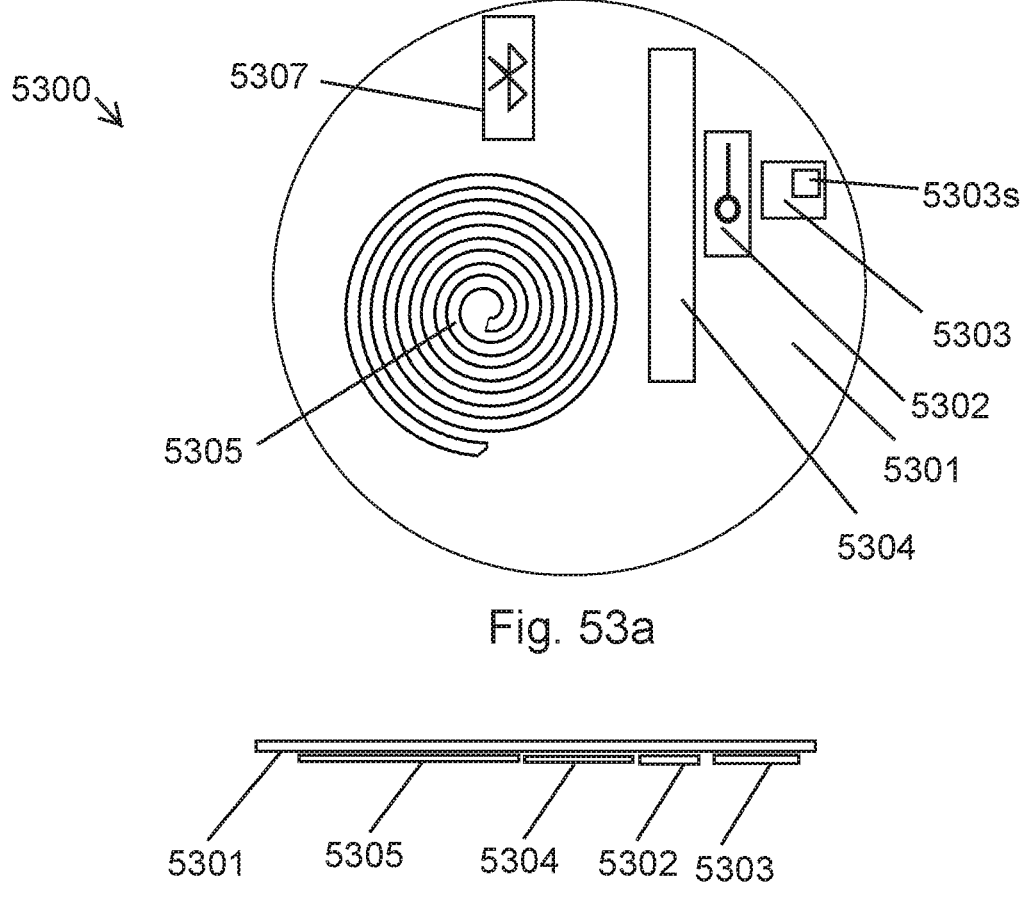
FIG. 53a depicts a top plane view of a compressible, subcutaneous implant, comprising a lighting screen.
FIG. 53b depicts a side view of an implant, illustrating how each of the elements may be coupled to the screen according to an embodiment.
FIG. 53*c* depicts a side view of the implant with a barrier element.

FIG. 53*a* depicts another example of a compressible, subcutaneous implant 5300. Implant 5300 comprises a light screen or sheet 5301, as previously mentioned, which may be configured to display images and/or videos. Implant 5300 may be useful, for example, as an internal tattoo, including the embodiments shown in FIGS. 49 and 50 described above. Implant 5300 may also be useful in connection with more therapeutic embodiments, such as implants used to deliver light therapy. Further details regarding such light treatments can be found in "Formation of Lumirubin During Light Therapy in Adults," Journal of Biological Sciences 4

(3): 357-360 (2004), which is incorporated herein in its entirety by reference. Implant 5300 may further comprise an antenna 5302 to allow for receipt of electromagnetic signals, which may be used to transmit data for use in displaying images on screen 5301. A CPU 5303 may also be provided, which may allow for processing of signals received via antenna 5302. A flexible battery 5304 may also be provided. For charging of flexible battery 5304, a wireless charging system may be provided, such as the wireless inductance assembly 5305 shown in FIG. 53*a*. Preferably, each of the elements of implant 5300 is either flexible and/or compressible, or is small enough on its own to fit within a minimally invasive entrance incision with other elements of implant 5300 compressed about it.

FIG. 53*b* is a side elevation view of implant 5300 illustrating how each of the elements may be coupled to screen 5301. As shown in FIG. 53*c*, preferably, each of the elements of implant 5300, including screen 5301, is sealed within a container or envelope 5306, which is preferably both waterproof and biocompatible. Examples of suitable materials for container 5306 include polyethylene, parylene-C, polyimide, and the like.

In some embodiments, a sensor 5303*s* may be provided, which in some embodiments may be used to detect the user's heartrate by, for example, electrical methods similar to electrocardiogrametric methods, and/or acoustic/vibrational methods, wherein the vibration of a pulse may be detected by sensor 5303*s*. This may be useful, for example, to display outwardly the pulse rate. This may be displayed by, for example, matching the light display on the implant with the heartrate, or having the light display pulse at a rate that is a multiple, or fraction, of the wearer's current heartrate. In other embodiments, sensor 5303*s* may comprise a pressure sensor, which may allow, for example, a user to actuate and/or change the light element(s) of the implant, such as actuating the lights of an internal tattoo, changing the color of the tattoo, changing the display properties of the lights (pulsing, for example), or actuating therapeutic lights, by applying pressure to a selected portion of the implant.

Implant 5300 may further comprise a wireless transceiver 5307, such as a Bluetooth® transceiver, which may allow for actuation of one or more features of the device wirelessly from, for example, a smartphone or the like.

FIG. 54*a* depicts another compressible implant system 5400 comprising implant 5401 and auxiliary implant 5408, which may be electrically coupled to implant 5401 via wire 5407. Providing an auxiliary implant 5408 may allow for certain components, such as sensitive electrical components, to be placed within a separate implant, which may be more protective of such components, such as being within a waterproof/sealed container, for example.

Implant 5401 may be similar to one or more of the implants previously discussed and may therefore comprise an inductance coil 5405, an antenna 5402*a*, and a laminate/wrapper 5406. The components contained within auxiliary implant 5408 may comprise an antenna 5402*b*, which may be provided instead of antenna 5402*a* or in addition to antenna 5402*a*, a CPU 5403, and a battery 5404. A seal, such as a wrapper, may be used to contain all of the elements of auxiliary implant 5408 therein. During implantation, the auxiliary implant 5408 may simply be inserted through the same entrance incision as the compressed implant 5401, either before or after implant 5401.

FIG. 54*b* depicts implant 5401 in its uncompressed configuration from the side, which shows inductance coil 5405 extending from one side of the implant 5401.

FIG. 54*c* depicts a full system comprising implant 5401 and auxiliary implant 5408. This figure also shows the use of a laminate/wrapper 5406, which may extend about the entirety of implant 5401.

FIG. 55*a* depicts a human patient's abdomen having subcutaneous, compressible mesh implants 5501 positioned in respective implant pockets 5505R and 5505L, wherein the dashed lines emanating from minimally invasive entrance incision 5504 indicate the edges of the undermined/tissue-dissected areas of the pockets. More particularly, each of the two, separate mesh implants 5501 shown in this figure are positioned within a respective implant pocket 5505R/5505L, each of which is delineated by the dashed lines and may be created by such methods as previously shown in FIG. 2. Again, implant pockets 5505R and 5505L are much "larger" (as described previously) than the entrance incision 5504 used to allow a lysing tip to enter the subcutaneous region of the body and to create the implant pockets. Similarly, mesh implants 5501 are in their deployed and/or uncom-pressed state, much "larger" than they are in their com-pressed state and much larger than the length and/or size of the entrance incision 5504. Macro positioning/instrument engaging holes 5503 may aid in implant placement as previously discussed. In some embodiments/implementa-tions, mesh implant 5501 may be Kevlar or Kevlar-like soldier/spy protective meshes comprising, for example, para-aramid synthetic fiber & fiber-PMMA (polymethyl-methacrylate (Acrylic)) composites wherein the aramid is biocompatible. In contemplated implementations, a second-ary coat of biocompatible plastic coating may be applied to the mesh, which coating may contain, in some cases, an antibiotic and/or antiseptic that may be released on impact to prevent/reduce infection, such as upon impact with a suffi-cient force and/or pressure and/or upon impact with a penetrating object, such as a bullet or other ballistic object or knife. In some embodiments/implementations, such as those configured for abdominal hernia repair, the mesh implant 5501 may be Kevlar or expanded polytetrafluoro-ethylene (ePTFE) & POL-Collagen, for example, to rein-force the abdominal wall against pressures on underlying weak tissues related to hernias.

FIG. 55*b* depicts a side view of a mesh implant 5501 with optional mesh implant peripheral folds 5501*f* which may aid in mitigating a penetrating wound, for example, if the mesh is an antiballistic, such as Kevlar, by catching a bullet at an edge rather than allowing edge slippage.

FIG. 55*c* depicts a side view of a mesh implant 5501 with optional zone of overlap 55010, which may be secured by binding element 5501*b*, such as a staple, suture, grommet, rivet, or the like. Overlap 55010 and binding element(s) 5501*b* may aid in mitigating a penetrating wound if the mesh is an antiballistic, such as Kevlar, by doubling the thickness at what otherwise would have been an edge with a direct weakened area/space to the underlying structures below.

FIG. 56*a* depicts a soldier who resembles a gingerbread man having multiple subcutaneous, compressible mesh implants 5601 positioned in implant pockets 5605 wherein the dashed lines emanating from minimally invasive entrance incisions 5604 indicate the edges of the under-mined/tissue-dissected areas of the pockets. More particu-larly, mesh implants 5601 are positioned within the implant pockets 5605, as previously discussed. Again, the implant pockets are much larger in one or more (in some cases, all) peripheral edge dimensions than the entrance incision 5604 measures along one or more, or all, such corresponding dimensions. It is noteworthy that multiple implant pockets 5605 may share a single minimally invasive entrance incision 5604. In some embodiments/implementations, mesh implant 5601 may be may be anti-ballistic/penetration resis-tant such as Kevlar or Kevlar-like soldier/spy protective meshes comprising, for example, para-aramid synthetic fiber & fiber-PMMA (polymethylmethacrylate (Acrylic) compos-ites wherein the aramid is a biocompatible material. Area 5601*e* may comprise electronic elements including, but not limited to, inductance coil, antenna, CPU/printed circuit board and sensors to receive power, and antennas to transmit status of soldier and sensors/wiring in mesh to determine compromise and relay data to allow remedy from onboard or remote CPU. In some embodiments, meshes may comprise sensors, wires, and/or fiberoptics to determine mesh integ-rity and/or soldier status. Although only one of the implants depicted in FIG. 56*a* comprises the aforementioned electri-cal component region 5601*e*, it should be understood that this region may be present on each of the implants if desired. In some embodiments, one or more implants, such as implant 5607, may be laminated (with or without mesh), and may comprise, for example, graphene In some embodi-ments, an outer laminate may comprise PTFE for biocom-patibility and to facilitate removal if necessary. Further embodiments may comprise peripheral placement holes and/or macro vascularization holes, as previously discussed.

In some embodiments, stacked graphene sheets may be used as a ballistic resistance layer. In some instances, individual graphene sheets may comprise one-atom-thick layers of carbon atoms arranged in a honeycomb structure. Given the extremely thin nature of each graphene layer, many graphene layers may be stacked to improve ballistic resistant properties. Additional details regarding such gra-phene armor may be found in 'Graphene Body Armor: Twice the Stopping Power of Kevlar, at a Fraction of the Weight', Anthony, extremetech.com, 2014, which is incor-porated herein by reference in its entirety.

In some embodiments, it may be preferable to only stack two single-atom thick sheets of graphene. Such configura-tions may result in a diamene (a stack of 2 sheets of graphene) that may harden into a diamond-like consistency upon impact. In the absence of mechanical pressure, diamene may retain a degree of flexibility; however, when subject to sudden mechanical pressure, diamene may tem-porarily harden. It may be preferable to stack only two single-atom-thick graphene layers, as the aforementioned properties are only observed in diamene. Additional details regarding the aforementioned diamene structure may be found in "This Ultra-Thin Material Can Stop Bullets by Hardening Like a Diamond', Ratner, Hard Science, Big Think, 2017, which is also incorporated herein by reference in its entirety.

In some embodiments, ballistic resistant articles may comprise hybrid materials comprising different fabric sec-tions. In a preferred embodiment, such an article may comprise 3 layers of fabric arranged into a gradient wherein the outermost, strike-facing sections of the article have the highest tenacity. In some embodiments, each layer may comprise a fibrous layer comprising one or more fibrous plies. The second fibrous material may comprise a lower tenacity than the first material, and the third fibrous material may comprise a tenacity lower than the second material. The first, second, and third fibrous materials may be bonded together to form a consolidated composite article. In some embodiments, the third fibrous material may comprise nylon fibers, polyester fibers, polypropylene fibers, polyolefin fibers, or a combination thereof. In some embodiments, the first fibrous material may comprise high molecular weight polyethylene fibers, the second fibrous material may comprise high molecular weight polyethylene fibers and/or aramid fibers, and the third fibrous material may comprise nylon fibers. In other embodiments, the first fibrous material may comprise a woven aramid fabric, the second fibrous material may comprise a non-woven aramid fabric, and the third fibrous material may comprise nylon fibers. In some instances, the first fibrous material may comprise a non-woven fabric of unidirectionally oriented fibers, the second fibrous material may comprise a non-woven fabric of unidirectionally oriented fibers, and the third fibrous material may comprise a non-woven fabric of unidirectionally oriented fibers, a woven fabric, a knitted fabric, and/or a felt. In some embodiments, the ballistic resistant composite may comprise a non-fibrous isotropic polymer layer attached to the third fibrous material such that the first, second, and third layers along with the fibrous isotropic polymer are bonded together to form a consolidated composite. Additional details regarding the disclosed ballistic resistant article may be found in U.S. Patent Application Publication 2019/0016089, titled "Materials Gradient within Armor for Balancing the Ballistic Performance", which is hereby incorporated herein in its entirety by reference.

In some embodiments, Kevlar may be used as a ballistic resistant article. Such articles may comprise stacked Kevlar layers in a 90/45/90 orientation relative to each other. It may be desirable to have 6 to 7 multiples of 3 layers (in a 90/45/90 configuration) of 200 GSM Kevlar (18-21 total layers) to effectively stop ballistic projectiles. It may be observed that it may require twice as many layers of Kevlar as the amount damaged to stop a ballistic projectile. Additional details regarding Kevlar body armor and bullet-proofing capabilities of Kevlar may be found in "Experimental Study of Bullet-Proofing Capabilities of Kevlar, of Different Weights and Number of Layers, with 9 mm Projectiles", Stopforth, Science Direct, Defense Technology, 2018, which is hereby incorporated in its entirety by reference.

FIG. 56*b* depicts two implants 5601 that are positioned within a shared subcutaneous pocket and overlap with one another to an extent, as indicated by the overlapping region 56010. This may be useful for certain applications. For example, a single larger implant may be effectively created from a plurality of smaller implants that may be inserted separately and will likely end up fusing together with the patient's tissue. This may present an option for more safely and/or efficiently reconstructing a larger implant within the body.

FIG. 57*a* depicts a human patient's abdomen having subcutaneous, compressible implants 5701 positioned in respective implant pockets 5705R and 5705L, wherein the dashed lines emanating from a single minimally invasive entrance incision 5704. Again, the outer dashed lines indicate the edges of the undermined/tissue-dissected areas of the pockets 5705R/5705L. Implant pockets 5705R and 5705L may be relatively elongated to accommodate elongated implants. In this embodiment, the bulk of the implant may be bioresorbable with RFID chips 5707 placed in random patterns so as to make them numerous and less predictable in location for an unwanted party to remove.

FIG. 57*b* depicts a top view of an implant 5701 containing RFID chips 5707 placed in less predictable patterns. Again, once the implant 5701 has been resorbed in the body, each of the RFID chips 5707 will be positioned at, preferably, random locations throughout the body such that removal of one chip, or multiple chips, is likely to result in retaining at least one or more chips absent knowledge of the location of all of the chips. For example, human traffickers and the like may find one RFID chip and be able to remove it to inhibit locating/identifying a victim, but having multiple RFID chips implanted, preferably at random locations, may be very difficult and/or cost-prohibitive—i.e., may require a surgeon, antibiotics, X-rays, specialized micro-metal detectors, etc. In preferred embodiments, RFID chips 5707 are each configured as plates or plate-like elements having flat upper and lower surfaces that are parallel, or at least substantially parallel, to each other.

Moreover, even if removal of a randomly positioned plurality of chips were attempted, risks of missing even one (which is all it takes to set off an alarm) would be present. Further, infection and tell-tale scarring from removal of such a plurality of chips may alert others—e.g., doctors or police—of RFID removal, thwarting human trafficking.

Radio frequency identification chips may be used in certain embodiments, which may, for example, be used as devices to track and/or monitor patient health. For example, the RFID device may be active or passive, with low power, long-range transceivers for location and movement tracking. The RFID circuit may be multi-functional in some embodiments. For example, the RFID circuit may comprise a circuit inductively coupled with devices, such as temperature sensors, which may be used to assess patient health. The tracking device may also, or alternatively, comprise a micro-controller, radio transceiver, antennae, and/or power sources. Further details regarding suitable RFID devices for use in connection with various embodiments disclosed herein may be found in U.S. Pat. No. 11,141,062 titled "System and Method for Animal Location Tracking and Health Monitoring Using Long Range RFID and Temperature Monitoring," which is hereby incorporated in its entirety by reference.

Certain RFID embodiments may comprise, for example, a ferromagnetic mass disposed near a coil and a resonator circuit coupled to said coil, which may be configured to resonate upon receiving current from the coil. An antenna may be coupled to the resonator circuit. In some embodiments, the device may contain a modulator coupled to the resonator circuit to modulate output. The ferromagnetic mass may slide in and out of the coil naturally with bodily movement, which may induce voltage in the coil, thereby providing power to the circuit, in some cases without need for an external power source at all. Further details which may be useful in connection with various embodiments disclosed herein may be found in U.S. Patent Application Publication No. 2015/0129664 titled "Implantable RFID Tag", which is hereby incorporated in its entirety by reference.

In certain embodiments, RFID chips may contain power stores which may be recharged in the presence of electromagnetic fields, such as electromagnetic fields generated by transceiver units. The power stores may comprise, for example, capacitors or batteries. The transponder unit may communicate via numerous frequencies, thereby improving real-time performance, identification, and/or compatibility. The transponder unit may further comprise transmission units, memory, and/or power circuitry. In some instances, the transponder unit may be coupled to one or more antennae. Some embodiments may comprise RFID devices wrapped to seal the device from surroundings. Further details regarding RFID chips and systems may be found in U.S. Patent Application Publication No. 2011/0169610 titled "Radio Frequency Animal Tracking System", which is hereby incorporated in its entirety by reference.

Some embodiments may comprise implantable RFID transceivers used for identification and tagging of medical devices, such as medical devices incorporated into the implants disclosed herein or medical devices communicatively coupled with such implants. Some embodiments may comprise tagging devices and related components, such as tagging devices with manufacturing, implant information, and/or patient identification information. For example, such RFID tags may be coupled with implanted defibrillators, pulse generators, and/or stents. In some instances, the RFID module may be integrated into the medical device for identification, data storage, and/or communication purposes. Additional details regarding such RFID implants may be found in U.S. Pat. No. 7,429,920, titled "Radio Frequency Identification and Tagging for Implantable Medical Devices and Medics Device Systems", which is hereby incorporated in its entirety by reference.

Some embodiments and implementations may comprise RFID chips for use with active implantable medical devices (AIMD). Such systems may comprise, for example, an interrogator and/or a hermetically sealed RFID device comprising a substrate, RFID chip, and antenna. In some instances, the RFID device may be used to store data such as patient information, manufacturing information, serial numbers, and the like. Further details may be found in U.S. Pat. No. 7,916,013 titled "RFID Detection and Identification System for Implantable Medical Devices,", which is hereby incorporated in its entirety by reference.

FIG. 58a depicts a minimally invasive electro-dissection device with a 2 bead tip 5804 according to some embodiments having two beads protruding distally from a shaft 5805 and handle 5806. Tip 5804 comprises a beaded structure that may be positioned at the distal end of a shaft. The device/system may further comprise an implant expelling cannula 5820, which may be fixedly or releasably attached (or may be entirely separate in other embodiments) to shaft 5805 and may comprise an implant expelling plunger 5821.

FIG. 58b depicts a human torso after having undergone comparative bilateral surgical procedures. On the patient's right side (the left side of the figure), a lysing tip, such as a lysing tip having beads and adjacent recesses for delivery of energy therefrom (for example in FIG. 58a), was used to form implant pockets 5803R and 5803L, with one or more dimensions substantially greater than that of the entrance incision 5850 (about 5 mm, for example) used to begin to create the pocket. The outward arrows depict the initial forward paths of the dissection device radiating along the axis of the shaft 5805 away from the entrance incision 5850; the device shown may also be configured to dissect in a rearward direction. However, for space considerations, rearward arrows are not shown. Implant pocket 5803L in FIG. 58b results from a human patient's abdomen having received subcutaneous, expellable implants 5801 deposited on either forward or rearward passage of the implant expelling cannula 5820. In this embodiment, expellable implants 5801 comprise RFID chips. In other contemplated embodiments expellable implants may comprise electronics or medicines or clusters of biologic materials, such as stem cells.

Although the implant pockets 5803L and 5803R are shown as having been formed with multiple strokes from instrument 5804, it should be understood that, in alternative implementations, a single stroke may be used. Thus, unlike most of the embodiments disclosed herein, implants 5801 need not be compressible and therefore need not be larger, or at least substantially larger, than the entrance incision 5850. Thus, a single stroke of instrument 5805 may be used to both create the path or paths into which the implants 5801 are inserted and to insert the implants. The pockets may therefore consist of a single stroke, or of multiple strokes that may be connected to form a larger, continuous pocket as shown in FIG. 58b or multiple pockets each defined by a single stroke emanating from the entrance incision 5850. To further illustrate, in another alternative implementation, a first stroke in a first direction may, if the backstroke is followed in the same path, form a first pocket defined by the first stroke alone, and a second stroke may extend at an angle relative to the first stroke, such as an angle of up to or even exceeding 90 degrees for example, so that the implants 5801 contained in the respective single-stroke pockets may be separated from one another by whatever distance may be desired. Unlike implants 5707, implants 5801 may be configured in a cylindrical or at least substantially cylindrical shape, or another shape unlike implants 5707 in that such a shape may lack opposing, flat surfaces that are parallel to one another.

FIG. 58c depicts a side view of an alternative embodiment of an implant expelling cannula 5820s that is configured to expel implants from a side opening 5820os rather than through the distal end of the device. As with the instrument depicted in FIG. 58a, this instrument may further comprise an implant expelling plunger 5821c, which is shown advancing each of a series of the expellable implants 5801, each comprising RFID chips 5801rf through opening 5820os after each expelled implant is redirected off the cannula axis by angular diversion 5820a, which may comprise, for example, a ramp structure. The device shown in FIG. 58c is shown without a coupled tissue dissecting instrument, although, as those of ordinary skill in the art will appreciate, this device could easily be mounted on or otherwise coupled together with such an instrument if desired.

FIG. 58d depicts a more detailed side view of a of implant expelling cannula 5820 fixedly or releasably attached to shaft 5805, again also depicting implant expelling plunger 5821, pushing each of a series of the expellable implants 5801 comprising RFID chips out through frontal/distal shaft opening 5820of.

FIG. 59a depicts a human torso after having undergone comparative bilateral surgical procedures whereupon minimally invasive stem cell incubator implant rectangular strips 5901 were placed in implant pockets 5903R and 5903L, with one or more dimensions substantially greater than that of the entrance incision 5950 (about 5 mm, for example) used to begin to create the pocket. Minimally invasive stem cell incubator implant rectangular strips 5901 may comprise, for example, an implant payload bay 5901p comprising living biologic cell clusters (such as stem cells), which may be ensconced within implant protective pouch 5901b, which may comprise smooth laminates, meshes, and/or semipermeable membranes as well as possible nutrients, hormones, biologics, medicines, antibiotics that may support the proper survival of the stem cells. A mesh may be preferred to encourage blood vessel growth into the cells contained therein. Hormones may be added to the mesh in some embodiments to further encourage such growth, such as, for example, proliferin, prolactin, growth hormone and placental lactogen. In order to recover the growing stem cells by surgical extraction, it may be preferable that such strip and/or pouch materials be non-biodegradable and non-bioresorbable so the item is intact for removal. However, it is conceivable that bioresorbable materials may be used in alternative embodiments and implementations. It is possible that by tissue matching donors and recipients stem cell surrogates may incubate cell clusters for other patients. The surrogate may also be non-human in some cases, such as a genetically modified pig the immune system of which will not damage or otherwise negatively affect the foreign stem cells. Macro positioning/instrument engaging holes 5901$h$ may facilitate placement and/or manipulation and/or fixation.

As mentioned above, prolactin, growth hormone, placental lactogen, proliferin, and proliferin-related protein share structural similarities and biological activities, including angiogenesis, and therefore it may be useful to incorporate one or more of these proteins/substances, or other known angiogenesis-promoting substances, into one of the more of the implants disclosed herein. Such substances may act both as circulating hormones and as paracrine/autocrine factors to either stimulate or inhibit various stages of the formation and remodeling of new blood vessels, including endothelial cell proliferation, migration, protease production and apoptosis. Such opposing actions can reside in similar but independent molecules, as is the case of proliferin and proliferin-related protein, which stimulate and inhibit angiogenesis respectively. The potential to exert opposing effects on angiogenesis can also reside within the same molecule as the parent protein can promote angiogenesis (i.e. prolactin, growth hormone and placental lactogen), but, after proteolytic processing, the resulting peptide fragment acquires anti-angiogenic properties (i.e. 16 kDa prolactin, 16 kDa growth hormone and 16 kDa placental lactogen). Thus, it may be possible to use both angiogenesis-promoting substances and angiogenesis-inhibiting substances in an implant to, for example, promote vessel and/or tissue growth on a lower surface/side of the implant where therapeutic agents may be released and inhibit vessel and/or tissue growth on the upper side of the implant. Angiogenesis-inhibiting substances, such as 16 kDa prolactin, 16 kDa growth hormone, and/or 16 kDa placental lactogen, or any other known angiogenesis-inhibiting substances, may be selectively applied to certain areas of an implant that are desired to be free from blood vessel and/or tissue formation. Additional details regarding both angiogenesis promoting and angiogenesis inhibiting substances that may be incorporated into various implants disclosed herein can be found in "Roles Of Prolactin And Related Members Of The Prolactin/Growth Hormone/Placental Lactogen Family In Angiogenesis," Corbacho A, Martinez G, Clapp C, Journal of Endocrinology (2002) 173, 219-238, which is incorporated herein by reference in its entirety.

In some instances, meshes, such as scaffolds, may be used to aid in tissue engineering. In a preferred embodiment, such scaffolds may be used for retention and deliverance of cells and biochemical factors for cell adhesion and migration. Such scaffolds may also be used, in some embodiments, for templates to, for example, guide tissue development. In certain embodiments, materials such as, for example, natural biomaterials, ceramics, synthetic biomaterials, and/or biomimetic natural polymers may be used for implantable scaffolds. In some instances, natural biopolymers may comprise, for example, proteins, polysaccharides, and the like. In some instances, synthetic polymers may comprise PLA, PGA, PLGA, and the like. In some embodiments, ceramics may be used as scaffolds, which ceramics may comprise, for example, hydroxyapatite, tricalcium phosphate, alumina, and the like. In some instances, scaffold properties such as, for example, biomaterial, biodegradability, incorporated ECM variants, porosity, shape, and the like, may be varied as desired according to the application of the implant(s). In certain embodiments, scaffolds may comprise, for example, hydrogel scaffolds, fibrous scaffolds, microsphere scaffolds, bioceramic scaffolds, mesoporous bioactive glass scaffolds, and the like. In some embodiments, a 3D cell culture system may be used to create an artificial environment, aiding in processes such as, for example, cell differentiation and morphogenesis. Additional details regarding such scaffolds may be found in "Scaffolds from Biomaterials: Advantages and Limitations in Bone and Tissue Engineering", Alaribe, Biologia; 353-367, 2016, which is hereby incorporated in its entirety by reference.

FIG. 59$b$ depicts a side view of minimally invasive stem cell incubator implant strip 5901, wherein implant payload bays 5901$p$ are ensconced within individual implant protective pouches 5901$b$. As shown in this figure, bays 5901$p$ and/or pouches 5901$b$ may be positioned on either or both sides of the implant/strip 5901.

FIG. 59$c$ depicts a side view of an alternative embodiment of a minimally invasive stem cell incubator implant 5901C wherein implant payload bays 5901$p$, along with their corresponding contents (stem cells, for example) are sandwiched within implant laminate layers 5901L1 and 5901L2.

FIG. 60$a$ depicts the right side of a torso of a human patient having a rectangular compressible subcutaneous electronic neuro stimulative (SQENS) implant system 6000 positioned in a respective implant pocket 6005 made via minimally invasive entrance incision 6010. More particularly, a SQENS implant 6001 is positioned within an implant pocket 6005, one or both of which may be similar to any of the other implants and/or implant pockets previously mentioned. Implant pocket 6005 may be made by methods described elsewhere within this application, including FIGS. 1 & 57. In some implementations, the series of SQENS implants may be oriented along the dermatomal, sclerotomal, myotomal, and/or nerve map areas. Implant 6001 may, in some embodiments, comprise a flexible, compressible sheet, or stack of sheets of electronics. Again, implant pocket 6005 is much "larger" (as described previously) than the entrance incision 6004 used to allow a lysing tip to enter the subcutaneous region of the body and to create the implant pocket 6005. Similarly, implant 6001 is, in its deployed and/or uncompressed state, much "larger" than it is in its compressed state and much larger than the length of the entrance incision 6004.

Implant system 6000 may further comprise an antenna 6007 to allow for receipt of electromagnetic signals, which may be used to transmit data to CPU/printed-circuit-board 6003 for use in activating peripherally based terminal electrodes 6012 and optional non-peripherally based terminal electrodes 6011 using energy derived from battery 6004 and inductance coil 6014. Peripheral terminal electrodes 6012 may, as shown on the figure, only be positioned partially on the implant 6001 itself, whereas the non-peripheral terminal electrodes 6011 may be wholly positioned on the implant 6001. An external transmitter may be adjusted by the patient or healthcare personnel to transmit signals to internal antenna 6007 that, in turn, may provide instructions to CPU 6003 to coordinate electrical output of electrodes 6011 and/or 6012. These external signals may, for example, be generated and/or received from a smartphone or other wireless communication device 6099. Battery 6004 may also be flexible. A wireless charging system may be provided, such as the wireless inductance assembly 6014 may charge flexible battery 6004. Preferably, each of the elements of implant 6001 is either flexible and/or compressible, or is small enough on its own to fit within a minimally invasive entrance incision with other elements of implant 6001 compressed about it.

FIG. 60$b$ is a side elevation view of implant 6001 of system 6000 illustrating how each of the elements may be coupled on implant 6001; however, in other embodiments, orientations and locations may vary. In some embodiments, each of the elements of implant 6001, possibly with the exception of terminal electrodes 6011 and 6012, may be sealed within a container or envelope, which is preferably both waterproof and biocompatible. Examples of suitable materials for said container include polyethylene, polyurethane, polypropylene, and the like. In some embodiments, various coatings, such as polymer coatings, may also, or alternatively, be used.

As shown in FIG. 60*b*, in some embodiments, a superstructure 6001*s* may also be provided. Preferably, such superstructure(s) are flexible and/or expandable. Such superstructure(s) may be located on the underside of the elements depicted in FIG. 60*b*, and may aid in fully unfolding/uncompressing the implant 6001, maintaining the shape and/or location of the implant 6001 as it nestles in the subcutaneous layers below. In some embodiments, superstructure 6001*s* may comprise biocompatible polymers that are selectively permeable. In some embodiments, superstructure 6001*s* is hollow, end-sealed, and/or may comprise a xerogel, which may expand as water passes through the selectively permeable polymers into the inside of the superstructure 6001*s* causing it to rigidify to varying degrees. This may be beneficial to reduce unwanted folding and/or migration.

FIG. 60*c* depicts a top plan view of the implant 6001 in its deployed/uncompressed state. Externally detectable macro positioning/instrument engaging holes 6023 (as described previously) may aid in the positioning of implant system 6000. In alternative embodiments, holes 6023 are not externally detectable. One or more printed circuit boards 6003 and/or CPUs, ancillary electronics 6024, including but not limited to a heart rate sensor and oxygen saturation monitor, may also be provided. During an episode of pain or discomfort, a patient's heart rate may elevate. An ancillary electronic heart rate sensor 6024 option may therefore detect an elevated heart rate, which may be used by the SQENS to signal/stimulate nerves upon detecting, for example, a threshold heart rate and/or a threshold increase in heart rate over a given period. In this manner, if pain is reduced by the implant 6001, the heart rate should lessen and cause the stimulation to cease. Internal or external programming may, in some embodiments, determine a preset heart rate diminution, which if not achieved by a programmable time threshold/limit, would cease the SQENS unit firing as another health cause may be the origin of the particular elevated heat rate sampling.

For comparative purposes, Percutaneous Electrical Nerve Stimulation (PENS), goes even deeper than Transcutaneous Electrical Nerve Stimulation (TENS, surface electrodes) although both have in common, small wires attached to a battery-powered electrical stimulator, PENS has needle electrodes deliver current closer to the nerves or the muscles beneath the skin, in the hopes of bypassing upper nerves and thus causing less skin transmission pain. PENS typically involves insertion of an acupuncture-like needle which probes into the soft tissues or muscles to electrically stimulate nerve fibers in the sclerotomal, myotomal, or dermatomal distribution corresponding to the patient's pain symptoms. However, needle insertion and even slight movements cause pain in PENS. Thus, outside of the implant procedure, SQENS may offer both conveniences of less needling and skin transmission pain.

FIG. 60*d* depicts a top plan breakaway view of an alternative implant in its deployed/uncompressed state. Also shown are peripherally based terminal electrodes 6012*a-d* and optional non-peripherally based terminal electrodes

6011*a-c* which each may be electrically coupled, directly or indirectly, to a CPU, such as CPU 6003 in FIG. 60*c*. If the electrodes are on independent circuits to the CPU then each may be programmed to fire at random or independently in a preprogrammed pattern so as to provide a differing stimulus pattern to the subject/recipient over time. This may provide an improved ability to avoid pain by changing, either randomly or based upon a preconfigured pattern, for example, the actuation of each of the various electrodes. Psychological and neurological studies have shown that a stimulus' effect may diminish based upon unchanging repetition over time (recipient's nervous system becomes jaded to a repetitive unchanging/boring stimulus). Thus preprogrammed or randomized or changing programmable stimuli may serve to enhance the effect of SQENS. Electrodes output may be individually addressed in terms of amplitude, frequency, and/or activation in order to achieve multiple stimuli.

A multiplicity of stacked inductance coils may increase the power transfer as well as increase of mutual inductance between coupled coils. Reference: 'Achieve High Power Density with Stacked Inductor Aug. 25, 2021, https://www-.electronicdesign.com'

In some embodiments, electrodes may be injected into the body using one or more of the techniques and/or in one or more of the implants disclosed herein. In a preferred embodiment, such electrodes may comprise an in-body curing polymer and metal composite. In some instances, such electrodes may be used in conjunction with neural stimulating devices. In certain embodiments, injected electrodes may comprise silicone-metal-particle composites. In some embodiments, the composite may comprise silicone elastomers and metallic silver flakes. Additional details regarding such injectable electrodes may be found in "An Injectable Neural Stimulation Electrode Made from an In-Body Curing Polymer/Metal Composite", Trevathan, Advanced Healthcare Materials, 2019, DOI: 10.1002/adhm.201900892, which is hereby incorporated herein in its entirety by reference.

FIG. 61*a* depicts the right side of a torso of a human patient having a spiral subcutaneous electronic neuro stimulative (SSENS) implant system 6100 having a plurality of implants each preferably positioned in a respective implant pocket made via minimally invasive entrance incision 6110. In this embodiment, a series of 3 SSENS spiral implants 6101*a*, 6101*b*, 6101*c* are positioned within respective implant pockets. More particularly, spiral implant 6101*c* (shown in dashed lines to indicate it has already been implanted below the skin) is positioned within an implant pocket 6122. Implant pocket 6122 may be made by methods described elsewhere within this application, including FIGS. 47*a-e*. In some implementations, the series of SSENS implants may be oriented along the dermatomal, sclerotomal, or myotomal, or nerve map areas. Spiral implants may be installed in minimally invasive entrance wounds by methods including those described in FIGS. 47*a-e*. More particularly, spiral implants 6101*a* & 6101*b* are shown without dashed lines to indicate they are being positioned before surgery above the prepped (with chlorhexidine and/or iodine) surgical site for the surgeon to assess optimal implant location, spacing and entrance wound distance for each implant prior to pocket formation or skin marking.

FIG. 61*b* shown as top view of a single 3 turn SSENS implant 6101 with outer terminal end 61010 and electrodes dispersed along one or more sides of the faces or sides of the spiral with outer arm band terminus 61010 and inner arm band terminus 6101*i* and space 6188 between adjacent bands. Spacing 6188 may be helpful for a variety of purposes, such as improving the ease with which spiral implants can be surgically implanted through a minimally invasive entrance incision. Spacing 6188 between adjacent bands of a spiral implant may also provide potential benefits to the implant following implantation, such as providing increased surface area for drug delivery or other purposes, and/or for providing features that project, either permanently or selectively, into this space 6188, for various purposes.

In some embodiments, spiral implant 6101 is circular in overall shape from a top plan view, as shown in FIG. 61b, and rectangular in cross section. As described below, however, various other shapes may be used in alternative embodiments as desired. Spiral implant 6101 may be rigid or, if preferred, more flexible. In some embodiments, the spiral implant 6101 may be compressible by being rollable and/or foldable. In some embodiments, spiral implant 6101 may comprise a metal, ceramic, cermet, glass, flexible plastic, organic polymer, biopolymer, or the like. Other embodiments may comprise a polymeric external lamination or containment to retain more dissolvable materials such as hydrogels and the like. Drugs, vitamins, or other chemicals, including biologics, may also be bound, dissolved, or otherwise present in a portion or all of the structure of spiral implant 6101 and/or elements contained therein. Also shown are terminal electrodes 611 1a-f which each may be hooked in series or parallel or independently directly or indirectly to CPU 6103pb, as shown in FIG. 61c. If the electrodes are on independent circuits to the CPU then each may be programmed to fire at random or independently in a preprogrammed pattern so as to provide a differing stimulus pattern to the subject/recipient over time. Psychological and neurological studies have shown that a stimulus' effect may diminish based upon unchanging repetition over time (recipient's nervous system becomes jaded to a repetitive unchanging/boring stimulus). Thus preprogrammed or randomized or changing programmable stimuli may serve to enhance the effect of SSENS. Electrodes output may be individually addressed in terms of amplitude, frequency, and/or activation in order to achieve multiple stimuli.

FIG. 61c is an enlarged view of a cross section at the location demarcated by the line intersecting the arrow in FIG. 61b near outer arm band terminus 61010 of one possible embodiment, wherein various layers/elements are depicted therein, including a metallic inductance coil 6114, battery 6104 (thin film in this embodiment), printed circuit board 6103pb (in some embodiments printed circuit board 6103pb is a CPU), antenna 6102b, ancillary electronics 6124, such as a heart rate sensor or oxygen saturation monitor, which may be positioned adjacent to protective outer sheath 6117. In other contemplated embodiments, additional metallic inductance coils 6114a may be stacked to enhance the capabilities of the implant. During an episode of pain or discomfort, a patient's heart rate may elevate. An ancillary electronic heart rate sensor 6124 option may detect elevated heart rate causing in the SSENS to signal/stimulate nerves whereupon if pain is reduced the heart rate should lessen. Internal or external programming may determine a preset heart rate diminution, which if not achieved by a programmable time threshold/limit, would cease the SSENS unit firing as another health cause may be the origin of the particular elevated heat rate sampling. Some contemplated embodiments may comprise multiple internal antennas. An external transmitter may be adjusted by the patient or healthcare personnel to transmit signals to internal antenna 6102b that, in turn, may provide instructions to printed circuit board 6103pb to coordinate electrical output of electrodes terminal electrodes 6111a-f. These external signals may, for example, be generated and/or received from a smartphone or other wireless communication device 6199

Each of the elements of implant 6101, except for terminal electrodes 6111 & 6112, may be sealed within a container or envelope (protective outer sheath 6117), which is preferably both waterproof and biocompatible. Examples of suitable materials for said container include polyethylene, polyurethane, polypropylene, and the like. Again, a superstructure 6101s, which is preferably flexible and/or expandable, may aid in fully unfolding/uncompressing the implant and/or maintaining the shape and location of the implant as it nestles in the subcutaneous layers below. In some embodiments, superstructure 6101s may comprise biocompatible polymers that are selectively permeable. In some embodiments, superstructure 6101s may be hollow, end-sealed and/or may comprise an expansive/expansile material, such a xerogel, which expands as water passes through the selectively permeable polymers into the inside of the flexible expandable superstructure 6101s causing expansive/expansile material to engorge in a limited space and thus relatively rigidify to varying degrees. This may be beneficial to reduce unwanted implant folding and/or migration.

Inductance coil/'group of stacked coils' may be present as per the coil cross section depicted in FIG. 37d.

A multiplicity of stacked inductance coils may increase the power transfer as well as increase of mutual inductance between coupled coils. Reference: 'Achieve High Power Density with Stacked Inductor Aug. 25, 2021, https://www-.electronicdesign.com'

To deliver proper alignment the maximal energy transfer per orientation of coil groups may be, in some embodiments, assessed by an internal or external CPU with a signaling when optimal alignment is approaching or departing, or made or lost. In some embodiments, the rate of maximal energy transfer may determine optimal position/orientation.

As per FIG. 37d, a temperature sensor such as 3719t may be present in implant 6101, which temperature sensor may be configured to detect tissue temperatures external to the coil and/or wrapper so that hardware and/or software in the system can alert the user/external coil to increase or decrease energy transmission as the case may be. In some embodiments, one or more threshold temperatures may be established, such as a shutoff temperature, which may be, for example, 45 degrees C., which may result in termination of energy delivery until the temperature returns to a second threshold temperature, such as 40 degrees C., at which point the energy delivery may resume.

In some embodiments, additional elements, such as electronic elements, may be coupled to the coil to make the coil more useful as a standalone implant, or an implant configured to standalone as a power supply to another, secondary implant. In some such embodiments, use of a unitary coil, as shown in FIG. 80a, may eliminate the need for an auxiliary implant altogether. In contemplated embodiments, a unitary coil may therefore be coupled with other implants, such as implants to which the unitary coil is providing energy, without the use of an auxiliary implant to aid the unitary coil in doing so. It is also contemplated, however, that some coil embodiments may have some, but not all, of the components that may be provided on an auxiliary implant, and may therefore be considered a "hybrid" coil implant.

FIG. 62a depicts the right side of a torso of a human patient having a flexible strand/string subcutaneous electronic neuro stimulative (FSQENS) implant system 6200 comprising implants positioned in respective implant pockets preferably made via minimally invasive entrance incision 6210. More particularly, implant system 6200 comprises a FSQENS flexible strand/string implant 6201, which may be positioned within an implant pocket 6205c comprising a canal that may be made by trocar, probe and/or beaded dissector as shown later. Inductance coil 6214 (with or without additional electronics attached) and auxiliary implant 6208 may be deposited in various implant pockets made similarly to others described by methods described elsewhere within this application, including FIGS. 1 & 57. In some implementations, the FSQENS implant may be oriented along the dermatomal, sclerotomal, or myotomal, or nerve map areas. Flexible strand/string implant 6201 may, in some embodiments, comprise a flexible tube or strand of electronics.

As used herein, a "flexible electronic string/strand" implant is a linear combination of multiple end effectors. In some such embodiments, the length of the flexible electronic string/strand implant exceeds the maximal width of the implant by a factor of at least 25. In some such embodiments, the length of the flexible electronic string/strand implant exceeds the maximal width of the implant by a factor of at least 50. As used herein, an "end effector" is any terminus for the discharge of energy into the body, including light, heat, electrical, or electromagnetic discharge.

Implant system 6200 may further comprise auxiliary implant 6208 elements previously similarly described in FIG. 54 a-c including but not limited to an antenna 6202b to allow for receipt of electromagnetic signals, which may be used to transmit data to CPU/printed-circuit-board 6203 for use in activating peripherally based terminal electrodes 6211, 6211a-g using energy derived from battery 6204, wiring 6215i, and inductance coil 6214. An external transmitter may be adjusted by the patient or healthcare personnel to transmit signals to internal antenna 6202b that in turn directs CPU 6203 to coordinate electrical output of electrodes 6211a-g. In some embodiments, the battery 6204 may also be flexible and/or installed within or along inductance coil 6214. A wireless charging system may be provided, such as the wireless inductance assembly 6214 may charge the battery 6204. Preferably, each of the elements of implant system 6200 is either flexible and/or compressible, or is small enough on its own to fit within a minimally invasive entrance incision 6210 with other elements of implant 6200 moved into their optimal positions in separate tissue pockets, such as enlarged tissue pocket 6205, which contains inductance coil 6214 in the depicted embodiment. Auxiliary implant 6208 may allow for certain components, such as sensitive electrical components, to be placed within a separate implant, which may be more protective of such components, such as being within a waterproof/sealed container, for example. A seal, such as a wrapper, may be used to contain all of the elements of auxiliary implant 6208 therein. An external transmitter may be adjusted by the patient or healthcare personnel to transmit signals to internal antenna 6202b that, in turn, may provide instructions to CPU/printed-circuit-board 6203 to coordinate output. These external signals may, for example, be generated and/or received from a smartphone or other wireless communication device 6299

In some embodiments, additional elements, such as electronic elements, may be coupled to the coil to make the coil more useful as a standalone implant, or an implant configured to standalone as a power supply to another, secondary implant. In some such embodiments, use of a unitary coil, as shown in FIG. 80a, may eliminate the need for an auxiliary implant altogether. In contemplated embodiments, a unitary coil may therefore be coupled with other implants, such as implants to which the unitary coil is providing energy, without the use of an auxiliary implant to aid the unitary coil in doing so. It is also contemplated, however, that some coil embodiments may have some, but not all, of the components that may be provided on an auxiliary implant, and may therefore be considered a "hybrid" coil implant.

FIG. 62b is a side elevation view of FSQENS flexible strand/string implant 6201 illustrating how each of the elements may be coupled on strand 6201; however, in other embodiments orientations & locations may vary. Not shown in FIG. 62b, is that preferably, each of the elements of implant 6201, except for terminal electrodes 6211, is sealed within a container or envelope, which is preferably both waterproof and biocompatible. Examples of suitable materials for said container include polyethylene, polyurethane, polypropylene, and the like. A wire 62150 may be used to couple the auxiliary implant 6208 with one or more (preferably all) of the various electrodes 6211a-g of the string implant 6201.

During an episode of pain or discomfort, a patient's heart rate may elevate. An ancillary electronic heart rate sensor 6224 option may detect elevated heart rate, causing in the FSQENS to signal/stimulate nerves whereupon if pain is reduced the heart rate should lessen. Internal or external programming may determine a preset heart rate diminution, which if not achieved by a programmable time threshold/limit, would cease the SQENS unit firing as another health cause may be the origin of the particular elevated heat rate sampling. Also shown are terminal electrodes 6211a-g which each may be electrically coupled, directly or indirectly, to a CPU 6203 and/or other suitable electrical circuitry.

FIG. 62c is an enlarged transparency view of FIG. 62b depicting an embodiment of a wiring scheme for various terminal electrodes 6211a-e along a flexible strand/string subcutaneous electronic neuro stimulative (FSQENS) implant 6201. In this embodiment, electrodes 6211a-e are all wired independently (for example, on wires such as 6211aw, which is coupled with electrode 6211a) of each other, thus allowing for different programmable control for each. In other contemplated embodiments the wiring may be in series, parallel or another form of independent wiring or a combination thereof. Firing may vary in terms of amplitude and time of firing and on-off cycle. Again, this may be random, controllable by the user, or both (selectively random or specific, as selected by the patient). If the electrodes are on independent circuits to the CPU then each may be programmed to fire at random or independently in a pre-programmed pattern so as to provide a differing stimulus pattern to the subject/recipient over time. Psychological and neurological studies have shown that a stimulus' effect may diminish based upon unchanging repetition over time (recipient's nervous system becomes jaded to a repetitive unchanging/boring stimulus). Thus preprogrammed or randomized or changing programmable stimuli may serve to enhance the effect of FSQENS. Electrodes output may be individually addressed in terms of amplitude, frequency, and/or activation in order to achieve multiple stimuli. The triangles used to represent the electrodes in FIGS. 62a-c are by no means restrictive or indicative of electrode shape. For example, in FIGS. 62b & 62c, internal wiring 6211aw is connected to a peripheral/circumferential electrode 6211a that may have several potential benefits. For example, providing a band-like/circumferential electrode may allow for a more widely distributed signal that may be less prone to missing a particular target nerve or other tissue region. However, it may be desirable for certain applications to form such an electrode such that it extends only partially about the periphery of the string and/or tube-like implant 6201. For example, it may be desirable to avoid the increased points of termination, such as corners, which may result from an incomplete circumferential electrode. It should be understood, however, that such points of termination may be preferred for certain applications, particularly since it may be desirable to vary the location, strength, and/or other parameters of the signal for certain applications, such as FSQENS applications.

Although electrode 6211*a* is shown projecting slightly from the peripheral wall of the implant 6201 in FIG. 62*c*, it should also be understood that it may be desirable to have the electrode flush with this exterior wall, which may be a hollow or solid tube, for example, instead, which may allow the implant to slide more easily through, for example, a trocar, adjacent tissues, and/or the entrance wound. The cross-sectional shape of the implant 6201 may vary as desired, such as from circular to oval to strap-like to polygonal in various contemplated embodiments.

Inductance coil/'group of stacked coils' may be present as per the coil cross section depicted in FIG. 37*d*.

A multiplicity of stacked inductance coils may increase the power transfer as well as increase of mutual inductance between coupled coils. Reference: 'Achieve High Power Density with Stacked Inductor Aug. 25, 2021, https://www-.electronicdesign.com'

To deliver proper alignment the maximal energy transfer per orientation of coil groups may be, in some embodiments, assessed by an internal or external CPU with a signaling when optimal alignment is approaching or departing, or made or lost.

As per FIG. 37*d*, a temperature sensor such as 3719*t* may be configured to detect tissue temperatures external to the coil and/or wrapper so that hardware and/or software in the system can alert the user/external coil to increase or decrease energy transmission as the case may be. In some embodiments, one or more threshold temperatures may be established, such as a shutoff temperature, which may be, for example, 45 degrees C., which may result in termination of energy delivery until the temperature returns to a second threshold temperature, such as 40 degrees C., at which point the energy delivery may resume.

FIG. 63*a* depicts the right side of a torso of a human patient having a flexible strand/string subcutaneous implant 6301 positioned in a respective implant pockets comprising elongated canals made adjacent minimally invasive entrance incisions 6310*a-c*. More particularly, implant system 6300 comprises a flexible strand/string implant 6301, which may be positioned within a canal that may be made by trocar, probe and/or beaded dissector as previously described.

Although most implant pockets described in this disclosure are shown as having been formed with multiple strokes from instrument 5804, in trocar/cannula implementations, a single stroke may be used. Thus, unlike most of the embodiments disclosed herein, implant 6301 need not be compressible and therefore need not be larger, or at least substantially larger, than the entrance incisions 6310*a-c*. Thus, a single stroke of trocars/cannulas 6331 and 6332 may be used to both create the path or paths into which the implant 6301 will come to rest.

Implant 6301 may be fed into the initial trocar/cannula 6331 prior to body insertion to extend no further than the internal ramp 6331*r*. The initial trocar/cannula 6331 is inserted through initial incision 6310*a*, usually in the subcutaneous tissues, in a vector directed toward a second entrance incision 6310*b* for an optional second trocar/ cannula 6332. The second entrance incision 6310*b* for a second trocar/cannula 6332 may become the exit incision for the initial trocar/cannula 6331. Alternatively, the initial trocar/cannula 6331 may be backed out of initial incision 6310*a* once the opening 63310 has allowed for passage of the cargo of implant 6301 therein. The proximal end of the implant 6301*p* may continue to be fed into the initial entrance wound until the desired length and placement is achieved. After sufficient amount/length of the implant has been fed into the second trocar/cannula 6332, the second trocar/cannula 6332 may be forced into second entrance incision 6310*b* along a vector 6333*v* headed toward an optional third entrance incision 6310*c* whereupon the process may be repeated except that the cannulas can no longer be conveniently backed out over the implant after the initial incision 6310*a*. In this manner, a string-like implant of any length may be implanted into any region of the body along any lines, whether straight or curved, as desired.

FIG. 63*b* depicts an upper plan view of an upright beveled relatively sharp tipped trocar 6331*c* with pointed tip 6331*p*.

FIG. 63*c* depicts a plan view rotated 90 degrees on its axis of the same trocar 6331*c* as in FIG. 63*b* with shaft opening/hole 6331*h* and pointed tip 6331*p*.

FIG. 63*d* depicts an upper plan view of an upright beveled relatively blunt spatula tipped trocar 6331*d* with blunt spatula tip 6331*b*.

FIG. 63*e* depicts a plan view rotated 90 degrees on its axis of the same trocar 6331*d* as in FIG. 63*d* with shaft opening 63310 and blunt spatula tip 6331*b*.

FIG. 63*f* depicts another alternative trocar 6331*f*, which may be similar to the trocars previously discussed and depicted aside from the shape of the trocar shaft, which may be curved. In some embodiments, the shaft may be permanently/rigidly curved or, alternatively, may be flexible to allow for obtaining a variety of curvatures within the constraints of the material. An opening/aperture 6331*a* and tip 6331*t*, which may be blunt or pointed, may also be present.

FIG. 63*g* depicts a side view of an implant expelling cannula 6331*b* that is configured to, and is shown, expelling a string-like implant 6301 from a side opening 63310. This figure also depicts a ramp 6331*r*, which may be configured to divert or redirect the implant 6301 out of opening 63310.

FIG. 64*a* depicts the front side of a torso of a human patient having one or more compressible subcutaneous electronic muscle stimulative (SQEMS) implants, which may be part of a system 6400, each of which may be positioned in one or more respective implant pockets, such as pockets 6405R & 6405L, preferably made via minimally invasive entrance incision 6410. In the depicted embodiment, a single minimally invasive entrance incision 6410 is used to form both implant pockets 6405R/6405L. However, if the proximity of the pockets is not sufficient, or for other reasons, a separate entrance incision may be used for each implant pocket if desired.

More particularly, a SQEMS implant 6401 is positioned within an implant pocket 6405R, one or both of which may be similar to any of the other implants and/or implant pockets previously mentioned. Implant pocket 6405R may be made by methods described elsewhere within this application, including FIGS. 1 & 57. In some implementations, one or more of the SQEMS implants may be oriented along the location of the rectus abdominis muscle or other abdominal muscles, or any other muscle group in alternative embodiments or implementations as desired. Implant 6401 may, in some embodiments, comprise a flexible, compressible sheet, or stack of sheets, of electronics. Again, implant pocket(s) 6405R and 6405L are preferably much "larger" (as described previously) than the entrance incision(s) 6410 used to allow a lysing tip to enter the subcutaneous region of the body and to create the implant pocket(s) 6405R/ 6405L. Similarly, implant 6401 is, preferably, in its deployed and/or uncompressed state, much "larger" than it is in its compressed state and much larger than the length of the entrance incision(s) 6410. The contralateral implant (not dashed to indicate it is resting above surgically prepped skin for planning purposes) illustrates various components of the implant. The dissection/implant pocket may differ for muscle stimulation because the muscle lies below the deepest part of the skin's subcutaneous fat layer in an investing fascia. Therefore implant configured for muscle stimulation may be placed deeper, such as in the lower layer of the fat that is adjacent to the muscle or directly upon the muscle and/or its adjacent fascia to excite the muscle tissue from a more proximate location. It may also be preferable for such embodiments to face the electrodes on the underside of the implant.

Implant(s) 6401 of system 6400 may further comprise an antenna 6407, as previously described, to allow for receipt and/or transmission of electromagnetic signals, which may be used to transmit data to CPU/printed-circuit-board 6403 or another suitable electrical components for use in activating peripherally based terminal electrodes 6412 and optional non-peripherally based terminal electrodes 6411 using, for example, energy derived from battery 6404 and/or inductance coil 6414, as also previously described. Peripheral terminal electrodes 6412 may, as shown on the figure, only be positioned partially on the implant 6401 itself, whereas the non-peripheral terminal electrodes 6411 may be wholly positioned on the implant 6401. An external transmitter may be adjusted by the patient or healthcare personnel to transmit signals to internal antenna 6407 that, in turn, may provide instructions to CPU 6403 to coordinate electrical output of electrodes 6411 and/or 6412. These external signals may, for example, be generated and/or received from a smartphone or other wireless communication device 6499. Battery 6404 may also be flexible. A wireless charging system may be provided, such as the wireless inductance assembly 6414, which may be used to charge flexible battery 6404 and/or provide more direct energy transfer, such as to a capacitor. Preferably, each of the elements of implant 6401 is either flexible and/or compressible, or is small enough on its own to fit within a minimally invasive entrance incision with other elements of implant 6401 compressed about it.

In some embodiments, one or more myoelectric sensors 6425 may also be provided. Such sensor(s) 6425 may be used to sense when muscle tissue is becoming fatigued, which may be used to adjust and/or terminate stimulation of the muscle to prevent damage to the tissue or simply provide a threshold for cessation of stimulation. In some embodiments, the user may be allowed to adjust this threshold according to, for example, a desired "workout" intensity or current mood.

Some embodiments may further comprise one or more externally detectable macro positioning/instrument engaging holes 6423 (as described previously), which may aid in the positioning of implant system 6400 during installation. In alternative embodiments, placement holes 6423 need not be externally detectable, or need not be present at all. One or more printed circuit boards/CPUs 6403 and/or ancillary electronics 6424 may also be provided as needed, including but not limited to a heart rate sensor, oxygen saturation monitor, and the like.

As a more specific example, during an episode of pain or discomfort, a patient's heart rate may elevate. An ancillary electronic heart rate sensor 6424 option may therefore detect an elevated heart rate, which may be used to by the SQEMS to cease or reduce further stimulation of nerves upon detecting, for example, a threshold heart rate and/or a threshold increase in heart rate over a given period. In this manner, if pain is being caused by the implant 6401, the implant 6401 may be configured to reduce or terminate stimulation of muscle to reduce or eliminate the pain and/or avoid tissue damage. As previously discussed for nerve stimulation, various terminal electrodes may be electrically coupled, directly or indirectly, to a CPU, such as CPU 6403. If the electrodes are on independent circuits to the CPU then each may be programmed to fire at random or independently in a preprogrammed pattern so as to provide a differing stimulus pattern to the subject/recipient over time. This may provide an improved ability to reduce pain or muscle fatigue by changing, either randomly or based upon a preconfigured pattern, for example, the actuation of each of the various electrodes. Allowing one portion of a muscle to relax whilst a different portion is activated may enhance the effect whilst allowing more comfort for the patient. Thus preprogrammed or randomized or changing programmable output may serve to enhance the effect of SQEMS. Electrodes output may be individually addressed in terms of amplitude, frequency, and/or activation in order to achieve multiple varying outputs. This effect may be enhanced, or alternatively achieved, by use of multiple implants. For example, in the depicted embodiment, the implant on the right may be configured to intermittently cease stimulation as the implant on the left fires, and vice versa. This may be accomplished as an alternative to firing multiple electrodes on a single implant intermittently, or randomly, or may be done in addition to independently firing multiple electrodes on a single implant.

FIG. 64b is a bottom plan view of implant 6401 of system 6400 illustrating how each of the elements may be coupled on implant 6401; however, in other embodiments, orientations and locations may vary. In some embodiments, each of the elements of implant 6400, possibly with the exception of terminal electrodes 6411 and 6412, may be sealed within a container or envelope, which is preferably both waterproof and biocompatible. In some embodiments, one or more of the electrodes may be exposed, such as by protruding through openings formed in the container/envelope. Examples of suitable materials for said container may include polyethylene, polyurethane, polypropylene, and the like. In some embodiments, various coatings, such as polymer coatings, may also, or alternatively, be used.

FIG. 64c depicts a front view of an abdominal tension detecting belt 6451 that may be optionally used in conjunction with implant 6401. Abdominal tension detecting belt 6451 may comprise antenna 6457, tension sensor 6458, CPU 6454, and battery 6453. Belt 6451 may be communicatively coupled with one or more implants 6401. For example, upon detecting a threshold tension, a signal may be generated to fire one or more electrodes of the one or more implants 6401. This may be used as a training tool to, for example, voluntarily or involuntarily train a user to avoid having the abdomen/stomach project outwardly to an undesired degree and/or avoid poor posture. For example, if the user has poor posture, the abdomen may be projecting outward, which may cause the sensor to reach a threshold tension. This threshold may cause firing of one or more electrodes, the sensation/pain of which may cause the user to suck or withdraw the abdomen inwardly to avoid the sensation, which may be used to train better posture over time.

Inductance coil/'group of stacked coils' may be present as per the coil cross section depicted in FIG. 37d.

A multiplicity of stacked inductance coils may increase the power transfer as well as increase of mutual inductance between coupled coils. Reference: 'Achieve High Power Density with Stacked Inductor Aug. 25, 2021, https://www-.electronicdesign.com'

To deliver proper alignment the maximal energy transfer per orientation of coil groups may be, in some embodiments, assessed by an internal or external CPU with a signaling when optimal alignment is approaching or departing, or made or lost.

As per FIG. 37d, a temperature sensor such as 3719t may be configured to detect tissue temperatures external to the coil and/or wrapper so that hardware and/or software in the system can alert the user/external coil to increase or decrease energy transmission as the case may be. In some embodiments, one or more threshold temperatures may be established, such as a shutoff temperature, which may be, for example, 45 degrees C., which may result in termination of energy delivery until the temperature returns to a second threshold temperature, such as 40 degrees C., at which point the energy delivery may resume.

FIG. 65a depicts the front side of a torso of a human patient having a plurality of spiral subcutaneous electronic muscular stimulative (SSEMS) implants 6501a-6501g, which may be part of a SSEMS system 6500. Each of the implants 6501a-6501g is preferably positioned in a respective implant pocket made via minimally invasive entrance incisions 6510a,b,n. As shown in this figure, a plurality of implants may be positioned in some pockets, whereas other pockets may contain only a single implant (i.e., implant 6501g in implant pocket 6522c). Of course, this may vary in other embodiments as desired. As previously mentioned, a single entrance incision may be used to form each of the implant pockets or, alternatively, a separate entrance incision may be used for each implant pocket, or for a subset of the implant pockets. In the depicted embodiment, however, a single entrance incision 6510a is used to form implant pockets 6522a and 6522b, whereas a separate incision 6510b is used to form the lower implant pocket 6522c. A circular/oval incision 6510n is also depicted as an optional alternative, whereby the incision may be hidden within the navel. Thus, the incision may be formed anywhere within the navel represented by this closed loop. In this embodiment, a series of 7 SSEMS spiral implants 6501a-g are positioned within respective implant pockets. More particularly, spiral implant 6501g (shown in dashed lines to indicate it has already been implanted below the skin) is positioned within an implant pocket 6522c. Implant pockets 6522a-c may be made by methods described elsewhere within this application, including FIGS. 47a-e. In some implementations, the series of SSEMS implants may be oriented along desired portions of the rectus abdominis muscle. Spiral implants may be installed in minimally invasive entrance wounds by methods including those described in FIGS. 47a-e. Spiral implant 6501g is shown in dashed lines to indicate it has already been implanted subcutaneously in pocket 6522c. More particularly, spiral implants 6501a-f are shown without dashed lines to indicate they are being positioned before surgery above the prepped (with chlorhexidine and/or iodine) surgical site for the surgeon to assess optimal implant location, spacing, and entrance wound distance for each implant prior to pocket formation or skin marking. As previously described, a portable electronic device, such as smartphone 6599, may be part of system 6500, and therefore may be communicatively coupled with one or more of the implants.

FIG. 65b depicts a plan view of a single 3 turn SSEMS implant 6501 with outer terminal end 65010 and electrodes dispersed along one or more sides of the faces or sides of the spiral with outer arm band terminus 65010 and inner arm band terminus 6501i and space 6588 between adjacent bands. Spacing 6588 may be helpful for a variety of purposes, such as improving the ease with which spiral implants can be surgically implanted through a minimally invasive entrance incision. Spacing 6588 between adjacent bands of a spiral implant may also provide potential benefits to the implant following implantation, such as providing increased surface area for drug delivery or other purposes, and/or for providing features that project, either permanently or selectively, into this space 6588, for various purposes.

In some embodiments, spiral implant 6501 is circular in overall shape from a top plan view, as shown in FIG. 65b, and/or oval in cross section, as shown in FIG. 65c. As described below, however, various other shapes may be used in alternative embodiments as desired. Spiral implant 6501 may be rigid or, if preferred, more flexible. In some embodiments, the spiral implant 6501 may be compressible by being rollable and/or foldable. However, due to the nature of the novel spiral structure and implantation techniques described herein, the implant 6501 may be non-compressible and/or non-foldable in some embodiments. In some embodiments, spiral implant 6501 may comprise a metal, ceramic, cermet, glass, flexible plastic, organic polymer, biopolymer, or the like. Other embodiments may comprise a polymeric external lamination or containment to retain more dissolvable materials such as hydrogels and the like. Drugs, vitamins, or other chemicals, including biologics, may also be bound, dissolved, or otherwise present in a portion or all of the structure of spiral implant 6501 and/or elements contained therein. Also shown are terminal electrodes 6511a-f which each may be electrically coupled, in some cases independently, directly or indirectly, to CPU 6503pb, as shown in FIG. 65c. If the electrodes are on independent circuits to the CPU then each may be programmed to fire at random or independently in a preprogrammed pattern so as to provide a differing stimulus pattern to the subject/recipient over time. Thus, preprogrammed or randomized or changing programmable stimuli may serve to enhance the effect of SSEMS. Electrode output may be individually addressed in terms of amplitude, frequency, and/or activation in order to achieve multiple stimuli.

FIG. 65c is an enlarged view of a cross section at the location demarcated by the line intersecting the arrow in FIG. 65b near outer arm band terminus 65010 of one possible embodiment, wherein various layers/elements are depicted therein, including a metallic inductance coil 6514, antenna 6502b, battery 6504 (thin film in this embodiment), printed circuit board 6503pb (in some embodiments, printed circuit board 6503pb may comprise a CPU), and ancillary electronics 6524, such as a heart rate sensor, oxygen saturation monitor, or the like, any of which may be positioned adjacent to protective outer sheath 6517. In other contemplated embodiments, additional metallic inductance coils 6514a and 6514b may be stacked to enhance the power generation capabilities of the implant. Some contemplated embodiments may comprise multiple internal antennas.

In some embodiments, additional elements, such as electronic elements, may be coupled to the coil to make the coil more useful as a standalone implant, or an implant configured to standalone as a power supply to another, secondary implant. In some such embodiments, use of a unitary coil, as shown in FIG. 80a, may eliminate the need for an auxiliary implant altogether. In contemplated embodiments, a unitary coil may therefore be coupled with other implants, such as implants to which the unitary coil is providing energy, without the use of an auxiliary implant to aid the unitary coil in doing so. It is also contemplated, however, that some coil embodiments may have some, but not all, of the components that may be provided on an auxiliary implant, and may therefore be considered a "hybrid" coil implant.

As previously mentioned, a myoelectric sensor 6525 may be provided in some embodiments, which may be used to provide feedback to the electrodes regarding the fatigue of the muscles being stimulated.

In some embodiments, each of the elements of implant 6501, with the possible exception of terminal electrodes 6511, may be sealed within a container or envelope (protective outer sheath 6517), which is preferably both waterproof and biocompatible. Examples of suitable materials for said container may include polyethylene, polyurethane, polypropylene, and the like. In addition, the depicted embodiment further comprises an implant superstructure 6501s. For purposes of this disclosure, an "implant superstructure" should be considered to encompass any structure that is formed upon and/or as an extension to an implant to add rigidity to the implant in its uncompressed form. Some implant superstructures may be inflatable with a liquid or another fluid, which may allow for selectively adding such rigidity, while others may be configured to provide such rigidity automatically, such as upon unfolding or otherwise decompressing the implant. Preferably, implant superstructures are flexible and/or expandable, which may aid in fully unfolding/uncompressing the implant and/or maintaining the shape and location of the implant as it nestles in the subcutaneous layers below. In some embodiments, superstructure 6501s may comprise biocompatible polymers that are selectively permeable. In some embodiments, superstructure 6501s may be hollow, end-sealed, and/or may comprise an expansive/expansile material, such a xerogel, which may be configured to expand as water or another liquid, such as body fluids, pass through the selectively permeable polymers into the inside of the flexible expandable superstructure 6501s, thereby causing an expansive/expansile material to engorge in a limited space and thus relatively rigidify to varying degrees. This may be beneficial to reduce unwanted implant folding and/or migration. Although superstructure 6501s is shown positioned within a lumen of the spiral implant 6501, it should be understood that similar superstructures may be formed at other locations as desired according to the type of implant, application, and desired rigidity modification. Thus, in some embodiments, the superstructure may be formed on an exterior surface of a spiral implant, which may provide the rigidity necessary to maintain the spiral shape in some cases.

Inductance coil/'group of stacked coils' may be present as per the coil cross section depicted in FIG. 37d.

A multiplicity of stacked inductance coils may increase the power transfer as well as increase of mutual inductance between coupled coils. Reference: 'Achieve High Power Density with Stacked Inductor Aug. 25, 2021, https://www-.electronicdesign.com'

To deliver proper alignment the maximal energy transfer per orientation of coil groups may be, in some embodiments, assessed by an internal or external CPU with a signaling when optimal alignment is approaching or departing, or made or lost.

As per FIG. 37d, a temperature sensor such as 3719t may be configured to detect tissue temperatures external to the coil and/or wrapper so that hardware and/or software in the system can alert the user/external coil to increase or decrease energy transmission as the case may be. In some embodiments, one or more threshold temperatures may be established, such as a shutoff temperature, which may be, for example, 45 degrees C., which may result in termination of energy delivery until the temperature returns to a second threshold temperature, such as 40 degrees C., at which point the energy delivery may resume.

FIG. 66a depicts a front side of a torso of a human patient having a flexible strand/string subcutaneous electronic muscular stimulative (FSQEMS) implant 6601, which may be part of a system 6600. Implant 6601 may be positioned in a respective implant pocket preferably made via a minimally invasive entrance incision 6610. More particularly, implant system 6600 comprises a FSQEMS flexible strand/string implant 6601, which may be positioned within an implant pocket that in this embodiment may comprise a canal rather than an enlarged pocket configured to receive an expandable implant. Pocket/canal 6605c may be made by, for example, a trocar, probe and/or beaded dissector, as previously discussed. System 6600 may further comprise inductance coil 6614 (with or without additional electronics attached) and/or auxiliary implant 6608, which may be deposited in various enlarged, non-canal implant pockets, such as pocket 6605, which may be made similarly to other methods described elsewhere within this disclosure, including FIGS. 1 & 57. In some embodiments and implementations, the FSQEMS string implant 6601 may be oriented along the location of the rectus abdominis muscle or other abdominal muscles, or any other muscle group as desired. Flexible strand/string implant 6601 may, in some embodiments, comprise a flexible tube and/or strand of electronics. The contralateral implant (not dashed to indicate it is resting above surgically prepped skin for planning purposes) illustrates various possible components of the implant. The dissection/implant pocket/canal for string implants may differ for muscle stimulation in that the muscle lies below the deepest part of the skin's subcutaneous fat layer in an investing fascia. Therefore, implants configured for muscle stimulation may be placed deeper, such as in the lower layer of the fat that is adjacent to the muscle or directly upon the muscle and/or its adjacent fascia to excite the muscle tissue from a more proximate location. It may also be preferable for such embodiments to face the electrodes on the underside of the implant. An external transmitter may be adjusted by the patient or healthcare personnel to transmit signals to internal antenna 6602b that, in turn, may provide instructions to CPU/printed-circuit-board 6603 to coordinate electrical output of electrodes 6611. These external signals may, for example, be generated and/or received from a smartphone or other wireless communication device 6699

As best illustrated in FIG. 66b, implant system 6600 may further comprise auxiliary implant 6608, various possible elements of which may be as described in FIGS. 54 a-c, including but not limited to an antenna 6602b to allow for sending and/or receipt of electromagnetic signals, which may be used to transmit data to CPU/printed-circuit-board 6603 for use in activating peripherally based terminal electrodes 6611a-f using energy derived from battery 6604 and/or inductance coil 6614, and wiring 6615i/6615o. Auxiliary implant 6608 may also comprise a capacitor 6626 and/or a lab-on-a-chip 6629. A lab-on-a-chip may be beneficial for, for example, diabetics to assess blood glucose levels pre, post, and/or during muscular activity. In some embodiments, microfluidic channels (not shown) may bring patient serum/blood/tissue fluid located outside of the protected encasement/wrapper in contact with lab-on-a-chip for analysis(es). An external transmitter may be adjusted by the patient or healthcare personnel to transmit signals to internal antenna 6602*b* that in turn, may direct CPU 6603 to coordinate electrical output of electrodes 6611*a-f*, which, again, may be actuated independently or together. In some embodiments, the battery 6604 may also be flexible and/or installed within or along inductance coil 6614. A wireless charging system may be provided, such as a wireless inductance assembly, which may be used to charge the battery 6604. Preferably, each of the elements of implant system 6600 is flexible and/or compressible, or is small enough on its own to fit within a minimally invasive entrance incision 6610 with other elements of implant 6600 moved into their optimal positions in separate tissue pockets. Auxiliary implant 6608 may allow for certain components, such as sensitive electrical components, to be placed within a separate implant, which may be more protective of such components, such as being within a waterproof/sealed container, for example. A seal, such as a wrapper, may be used to contain all of the elements of auxiliary implant 6608 therein.

In some embodiments, additional elements, such as electronic elements, may be coupled to the coil to make the coil more useful as a standalone implant, or an implant configured to standalone as a power supply to another, secondary implant. In some such embodiments, use of a unitary coil, as shown in FIG. 80*a*, may eliminate the need for an auxiliary implant altogether. In contemplated embodiments, a unitary coil may therefore be coupled with other implants, such as implants to which the unitary coil is providing energy, without the use of an auxiliary implant to aid the unitary coil in doing so. It is also contemplated, however, that some coil embodiments may have some, but not all, of the components that may be provided on an auxiliary implant, and may therefore be considered a "hybrid" coil implant.

In some embodiments, one or more myoelectric sensors 6625 may also be provided. Such sensor(s) 6625 may be used to sense when muscle tissue is becoming fatigued, which may be used to adjust and/or terminate stimulation of the muscle to prevent damage to the tissue or simply provide a threshold for cessation of stimulation. In some embodiments, the user may be allowed to adjust this threshold according to, for example, a desired "workout" intensity or current mood.

As a more specific example, during an episode of pain or discomfort, a patient's heart rate may elevate. An ancillary electronic heart rate sensor 6624 option may therefore detect an elevated heart rate, which may be used to by the FSQEMS to cease or reduce further stimulation of muscles upon detecting, for example, a threshold heart rate and/or a threshold increase in heart rate over a given period. In this manner, if pain is being caused by the implant 6601, the implant 6601 may be configured to reduce or terminate stimulation of muscle to reduce or eliminate the pain and/or avoid tissue damage. As previously discussed for nerve stimulation, various terminal electrodes may be electrically coupled, directly or indirectly, to a CPU, such as CPU 6603. If the electrodes are on independent circuits to the CPU then each may be programmed to fire at random or independently in a preprogrammed pattern so as to provide a differing stimulus pattern to the subject/recipient over time. This may provide an improved ability to reduce pain or muscle fatigue by changing, either randomly or based upon a preconfigured pattern, for example, the actuation of each of the various electrodes. Allowing one portion of a muscle to relax whilst a different portion is activated may enhance the effect whilst allowing more comfort for the patient. Thus preprogrammed or randomized or changing programmable output may serve to enhance the effect of FSQEMS. Electrode output may be individually addressed in terms of amplitude, frequency, and/or activation in order to achieve multiple varying outputs. This effect may be enhanced, or alternatively achieved, by use of multiple implants. For example, in the depicted embodiment, the implant on the right may be configured to intermittently cease stimulation as the implant on the left fires, and vice versa. This may be accomplished as an alternative to firing multiple electrodes on a single implant intermittently, or randomly, or may be done in addition to independently firing multiple electrodes on a single implant.

FIG. 66*b* is a side elevation view of FSQEMS flexible strand/string implant 6601 illustrating how each of the elements may be coupled on strand 6601; however, in other embodiments, orientations & locations may vary. In some embodiments, each of the elements of implant 6601, with the possible exception of the electrodes 6611*a-f*, may be sealed within a container or envelope, which is preferably both waterproof and biocompatible. Examples of suitable materials for said container include polyethylene, polyurethane, polypropylene, and the like. A wire 6615*o* may be used to couple the auxiliary implant 6608 with one or more (preferably all) of the various electrodes 6611*a-f* of the string implant 6601.

FIG. 66*c* is an enlarged transparency view of FIG. 66*b* depicting an embodiment of a wiring scheme for various terminal electrodes 6611*a-e* along a flexible strand/string subcutaneous electronic muscle stimulative (FSQEMS) implant 6601. In this embodiment, electrodes 6611*a-e* are all wired independently (for example, on wires such as 6611*aw*, which is coupled with electrode 6611*a*) of each other, thus allowing for different programmable control for each. In other contemplated embodiments, the wiring may be in series, parallel or another form of independent wiring or a combination thereof. Firing may vary in terms of amplitude, time of firing, and/or on-off cycle. Again, this may be random, controllable by the user, or both (selectively random or specific, as selected by the patient). If the electrodes are on independent circuits to the CPU, then each may be programmed to fire at random intervals or independently in a preprogrammed pattern so as to provide a differing stimulation pattern to the subject/recipient over time. Thus preprogrammed or randomized or changing programmable stimuli may serve to enhance the effect of FSQEMS. Electrode output may be individually addressed in terms of amplitude, frequency, and/or activation in order to achieve multiple stimuli. The triangles used to represent the electrodes in FIGS. 66*a-c* are by no means restrictive or indicative of electrode shape. In FIGS. 66*b* & 66*c*, internal wiring 6611*aw* may be connected to a peripheral/circumferential electrode 6611*a*, which may have several potential benefits. For example, providing a band-like/circumferential electrode may allow for a more widely distributed signal that may be less prone to missing a particular target nerve or other tissue region. However, it may be desirable for certain applications to form such an electrode such that it extends only partially about the periphery of the string and/or tube-like implant 6601. For example, it may be desirable to avoid the increased points of termination, such as corners, which may result from an incomplete circumferential electrode. It should be understood, however, that such points of termination may be preferred for certain applications, particularly since it may be desirable to vary the location, strength, and/or other parameters of the signal for certain applications, such as FSQEMS applications.

Although electrode 6611*a* is shown projecting slightly from the peripheral wall of the implant 6601 in FIG. 66*c*, it should also be understood that it may be desirable instead to have the electrode flush with this exterior wall, which may be a hollow or solid tube, for example, which may allow the implant to slide more easily through, for example, a trocar, adjacent tissues, and/or the entrance wound. As well, a flush match between these elements may reduce the chance of tissue trauma/shear between an implant with a hard protrusion and a tissue structure such as a blood vessel or nerve. The cross-sectional shape of the implant 6601 may vary as desired, such as from circular to oval to strap-like to polygonal in various contemplated embodiments.

The implant system 6600 may also comprise, as in FIG. 64c, an abdominal tension detecting belt that may be optionally used in conjunction with implant 6601. This may be used as a training tool to, for example, voluntarily or involuntarily train a user to avoid having the abdomen/stomach project outwardly to an undesired degree and/or avoid poor posture. For example, if the user has poor posture, the abdomen may be projecting outward, which may cause the sensor to reach a threshold tension. This threshold may cause firing of one or more electrodes, the sensation/pain of which may cause the user to suck or withdraw the abdomen inwardly to avoid the sensation, which may be used to train better posture over time.

Implant system 6600 may be particularly useful in connection with treatment of patients who have been immobile or bedridden for prolonged periods. For example, use of system 6600 in treatment of stroke or other trauma victims may tone muscle and/or help metabolize sugars. In addition, similar to the manner in which EMS (Electrical Muscle Stimulation) and PEMs (percutaneous electrical muscle stimulation) may aid type 2 diabetics by lowering postprandial glucose (Diabetes Res. Clin. Pract. 2012 June; 96 (3): 306-12), in some alternative implementations, an embodiment of an FSQEMS system may be used for such treatment, but without the painful needles of PEMs. Although FSQEMS is shown here associated with the rectus abdominis musculature, it may be appreciated that use with many other voluntary muscle groups may be practical. Inductance coil/'group of stacked coils' may be present as per the coil cross section depicted in FIG. 37d.

A multiplicity of stacked inductance coils may increase the power transfer as well as increase of mutual inductance between coupled coils. Reference: 'Achieve High Power Density with Stacked Inductor Aug. 25, 2021, https://www-.electronicdesign.com'

To deliver proper alignment the maximal energy transfer per orientation of coil groups may be, in some embodiments, assessed by an internal or external CPU with a signaling when optimal alignment is approaching or departing, or made or lost.

As per FIG. 37d, a temperature sensor such as 3719t may be configured to detect tissue temperatures external to the coil and/or wrapper so that hardware and/or software in the system can alert the user/external coil to increase or decrease energy transmission as the case may be. In some embodiments, one or more threshold temperatures may be established, such as a shutoff temperature, which may be, for example, 45 degrees C., which may result in termination of energy delivery until the temperature returns to a second threshold temperature, such as 40 degrees C., at which point the energy delivery may resume.

In some embodiments, lab-on-a-chip devices may be incorporated into one or more of the implants disclosed herein, which devices may comprise microfluidic chips. In some embodiments, microfluidic chips may comprise channel systems connected to liquid reservoirs by, for example, tubing systems. In some embodiments, sensors, detectors, optical components, and the like may be integrated on-chip. In some instances, miniaturization technology and/or reduction of reaction volume may decrease the absolute amount of analytes, allowing for the analysis of small compounds out of a flowing bulk sample. In some embodiments, fluorescence analysis may allow for real time measurements due to its high temporal resolution and sensitivity. Such microchips may be used for applications such as, for example, enzymatic assays, photo-induced protein conversion, analysis of DNA, and the like. In some embodiments, merging channel geometries may be used to regulate the concentrations of reagents. Additionally, in some instances, temperature may also be regulated. In some embodiments, such chips may comprise continuous flow microreactors, which may facilitate multi-step reactions, allowing for the combination of multiple reaction steps and on-line analysis. In some embodiments, such chips may be used for high throughput screening and/or cell sorting. In some embodiments, chips may be constructed to detect and/or sort DNA fragments and/or bacterial cells, preferably with high throughput rates. Combining appropriate biological assays with high-sensitivity detection techniques may facilitate the identification and isolation of targeted cells and/or molecules. In some embodiments, small liquid volumes may be generated such that the supply of reagents may be regulated in precise reactions, such as protein crystallization or molecular evolution. In some instances, said volumes may be formed by aqueous droplets in a carrier medium. In some embodiments, chips may be used for microfluidic cell treatment, as reaction volumes may approach volumes analogous to those found in cells, allowing for manipulation of objects of cellular size in a controlled environment. Additional details regarding such lab-on-a-chip devices may be found in "Lab-on-a-chip: Microfluidics in Drug Discovery", Dittrich, Nature, Vol. 5, 210-218, 2006, which is hereby incorporated herein in its entirety by reference.

FIG. 67a depicts an embodiment of a spiral implant 6701 comprising a plurality of LEDs 6711 interspersed throughout the implant 6701, such as LEDs, OLEDs, and/or mLEDs, each of which may be positioned inside the lumen of the spiral implant 6701 or on an outer surface thereof. Spiral implant 6701 comprises an inner terminus 6701i and an outer terminus 67010, and may comprise space 6788 between each pair of adjacent spiral arms. The embodiment depicted by FIG. 67a may be useful for illuminating a preexisting ink tattoo through the skin surface. Other uses may include implantation for mood improvement, as previously discussed. Some implementations may include uses for illumination of overlying traditional tattoos from an illuminated subcutaneous implantable spiral which may optionally be controllable from an external device. Other implementations may include illuminated subcutaneous implantable spirals themselves are the implantable tattoo art which may optionally be controllable from an external device; a combination of these uses may be possible. Any of the LEDs or other light sources shown or discussed as being used on a compressible implant may be used on a spiral/non-compressible implant in various contemplated embodiments.

Further implementations may include uses for treating bilirubin or chemicals derived therefrom in liver disease, cancer, or other disease states. LEDs or other light sources shown or discussed as being used on a compressible implant may be used on a spiral/non-compressible implant in various contemplated embodiments and may be therapeutic. For example, phototherapy may produce specific changes in bile acid metabolism and may reduce itching in liver disease patients by altering the cutaneous bile acid pool. Additional details may be found in 'Effects Of Phototherapy On Hepatic Function In Human Alcoholic Cirrhosis', Knodell, Gastro-enterology, 70:1112, 1976 which is hereby incorporated in its entirety by reference. Phototherapy results in transfor-mation of bilirubin to more water-soluble isomers. Effective bilirubin altering wavelengths in vitro (i.e., leading to greater than 25% photoisomer) were in the blue spectrum from approximately 390 to 470 nm. Green light (530 nm) was not only ineffective for production of photoisomer, but may reverse the reaction. The results indicate that clinically useful phototherapy units should include the blue portion of the visible spectrum, with increasing effectiveness by elimi-nating of green light. Additional details may be found in 'Phototherapy For Neonatal Jaundice: Optimal Wavelengths Of Light', Ennever, J Pediatr, 103:295, 1983 which is hereby incorporated in its entirety by reference. Thus, blue LED light may reduce bilirubin in liver disease patients.

In some embodiments, additional elements, such as elec-tronic elements, may be coupled to the coil to make the coil more useful as a standalone implant, or an implant config-ured to standalone as a power supply to another, secondary implant. In some such embodiments, use of a unitary coil, as shown in FIG. 80a, may eliminate the need for an auxiliary implant altogether. In contemplated embodiments, a unitary coil may therefore be coupled with other implants, such as implants to which the unitary coil is providing energy, without the use of an auxiliary implant to aid the unitary coil in doing so. It is also contemplated, however, that some coil embodiments may have some, but not all, of the components that may be provided on an auxiliary implant, and may therefore be considered a "hybrid" coil implant.

In some embodiments, the coil/spiral implant may com-prise an arm extending along at least 2 complete turns to form the spiral shape. In some such embodiments, the coil/spiral implant may comprise an arm extending along at least 10 complete turns to form the spiral shape. In some such embodiments, the coil/spiral implant may comprise an arm extending along at least 15 complete turns to form the spiral shape. In some such embodiments, the coil/spiral implant may comprise an arm extending along at least 20 complete turns to form the spiral shape. In some such embodiments, the coil/spiral implant may comprise an arm extending along at least 25 complete turns to form the spiral shape.

FIG. 67b depicts a cross-sectional view of an embodiment of a spiral implant with rectangular cross-section 6701re taken from FIG. 67a as demarcated by the line and arrow.

FIG. 67c depicts a cross-sectional view of another embodiment of a spiral implant 6701fL with a relatively flat cross-sectional shape.

FIG. 67d depicts a cross-sectional view of still another embodiment of a spiral implant 6701ov having an oval cross-sectional shape.

FIG. 67e depicts a cross-sectional view of yet another embodiment of a spiral implant 6701pe with a pentagonal cross-sectional shape. In further anticipated embodiments, the cross sectional shapes may be any geometric shape, including, but not limited to polygons.

FIG. 67f is a side view of another alternative embodiment of a portion of a spiral implant 6701if showing the inner terminus, which comprises an open loop end or handle 6750f projecting therefrom. Loop 6750f may facilitate the place-ment of, for example, a fixating suture or a guide suture by a surgeon. In the case of a spiral implant, as the implant pockets are often slightly larger than the size of the implant, if a surgeon wishes to limit the mobility of the implant before the body seals it in place, a suture may be helpful.

FIG. 67g is a side view of another alternative embodiment of a spiral implant 6701ig showing the inner terminus of the implant, which inner terminus comprises a notch 6750g, which may facilitate the placement of a suture or other similar structure that may be coupled with the implant to facilitate affixing the implant at a desired location within an implant pocket. For example, in some implementations, the implant pocket may be significantly larger than the implant and the implant may therefore be prone to shifting within the pocket. In order to maintain the implant at a desired location, such as directly under an ink tattoo, a surgeon may wrap a suture about the notch 6750g and couple the suture to the skin at that location to prevent the implant from shifting. Notch 6750g may also, or alternatively, be used to facilitate movement of the implant by, for example, allowing a surgeon to pull the implant with the suture similar to a tether.

FIG. 67h depicts a cross-sectional view of another example of a spiral implant 6701h. Implant 6701h is similar to the spiral implant of FIG. 67b, but further comprises a superstructure 6751h, which may extend along the entire length of the implant 6701h or, alternatively, just a portion thereof, to provide added structure to the implant 6701h. Superstructure 6751h may, in some embodiments, be adhered to one side and/or surface of the spiral implant 6701h and, although shown as a semicircle in the figure, may comprise any shape as desired.

FIG. 67i depicts a cross-sectional view of a similar spiral implant 6701ii also having a superstructure 6751i, but in this case the superstructure 6751i is positioned within a lumen of the implant rather than coupled to an outer surface thereof. In contemplated embodiments, superstructures that are cross sectionally circular may be a variety of other shapes, includ-ing ovals and/or polygons.

FIG. 67j depicts a cross-sectional view of another similar spiral implant 6701j comprising a fully contained super-structure 6751j positioned in a lumen thereof. However, in this embodiment, the superstructure 6751j is sandwiched between various other elements of the implant, such as battery 6704 and inductance coil 6714. It should be under-stood, however, that the superstructure may be coupled to and/or sandwiched between any other elements of the assembly, including other functional elements, or alterna-tively, elements the sole purpose of which may be to couple the superstructure 6751j to the implant, such as laminate and/or adhesive layers, for example.

FIG. 67k depicts a cross-sectional view of another spiral implant 6701k comprising an externally attached superstruc-ture 6751k, which, as shown in the figure, may be coupled to an outer side/surface of the implant.

FIG. 67L depicts a cross-sectional view of still another spiral implant 6701L comprising a fully contained semicir-cular superstructure 6751L.

FIG. 67m depicts a cross-sectional view of yet another spiral implant 6701m comprising an externally coupled superstructure 6751m. Implant 6701m differs from implant 6701h in that the superstructure is coupled to an opposite side (inner vs. outer, for example) of the implant relative to implant 6701h.

FIG. 67n depicts a cross-sectional view of a spiral implant 6701n comprising a superstructure 6751n positioned on the upper and lower surfaces of the implant. Of course, in alternative embodiments, the superstructure 6751n may only be positioned on the top, or only the bottom, of the implant.

FIG. 68a depicts a top plan view of an embodiment of a compressible implant 6801, which may comprise a semisolid implant, and which further comprises a peripheral superstructure 6851*b*. Implant 6801 further comprises macro positioning/instrument engaging holes 6803 and reinforcement areas 6802.

As shown in FIGS. 68*b*-68*e*, each of which is a cross-sectional view of a possible iteration of the general embodiment of FIG. 68*a*, superstructures 6851*b*-6851*e*, which are variations of the superstructure 6851*b* shown in FIG. 68*a*, may either extend along the outer peripheral edge of implants 6801, 6801*c*, 6801*d*, as shown in FIGS. 68*b*, 68*c*, and 68*d*, or may extend inside the implant 6801*e* (e.g., between upper and lower surfaces thereof) to define or be adjacent to the peripheral edge of the implant, as shown in FIG. 68*e*.

Any of the aforementioned superstructures, such as superstructures 6851*b*-6851*e*, may comprise, for example, a bladder-like structure that may be inflatable in some embodiments. Similarly, in some embodiments, the implant itself may comprise a bladder-like structure, as shown in FIG. 68*c*, which depicts an implant 6801*c* having a central space peripherally bound at opposing ends by superstructure 6851*c*. Such bladder-like implants may, in some embodiments and implementations, be configured with electronic control, an energy source, and/or pumping/drug delivery systems to infuse drugs/chemicals directly into the blood supply of a target tissue such as, for example, chemotherapy into a cancer. Superstructures, such as but not limited to superstructures 6851*b*-6851*e*, may also be configured to reduce or eliminate potentially problematic edges and/or relatively sharp points, which, as discussed above, may result in inflammation and/or other problems. Thus, preferred embodiments may be specifically configured solely, or at least primarily, with smooth and/or softened edges, surfaces, and/or points to reduce or eliminate these issues.

FIG. 69 depicts a spiral implant 6900 comprising spiral arms 6901*a* having little to no space between each adjacent pair of spiral arms 6901*a*, as indicated at 6988. This type of shape may be manufactured, for example, by simply cutting a spiral out of a planar substrate with no space in between arms. For this type of spiral to be implanted in a relatively easy manner, however, the material of the implant may be sufficiently flexible so that the spirals created by cutting may be bent/flexed away from each other in order to fit through the preferably minimally invasive entrance wound, as shown by the techniques previously disclosed. As per FIG. 47, this spiral implant 6900 may be rotated into an incision from either the inner or outer terminus.

Inductance coil/'group of stacked coils' may be present as per the coil cross section depicted in FIG. 37*d*.

A multiplicity of stacked inductance coils may increase the power transfer as well as increase of mutual inductance between coupled coils. Reference: 'Achieve High Power Density with Stacked Inductor Aug. 25, 2021, https://www-.electronicdesign.com'

To deliver proper alignment the maximal energy transfer per orientation of coil groups may be, in some embodiments, assessed by an internal or external CPU with a signaling when optimal alignment is approaching or departing, or made or lost.

As per FIG. 37*d*, a temperature sensor such as 3719*t* may be configured to detect tissue temperatures external to the coil and/or wrapper so that hardware and/or software in the system can alert the user/external coil to increase or decrease energy transmission as the case may be. In some embodiments, one or more threshold temperatures may be established, such as a shutoff temperature, which may be, for example, 45 degrees C., which may result in termination of energy delivery until the temperature returns to a second threshold temperature, such as 40 degrees C., at which point the energy delivery may resume.

FIG. 70*a* depicts a front view of a torso, especially the lower abdomen and genital region, of a human patient having a flexible strand/string electronic genital stimulative (FSEGS) implant system 7000 comprising one or more implants positioned in respective implant pockets preferably made via one or more minimally invasive entrance incisions 7010. More particularly, implant system 7000 comprises a FSEGS flexible strand/string implant 7001, which may be positioned within an implant pocket 7005*c*, which may comprise a canal that may be made by a trocar, probe, and/or beaded dissector as shown previously. System 7000 may further comprise connecting wires 7015*i*, inductance coil 7014 (with or without additional electronics attached) and/or auxiliary implant 7008, each of which may be deposited in various implant pockets, either their own individual implant pockets or an implant pocket shared with another implant of the system, which may be made similarly to others described by methods described elsewhere within this application, including FIGS. 1 & 57. In some implementations, the primary FSEGS implant 7001 of system 7000 may be oriented in or about the clitoral or crus clitoral tissues, or in or adjacent to the penis. Flexible strand/string implant 7001 may, in some embodiments, comprise a flexible tube or strand of electronics.

In some embodiments, inductance coils may be replaced by other power generating and/or yielding devices, such as, thermoelectric generators, flexible piezoelectric energy harvesters, capacitive coupling transmission, magnetodynamic coupling transmission, microwave power transmission, and the like, depending on the subject patient and safety guidelines.

It may be beneficial to have not only electrode stimulation of the nerve supply to the genitalia, but a simultaneous or rhythmic interrupted stimulation of the genital tissues themselves by, for example, vibrational mechanical means, such as piezoelectric means 7071*a*. In further contemplated embodiments, the piezoelectric generator/actuator/means 7071*a* may be replaced with, for example, miniaturized eccentric rotating mass motors, linear resonant actuators, solenoids, and the like.

As best depicted in FIG. 70*b*, implant system 7000 may further comprise auxiliary implant 7008, which may comprise any of the elements previously described in FIGS. 54 *a*-*c*, including but not limited to an antenna 7002*b* to allow for receipt of electromagnetic signals, which may be used to transmit data to CPU/printed-circuit-board 7003 for use in activating peripherally based terminal electrodes 7011*a*-*e* using energy derived from battery 7004 and/or inductance coil 7014. An external transmitter may be adjusted by the patient or healthcare personnel to transmit signals to internal antenna 7002*b* that in turn directs CPU 7003 to coordinate electrical output of electrodes 7011*a*-*e*. In some embodiments, the battery 7004 may also be flexible and/or installed within or along inductance coil 7014. A wireless charging system may be provided, as previously described, and which may be configured to wirelessly charge the battery 7004 via inductance coil 7014. Preferably, each of the elements of implant system 7000 is either flexible and/or compressible, or is small enough on its own to fit within a minimally invasive entrance incision 7010 with other elements of implant 7000 moved into their optimal positions in separate tissue pockets, such as pocket 7005, which contains inductance coil 7014 in the depicted embodiment. Auxiliary implant 7008 may allow for certain components, such as sensitive electrical components, to be placed within a separate implant, which may be more protective of such components, such as being within a waterproof/sealed container, for example. A seal, such as a wrapper, may be used to contain all of the elements of auxiliary implant 7008 therein.

In further contemplated embodiments, the implant system may comprise an auxiliary implant with any element including, but not limited to, those mentioned for the auxiliary implant described in FIG. 66, for example, CPU(s)/printed-circuit-board(s), battery(ies), memory/data storage element(s), antenna(e), capacitor(s), electronic heart rate sensor(s), lab-on-a-chip element(s). In other contemplated embodiments, either coils or auxiliary implants may comprise pulse oximetry elements. Although some auxiliary implants shown in the figures are cylindrical in shape, in further contemplated embodiments they may comprise a variety of shapes including, but not limited to, ovoids, polygonal prisms, pads, pillow-like, purse-like, with or without various cavities or convexities.

The electrode termini may be positioned and configured to stimulate in and/or adjacent to the genitalia (e.g., the clitoris or penis), in some cases along with and its associated tissues, such as branches of the pudendal nerve. For example, some implementations may involve stimulation of the dorsal nerve of the clitoris and labial nerves or the dorsal nerve of the penis, the genital femoral nerve, and/or other nerve branches that may be supplied by the sacral plexus, for example, or any other nerve capable of sexual stimulation.

An external transmitter may be adjusted by the patient or healthcare personnel to transmit signals to internal antenna 7007 that, in turn, may provide instructions remotely to CPU 7003 to coordinate electrical output of electrodes 7011*a-e*. These external signals may, for example, be generated and/or received from a smartphone or other wireless communication device 7099. The smartphone/wireless communication device may comprise a CPU and software capable of interpreting and/or sending signals to and from the implantable CPU 7003. The external CPU and/or the internal CPU may contain programming sequences that will elicit the electrode firing in predetermined patterns that may be desirably stimulative. For example, sexual stimulations that occur in a wave-like pattern wherein a distal set of electrodes fires and then turns off and the next set of more proximal electrodes fires and then turns off and then the next set of even more proximal electrodes fires and then turns off, may be more pleasurable in some subjects than if all the electrodes fire at once.

In some embodiments, devices may be implanted to stimulate the clitoris in patients possessing vaginas. Some systems may include, for example, devices implanted near the dorsal nerves of the clitoris. In some instances, signal generators may be activated on command to generate energy pulses and stimulate the dorsal nerves. Such pulses may be generated in a controlled manner via stored programs and internal sensors, and/or may be dynamically controlled by an external device. In some instances, generated energy may include ultrasonic energy, electrical energy, chemical energy, and the like. Further details regarding such clitoral stimulation devices may be found in U.S. Patent Application Publication No. 2009/0259095, titled "System and Method for Treatment of Hypo-Orgasmia and Anorgasmia", which is hereby incorporated herein in its entirety by reference.

Certain embodiments may comprise systems to aid in achieving the enlarged state of female erectile tissue. In some instances, a device may be implanted within the female erectile tissue, such that, upon activation, fluid may be pumped from a subcutaneous reservoir into the device, enlarging the device, which may aid in achieving enlarged state of female erectile tissue. Some embodiments may comprise devices that may be controlled or recharged via external devices. Such systems may be used to aid in achieving female orgasm. Additional details regarding such systems may be found in U.S. Pat. No. 10,568,804, titled "System, an Apparatus, and a Method for Treating a Sexual Dysfunctional Female Patient", and U.S. Patent Application Publication No. 2020/0390643, titled "System, an Apparatus, and a Method for Treating a Sexual Dysfunctional Female Patient", both of which are hereby incorporated herein in their entireties by reference.

Some embodiments may include systems comprising distributed implanted devices that may selectively stimulate different nerves, which may, in some cases, provide aid to patients with sexual and urinary activity disorders. In some instances, a master controller may communicate with each stimulating device, preferably wirelessly, to transmit control commands. The master controller device and/or individual stimulators may be configured to respond to signals created from sensing devices in some embodiments. Examples of stimulation may include electrical stimulation of selected devices at selected intervals to achieve various phases of sexual arousal. Further details regarding such implants and systems may be found in U.S. Patent Application Publication No. 2006/0020297, titled "Neurostimulation System with Distributed Stimulators", which is hereby incorporated herein in its entirety by reference.

Implantable vaginal stimulators may be used in certain embodiments to enhance sexual response to stimuli. In some instances, an implantable system may comprise an operation device for control over the stimulating device. Movement/vibration of the stimulating device may be configured to be generated by, for example, an electromagnetic device, an electric motor, or the like. Furthermore, the system may comprise, in some embodiments, an implantable switch/wireless remote control for manual control and/or one or more sensors configured for detecting physical parameters for automatic control. Further details regarding such devices and systems may be found in U.S. Pat. No. 9,107,796, titled "Apparatus, System and Operation Method for the Treatment of Female Sexual Dysfunction", which is hereby incorporated herein in its entirety by reference.

Some embodiments of a system for enhanced female arousal may comprise an implant and/or system configured for restricting blood flow exiting the erectile tissue. Such systems may, in some embodiments, utilize a two-stage restriction of blood flow exiting a patient's erectile tissue, such as an initial stimulation of an erectile tissue to cause contraction and initially reduce blood flow leaving the erectile tissue, which may be coupled with additional gentle constriction of blood flow leaving the erectile tissue to further aid in the erectile tissues' engorgement with blood. Additional details regarding such devices and systems may be found in U.S. Pat. No. 8,795,153, titled "Method for Treating Female Sexual Dysfunction", which is hereby incorporated herein in its entirety by reference.

In some instances, electrical stimulators may be implanted within the body using the techniques and/or on the implants disclosed herein. In some embodiments, such electrical stimulators may comprise inductance coils, which may be used for purposes such as, for example, wireless data and power transmission. Additional details regarding such electrical stimulators may be found in "Implantable Functional Electrical Stimulation with Inductive Power and Data Transmission System", Lee, 2007, doi.org/10.12701/YUJM.2007.24.2.97, which is incorporated herein by reference in its entirety.

In some embodiments, implanted stimulators may comprise external casings comprising a first metal portion and a second portion, which may comprise a plastic/polymer portion. Some embodiments may comprise inductance coils embedded within the polymer/plastic portion of the casing. Additional details regarding such casings may be found in U.S. Pat. No. 7,376,466, titled "Casings for Implantable Stimulators and Methods of Making the Same", which is hereby incorporated herein in its entirety by reference.

Implanted lead connectors may be used, in some embodiments, to interconnect multiple devices and/or channel electrical signals between said devices and/or target organs. Some embodiments may comprise lead connectors comprising, for example, first and second ports configured to each receive signals suitable for tissue stimulation and a third port configured to connect to an organ. Additional details regarding such lead connectors may be found in U.S. Pat. No. 8,706,230, titled "Implantable Lead Connector", which is hereby incorporated herein in its entirety by reference.

In some embodiments, electrical stimulation systems may comprise implantable control modules. Such modules may comprise, for example, a housing comprising an electronic subassembly, an antenna, and/or a plurality of connectors. Some embodiments may comprise, for example, a control module, a connector receptacle, and/or leads including a plurality of electrodes on a distal end and a plurality of contacts on the proximal end. In some embodiments, a proximal end of the lead may be positioned in a connecter electrically coupled via, for example lead spring contacts to a control module. Additional details regarding such control modules may be found in U.S. Pat. No. 7,803,021, titled "Implantable Electrical Stimulation Systems with Leaf Spring Connective Contacts and Methods of Making and Using", and in U.S. Pat. No. 8,983,608, titled "Lead Connector for an Implantable Electric Stimulation System and Methods of Making and Using", both of which are hereby incorporated herein in their entireties by reference.

Some electrical stimulation devices involve the use of passive electrical conductors that may extend from subcutaneous tissue to the target tissue. Such devices may comprise, for example, superficial electrodes positioned in the upper lower subcutaneous electrodes forming a pick-up end, which preferably has a sufficient surface area to allow a sufficient portion of the current to flow from the surface electrodes through the fat and to the pick-up electrodes. In some embodiments, such devices may have functions such as, for example, blocking/activating neural impulses and/or stimulating a target tissue. Additional details regarding such methods and devices for electrical stimulation may be found in U.S. Pat. No. 9,072,886, titled "Method of Routing Electrical Current to Bodily Tissues via Implanted Passive Conductors", which is hereby incorporated herein in its entirety by reference.

In some embodiments, implanted electrical stimulation devices may be configured to deliver electrical stimulation therapy by using, for example, controlled current pulses to emulate controlled voltage pulses. In some instances, the current and/or voltage levels may be modulated. Some devices may be configured as controlled-current and/or controlled-voltage devices, preferably being configured to deliver current or voltage on a selective basis to electrodes implanted within the patient. Additional details regarding such stimulation devices may be found in U.S. Pat. No. 9,259,578, titled "Electrical Stimulator with Voltage Mode Emulation Using Regulated Current", which is hereby incorporated herein in its entirety by reference.

In some embodiments, implantable stimulator devices may comprise arrays of electrodes used, for example, to stimulate muscles and nerves. In some instances, the stimulator may comprise at least one array of electrodes that may serve as inputs and/or outputs. Some embodiments of the stimulator may comprise, for example, an integrated circuit to control the stimulator, a memory chip, a power source, and/or a transceiver. In certain embodiments, each element may be wrapped in a bio-compatible encasement and be connected with flexible wiring. In certain instances, the electrodes may comprise a flexible array of electrical contacts, which may be dynamically selected. Certain embodiments may also comprise sensors to detect physiological conditions. Additional details regarding such stimulators may be found in U.S. Patent Application Publication No. 2020/0406030, titled "Implantable Electrical Stimulator", which is hereby incorporated herein in its entirety by reference.

In some embodiments, miniature implantable stimulators may be used to produce unidirectionally propagating action potentials. Some configurations may comprise, for example, microstimulators arresting action potentials travelling in one direction along large and/or small nerves. Such devices may comprise, for example, electrodes for applying stimulating current; electrical/mechanical components hermetically encapsulated in biocompatible materials; an electrical coil for receiving energy and/or transmitting information; and/or means for storing electrical energy. In certain embodiments, such microstimulators may be configured to operate independently or in cooperation with other implanted devices. Additional details regarding such microstimulators may be found in U.S. Pat. No. 9,823,394, titled "Implantable Microstimulators and Methods for Unidirectional Propagation of Action Potentials", which is hereby incorporated herein in its entirety by reference.

Some embodiments comprising electrical stimulators may comprise electrodes including a porous substrate comprising bio-compatible materials, which may be configured to mimic extracellular matrix embedding. Such substrates may have an adjustable pore size configured to control tissue in growth. Such electrodes may, in some embodiments, be coupled with a pulse generator to generate an electric field around a target tissue. Additional details regarding the disclosed stimulation device may be found in U.S. Pat. No. 10,780,275, titled "Implantable Neuro-Stimulation Device", which is hereby incorporated herein in its entirety by reference.

In some instances, electrical stimulation may be delivered in current-based waveforms via implanted electrodes. Such devices may support selective control of stimulation, which may occur, for example, via a combination of two or more electrodes coupled to regulated current paths and/or at least one electrode coupled to an unregulated current path. In some instances, an unregulated current may balance current that would otherwise be unbalanced between regulated current paths. Additional details regarding such stimulators may be found in U.S. Pat. No. 9,987,493, titled "Medical Devices and Methods for Delivery of Current-Based Electrical Stimulation Therapy", which is hereby incorporated herein in its entirety by reference.

Some implanted neurostimulating devices may favor very thin electrodes and backings that may be conformable to an arciform area of the body; however, implants under pressure may be subject to migration and, if not sufficiently rigidified during a relatively large time period of tissue fibrosis and 'healing-in,' small, very flexible implants may be susceptible to folding, flipping, and/or unwanted migration. Unwanted migration of a sharp edge of a piece of electronics, even on a plastic backing, adjacent a delicate nerve or even a thick blood vessel, can cause inflammation leading to pain in the nerve or weakening of the blood vessel wall, which may lead to rupture. Additional details regarding such implants may be found in U.S. Pat. No. 10,653,888, titled "Wireless Neurostimulators", and U.S. Patent Application Publication No. 2020/0254266, titled "Wireless Neurostimulators," which is incorporated herein by reference in its entirety. It is also noted that, in this reference, FIG. 13 provides an indication of how small the implant may be, which in some instances may restrict some function.

With current technology, alternative embodiments/implementations may allow the smartphone or other wireless communication device 7099 to display video or image sites of pornography in a pattern or quality that may be synchronized with sexual stimulation output from system 7000. Further contemplated embodiments/implementations may allow for the synchronization of sound and sexual stimulation in system 7000. For example, in some embodiments and implementations, particular scenes from a movie may be linked to system 7000 in a manner such that stimulation is generated automatically upon starting a particular scene. Similarly, particular portions of a scene may result in increased or decreased stimulation to allow for synchronization of particular portions of the scene, rather than the entire scene itself, to system 7000.

It is noteworthy that what now is considered an external smartphone or other wireless communication device 7099 may, in some embodiments, be internalized by, for example, removing the screen and/or traditional protective components and implanting the battery, CPU, antenna, and other necessary electronics using methods such as those described herein. Therefore it is to be understood that system 7000 may also comprise this type of traditionally external device into an internalized location with internalized function. These parts may be not limited to those discussed, but may also include, for example, eye glasses/corrective lenses that are communicative with the system as well as hearing aids or implantable hearing devices. Eventually, the so called 'Metaverse' may become highly miniaturized, but until that time, many devices may require amounts of power and wireless charging that necessitate relatively large space and/or surface areas that may be accommodated by the devices and methods described herein, examples of which are discussed below.

In some embodiments, additional elements, such as electronic elements, may be coupled to the coil to make the coil more useful as a standalone implant, or an implant configured to standalone as a power supply to another, secondary implant. In some such embodiments, use of a unitary coil, as shown in FIG. 80a, may eliminate the need for an auxiliary implant altogether. In contemplated embodiments, a unitary coil may therefore be coupled with other implants, such as implants to which the unitary coil is providing energy, without the use of an auxiliary implant to aid the unitary coil in doing so. It is also contemplated, however, that some coil embodiments may have some, but not all, of the components that may be provided on an auxiliary implant, and may therefore be considered a "hybrid" coil implant.

FIG. 70b is a side elevation view of FSEGS flexible strand/string implant 7001 illustrating how each of the elements may be coupled on strand implant 7001; however, in other embodiments, orientations and/or locations may vary. In some embodiments, one or more, or each, of the elements of implant 7001, with the possible exception of terminal electrodes 7011a-e, may be sealed within a container or envelope, which is preferably both waterproof and biocompatible. Examples of suitable materials for said container include polyethylene, polyurethane, polypropylene, and the like. A wire 70150 may be used to couple the auxiliary implant 7008 with one or more (preferably all) of the various electrodes 7011a-e of the string implant 7001. In some embodiments, string implant 7001 may also comprise piezoelectric elements 7071a-e. Said piezoelectric elements may also comprise flexible piezoelectrics comprising, for example, PbZr0.52Ti0.48O3, LiNbO3, LiTaO3, PZT/PVDF composites, and/or the like. In further contemplated embodiments, string implant 7001 may further comprise LEDs 7081a-c, such as LED/OLED/mLEDs, which may further pleasure the patient or the patient's partner by providing programmable illumination.

In some embodiments, piezoelectric energy harvesters may be based on polyimide (PI)/Bi,La)FeO3-PbTiO3(BLF-PT)0-3 composites. Such piezoelectric energy harvesters may be flexible, lightweight, and/or free-standing. Additional details regarding such piezoelectrics may be found in "Flexible Piezoelectric Energy Harvester/Sensor with High Voltage Output over Wide Temperature Range", Sun, Nanoenergy, 2019, doi.org/10.1016/j.nanoen.2019.04.055, which is hereby incorporated herein in its entirety by reference.

In some embodiments, piezoelectric energy harvesters may comprise a sandwich structure comprising, for example, PVDF film filled with FeTiNbO6 (FTN) semiconductor particles, one or more intermediate layers, and/or pure PVDF films as upper and lower barriers. Such piezoelectrics may be prepared by hot pressing technology, and in some instances, may be flexible. Additional details regarding such piezoelectric devices may be found in "Flexible Piezoelectric Energy Harvester with Extremely High Power Generation Capability by Sandwich Structure Design Strategy", Fu, Applied Math & Interfaces, 2020, DOI: 10.1021/acsami.9b21201, which is hereby incorporated herein in its entirety by reference.

In some embodiments, piezoelectric devices may comprise all-inorganic compounds, such as, for example, Pb(Zr0.52Ti0.48)O3. In certain instances, such piezoelectrics may be flexible. In certain embodiments, such piezoelectrics may be based on two-dimensional mica substrates via a sol-gel method. Additional details may be found in "All-Inorganic Flexible Piezoelectric Energy Harvester Enabled by Two-Dimensional Mica", Wang, Nanoenergy, 2017, doi.org/10.1016/j.nanoen.2017.11.037, which is hereby incorporated herein in its entirety by reference.

In some embodiments, piezoelectric devices may comprise multimaterial piezoelectric fibers. In some instances, such piezoelectric devices may be shaped like hollow cylinders. Such devices may comprise, for example, poly (vinylidene difluoride-trifluoroethylene) shells, which may also comprise carbon-loaded poly(carbonate)/indium electrodes and/or poly(carbonate) cladding. In some embodiments, piezoelectric devices may comprise perovskite, having a general formula of ABX3. Examples may comprise materials such as LaAlO3, NaWO3, and the like. In a preferred embodiment, a piezoelectric device may have high-electromechanical coupling properties while exhibiting low dielectric loss. Suitable materials for such uses may include, for example, PbMg1/3Nb2/3O3-PbTiO3, PbZn1/3Nb2/3O3-PbTiO3, and the like. In some embodiments, piezoelectric crystals may also be used, due to their high piezoelectric performance. Additional details regarding piezoelectric devices may be found in "Developments of Immobilized Surface Modified Piezoelectric Crystal Biosensors for Advanced Applications", Pramanik, International Journal of Electrochemical Science, 2013, researchgate.net/publication/258052187, which is hereby incorporated herein in its entirety by reference.

During sexual arousal or stimulation, a patient's heart rate may change. An ancillary electronic heart rate sensor 7024 option may therefore be configured to detect heart rate, whereupon a preprogrammed FSEGS may signal a desired change in stimulation or stimulation pattern. As a safety precaution, internal or external programming may determine a preset heart rate, the reaching of which may cease the FSEGS unit firing. An ancillary pulse oximeter 7025 may also be coordinated with a stimulation pattern.

Terminal electrodes 7011a-e and/or piezoelectric elements 7071a-e may be electrically coupled, directly or indirectly, to a CPU 7003 and/or other suitable electrical circuitry. Additionally, the firing of the LEDs 7081a-c may be programmable.

FIG. 70c is an enlarged transparency view of FIG. 70b depicting an embodiment of a wiring scheme for various terminal electrodes 7011a-e along a flexible strand/string electronic genital stimulative (FSEGS) implant 7001. In this embodiment, electrodes 7011a-e are all wired independently (for example, on wires such as 7011aw, which is coupled with electrode 7011a) of each other, thus allowing for different programmable control for each. In this embodiment, piezoelectrics 7071a-e may also be wired independently of each other, thus allowing for different programmable control for each. In other contemplated embodiments, the wiring may be in series, parallel or another form of independent wiring or a combination thereof. Firing may vary in terms of amplitude and time of firing and on-off cycle. Again, this may be random, controllable by the user, or both (selectively random or specific, as selected by the patient). If the electrodes are on independent circuits to the CPU then each may be programmed to fire at random or independently in a preprogrammed pattern so as to provide a differing stimulus pattern to the subject/recipient over time. Psychological and neurological studies have shown that a stimulus' effect may diminish based upon unchanging repetition over time (recipient's nervous system becomes jaded to a repetitive unchanging/boring stimulus). Thus, preprogrammed or randomized or changing programmable stimuli may serve to enhance the effect of FSEGS. Electrode output may be individually addressed in terms of amplitude, frequency, and/or activation in order to achieve multiple stimuli. The triangles used to represent the electrodes in FIGS. 70b-c are by no means restrictive or indicative of electrode shape. For example, in FIGS. 70b and 70c, internal wiring 7011aw is connected to a peripheral/circumferential electrode 7011a that may have several potential benefits. For example, providing a band-like/circumferential electrode may allow for a more widely distributed signal that may be less prone to missing a particular target nerve or other tissue region. However, it may be desirable for certain applications to form such an electrode such that it extends only partially about the periphery of the string and/or tube-like implant 7001. For example, it may be desirable to avoid the increased points of termination, such as corners, which may result from an incomplete circumferential electrode. It should be understood, however, that such points of termination may be preferred for certain applications, particularly since it may be desirable to vary the location, strength, and/or other parameters of the signal for certain applications, such as FSEGS applications.

Although electrode 7011a is shown projecting slightly from the peripheral wall of the implant 7001 in FIG. 70c, it should also be understood that it may be desirable instead to have the electrode flush with this exterior wall, which may be a hollow or solid tube, for example, which may allow the implant to slide more easily through, for example, a trocar, adjacent tissues, and/or the entrance wound. The cross-sectional shape of the implant 7001 may vary as desired, such as from circular to oval to strap-like to polygonal in various contemplated embodiments.

FIGS. 70d-70g depict various implantation sites that may be particularly desirable for use in connection with the FSEGS systems disclosed herein. For example, FIG. 70d depicts a string implant 7001 extending into the clitoris within an implant pocket 7005c. In preferred embodiments and implementations, the implant 7001 may extend directly into the glans 7069g, as shown in FIG. 70d. Alternatively, or additionally, implants may extend into the crux 7069c of the clitoris, as shown in FIG. 70e, which depicts the results of an implementation involving a first implant 7001a extending into the shaft and/or glans 7069g of the clitoris, a second implant 7001b extending into a first side/wing of the crux 7069c, and a third implant 7001c extending into a second side/wing of the crux 7069c. Although not shown in this figure, it should be understood that each implant may extend within a respective implant pocket, which may comprise an implant canal, as needed.

FIGS. 70f and 70g depict FSEGS implants positioned within male genitalia. More particularly, FIG. 70f depicts an implant 7001 positioned within an implant pocket 7005c extending down the shaft of a patient's penis 7096s and at least partially into the glans 7096g of the penis 7096s. Similarly, FIG. 70g depicts the results of an alternative implementation in which two implants 7001 have been positioned within the penis 7096s side by side. Again, implant pockets are not shown in this figure but it should be understood that they may be present.

Inductance coil/'group of stacked coils' may be present as per the coil cross section depicted in FIG. 37d.

A multiplicity of stacked inductance coils may increase the power transfer as well as increase of mutual inductance between coupled coils. Reference: 'Achieve High Power Density with Stacked Inductor Aug. 25, 2021, https://www-.electronicdesign.com'

To deliver proper alignment the maximal energy transfer per orientation of coil groups may be, in some embodiments, assessed by an internal or external CPU with a signaling when optimal alignment is approaching or departing, or made or lost.

As per FIG. 37d, a temperature sensor such as 3719t may be configured to detect tissue temperatures external to the coil and/or wrapper so that hardware and/or software in the system can alert the user/external coil to increase or decrease energy transmission as the case may be. In some embodiments, one or more threshold temperatures may be established, such as a shutoff temperature, which may be, for example, 45 degrees C., which may result in termination of energy delivery until the temperature returns to a second threshold temperature, such as 40 degrees C., at which point the energy delivery may resume.

FIG. 71a depicts an example of a sensory-processing-feedback-system 7100 comprising, in the depicted embodiment, a flexible strand/string electronic implant (FSEI). System 7100 comprises one or more implants positioned in respective implant pockets preferably made via one or more minimally invasive entrance incisions 7110. More particularly, implant system 7100 comprises flexible strand/string implant(s) (FSEI) 7101, which may be positioned within an elongated implant pocket(s) 7105c comprising a canal that may be made by a trocar, probe and/or beaded dissector as shown previously. System 7100 may further comprise inductance coil 7114 (with or without additional electronics attached) and/or auxiliary implant 7108, each of which may be deposited in various implant pockets 7105, their own individual implant pockets, or an implant pocket shared with another implant of the system, which may be made similarly to others described by methods described elsewhere within this application, including FIGS. 1 & 57. Inductance coil 7114 may be connected to auxiliary implant 7108 by an incoming wire 7115i, and auxiliary implant 7108 may be connected to the FSEI 7101 by outgoing wires 7115O. In some embodiments and implementations, the primary FSEI implant 7101 of system 7100 may be oriented in, about, or toward a target zone of a distant/distal auxiliary implant 7141 that may be placed in the subcutaneous tissues of the upper body, or another remote location on the body relative to the entrance incision and/or other implants of the system 7100. The distant/distal auxiliary implant(s) 7141 may comprise, for example, a wireless communication device/antenna 7141a and/or a transcutaneous sound receiver 7141s, such as a subcutaneously implanted microphone.

Flexible strand/string implant 7101 may, in some embodiments, comprise a flexible tube or strand of electronics, wires, and/or fiber optics. In some embodiments, inductance coils may be replaced by other power generating and/or yielding devices, such as, thermoelectric generators, flexible piezoelectric energy harvesters, capacitive coupling transmission, magnetodynamic coupling transmission, microwave power transmission, and the like, depending on the subject patient and safety guidelines. In some implementations, fiber optics may transfer data and/or energy.

In some embodiments, thermoelectric generators may comprise, for example, SiGe, CoSb3, Bi2Te3, PbTe, and the like. In certain embodiments, materials such as Bi2Te3 may be mixed with nanomaterials to reduce the lattice thermal conductivity. In some instances, such thermoelectric generators may be flexible. Such thermoelectric generators may comprise, for example, polymers, such as polyaniline, which exhibits good thermoelectric properties. In certain instances, thermoelectric properties may be enhanced by incorporating conductive additives such as, for example, carbon nanotubes with Au nanoparticles. In some embodiments, a TEG may be fabricated from a hybrid material comprising granulated carbon nanotubes granulated into p/n-type bismuth telluride, which may be distributed within a flexible material, such as polydimethylsiloxane. In certain embodiments, TEGs may be cylindrical, or even thin-film, in some cases a few micrometers thick. TEGs may be cooled via active/passive cooling methods. In a preferred embodiment, multi-stage TEGs may be used to generate higher power compared to a single TEG for a given temperature gradient. To enhance biocompatibility, TEGs may be coated in a biocompatible membrane. Additional details regarding thermoelectric generators may be found in "The Design of a Thermoelectric Generator and Its Medical Applications", Kumar, MDPI, 2019, DOI: 10.3390/designs3020022, which is hereby incorporated herein in its entirety by reference.

In some embodiments, thermoelectric generators may comprise DC-DC rectifiers in order to yield a current/potential, which may be used to charge a battery.

In some embodiments, the orientation of the top electrodes of a thermoelectric generator module may be oriented in a way which may increase unidirectional flexibility. In a preferred embodiment, all of the top electrodes may be integrated in parallel to increase flexibility. In some instances, small thermoelectric semiconductor chips may be mounted on a substrate at a high packaging density, realizing efficient power recovery while maintaining stable adhesion and flexibility. Additional details regarding such electrodes may be found in "Flexible Thermoelectric Generator Module: A Silver Bullet to Fix Waste Energy Issues", Osaka University, 2018, from phys.org/news/2018-12-flexible-thermoelectric-module-silver-bullet.html, which is hereby incorporated herein in its entirety by reference.

In some embodiments, thermoelectric generators may comprise polydimethylsiloxane substrates and/or thermocouples. PDMS may provide flexibility and low thermal conductivity to the TEG. A lower thermal conductivity may aid in reducing losses in the heat flowing through thermocouples. Additional details regarding implantable thermoelectric devices may be found in "Human Body Heat Energy Harvesting Using Flexible Thermoelectric Generator for Autonomous Microsystems", Kim, Materials Science, 2012, which is hereby incorporated herein in its entirety by reference.

In some embodiments, electrostatic generators may be used to produce energy via electrostatic induction. Such devices may convert mechanical vibration into electrical energy by moving part of the transducer relative to an electric field. In some embodiments, kinetic generators based on electrostatic transducers may comprise variable capacitors. In some embodiments, magnetic induction generators may be used to produce electricity. Such devices may induce flux changes by, for example, rotating a circuit along an axis, thereby changing the surface associated with magnetic flux. Such devices may comprise, for example, eccentric masses, permanent magnet rings, and/or planar coils. In some embodiments, thermo-electric harvesters may be used to produce electricity. Such devices may comprise thermocouples, which may be electrically connected in series with high thermal resistance while being thermally connected in parallel. Such devices may use differences in temperature to produce power. In some embodiments, environmental energy harvesting may be used to power implanted devices. In some such embodiments, one such harvesting method may comprise a capacitive coupling link, which may involve two parallel plates acting as capacitors. The first plate may be outside the body while the second plate in implanted within the body. Such capacitive coupling devices may be used to transfer data and/or power. In some instances, piezoelectric devices may be used to convert mechanical motion/strain into electrical energy. Additional details regarding such energy harvesting methods may be found in "Energy Harvesting for the Implantable Biomedical Devices: Issues and Challenges", Hannan, BioMedical Engineering Online, 2014, 13:79, which is hereby incorporated herein in its entirety by reference.

In some embodiments, batteries, such as, for example, lithium-based batteries, may be used to power implanted devices. In certain instances, bio-fuel cells may be used to generate electrical power. Bio-fuel cells may generate power from sources such as, for example, glucose and/or amylum from within the body. In certain embodiments, thermoelectric generators may be used to generate power by exploiting the difference in temperatures around the body. In some instances, transcutaneous power transmission via inductive coupling may be used to charge/power implanted devices. In certain embodiments, kinetic energy from the body's movement may be converted into electrical energy. Additional details regarding such powering methods may be found in "Power Approaches for Implantable Medical Devices", Amar, Sensors, 2015; 15:28889-28914, which is hereby incorporated herein in its entirety by reference.

System 7100 also may comprise smart glasses 7142, capable of transmitting optical information to and from the wearer. System 7100 may also comprise acoustic implant 7143, which may be positioned, for example, within the ear and/or within the adjacent tissues. The purpose for having implant 7141 positioned relatively distant from the inductance coil and/or other associated electronics/implants relative to implants previously discussed is that the lower abdomen is an area that is usually clothed and may have sufficient subcutaneous tissue in which to contain, cushion, and/or hide a relatively larger implant. In addition, the tissue in this region of the body is relatively inert, thereby possibly reducing the risk of electromagnetic carcinogenesis. Thus, ongoing visual signals, which may currently be transmitted by Bluetooth® or another wireless communication protocol, may not penetrate through the skin at various postural angles, and placing an auxiliary implant 7141 may reduce the distance and energies necessary to transmit signals from eyeglasses or hearing aids/speakers, thus improving the quality of the signals. In some contemplated embodiments, inductance coil 7114, when not receiving transmitted wireless energy, may also be configured to act as a transmitting and/or receiving antenna. In some embodiments and implementations, the incision, or one of the incisions, may be made in the region of the patient's navel 7110*n*.

In some embodiments, additional elements, such as electronic elements, may be coupled to the coil to make the coil more useful as a standalone implant, or an implant configured to standalone as a power supply to another, secondary implant. In some such embodiments, use of a unitary coil, as shown in FIG. 80*a*, may eliminate the need for an auxiliary implant altogether. In contemplated embodiments, a unitary coil may therefore be coupled with other implants, such as implants to which the unitary coil is providing energy, without the use of an auxiliary implant to aid the unitary coil in doing so. It is also contemplated, however, that some coil embodiments may have some, but not all, of the components that may be provided on an auxiliary implant, and may therefore be considered a "hybrid" coil implant.

As depicted the perspective view of FIG. 71*b*, implant system 7100 may further comprise auxiliary implant 7108, which may comprise any of the elements previously described in FIGS. 54 *a-c*, including but not limited to an antenna 7102*b* to allow for receipt of electromagnetic signals, which may be used to transmit data to CPU/printed-circuit-board 7103. An external transmitter may be adjusted by the patient or healthcare personnel to transmit signals to internal antenna 7102*b* that, in turn, directs CPU 7103 to coordinate electrical output of wiring contained in implant 7101. In some embodiments, the battery 7104 may also be flexible and/or installed within or along inductance coil 7114. A wireless charging system may be provided, as previously described, which may be configured to wirelessly charge the battery 7104 via inductance coil 7114. Preferably, one or more of the elements of implant system 7100 is either flexible and/or compressible, or is small enough on its own to fit within a minimally invasive entrance incision 7110 with other elements of implant 7100 moved into their optimal positions in separate tissue pockets, such as pocket 7105, which contains inductance coil 7114 in the depicted embodiment. However, some components, such as the string-like implant 7101, need not be compressible. Similarly, in some embodiments, the inductance coil 7114 may be rigid but may, due to the techniques for insertion of spiral implants disclosed herein, be inserted into a larger implant pocket, as previously discussed. Auxiliary implant 7108 may allow for certain components, such as sensitive electrical components, to be placed within a separate implant, which may be more protective of such components, such as being within a waterproof/sealed container, for example. A seal, such as a wrapper, may be used to contain all of the elements of auxiliary implant 7108 therein. Auxiliary implant 7108 may further comprise, for example, a memory/data storage element 7125.

In further contemplated embodiments, the implant system may comprise an auxiliary implant with any element including, but not limited to, those mentioned for the auxiliary implant described in FIG. 66, for example, CPU(s)/printed-circuit-board(s), battery(ies), memory/data storage element(s), antenna(e), capacitor(s), electronic heart rate sensor(s), lab-on-a-chip element(s). In other contemplated embodiments, either coils or auxiliary implants may comprise pulse oximetry elements. Although some auxiliary implants shown in the figures are cylindrical in shape, in further contemplated embodiments they may comprise a variety of shapes including, but not limited to, ovoids, polygonal prisms, pads, pillow-like, purse-like, with or without various cavities or convexities.

As previously mentioned, in some embodiments, system 7100 may further comprise and/or be a replacement for various other functional elements such as, for example, eye glasses/corrective lenses that are communicative with the system, hearing aids, and/or implantable hearing devices. In some embodiments, antenna 7141*a* may be configured to communicate with various sensory feedback elements of the system 7100, such as eyeglasses 7142 and/or hearing aid 7143.

FIG. 71*c* is a side perspective view of auxiliary implant 7141, which may be positioned at the terminus of the FSEI(s) 7101. In this embodiment, auxiliary implant 7141 may comprise antenna 7141*a* and transcutaneous audio receiver 7141*s*. In some embodiments, two separate implants 7141 may be provided to, for example, decrease the distance that signals must travel to and/or from the various sensory devices, such as glasses 7142 and/or hearing aids/speakers 7143.

In some embodiments, inductance coils may be replaced by other power generating and/or yielding devices, such as, thermoelectric generators, flexible piezoelectric energy harvesters, capacitive coupling transmission, magnetodynamic coupling transmission, microwave power transmission, and the like, depending on the subject patient and safety guidelines.

Inductance coil/'group of stacked coils' may be present as per the coil cross section depicted in FIG. 37*d*.

A multiplicity of stacked inductance coils may increase the power transfer as well as increase of mutual inductance between coupled coils. Reference: 'Achieve High Power Density with Stacked Inductor Aug. 25, 2021, https://www.electronicdesign.com'

To deliver proper alignment the maximal energy transfer per orientation of coil groups may be, in some embodiments, assessed by an internal or external CPU with a signaling when optimal alignment is approaching or departing, or made or lost.

As per FIG. 37*d*, a temperature sensor such as 3719*t* may be configured to detect tissue temperatures external to the coil and/or wrapper so that hardware and/or software in the system can alert the user/external coil to increase or decrease energy transmission as the case may be. In some embodiments, one or more threshold temperatures may be established, such as a shutoff temperature, which may be, for example, 45 degrees C., which may result in termination of energy delivery until the temperature returns to a second threshold temperature, such as 40 degrees C., at which point the energy delivery may resume.

FIG. 72a depicts an example of a Subcutaneous Electrocardiogram (ECG=EKG) system 7200 comprising, in the depicted embodiment, a flexible strand/string electronic (FSEI-EKG) implant of Subcutaneous Electrocardiogram Leads 7201a-c. System 7200 comprises one or more implants positioned in respective implant pockets 7205, preferably made via one or more minimally invasive entrance incisions 7210. More particularly, implant system 7200 comprises an FSEI-EKG implant 7201 comprising three leads, namely, leads 7201a, 7201b and 7201c, which may be positioned within an elongated implant pocket 7205c comprising a canal that may be made by trocar, probe and/or beaded dissector as shown previously. In some embodiments, of course, more or fewer than three leads may be used. Similarly, although in a preferred embodiment, each of the leads may be packaged together in a single implant; in alternative embodiments, each lead may comprise a separate implant. System 7200 may further comprise inductance coil 7214 (with or without additional electronics attached) and/or auxiliary implant 7208, each of which may be deposited in various implant pockets 7205, their own individual implant pockets, or an implant pocket shared with another implant of the system, which may be made similarly to others described by methods described elsewhere within this application, including FIGS. 1 & 57. Inductance coil 7214 may be connected to auxiliary implant 7208 by an incoming wire or wires 7215i, and auxiliary implant 7208 may be connected to the FSEI-EKG 7201a-c by an outgoing wire or wires 7215o. The Subcutaneous Electrocardiogram Leads 7201a, 7201b and 7201c of flexible strand/string electronic (FSEI-EKG) implant 7201 may each terminate in a respective lead terminals 7221a, 7221b and 7221c on heart 7220.

Although traditional external, skin-attached ECGs typically refer to a 12-lead ECG, it commonly uses only 10 electrodes. Certain electrodes are part of two pairs and thus provide two leads. However, it is contemplated that fewer leads may be used for subcutaneous implants. Thus, for example, using the embodiment depicted in FIG. 72a and variations thereof, a three-lead subcutaneous ECG may be used to provide sufficient data for pacing or defibrillation. In some embodiments, subcutaneous implantable cardiac defibrillators (S-ICD) sometimes utilize electrograms recorded between one or two sensing electrodes and the pulse generator for ventricular sensing. Additional details regarding electrode requirements may be found in 'How many patients fulfil the surface electrocardiogram criteria for subcutaneous implantable cardioverter-defibrillator implantation?', Randles D A, EP Europace, Volume 16:1015-1021, 2014, which is hereby incorporated in its entirety by reference.

Flexible strand/string implant 7201 may, in some embodiments, comprise a flexible tube or strand of electronics, wires, and/or fiber optics. In some embodiments, inductance coils may be replaced by other power generating and/or yielding devices, such as, thermoelectric generators, flexible piezoelectric energy harvesters, capacitive coupling transmission, magnetodynamic coupling transmission, microwave power transmission, and the like, depending on the subject patient and safety guidelines. The purpose for having the inductance coil and/or other associated electronics/implants in the subcutaneous fat of the lower abdomen is an area that is usually clothed and may have sufficient subcutaneous tissue in which to contain, cushion, and/or hide a relatively larger implant. In addition, the tissue in this region of the body is relatively inert, thereby possibly reducing the risk of electromagnetic carcinogenesis. In some contemplated embodiments, inductance coil 7214, when not receiving transmitted wireless energy, may also be configured to act as a transmitting and/or receiving antenna. In some embodiments and implementations, the incision, or one of the incisions, may be made in the region of the patient's navel 7210n.

In some embodiments, additional elements, such as electronic elements, may be coupled to the coil to make the coil more useful as a standalone implant, or an implant configured to standalone as a power supply to another, secondary implant. In some such embodiments, use of a unitary coil, as shown in FIG. 80a, may eliminate the need for an auxiliary implant altogether. In contemplated embodiments, a unitary coil may therefore be coupled with other implants, such as implants to which the unitary coil is providing energy, without the use of an auxiliary implant to aid the unitary coil in doing so. It is also contemplated, however, that some coil embodiments may have some, but not all, of the components that may be provided on an auxiliary implant, and may therefore be considered a "hybrid" coil implant.

FIG. 72b is a perspective view of auxiliary implant 7208, which may comprise any of the elements previously described in FIGS. 54 *a-c*, including but not limited to an antenna 7202b to allow for receipt of electromagnetic signals, which may be used to transmit data to CPU/printed-circuit-board 7203. An external transmitter may be adjusted by the patient or healthcare personnel to transmit signals to internal antenna 7202b that, in turn, directs CPU 7203 to coordinate electrical output of wiring contained in implant 7201. In some embodiments, the battery 7204 may also be flexible and/or installed within or along inductance coil 7214. A wireless charging system may be provided, as previously described, and which may be configured to wirelessly charge the battery 7204 via inductance coil 7214. Although in the depicted embodiment, each of the implants of system 7200 may, due to their nature and/or the unique structures and/or implantation techniques disclosed herein, need not be compressible, it is contemplated that, in some embodiments, one or more of the elements of implant system 7200 is either flexible and/or compressible, or is small enough on its own to fit within a minimally invasive entrance incision 7210 with other elements of implant 7200 moved into their optimal positions in separate tissue pockets, such as pocket 7205, which contains inductance coil 7214 in the depicted embodiment. However, again, some components, such as the string-like implant 7201, need not be compressible. Similarly, in some embodiments, the inductance coil 7214 may be rigid but may, due to the techniques for insertion of spiral implants disclosed herein, be inserted into a larger implant pocket, as previously discussed. Auxiliary implant 7208 may allow for certain components, such as sensitive electrical components, to be placed within a separate implant, which may be more protective of such components, such as being within a waterproof/sealed container, for example. A seal, such as a wrapper, may be used to contain all of the elements of auxiliary implant 7208 therein. Auxiliary implant 7208 may further comprise, for example, a memory/data storage element 7225.

FIG. 72c depicts an alternative embodiment of a component of a Subcutaneous Electrocardiogram (ECG=EKG) system that, in some embodiments, may be configured to be coupled with the distal end of implant 7201 or may be configured to replace implant 7201. In the depicted embodiment, this component or sub-system comprises a dendritic and preferably resiliently flexible subcutaneous implant, which may be configured to be positioned in an implant pocket 7910c preferably made via a minimally invasive entrance incision 7210c. This dendritic subcutaneous implant comprises branches 7231c that may extend at various angles relative to the implant axis, in this case terminating with electrodes 7241c in locations approximating a desired 5 lead EKG. In preferred embodiments, each of the branches/leads may be preconfigured in a particular shape/configuration, which in some cases may be specifically designed for a particular patient, which may vary/depend on the patient's size and/or heart. In some such embodiments, the leads/branches may be resiliently flexible, such that the implant comprising the leads may be delivered in a compressed configuration through a minimally invasive entrance incision and then may be configured to automatically be decompressed, once delivered into an implant pocket, into its original shape with each of the branches/leads extending in desired/preconfigured directions and/or in desired/preconfigured distances that may be most useful for a particular patient (or a category of patients, such as "children aged X-Y" or "adults having a relatively normal heart size", for example). Thus, the leads of an EKG implant, which may comprise an implant configured to be coupled with a string implant coupled with a spiral implant/inductance coil or may be coupled directly with a spiral implant/inductance coil, may be configured with a plurality of leads in a configuration targeting a particular patient/heart configuration or may be configured to target a range of patients/heart configurations The depicted alternative embodiment further comprises distal and proximal end positioning holes/rings 7251, one or more inductance coils 7214c, which may be configured for receiving external wireless energy and/or signal reception/transmission, preferably along with a battery and/or PCB/CPU 7204c. Element 7204c may comprise a separate piece of the system that may be electrically coupled with the dendritic/EKG implant or, alternatively, may be part of the dendritic implant, such as positioned on/in and/or otherwise coupled with the trunk of the dendritic/EKG implant. The system may further comprise an external antenna 7202c and/or PCB/CPU 7204d, which may be incorporated into a cellphone or watch or wearable electronic or the like may communicate in delayed or real time the EKG to a health professional or AI for assessment. It is contemplated, in alternative embodiments, one or more of the branches 7231c may comprise circumferential electrodes which may be positioned to encircle or otherwise extend about a portion of one or more of the various branches 7231c, as previously described in connection with other embodiments. Further embodiments may comprise other numbers of branches and/or leads, such as, for example, between 3 and 12 branches/leads. In contemplated embodiments, holes/rings 7251 may comprise a luminescent material, such as phosphorescent, chemiluminescent, bioluminescent, and/or radioluminescent material, to assist a surgeon in identifying implant location to facilitate implant placement/fixation via suturing with external lighting dimmed transiently. This feature may, of course, be applied to and/or used with any of the other embodiments disclosed herein to facilitate stable positioning of an implant in a desired location, preferably within an implant pocket. In further embodiments and implementations, the implant's branch size and location may be custom designed/fitted for differing patient scenarios such as cardiomegaly, vertical heart, etc. via, for example, 3-D printing guide by a chest x-ray, ultrasound, or other technique, such as MRI. In further implementations, the implant may temporarily be encased in a removable sheath to accompany the implant a sufficient distance through the entrance incision and to compress the branches into a manageable shape for insertion/passage.

In further contemplated embodiments, the implant system may comprise an auxiliary implant with any element including, but not limited to, those mentioned for the auxiliary implant described in FIG. 66, for example, CPU(s)/printed-circuit-board(s), battery(ies), memory/data storage element(s), antenna(e), capacitor(s), electronic heart rate sensor(s), lab-on-a-chip element(s). In other contemplated embodiments, either coils or auxiliary implants may comprise pulse oximetry elements. Although some auxiliary implants shown in the figures are cylindrical in shape, in further contemplated embodiments they may comprise a variety of shapes including, but not limited to, ovoids, polygonal prisms, pads, pillow-like, purse-like, with or without various cavities or convexities.

In some embodiments, inductance coil 7214 may be replaced by other similar devices, such as In some embodiments, inductance coils may be replaced by other power generating and/or yielding devices, such as, thermoelectric generators, flexible piezoelectric energy harvesters, capacitive coupling transmission, magnetodynamic coupling transmission, microwave power transmission, and the like, depending on the subject patient and safety guidelines.

Inductance coil/'group of stacked coils' may be present as per the coil cross section depicted in FIG. 37d.

A multiplicity of stacked inductance coils may increase the power transfer as well as increase of mutual inductance between coupled coils. Reference: 'Achieve High Power Density with Stacked Inductor Aug. 25, 2021, https://www-.electronicdesign.com'

To deliver proper alignment the maximal energy transfer per orientation of coil groups may be, in some embodiments, assessed by an internal or external CPU with a signaling when optimal alignment is approaching or departing, or made or lost.

As per FIG. 37d, a temperature sensor such as 3719t may be configured to detect tissue temperatures external to the coil and/or wrapper so that hardware and/or software in the system can alert the user/external coil to increase or decrease energy transmission as the case may be. In some embodiments, one or more threshold temperatures may be established, such as a shutoff temperature, which may be, for example, 45 degrees C., which may result in termination of energy delivery until the temperature returns to a second threshold temperature, such as 40 degrees C., at which point the energy delivery may resume.

FIG. 73a depicts an example of a Subcutaneous Power Delivery System 7300, which may be used, for example, to provide power for an Implantable Cardiac Pacemaker. In the depicted embodiment, system 7300 comprises a flexible strand/string electronic (FSEI) implant 7301. System 7300 may further comprise one or more other implants positioned in respective implant pockets, preferably made via one or more minimally invasive entrance incisions 7310. As shown in this figure, the entrance incision 7310 used to make implant pocket 7305a is at an arbitrary angle relative to the pocket, which illustrates that the devices and techniques disclosed herein may allow for creation of an implant pocket directed in any direction a full 360 degrees from the angle of the incision as desired. More particularly, implant system 7300 comprises an FSEI implant 7301, which may be positioned within an elongated implant pocket 7305c comprising a canal that may be made by trocar, probe and/or beaded dissector as shown previously. System 7300 may further comprise inductance coil 7314a (with or without additional electronics attached) and/or auxiliary implant 7308, each of which may be deposited in various implant pockets 7305a/7305c, either their own individual implant pockets or an implant pocket shared with another implant of the system, which may be made similarly to others described by methods described elsewhere within this application, including FIGS. 1 & 57. Inductance coil 7314a may be connected to auxiliary implant 7308 by an incoming wire(s) 7315i, and auxiliary implant 7308 may be connected to the FSEI 7301 by outgoing wire(s) 73150. The flexible strand/string electronic (FSEI) 7301 terminate in a second inductance coil 7314b which may also, in some embodiments, be configured to function as an antenna as well. Inductance coil 7314b may be positioned in a second implant pocket 7305b. Inductance coil 7314b may be configured and positioned to emit wireless energy to a third inductance coil 7314c, which may be part of an implantable/implanted cardiac pacemaker 7321, which may be placed on a cardiac vein of heart 7320. It should be understood that, in some embodiments, pacemaker 7321 may therefore be considered part of a different system that is simply powered by system 7300. Alternatively, however, it is contemplated that pacemaker 7321 may be considered part of system 7300 in some embodiments.

Flexible strand/string implant 7301 may, in some embodiments, comprise a flexible tube or strand of electronics, wires, and/or fiber optics. The purpose for having the inductance coil and/or other associated electronics/implants in the subcutaneous fat of the lower abdomen is an area that is usually clothed and may have sufficient subcutaneous tissue in which to contain, cushion, and/or hide a relatively larger implant. In addition, the tissue in this region of the body is relatively inert, thereby possibly reducing the risk of electromagnetic carcinogenesis. In some contemplated embodiments, inductance coil 7314a, when not receiving transmitted wireless energy, may also be configured to act as a transmitting and/or receiving antenna. In some embodiments and implementations, the incision, or one of the incisions, may be made in the region of the patient's navel 7310n.

As depicted the perspective view of FIG. 73b, implant system 7300 may further comprise auxiliary implant 7308, which may comprise any of the elements previously described in FIGS. 54 a-c, including but not limited to an antenna 7302b to allow for receipt of electromagnetic signals, which may be used to transmit data to and/or receive data from CPU/printed-circuit-board 7303. An external transmitter may be adjusted by the patient or healthcare personnel to transmit signals to internal antenna 7302b that, in turn, directs CPU 7303 to coordinate electrical output of wiring contained in implant 7301. In some embodiments, the battery 7304 may also be flexible and/or installed within or along inductance coil 7314. A wireless charging system may be provided, as previously described, and which may be configured to wirelessly charge the battery 7304 via inductance coil 7314a. Optionally, one or more of the elements of implant system 7300 is either flexible and/or compressible, or is small enough on its own to fit within a minimally invasive entrance incision 7310 with other elements of implant 7300 moved into their optimal positions in separate tissue pockets. However, some components, such as the string-like implant 7301, need not be compressible. Similarly, in some embodiments, the inductance coils may be rigid but may, due to the techniques for insertion of spiral implants disclosed herein, be inserted into a larger implant pocket, as previously discussed. Auxiliary implant 7308, which may be compressible to allow it to fit within the preferably minimally invasive entrance incision 7310, may allow for certain components, such as sensitive electrical components, to be placed within a separate implant, which may be more protective of such components, such as being within a waterproof/sealed container, for example. A seal, such as a wrapper, may be used to contain all of the elements of auxiliary implant 7308 therein. Auxiliary implant 7308 may further comprise, for example, a memory/data storage element 7325.

In further contemplated embodiments, the implant system may comprise an auxiliary implant with any element including, but not limited to, those mentioned for the auxiliary implant described in FIG. 66, for example, CPU(s)/printed-circuit-board(s), battery(ies), memory/data storage element(s), antenna(e), capacitor(s), electronic heart rate sensor(s), lab-on-a-chip element(s). In other contemplated embodiments, either coils or auxiliary implants may comprise pulse oximetry elements. Although some auxiliary implants shown in the figures are cylindrical in shape, in further contemplated embodiments they may comprise a variety of shapes including, but not limited to, ovoids, polygonal prisms, pads, pillow-like, purse-like, with or without various cavities or convexities.

Cardiac devices usable in connection with one or more embodiments may comprise a pulse generator, which may be implanted in, for example, a prepectoral subcutaneous pocket, along with a number of transvenous leads. Each lead may be attached proximally to the can and fixated distally to the endocardial aspect of the heart. Implantation of the lead may require venous puncture, with the subclavian, axillary and cephalic veins frequently used. Device implantation, however, is often associated with infection, hematoma, inadvertent arterial puncture, pneumothorax, hemothorax and cardiac tamponade. Late complications associated with transvenous systems include lead fracture, lead displacement, venous obstruction and infective endocarditis. Additional details regarding devices and methods that may be useful in connection with various energy delivery embodiments disclosed herein in the context of pacemakers and/or defibrillators may be founds in 'Update On Leadless Cardiac Devices For General Physicians', Wiles B M, Clin Med (Lond) 17:33-36, 2017, which is hereby incorporated in its entirety by reference.

Some embodiments disclosed herein may be particularly useful in connection with some existing wireless/leadless devices, which may be configured for implantation external to the cardiac chambers to avoid high intra-cardiac pressure gradients, while enabling intravascular deployment of the device to the anterior cardiac vein. Various embodiments herein may be configured to improve upon these systems by providing a more convenient and/or less invasive method for powering such devices. The devices and methods disclosed herein may also allow for increasing the amount of electrical energy that can be generated and/or delivered to various cardiac implants, such as pacemakers, ECG implants, and/or defibrillators. Additional details regarding such cardiac devices can be found in "Inductively Powered Wireless Pacing Via A Miniature Pacemaker And Remote Stimulation System". P. Control Abiri Sci Rep. 7:6180, 2017 ncbi.nlm.nih.gov/pmc/articles/PMC5522478/, which is incorporated herein in its entirety by reference.

Inductance coil/'group of stacked coils' may be present as per the coil cross section depicted in FIG. 37d.

A multiplicity of stacked inductance coils may increase the power transfer as well as increase of mutual inductance between coupled coils. Reference: 'Achieve High Power Density with Stacked Inductor Aug. 25, 2021, https://www.electronicdesign.com'

To deliver proper alignment the maximal energy transfer per orientation of coil groups may be, in some embodiments, assessed by an internal or external CPU with a signaling when optimal alignment is approaching or departing, or made or lost.

As per FIG. 37d, a temperature sensor such as 3719t may be configured to detect tissue temperatures external to the coil and/or wrapper so that hardware and/or software in the system can alert the user/external coil to increase or decrease energy transmission as the case may be. In some embodiments, one or more threshold temperatures may be established, such as a shutoff temperature, which may be, for example, 45 degrees C., which may result in termination of energy delivery until the temperature returns to a second threshold temperature, such as 40 degrees C., at which point the energy delivery may resume.

In some embodiments, inductance coil 7314 may be replaced by other similar devices, such as, in some implementations, the wireless charging of the inductance coil 7314 may be replaced by, for example, thermoelectric generators, flexible piezoelectric energy harvesters, capacitive coupling transmission, magnetodynamic coupling transmission, microwave power transmission, and the like, depending on the subject patient and safety guidelines. It is anticipated that some embodiments of these devices may be configured in a spiral shape similar to that of inductance coils already discussed and thus benefit form similar minimally invasive implantation techniques.

FIG. 73c is a side elevation view of another embodiment of a powering system 7300 that may be used to provide electrical energy to any of the various implants and/or systems disclosed herein. System 7300 depicts an almost fully implanted thermoelectric implant 7314t (shown in dashed lines to indicate its presence below the skin) which was repositioned into a patient's implant pocket 7305t through incision 7310t, which may, in some implementations, be done in a manner similar to that depicted in FIGS. 47a-e. However, when the hairpin (180 degree curved) central inner coil 73180 of implant 7314t is reached, the surgeon may merely reverse the direction of rotation to maintain insertion into the patient. As previously discussed in connection with FIG. 47b, wires/wiring elements may, in some embodiments, be coupled to the inner and/or outer coil termini, which may be left in place as the coil is repositioned into place within the implant pocket 7305t. The wires/wiring elements may remain passing through incision 7310t and, if sufficiently flexible and dynamically connected, may rotate with the implant 7314t as it turns and is repositioned from outside of the body to within implant pocket 7305t through minimally invasive entrance incision 7310t. In some embodiments, additional elements, such as electronic elements, may be coupled to the coil to make the coil more useful as a standalone implant, or an implant configured to standalone as a power supply to another, secondary implant. In some such embodiments, use of a unitary coil, as shown in FIG. 80a, may eliminate the need for an auxiliary implant altogether. In contemplated embodiments, a unitary coil may therefore be coupled with other implants, such as implants to which the unitary coil is providing energy, without the use of an auxiliary implant to aid the unitary coil in doing so. It is also contemplated, however, that some coil embodiments may have some, but not all, of the components that may be provided on an auxiliary implant, and may therefore be considered a "hybrid" coil implant.

FIG. 74a depicts an example of a Subcutaneous Power Delivery System and a Subcutaneous Implantable Cardioverter Defibrillator (SICD) system 7400 comprising, in the depicted embodiment, a flexible strand/string electronic implant (FSEI) 7401 that terminates in a Subcutaneous Implantable Cardioverter Defibrillator (SICD). System 7400 comprises one or more implants positioned in respective implant pockets, each of which is preferably made via one or more minimally invasive entrance incisions 7410. More particularly, implant system 7400 comprises an FSEI implant 7401, which may be positioned within an elongated implant pocket 7405c comprising a canal that may be made a by trocar, probe and/or beaded dissector, as shown and discussed previously. System 7400 may further comprise inductance coil 7414 (with or without additional electronics attached) and/or auxiliary implant 7408, each of which may be deposited in various implant pockets 7405, either their own individual implant pockets or an implant pocket shared with another implant of the system, which may be made similarly to others described by methods described elsewhere within this application, including FIGS. 1 & 57. Inductance coil 7414 may be connected to auxiliary implant 7408 by an incoming wire or wires 7415i and auxiliary implant 7408 may be connected to the FSEI 7401 by one or more outgoing wires 74150.

Flexible strand/string implant 7401 may, in some embodiments, comprise a flexible tube or strand of electronics, wires, and/or fiber optics. The purpose for having the inductance coil and/or other associated electronics/implants in the subcutaneous fat of the lower abdomen, as it is an area that is usually clothed and may have sufficient subcutaneous tissue in which to contain, cushion, and/or hide a relatively larger implant. In addition, the tissue in this region of the body is relatively inert, thereby possibly reducing the risk of electromagnetic carcinogenesis. In some contemplated embodiments, inductance coil 7414, when not receiving transmitted wireless energy, may also be configured to act as a transmitting and/or receiving antenna. In some embodiments and implementations, the incision, or one of the incisions, may be made in the region of the patient's navel 7410n.

As depicted in the perspective view of FIG. 74b, implant system 7400 may further comprise auxiliary implant 7408, which may comprise any of the elements previously described in FIGS. 54 a-c, including, but not limited to an antenna 7402b to allow for receipt of electromagnetic signals, which may be used to transmit data to CPU/printed-circuit-board 7403. An external transmitter may be adjusted by the patient or healthcare personnel to transmit signals to internal antenna 7402b that may, in turn, direct CPU 7403 to coordinate electrical output of wiring contained in implant 7401. In some embodiments, the battery 7404 may also be flexible and/or installed within or along inductance coil 7414. A wireless charging system may be provided, as previously described, and may be configured to wirelessly charge the battery 7404 via inductance coil 7414. Preferably, one or more of the elements of implant system 7400 is either flexible and/or compressible, or is small enough on its own to fit within a minimally invasive entrance incision 7410 with other elements of implant 7400 moved into their optimal positions in separate tissue pockets, such as pocket 7405, which contains inductance coil 7414 in the depicted embodiment. However, some components, such as the string-like implant 7401 and/or the coil 7414, need not be compressible. Similarly, in some embodiments, the inductance coil 7414 may be rigid but may, due to the techniques for insertion of spiral implants disclosed herein, be inserted into a larger implant pocket, as previously discussed. Auxiliary implant 7408 may allow for certain components, such as sensitive electrical components, to be placed within a separate implant, which may be more protective of such components, such as being within a waterproof/sealed container, for example. A seal, such as a wrapper, may be used to contain all of the elements of auxiliary implant 7408 therein. Auxiliary implant 7408 may further comprise, for example, a memory/data storage element 7425.

In further contemplated embodiments, the implant system may comprise an auxiliary implant with any element including, but not limited to, those mentioned for the auxiliary implant described in FIG. 66, for example, CPU(s)/printed-circuit-board(s), battery(ies), memory/data storage element(s), antenna(e), capacitor(s), electronic heart rate sensor(s), lab-on-a-chip element(s). In other contemplated embodiments, either coils or auxiliary implants may comprise pulse oximetry elements. Although some auxiliary implants shown in the figures are cylindrical in shape, in further contemplated embodiments they may comprise a variety of shapes including, but not limited to, ovoids, polygonal prisms, pads, pillow-like, purse-like, with or without various cavities or convexities.

In the depicted embodiment, part of implant 7401 may be insulated, such as portion 7401*i*, and another portion may be non-insulated or bare, such as portion 7401*c*, which may need to be exposed to deliver sufficient energy to serve as a defibrillator.

Cardiac devices traditionally comprise two components: a pulse generator (also known as a 'can'), most commonly implanted in a prepectoral subcutaneous pocket, and one or more transvenous leads. Each lead is attached proximally to the can and fixated distally to the endocardial aspect of the heart. Implantation of the lead, however, typically requires venous punctures, with the subclavian, axillary and cephalic veins frequently used. Such device implantation is often associated with infection, hematoma, inadvertent arterial puncture, pneumothorax, hemothorax, and cardiac tamponade. Late complications associated with transvenous systems include lead fracture, lead displacement, venous obstruction, infective endocarditis, or the like. Subcutaneously implantable cardioverter defibrillators (S-ICD), by contrast, typically require greater defibrillation energy (80 Joules, for example) than a transvenous implantable cardioverter defibrillator (TV-ICD) (35 Joules, for example). These higher energy requirements result in longer charge times and necessitate a larger and heavier can. The S-ICD in also may have extremely limited pacing capabilities. Subcutaneous pacing is similar to transcutaneous pacing in that it is significantly uncomfortable for the patient and is associated with mechanical capture of skeletal muscle. Additional details regarding implantable defibrillators that may be useful in connection with various systems and methods disclosed herein can be found in 'Update On Leadless Cardiac Devices For General Physicians', Wiles B M, Clin. Med. (Lond) 17:33-36, 2017, which is incorporated herein by reference in its entirety.

Although only a single lead/implant 7401 is shown in the depicted embodiment, it should be understood that other embodiments may have multiple leads and/or multiple implants (in some embodiments, a single implant may comprise multiple leads and in others each lead may be part of a separate implant). For example, some embodiments may additionally, or alternatively, be configured to serve as an EKG. Thus, it is contemplated that some embodiments may be coupled with another system, such as the system depicted in FIGS. 72*a*-72*b*, which may allow for coupling of these two features in a single system.

In some embodiments, inductance coils may be replaced by other power generating and/or yielding devices, such as, for example, thermoelectric generators, flexible piezoelectric energy harvesters, capacitive coupling transmission, magnetodynamic coupling transmission, microwave power transmission, and the like, depending on the subject patient and safety guidelines.

Inductance coil/'group of stacked coils' may be present as per the coil cross section depicted in FIG. 37*d*.

A multiplicity of stacked inductance coils may increase the power transfer as well as increase of mutual inductance between coupled coils. Reference: 'Achieve High Power Density with Stacked Inductor Aug. 25, 2021, https://www-.electronicdesign.com'

To deliver proper alignment the maximal energy transfer per orientation of coil groups may be, in some embodiments, assessed by an internal or external CPU with a signaling when optimal alignment is approaching or departing, or made or lost.

As per FIG. 37*d*, a temperature sensor such as 3719*t* may be configured to detect tissue temperatures external to the coil and/or wrapper so that hardware and/or software in the system can alert the user/external coil to increase or decrease energy transmission as the case may be. In some embodiments, one or more threshold temperatures may be established, such as a shutoff temperature, which may be, for example, 45 degrees C., which may result in termination of energy delivery until the temperature returns to a second threshold temperature, such as 40 degrees C., at which point the energy delivery may resume.

In some embodiments, additional elements, such as electronic elements, may be coupled to the coil to make the coil more useful as a standalone implant, or an implant configured to standalone as a power supply to another, secondary implant. In some such embodiments, use of a unitary coil, as shown in FIG. 80*a*, may eliminate the need for an auxiliary implant altogether. In contemplated embodiments, a unitary coil may therefore be coupled with other implants, such as implants to which the unitary coil is providing energy, without the use of an auxiliary implant to aid the unitary coil in doing so. It is also contemplated, however, that some coil embodiments may have some, but not all, of the components that may be provided on an auxiliary implant, and may therefore be considered a "hybrid" coil implant.

FIG. 75*a* depicts frontal side view of an example of a Subcutaneous Power Delivery System 7500, which may be used, for example, to provide power for a variety of implantable devices. In the depicted embodiment, system 7500 comprises a flexible strand/string electronic implant (FSEI) 7501. System 7500 may further comprise one or more other implants positioned in respective implant pockets, preferably made via one or more minimally invasive entrance incisions 7510. As shown in this figure, the entrance incision 7510 used to make implant pocket 7505*a* is at an arbitrary angle relative to the pocket, which illustrates that the devices and techniques disclosed herein may allow for creation of an implant pocket directed in any direction a full 360 degrees from the angle of the incision as desired. Implant system 7500 comprises one or more FSEI implants 7501, each of which may be positioned within an elongated implant pocket 7505*c* comprising a canal that may be made by a trocar, probe and/or beaded dissector as shown previously. System 7500 may further comprise inductance coils or groups of stacked coils 7514*a* (with or without additional electronics attached) and/or auxiliary implant 7508, each of which may be deposited in various implant pockets 7505*a*/7505*c*, either their own individual implant pockets, or an implant pocket shared with another implant of the system, which may be made similarly to others described by methods described elsewhere within this application, including FIGS. 1 & 57. Inductance coil 7514*a* may be connected to auxiliary implant 7508 by one or more incoming wires 7515*i*, and auxiliary implant 7508 may be connected to the FSEI 7501 by one or more outgoing wires 75150. The flexible strand/string electronic (FSEI) 7501 may be coupled with a second inductance coil 7514*x* and antenna 7502*x*. In some embodiments, inductance coil 7514*x*, be configured to function as an antenna as well.

Inductance coil 7514*x* may be positioned in a second implant pocket, preferably at a location adjacent to another implant 75*x*, which may be located at various positions about the body as desired, and as represented by the examples of FIGS. 75*c*-75*g*, each of which represents a possible specific implant for generic implant 75*x* of FIG. 75*a*. Inductance coil 7514*x* may be configured and positioned to emit wireless energy to a third inductance coil 7524*c*-*g*, which may be part of a selection of implantable/implanted devices denoted by the starred black box 75*x* seen above the depicted patient's left shoulder. The 'x' may denote the various configurations c through g. Box 75*x* may represent various implantable surgical systems/devices which may be placed in/around a variety of organs/locations depicted, but not limited to those shown in FIGS. 75*c*-*g*, typically at a deeper or otherwise less accessible location. Thus, the elements of system 7500 may be preferably positioned more superficially and/or more accessible relative to the various possible implants denoted by box 75*x*, or more specifically by the examples of FIGS. 75*c*-*g*. It should be understood that, in some embodiments, the selection of implantable/implanted systems/devices in FIGS. 75*c*-*g* may therefore be considered part of a different system that is simply powered by system 7500. Alternatively, however, it is contemplated that the selection of implantable/implanted systems/devices in FIGS. 75*c*-*g* may be considered part of system 7500 in some embodiments. Antenna 7502*x* may communicate with one or more of the selection of implantable/implanted devices.

The system of body cavity or organ 'leapfrog' with multiple inductance coils may be of benefit in that suggested electric wiring/fiber optic transmission may be placed into and/or through the subcutaneous fat where the fatty cushion and relatively low reactance may be of benefit; this also may avoid long-standing wires passing into/through/between critical cavities/anatomical barriers. Power transmission via wire is more efficient than wireless currently but there may be benefit to wirelessly crossing critical anatomy to power a small power efficient device or battery. In some embodiments and implementations, magnetic alignment may be helpful to avoid misalignment between the external power delivery coil and/or the first internal power receiving coil, which may stop or reduce power transmission to a critical device. In contemplated embodiments, a CPU or other programmable device within or external to the system may assess the maximum/peak power levels being transmitted and/or received between wireless pairs or groups and then alert those involved in the immediate surgical, convalescent, and/or postoperative positioning of the devices as to whether optimal alignment is being maintained.

Flexible strand/string implant 7501 may, in some embodiments, comprise a flexible tube or strand of electronics, wires, and/or fiber optics. It may be beneficial to place an inductance coil and/or other associated electronics/implants in the subcutaneous fat of the lower abdomen, as it is an area that is usually clothed and may have sufficient subcutaneous tissue in which to contain, cushion, and/or hide a relatively larger implant. In addition, the tissue in this region of the body is relatively inert, thereby possibly reducing the risk of electromagnetic carcinogenesis. In some contemplated embodiments, inductance coils, when not receiving transmitted wireless energy, may also be configured to act as a transmitting and/or receiving antenna. In some embodiments and implementations, the incision, or one of the incisions, may be made in the region of the patient's navel 7510*n*.

As depicted the perspective view of FIG. 75*b*, implant system 7500 may further comprise auxiliary implant 7508, which may comprise CPU/printed-circuit-board 7503, battery 7504, memory/data storage element 7525, antenna 7502*b*, capacitor 7526, electronic heart rate sensor 7024, and lab-on-a-chip 7527. Auxiliary implant 7508 may also comprise any of the elements previously described in FIGS. 54 *a-c*, including but not limited to an antenna 7502*b* to allow for receipt of electromagnetic signals, which may be used to transmit data to and/or receive data from CPU/printed-circuit-board 7503. An external transmitter may be adjusted by the patient or healthcare personnel to transmit signals to internal antenna 7502*b* that, in turn, directs CPU 7503 to coordinate electrical output of wiring contained in implant 7501. In some embodiments, the battery 7504 may also be flexible and/or installed within or along inductance coil 7514*a*. A wireless charging system may be provided, as previously described, which may be configured to wirelessly charge the battery 7504 via inductance coil 7514*a*. Optionally, one or more of the elements of implant system 7500 is either flexible and/or compressible, or is small enough on its own to fit within a minimally invasive entrance incision 7510 with other elements of implant system 7500 moved into their optimal positions in separate tissue pockets. However, some components, such as the string-like implant 7501, need not be compressible. Similarly, in some embodiments, inductance coils may be rigid but may, due to the techniques for insertion of spiral implants disclosed herein, be inserted into a larger implant pocket, as previously discussed. Auxiliary implant 7508, which may be compressible to allow it to fit within the preferably minimally invasive entrance incision 7510, may allow for certain components, such as sensitive electrical components, to be placed within a separate implant, which may be more protective of such components, such as being within a waterproof/sealed container, for example. A seal, such as a wrapper, may be used to contain all of the elements of auxiliary implant 7508 therein. Auxiliary implant 7508 may further comprise, for example, a memory/data storage element 7525.

In further contemplated embodiments, the implant system may comprise an auxiliary implant with any element including, but not limited to, those mentioned for the auxiliary implant described in FIG. 66, for example, CPU(s)/printed-circuit-board(s), battery(ies), memory/data storage element(s), antenna(e), capacitor(s), electronic heart rate sensor(s), lab-on-a-chip element(s). In other contemplated embodiments, either coils or auxiliary implants may comprise pulse oximetry elements. Although some auxiliary implants shown in the figures are cylindrical in shape, in further contemplated embodiments they may comprise a variety of shapes including, but not limited to, ovoids, polygonal prisms, pads, pillow-like, purse-like, with or without various cavities or convexities.

In some embodiments, inductance coils may be replaced by other power generating and/or yielding devices, such as thermoelectric generators, flexible piezoelectric energy harvesters, capacitive coupling transmission, magnetodynamic coupling transmission, microwave power transmission, and the like, depending on the subject patient and safety guidelines.

FIG. 75c depicts a side view of an example of a wirelessly powered gastric/stomach implant 7524c, which may comprise an inductance coil, along with a more superficial inductance coil 7514c positioned within an implant pocket 7521c. Implant 7524c may, for example, comprise electrodes implanted into the nearby stomach 7520c and/or smooth muscle in the gastric antrum. Implant 7524c may be configured to be wirelessly powered by implant coil 7514c located in the relatively nearby implant pocket 7521c (not visible through the surface skin and thus depicted in dashed lines) in subcutaneous fat 7523c. Implant 7514c may, in turn, be powered by the electrical output of wiring contained in implant 7501 from implanted coil(s) 7514a, which, again, may be positioned in implant pocket 7505a, which may be in a position that allows for use of a larger inductance coil generating more electrical power/energy than the remote coil 7514c. An example of an implant that system 7500 may be configured to power is the Exilis™ gastric electrical stimulation (GES) system manufactured be Medtronic.

FIG. 75d depicts a side view of an example of a wirelessly powered foot drop/leg motor nerve implant 7524d, which may comprise an inductance coil and may comprise electrodes implanted onto a nearby motor nerve, such as the common peroneal nerve 7520d which may, in some cases, ameliorate foot drop. Implant 7524d may be configured to be wirelessly powered by system 7500. More particularly, implant 7514d may directly power implant 7524d and may itself receive energy from implanted coil(s) 7514a. Implant 7514d may be positioned in a more proximate and/or adjacent implant pocket 7521d, preferably in subcutaneous fat 7523d. Implant 7514d may be, in turn, powered by the electrical output of wiring contained in implant 7501 via coil(s) 7514a. An example of an implant that system 7500 may be configured to power in this context is the ActiGait, which is a product of nstim Services GmbH+Neurodan A/S. However, other similar devices are manufactured by Arthrex, Bioness, Finetech Medical, Ottobock, Stryker, and Wright Medical.

FIG. 75e depicts a side view of an example of a wirelessly powered drug/chemical pump implant 7524e. Implant 7524e may comprise, for example, an insulin releasing or other drug releasing, such as an opioid-releasing or Narcan-releasing, pump comprising electrodes implanted into a pump motor/magnetic/hydraulic drive system 7520e. Implant 7524e may be wirelessly powered by implant 7514e, which may comprise an inductance coil and/or may be positioned in a more proximate and/or adjacent implant pocket 7521e, preferably in subcutaneous fat 7523e. Implant 7514e may be, in turn powered by the electrical output of wiring contained in implant 7501 via coil(s) 7514a.

FIG. 75f depicts a side view of an example of a wirelessly powered brain/nervous system implant 7524f, which may comprise electrodes implanted into the nervous tissue of the brain 7520f. Implant 7524f may be wirelessly powered by implant 7514f, which may be positioned in a more proximate and/or adjacent implant pocket 7521f, preferably in subcutaneous fat and/or galea aponeurotica 7523f. Implant 7514f may be, in turn, powered by the electrical output of wiring contained in implant 7501 via coil(s) 7514a. Examples of suitable deep brain stimulation implants for this purpose are manufactured by, for example, Abbott, Medtronic, and Boston Scientific.

FIG. 75g depicts a side view of an example of a wirelessly powered ear/internal-stimulator portion of a cochlear implant 7524g, which may comprise electrodes implanted into the nearby cochlea 7520g. Implant 7524g may be wirelessly powered by implant 7514g, which may be positioned in a more proximate and/or adjacent implant pocket 7521g, preferably in subcutaneous fat 7523g. Implant 7514g may be, in turn, powered by the electrical output of wiring contained in implant 7501 via coil(s) 7514a. In some contemplated embodiments, it may be possible that, in some patients, the traditional external components of the cochlear implant, which normally comprise an external microphone and speech processor worn behind the ear and which convert soundwaves into an electric signal, may be substituted for by similar hardware/software located in, for example, auxiliary implant 7508, wherein a nearby or overlying transcutaneous microphone may provide some sound data/signal to be processes and relayed via implants 7501 and 7514g to the more traditional internal receiver-stimulator components of the cochlear implant, which may convert the signals into rapid electrical impulses distributed to multiple electrodes on the implant electrode array that stimulates spiral ganglion cells along the cochlear canals causing auditory nerve excitement for brain processing. Examples of cochlear implants that may be useful for this purpose include those manufactured by Cochlear Corp, Advanced Bionics Corp, and Med-El Corp.

Inductance coil/'group of stacked coils' may be present as per the coil cross section depicted in FIG. 37d.

A multiplicity of stacked inductance coils may increase the power transfer as well as increase of mutual inductance between coupled coils. Reference: 'Achieve High Power Density with Stacked Inductor Aug. 25, 2021, https://www.electronicdesign.com To deliver proper alignment the maximal energy transfer per orientation of coil groups may be, in some embodiments, assessed by an internal or external CPU with a signaling when optimal alignment is approaching or departing, or made or lost.

As per FIG. 37d, a temperature sensor such as 3719t may be configured to detect tissue temperatures external to the coil and/or wrapper so that hardware and/or software in the system can alert the user/external coil to increase or decrease energy transmission as the case may be. In some embodiments, one or more threshold temperatures may be established, such as a shutoff temperature, which may be, for example, 45 degrees C., which may result in termination of energy delivery until the temperature returns to a second threshold temperature, such as 40 degrees C., at which point the energy delivery may resume.

In some embodiments, additional elements, such as electronic elements, may be coupled to the coil to make the coil more useful as a standalone implant, or an implant configured to standalone as a power supply to another, secondary implant. In some such embodiments, use of a unitary coil, as shown in FIG. 80a, may eliminate the need for an auxiliary implant altogether. In contemplated embodiments, a unitary coil may therefore be coupled with other implants, such as implants to which the unitary coil is providing energy, without the use of an auxiliary implant to aid the unitary coil in doing so. It is also contemplated, however, that some coil embodiments may have some, but not all, of the components that may be provided on an auxiliary implant, and may therefore be considered a "hybrid" coil implant.

FIG. 76a depicts frontal side view of an example of a Subcutaneous Power Delivery System 7600, which may be used, for example, to provide power to implantable motor units. In the depicted embodiment, system 7600 comprises a flexible strand/string electronic implant (FSEI) 7601. System 7600 may further comprise one or more other implants positioned in respective implant pockets, preferably made via one or more minimally invasive entrance incision(s) 7610*a*. As shown in this figure, the initial entrance incision 7610*a* used to make implant pocket 7605*a* is at an arbitrary angle relative to the pocket, which illustrates that the devices and techniques disclosed herein may allow for creation of an implant pocket directed in any direction a full 360 degrees from the angle of the incision as desired. Implant system 7600 comprises an FSEI implant 7601 comprising multiple sections extending at relatively large angles relative to one another to allow the implant 7601 to extend up to the shoulder and then down the arm. Implant 7601 may therefore be positioned within multiple implant pockets that are adjacent to one another, as shown in the figure. Both the initial implant pocket 7605*b* and the secondary implant pocket 7605*c*, which may be made using another entrance incision 7610*b* positioned at or adjacent to the distal end of pocket 7605*b*. Implant pockets 7605*b* and 7605*c* may comprise a canal that may be made by trocar, probe and/or beaded dissector as shown previously. System 7600 may further comprise one or more inductance coils, including inductance coil(s) 7614*a*. System 7600 may further comprise an auxiliary implant 7608, as previously discussed. Again, each of these various implants may be deposited in various implant pockets 7605*a*/7605*b*/7605*c*, either their own individual implant pockets or an implant pocket shared with another implant of the system, which may be made similarly to others by methods described elsewhere within this application, including FIGS. 1 & 57. Inductance coil 7614*a* may be connected to auxiliary implant 7608 by incoming wire(s) 7615*i*, and auxiliary implant 7608 may be connected to the FSEI 7601 by outgoing wire(s) 7615*0*. The flexible strand/string electronic (FSEI) 7601 may be coupled to one or more motor drives, such as motor drives 7621 and/or 7623, to mimic or aid the musculoskeletal system, the muscles of which typically work in opposing pairs across a joint. It should be understood that, in some embodiments, selection of implantable/implanted motor drive systems/devices 7621/7623 may therefore be considered part of a different system that is simply powered by system 7600. Alternatively, however, it is contemplated that selection of implantable/implanted motor drive systems/devices 7621/7623 may be considered part of system 7600 in some embodiments.

Flexible strand/string implant 7601 may, in some embodiments, comprise a flexible tube or strand of electronics, wires, and/or fiber optics. It may be beneficial to place an inductance coil and/or other associated electronics/implants in the subcutaneous fat of the lower abdomen, as it is an area that is usually clothed and may have sufficient subcutaneous tissue in which to contain, cushion, and/or hide a relatively larger implant. In addition, the tissue in this region of the body is relatively inert, thereby possibly reducing the risk of electromagnetic carcinogenesis. In some contemplated embodiments, inductance coil 7614*a*, when not receiving transmitted wireless energy, may also be configured to act as a transmitting and/or receiving antenna. In some embodiments and implementations, the incision, or one of the incisions, may be made in the region of the patient's navel 7610*n*.

As depicted the perspective view of FIG. 76*b*, implant system 7600 may further comprise auxiliary implant 7608, which may comprise CPU/printed-circuit-board 7603, battery 7604, memory/data storage element 7625, antennas 7602*b*. Auxiliary implant 7608 may also comprise any of the elements previously described in FIGS. 54 *a-c*, including but not limited to an antenna 7602*b* to allow for receipt of electromagnetic signals, which may be used to transmit data to and/or receive data from CPU/printed-circuit-board 7603.

An external transmitter may be adjusted by the patient or healthcare personnel to transmit signals to internal antenna 7602*b* that, in turn, directs CPU 7603 to coordinate electrical output of wiring contained in implant 7601. In some embodiments, the battery 7604 may also be flexible and/or installed within or along inductance coil 7614*a*. A wireless charging system may be provided, as previously described, which may be configured to wirelessly charge the battery 7604 via inductance coil(s) 7614*a*. Optionally, one or more of the elements of implant system 7600 is either flexible and/or compressible, or is small enough on its own to fit within a minimally invasive entrance incision 7610*a* with other elements of implant 7600 moved into their optimal positions in separate tissue pockets. However, some components, such as the string-like implant 7601, need not be compressible. Similarly, in some embodiments, the inductance coil(s) 7614*a* may be rigid but may, due to the techniques for insertion of spiral implants disclosed herein, be inserted into a larger implant pocket, as previously discussed. Auxiliary implant 7608, which may be compressible to allow it to fit within the preferably minimally invasive entrance incision 7610*a*, may allow for certain components, such as sensitive electrical components, to be placed within a separate implant, which may be more protective of such components, such as being within a waterproof/sealed container, for example. A seal, such as a wrapper, may be used to contain all of the elements of auxiliary implant 7608 therein. Auxiliary implant 7608 may further comprise, for example, a memory/data storage element 7625.

In further contemplated embodiments, the implant system may comprise an auxiliary implant with any element including, but not limited to, those mentioned for the auxiliary implant described in FIG. 66, for example, CPU(s)/printed-circuit-board(s), battery(ies), memory/data storage element (s), antenna(e), capacitor(s), electronic heart rate sensor(s), lab-on-a-chip element(s). In other contemplated embodiments, either coils or auxiliary implants may comprise pulse oximetry elements. Although some auxiliary implants shown in the figures are cylindrical in shape, in further contemplated embodiments they may comprise a variety of shapes including, but not limited to, ovoids, polygonal prisms, pads, pillow-like, purse-like, with or without various cavities or convexities.

In some embodiments, motor drives for the musculoskeletal system may comprise, for example, hydraulic and/or magnetic movement systems and the like. As natural muscles work in opposing pairs across a joint, a synthetic muscle, similar to motorized robotics, may create work across a moveable interface, which in the depicted embodiment is the lower arm 7620 (ulna) across the finger joints, with ulnar attachment by natural or synthetic tendon 7629 and proximal motor portion 7621 drawing together (or repelling to reset) distal motor portion 7623 which is, in turn, attached to a ventral portion of a phalanx by natural or synthetic tendon 7624. These surgeries may occur separately or in concert with surgery to create pockets 7605*a*, 7605*b*, & 7605*c* and implant the depicted elements.

The motor(s) or other elements may derive their respective instructions and/or power from implant 7601, which reaches the arm via incisions 7610*a* and 7610*b*, and terminates near incision 7610*c* as discussed previously in FIG. 63 and the like.

Ultimately, energy may be wirelessly fed into coil(s) 7614*a* via an external coil and the system may store and feed energy to motor(s)/groups as needed.

In some embodiments, prosthetic devices may use sensored brushless motors for actuation. Such sensored brushless motors may comprise brushless motors, field oriented control systems, rotary encoders, and gearboxes. In certain embodiments, the rotary encoder may comprise a tunneling magnetoresistance sensor. In some instances, each motor may be individually actuatable. Additional details regarding the disclosed prosthetic device may be found in US Patent Publication Application No. 2020/0306059, titled "System and Method for a Prosthetic Hand Having Sensored Brushless Motors", which is hereby incorporated in its entirety by reference.

In some embodiments, powered prosthetic devices (such as prosthetic thighs), may use computer controlled actuators to rotate the prosthetic thigh. In a preferred embodiment, a computer controlled actuator may be configured to rotate the prosthetic thigh along a sagittal plane relative to the socket. In certain embodiments, the actuator may increase stiffness of the joint if the foot is in contact with the ground and may decrease stiffness if the foot is in not in contact with the ground. Additional details regarding the disclosed prosthetic device may be found in US Patent Publication Application No. 2013/0261766, titled "Powered Prosthetic Hip Joint", which is hereby incorporated in its entirety by reference.

In some instances, actuators may be used to augment joint function. Such actuators may involve, for example, energizing a transverse flux motor to apply torque to a joint. In some instances, the motor may be directly couple to a low-reduction ratio transmission system, which is connected to an elastic element that is connected to the joint to supply torque, equilibrium, and/or impedance to a joint. Additional details regarding the disclosed actuating joint may be found in U.S. Pat. No. 10,143,570, titled "Biomimetic Joint Actuators", which is hereby incorporated in its entirety by reference.

In some instances, powered ankle-foot prostheses may be used to increase amputees' metabolic walking economy. Such devices may comprise, for example, a controller including an electromyographic processing unit, which may be coupled to an electromyographic sensor, which may be coupled to a plurality of servo controllers, which may link the controllable powered actuators and the controller. In some instances the servo controllers may comprise torque controllers, impedance controllers, and/or position controllers. In some embodiments, unidirectional springs may be configured in parallel with the controllable actuators. Additional details regarding the disclosed ankle joint may be found in U.S. Pat. No. 10,137,011, titled "Powered Ankle-Foot Prosthesis", which is hereby incorporated in its entirety by reference.

In some embodiments, knee prostheses may comprise agonist-antagonist arrangements of two series-elastic actuators in parallel, a knee joint, and a controller for independently energizing the actuators. In a preferred embodiment, the first rotary actuator may be connected to a first linear ball screw, which may be linked to the mechanical knee joint via a link which may comprise a first ball-nut threadably engaged with the first linear screw. In such an embodiment, the second rotary actuator may be connected to a second linear ball screw, which may be linked to the mechanical knee joint via a link which may comprise a second ball-nut threadably engaged with the second linear screw. Upon actuation of the rotary actuator, the linear screw rotates, causing the link to move along the linear screw causing rotation of the joint. Additional details regarding the disclosed knee joint may be found in U.S. Pat. No. 9,149,370, titled "Powered Artificial Knee with Agonist-Antagonist Actuation", which is hereby incorporated in its entirety by reference.

In some instances, prosthetic legs may comprise electronically controlled, power generating knee joints. In certain instances, the knee may either be passive, or it may be active, assisting or completely controlling gait. In either active/passive mode, the knee may still generate electrical energy. In certain embodiments, the prosthetic leg may comprise an electronic control system for overall operation of the leg, and storage devices for excessively generated electrical energy. Additional details regarding the disclosed prosthetic leg may be found in U.S. Pat. No. 7,485,152, titled "Prosthetic Leg Having Electronically Controlled Prosthetic Knee with Regenerative Braking Feature", which is hereby incorporated in its entirety by reference.

Agonist-antagonist actuators may be used for artificial joints in artificial limbs, which may be used in, for example, orthotic, prosthetic, or exoskeletal applications. In some embodiments, a flexion actuator may include a series combination of a first active element and a first elastic element; an extension actuator may comprise a second active element and a second elastic element. In some embodiments, series elasticity may be used for mechanical power amplification. Additional details regarding the disclosed joint may be found in U.S. Pat. No. 8,870,967, titled "Artificial Joints Using Agonist-Antagonist Actuators", which is hereby incorporated in its entirety by reference.

In some embodiments, prosthetic leg devices may comprise powered knee and ankle joints with motor units for delivering power to each joint. Such prosthetics may comprise, for example, sensors for measuring real-time inputs and controllers for controlling movement. The control system may comprise, for example, a processor, memory for storing instructions, and means for generating control signals for each powered joint. Additional details regarding the disclosed prosthetic device may be found in U.S. Pat. No. 8,652,218, titled "Powered Leg Prosthesis and Control Methodologies for Obtaining Near Normal Gait", which is hereby incorporated in its entirety by reference.

In some embodiments, implanted devices may comprise motors. Such motors may be, for example, coreless. Eliminating the ferromagnetic core may offer, in some instances, reduced mass, lower electrical time constant, high power efficiency, low noise, et al. Additionally, core-free motors may lead to longer battery life and more rapid cycling. In a preferred embodiment, a permanent magnet motor may comprise high energy density, increased oxidation resistance, and stable magnetization curves. In some instances, sintered ceramic bearings may provide more precision when compared to traditional motors. For internal applications, it may be preferred, in some embodiments, to use hydrodynamic or magnetic bearings due to their longer lifespans. Additional details regarding the disclosed motors may be found in 'Electric Motors for Medical and Clinical Applications', Gieras, 2008, researchgate.net/publication/245024769, which is hereby incorporated in its entirety by reference.

Inductance coil/'group of stacked coils' may be present as per the coil cross section depicted in FIG. 37d.

A multiplicity of stacked inductance coils may increase the power transfer as well as increase of mutual inductance between coupled coils. Reference: 'Achieve High Power Density with Stacked Inductor Aug. 25, 2021, https://www.electronicdesign.com'

To deliver proper alignment the maximal energy transfer per orientation of coil groups may be, in some embodiments, assessed by an internal or external CPU with a signaling when optimal alignment is approaching or departing, or made or lost.

As per FIG. 37*d*, a temperature sensor such as 3719*t* may be configured to detect tissue temperatures external to the coil and/or wrapper so that hardware and/or software in the system can alert the user/external coil to increase or decrease energy transmission as the case may be. In some embodiments, one or more threshold temperatures may be established, such as a shutoff temperature, which may be, for example, 45 degrees C., which may result in termination of energy delivery until the temperature returns to a second threshold temperature, such as 40 degrees C., at which point the energy delivery may resume.

In some embodiments, additional elements, such as electronic elements, may be coupled to the coil to make the coil more useful as a standalone implant, or an implant configured to standalone as a power supply to another, secondary implant. In some such embodiments, use of a unitary coil, as shown in FIG. 80*a*, may eliminate the need for an auxiliary implant altogether. In contemplated embodiments, a unitary coil may therefore be coupled with other implants, such as implants to which the unitary coil is providing energy, without the use of an auxiliary implant to aid the unitary coil in doing so. It is also contemplated, however, that some coil embodiments may have some, but not all, of the components that may be provided on an auxiliary implant, and may therefore be considered a "hybrid" coil implant.

FIG. 77 depicts a top plan partially transparent view of a flexible tissue implant facilitating system (FTIFS) 7700 and devices comprising an instrument comprising blunt introducing tip 7709, dilator 7708, clockwise screw threads 7711 positioned on a tapering portion of dilator 7708. Tip 7709 is coupled to a distal portion of shaft 7714. Clockwise rolled implant 7704 is in rolled up into a compressed configuration and has been inserted in tissue pocket 7705, which is depicted in dashed lines indicating these elements lie below the skin surface adjacent minimally invasive entrance wound/incision 7710. The depicted as internal portion of a suture 7751*i* was previously affixed to implant macro positioning/instrument engaging hole 7703 when the implant was outside of body (preinstallation). When the implant was outside of incision 7710, the non-needle bound end of the suture was tied to hole 7703; then an endoscopic needle driver delivered the suture needle and accompanying distal suture through the skin from inside to out preferably a distant region of the implant pocket (distant from the entrance incision), such as at one or more corners of the implant pocket, resulting in an externalized portion of the suture 7751*e* extending from within the implant pocket 7705 through one or more openings that may have been, as mentioned above, made via an endoscopic needle driver in some preferred implementations, to be accessible for grasping by a surgeon and/or grasping instrument. The external portion suture(s) 7751*e* may then be pulled, preferably with a suitable instrument, as the handle 7715 and releasably bound shaft turn the remaining implant 7704 counterclockwise to unfurl implant 7704 like a flag. Suture materials may be nonabsorbable for example polypropylene or absorbable such as poliglecaprone and optionally secured by tying after exiting the skin a desired distance. Once unwound from the implant, the unbound/untethered FTIFS components may exit the incision/entrance wound 7710 leaving the implant in place. Any holes with attached sutures remaining may penetrate the skin in a similar fashion from inside out via an endoscopic needle driver for be sutured to opposite corners; this is possible if holes 7703 have been loaded with stitch prior to loading/winding the implant on shaft 7714 before the insertional process began (such holes may be the ones adjacent to the shaft and any protruding attachment elements, as stitch may be relatively small, taking little space). In some embodiments, screw threads 7711 on dilators may be manufactured counterclockwise to suit a surgeon/patient's needs.

FIG. 78*a* depicts an example of a wireless charging system 7800 comprising an external/transmitting inductance coil device 7814*e* that may be used to, for example, recharge or otherwise provide power to an internal implant 7814*i*. External/transmitting inductance coil device 7814*e* may be positioned adjacent to a corresponding receiving/internal inductance coil 7814*i*, which may be a standalone coil or part of an implant, to wirelessly transfer power to an implant as needed. However, human skin epidermis/dermis 7840*e* and subcutaneous fat 7840*s* lie between the coils which may heat the skin structures. In some embodiments and implementations, inductance coil 7814*e* and/or 7814*i* may comprise multiple coils, which may enhance the efficiency and/or functionality of the system. For example, in some embodiments, a butterfly inductance coil may be used to facilitate communication and/or transfer of power to the implant. Additional details regarding such butterfly coils may be found in U.S. Patent Application Publication No. 2008/0027513 titled "Systems and Methods for Using a Butterfly Coil to Communicate with or Transfer Power to an Implantable Medical Device", which is hereby incorporated herein in its entirety by reference. Due to the potential heating of skin and/or surrounding tissues, FIG. 78*b* depicts optional elements to system 7800 comprising plastic bladder 7860 with water/fluid inlet port 7861*i* and outlet port 78610 to circulate cool water/fluid thus cooling the skin to reduce the effects of heating from wireless energy transfer. In some implementations, the plastic bladder may be flexible. However, in other embodiments and implementations, the bladder may be rigidified.

FIG. 79*a* depicts a branched/dendritic flexible subcutaneous electronic neuro stimulative (FSQENS) implant 7901*a* comprising an auxiliary implant unit 7908*a* positioned in an implant pocket 7905*a* preferably made via a minimally invasive entrance incision. In further contemplated embodiments, a similar configuration may be used as a branched/dendritic flexible subcutaneous electronic muscular stimulative (FSQEMS) implant. More particularly, implant 7901*a* may be positioned within implant pocket 7905*a* that may be made by a minimally invasive dissection and/or beaded dissector as previously described. A coil (for example as shown in FIG. 62 but not shown here for space considerations) with or without additional electronics such as auxiliary implant 7908*a* may be deposited in various implant pockets made similarly to others described by methods described elsewhere within this application, including FIGS. 1 & 57 and connected via wiring/connection 7915*a*. In some implementations, the branched/dendritic FSQENS implant may be oriented along the dermatomal, sclerotomal, or myotomal, or nerve map areas.

In this embodiment, dendrite/branches, such as branches 7921*a*, may extend from the primary, elongated axis of implant 7901*a*. In the depicted embodiment, these branches 7921*a* may extend perpendicular, or at least substantially perpendicular, to the axis of implant 7901*a*. Implant 7901*a* may comprise terminal electrodes 7911*a*, optional peripheral/circumferential electrode 7912*a*, and positioning ring/hole 7922*a*, external coupler/adapter 7923*a*, and internal coupling 7909*a*. Positioning ring/hole 7922*a* may be used for positioning, suturing, fixation or as per the other positioning holes discussed elsewhere herein. The unit may be sealed within a container or envelope, which is preferably both waterproof and biocompatible. Terminal electrodes 7911a each may be electrically coupled, directly or indirectly, to a CPU and/or other suitable electrical circuitry and/or may also be wired independently of each other, thus allowing for different programmable control for each. In other contemplated embodiments, the wiring may be in series, parallel or another form of independent wiring or a combination thereof.

FIG. 79b depicts an alternative embodiment of a branched/dendritic flexible subcutaneous electronic neuro stimulative (FSQENS) implant 7901b positioned in an implant pocket 7905b preferably made via a minimally invasive entrance incision. In further contemplated embodiments, a similar configuration may be used as a branched/dendritic flexible subcutaneous electronic muscular stimulative (FSQEMS) implant. Unlike implant 7901a, implant 7901b comprises branches 7921b that extend at an acute angle relative to the implant axis, preferably with both opposing branches pointing towards the distal end of the implant having positioning hole/ring 7922b, as shown in the figure, which may facilitate insertion of the implant. It is contemplated, however, that in alternative embodiments one or more of the branches may extend towards, rather than away from, this distal end. Otherwise, implant 7901b may be similar to implant 7901a and may comprise, for example, one or more terminal electrodes 7911b, which may be positioned at or adjacent to the tips of each, or at least a subset, of the various branches 7921b, along with one or more circumferential electrodes 7912b, which may be positioned to encircle or otherwise extend about a portion of one or more of the various branches 7921b.

In some embodiments, a plurality of branches 7911b may be used as leads for an ECG implant. Thus, the embodiment of FIG. 79b may be modified to include, for example, 3-12 branches/leads, which may be much longer than the branches depicted in this figure if needed in order to be positioned at desired locations adjacent a patient's heart.

FIG. 79c depicts a serpentine/sinuous flexible subcutaneous electronic neuro stimulative (FSQENS) implant 7901c, positioned in an implant pocket 7905c preferably made via a minimally invasive entrance incision. In further contemplated embodiments, a similar configuration may instead be used as a serpentine/sinuous flexible subcutaneous electronic muscular stimulative (FSQEMS) implant. More particularly, implant 7901c may be positioned within implant pocket 7905c that may be made by a minimally invasive dissection and/or beaded dissector as previously described.

In this embodiment, alternating bends such as bend 7921c, may be formed such that the implant meanders back and forth in a periodic manner. In some embodiments, the implant may form, or at least substantially form, a sinusoidal shape, at least in part, as shown in FIG. 79c. Each of the various bends or periods of the implant may be substantially angled relative to the overall implant axis, which is represented by the proximal implant terminus. Again, the distal end of the implant may comprise a positioning ring/hole 7922c, and the implant 7901c may comprise terminal electrodes 7911c, which may be positioned at the apex of each, or at least a subset, of the various bends/periods of the implant. Optional peripheral/circumferential electrodes 7912c may also be used if desired, as discussed above. Each of the various electrodes, such as electrodes 7911c and/or electrodes 7912c, may be electrically coupled, directly or indirectly, to a CPU and/or other suitable electrical circuitry and/or may also wired independently of each other, thus allowing for different programmable control for each. In other contemplated embodiments the wiring may be in series, parallel or another form of independent wiring or a combination thereof.

Preferably, each of the peaks of the sinusoidal shape of implant 7901c, or at least a subset of these peaks, comprises an electrode, which may maximize the distance between opposing and/or adjacent electrodes. Also, preferably, the implant 7901c is configured to maintain its shape without requiring the surgeon to reconfigure the implant 7901c in this shape. Implant 7901c may therefore comprise a rigid material or a resiliently flexible material, such as a material having shape memory.

FIG. 80a depicts a top view of a circular, spiral implant (or minimally invasive rotatably implantable unitary coil) 8001 with outer arm band terminus 8012 and inner arm band terminus 8011 and space 8010 between the bands. In some embodiments, spiral implant 8001 may be circular in overall shape and rectangular in cross section. However, various other shapes may be used in alternative embodiments. Spiral implant 8001 may be rigid or, if preferred, more flexible. In some embodiments, the spiral implant 8001 may be compressible by being rollable and/or foldable. In some embodiments, spiral implant 8001 may comprise a metal, ceramic, cermet, glass, flexible plastic, organic polymer, biopolymer, or the like, and therefore, due to the unique insertion methods disclosed herein, need not be compressible. Other embodiments may comprise a polymeric external lamination or containment to retain more dissolvable materials such as hydrogels and the like. Drugs, vitamins, or other chemicals, including biologics, may also be bound, dissolved, or otherwise present in a portion or all of the structure of spiral implant 8001 and/or elements contained therein. In some embodiments, antibiotics/antimicrobials may be coated or otherwise incorporated on and/or into the implant to prevent or at least inhibit microbial growth on the implant. Use of a unitary coil, as shown in FIG. 80a, may eliminate the need for an auxiliary implant altogether. In contemplated embodiments, a unitary coil may therefore be coupled with other implants, such as implants to which the unitary coil is providing energy, without the use of an auxiliary implant to aid the unitary coil in doing so. It is also contemplated, however, that some coil embodiments may have some, but not all, of the components that may be provided on an auxiliary implant, and may therefore be considered a "hybrid" coil implant.

Different regions and/or portions of spiral implant 8001 may also have different medications or chemicals printed or otherwise designed into them. In addition, electronics, micro-pumps, and/or printed circuit boards may be present in the spiral implant 8001 when properly protected. Radiographically, sonically, and/or electromagnetically identifiable material may also be present in implant 8001 to aid in locating and/or manipulating the implant. Spiral implants may be inserted by rotating/winding the implant into a minimally invasive entrance wound, as will be discussed and depicted later in greater detail. Spiral implants may also lend themselves to carrying electronics, such as inductance coils, thin film batteries, printed circuit boards as well as chemicals, medicines, and/or biopolymers. From the inner terminus of the coil 8011, wiring/connector 8015i may be electrically coupled to one or more of the components of the implant 8001. Similarly, the outer terminus of the coil 8012 may comprise wiring/connector 80150, which may be joined/coupled to various portions of the coil to complete circuitry after, for example, a portion of the implant has cleared the entrance incision.

FIG. 80*b* depicts a cross-sectional view of spiral implant 8001 taken from FIG. 80*a* along the line and arrow depicted therein. The cross-sectional view of spiral implant 8001 also depicts electromagnetic interference (EMI) suppression elements comprising magnet 8031 and shielding via ferro-metallic element 8032, which may comprise 270 degree shielding in some embodiments. In further contemplated embodiments, ferro-metallic shielding element 8032 may be positioned and configured such that this element lacks portions running down one or both sides and therefore need not envelope any elements laterally as shown in the figure. In further embodiments, EMI suppression may comprise a magnet. The cross-sectional view of spiral implant 8001 also depicts superstructure 8019 positioned on the upper surface of the implant. Of course, in alternative embodiments, the superstructure 8019 may be positioned on any other side and/or portion of the implant. Spiral implant 8001 may also comprise temperature sensor 8019*t*, which may protrude from another location on implant 8001. The depicted embodiment also comprises various layers/elements, including a metallic inductance coil 8021, battery 8022 (thin film in this embodiment), printed circuit board/CPU 8023, one or more additional inductance coils 8021*a*, capacitor 8026, data storage 8027, lab-on-a-chip 8029, ancillary electronics 8024, such as a heating element, thin film resistors, etc., and polymeric protective inner sheath 8025*i*, which may be positioned adjacent to protective outer sheath 8025*o*. Ancillary electronics 8024 may also be used if desired, which may comprise, for example, a heart rate sensor, oxygen saturation monitor, or the like, any of which may be positioned adjacent to protective outer sheath 8025*o*. In other contemplated embodiments, one or more additional metallic inductance coils 8021*a* may be stacked to enhance the power generation capabilities of the implant. As also shown in this figure, a hollow space may be created between inner and outer sheaths 8025*i*/8025*o*, which may be used to contain a fluid and/or gel, for example, which may serve as a protective sheath/seal, a superstructure, and/or a location for drug containment and/or delivery. In some embodiments, microfluidic channels (not shown later as 8029*m*) may be used, which may be configured to deliver patient serum/blood/tissue fluid located outside of the protected encasement/wrapper in contact with lab-on-a-chip for analysis(es). In further contemplated embodiments, temperature sensors may be placed in one or more locations on the inside and/or outside of spiral implant 8001 or any of the other implants disclosed herein. Temperature sensors located on the outside may, in some embodiments, be configured to send temperature data to a CPU, which may be programmed with a set temperature threshold such as, for example, 45° C., to possibly shut down or reduce external wireless inductance coil charging to protect delicate adjacent tissue. Once external temperatures return to a preset safe threshold, for example 42° C., wireless charging may recommence. Temperature sensors placed internally in the spirals may have preset thresholds to alter the charging parameters to protect one or more of the aforementioned internal elements of the spiral coil 8001. An external transmitter may be adjusted by the patient or healthcare personnel to transmit signals to internal antenna 8002*b* that in turn, may direct CPU 8023 to coordinate functions of the implant. Some contemplated embodiments may comprise multiple internal antennas.

FIG. 80*c* depicts a cross-sectional view of an alternative embodiment comprising (EMI) suppression elements comprising magnet 8031 and shielding via ferro-metallic element 8032*c*, which comprises planar shielding. The embodiment further comprises inductance coil 8021, one or more additional inductance coils 8021*a*, battery 8022, printed circuit board/CPU 8023, antenna 8002*b*, capacitor 8026, data storage 8027, lab-on-a-chip 8029, ancillary electronics 8024 (such as a heating elements, thin film resistors, etc.) and polymeric protective inner sheath 8025*i*, which may be positioned adjacent to protective outer sheath 8025*o*. Microfluidic channels 8029*m* may be configured to deliver patient serum/blood/tissue fluid located outside of the protected encasement/wrapper in contact with lab-on-a-chip 8029 for analysis(es). Fiberoptics 80290 may be configured to analyze patient serum/blood/tissue fluid located outside of the protected encasement/wrapper in concert with the lab-on-a-chip 8029. As vascularization may occur through the implant from below to nourish the tissues overlying the implant (for example, if the implant is placed subcutaneously), placement of Microfluidic channels 8029*m* and/or fiberoptics 80290 facing the spaces 8010 between the spiral arm/bands may be beneficial for measurements following vascularization. In further contemplated embodiments, placing the fiberoptics and/or microfluidic termini away from the spaces may provide for more immediate analyses until neovascularization occurs within these spaces.

FIG. 80*d* depicts a cross-sectional view of an alternative embodiment comprising (EMI) suppression elements comprising magnet 8031 and shielding via ferro-metallic element 8032*d*, which, in the depicted embodiment, comprises wraparound, 360 degree shielding for one or more selected elements. The embodiment further comprises inductance coil 8021, one or more additional inductance coils 8021*a*, battery 8022, printed circuit board/CPU 8023, antenna 8002*b*, capacitor 8026, data storage 8027, lab-on-a-chip 8029, ancillary electronics 8024 (such as a heating elements, thin film resistors, etc.) and polymeric protective inner sheath 8025*i*, which may be positioned adjacent to protective outer sheath 8025*o*.

In some embodiments, wireless power transfer systems may require electromagnetic interference (EMI) suppression shields to protect electronic components from unwanted magnetic field fluctuations. In some embodiments, such EMI suppression shields may involve ferrite films, metal films, and/or a hybrid material comprising both a metal and ferrite component. Additional details regarding EMI suppression shields may be found in 'Electromagnetic Interference Shielding Effects in Wireless Power Transfer Using Magnetic Resonance Coupling for Board-to-Board Level Interconnections', Kim, InCompliance Magazine, 2013, which is hereby incorporated by reference in its entirety.

In some embodiments, EMI suppression shields may comprise thin, flexible magnetic shields. It some instances, it may be beneficial to use a material having a high permeability, which may lead to improved shielding performance through magnetic field containment/absorption. In other embodiments, it may be beneficial to use a material having a higher resistance, which may lead to better noise suppression; however, particular caution may be required, as even though higher resistance values may absorb more magnetic field noise, they may create more heat. In some instances, metallic shields may be used as EMI suppression shields, as they can reflect such noise energy. In other instances, magnetic shields may be used as they may absorb such noise energy and convert it to heat. In some embodiments, hybrid materials (for example, a ferrite material and copper), which may comprise a magnetic sheet with a metallized back layer, may be used to increase such EMI suppression effects. In some embodiments, having a low permeability and a high resistance may be desired. Such embodiments may include those in which such EMI suppression shields are in close proximity with inductance coils. In some instances, hybrid materials may comprise a stack comprising an insulating layer, a conductive layer, and a magnetic sheet. Additional details regarding EMI suppression devices and materials may be found in 'EMI Suppression Shields: Understanding the Basics', Burket, Electronic Design, TechXchange: Delving into EMI, EMC, and Noise, 2020, which is hereby incorporated by reference in its entirety.

In some embodiments, magnetic flux diversion may be used to shield components from EMI. In some embodiments, shields may be constructed with high permeability, which may be used to concentrate magnetic flux. In some embodiments, such highly permeable metals may comprise nickel-iron alloys comprising small percentages of copper, chromium and/molybdenum. Additional details regarding magnetic flux diversion shielding may be found in 'Inductive Power Transmission Shielding', Electronics Notes, https://www.electronics-notes.com/articles/equipment-items-gadgets/wireless-battery-charging/inductive-power-transmission-shielding.php, which is hereby incorporated by reference in its entirety.

In some embodiments, passive and/or active cancellation loops may be used to mitigate EMI. Such loops may produce a magnetic field opposing an initial magnetic field. If a passive loop is excited by a varying magnetic field, the loop may acquire an EMF, generating a current in the loop, therefore generating a magnetic field. In some instances, to enhance shielding performance, a series capacitor may be used to induce a current within the loop. Additional details regarding such EMI suppression methods may be found in 'Active Shielding Design for Wireless Power Transfer Systems', Cruciani, IEEE Transactions on Electromagnetic Compatibility, Vol. 61, Issue 6, 2019, which is hereby incorporated by reference in its entirety.

In some embodiments, nanomagnetic structures may be used for EMI suppression. In some embodiments, such structures may comprise vertically aligned magnetic composite structures as coupling inductors. In some embodiments, magnetic nanoparticles may be surrounded by an amorphous insulating matrix, which may comprise, for example, Fe and Co-based thin films. In other embodiments, such structures may comprise stacked layers of ferromagnetic fields alternating with and separated by thin insulating polymer dielectric layers. In some instances, the ferromagnetic layer may comprise NiFe, NiFeMo, and/or CoZrO. In some embodiments, insulators used within such stacks may comprise, for example, alumina. Such insulator layers may be used to increase reflection loss. Additional details regarding such EMI suppression shields may be found in 'Nanomagnetic Structures for Inductive Coupling and Shielding in Wireless Charging Applications', Mishra, IEEE, DOI: 10.1109/ECTC.2015.7159707, 2015, which is hereby incorporated by reference in its entirety.

In some embodiments, fiber optics may be used in chemical sensing devices. In some embodiments, connectors between the fiber optic cable and the sensor head may comprise a sapphire ball lens, retainer, a spring-giving focus/collimation, and the like. Such arrangements may be used to launch and receive beams of diameters such as 5 mm. In some instances, certain emitted wavelengths may cause tissue damage, so it may be beneficial to block such wavelengths with a filter. In order to minimize unforeseen variations in specification, collection fibers may have diameters of 200 or 400 micrometers. In some embodiments, errors may arise due to variations in the intensity of the xenon arc lamp light source; to minimize such errors, a light intensity controller may be used. Additional details regarding the aforementioned fiber optic device may be found in 'Optical Fiber-Coupled Ocular Spectrometer for Measurements of Drug Concentration in the Anterior Eye—Applications in Pharmaceuticals Research', Miller, IEEE Transactions on Biomedical Engineering, Vol. 57, No. 12, December 2010, which is hereby incorporated in its entirety by reference.

In some embodiments, fiber optic sensors may comprise interferometric sensors, which may respond to an external stimulus by a change in the optical path length, resulting in a phase difference in the interferometer. In other embodiments, fiber optic sensors may comprise intrinsic fiber optic sensors based on the evanescent wave absorption effect. Such intrinsic evanescent wave-based fiber optic sensors may use LED light sources. In some embodiments, fiber optic cables used in conjunction with intrinsic evanescent sensors may comprise multimode optical fibers with silica cores and plastic cladding. In some instances, functional coatings of fiber optic cables may comprise dip- and spin-coatings, layer-by-layer deposition, electrostatic self-assembly, chemical and physical vapor deposition, and the like. In preferred embodiments, the outermost layer of the coating may comprise porphyrin (TSPP). In preferred embodiments, porphyrin films/compounds may be used as sensitive elements for optical sensors due to their high sensitivity and optical properties which depend on the environmental conditions (in which the target molecule is present). In some embodiments, fiber optic sensors may comprise tapered optical fibers, the optical properties of which may be influenced by the profile of the conical tapering sections. In some instances, the optical fiber may act as a platform that may be exploited to facilitate the detection of different chemicals by coating the fiber with appropriate functional materials (such as mesoporous $PDDA/SiO_2$ nanoparticles for ammonia). In some embodiments, optical fiber coatings may comprise a $PAH/SiO_2$ film (allowing for greater versatility of the sensor) for the detection of organic compounds. Additional details regarding the aforementioned fiber optic devices may be found in "Fibre-Optic Chemical Sensor Approaches Based on Nanoassembled Thin Films: A Challenge to Future Sensor Technology", Korposh, 13 Jun. 2013, DOI: 10.5772/53399, which is hereby incorporated in its entirety by reference.

In some embodiments, Vascular Endothelial Growth Factor (VEGF) may be used to increase blood vessel proliferation. VEGF has been shown to significantly augment collateral vessel as well as capillary development. VEGF has four homodimeric species, each monomer having 121, 165, 189, or 206 amino acids. $VEGF_{121}$ and $VEGF_{165}$ are diffusible after secretion, while $VEGF_{189}$ and $VEGF_{206}$ are secreted but tend to be bound to heparin-containing polyglycans. VEGF stimulates angiogenesis, and even in neovascularization, as VEGF and VEGF receptors colocalize with sites of neovascularization. It should be noted that $VEGF_{165}$ demonstrates substantial affinity for heparin. Circulating alpha2-macroglobulin covalently binds to and inactivates VEGF; however, heparin may be used to inhibit the binding and inactivation of VEGF by alpha2-macroglobulin. Additional details regarding VEGF may be found in 'Therapeutic Angiogenesis', Takeshita, Journal of Clinical Investigation, Vol. 93, pp. 662-670, 1994, which is hereby incorporated in its entirety by reference.

Positive angiogenic factors may aid in blood vessel proliferation. Positive angiogenic factors may also include aFGF, bFGF, VEGF, angiogenin, and others. Additional details regarding angiogenic factors may be found in 'Angiogenesis in Cancer, Vascular Rheumatoid and other Disease', Folkman, Nature Medicine, Vol. 1, No. 1, 1995, which is hereby incorporated in its entirety by reference.

FIG. 81*a* is a top plan view of a composite system 8100 comprising a minimally invasive implant for prolonged and/or controlled drug/chemical delivery, which comprises a unitary coil 8114, segmentation pod implants 8171*a*, 8171*b*, auxiliary implant 8108*a*, and/or a bladder-like compressible implant 8101. Prolonged implantable drug administration of water soluble medicines may require highly concentrated fluids or powdered anhydrous storage if such a system is not to be recharged/refilled. However, direct release of such concentrations may be locally caustic, generally toxic and/or lethal. Water insoluble medicines may therefore be stored concentrated in liposomes or other means, mixed with water as per 'Liposomes for Enhanced Bioavailability of Water-Insoluble Drugs: In Vivo Evidence & Recent Approaches, Pharmaceutics 2020, vol. 12, 264, which is hereby incorporated in its entirety by reference. System 8100 may therefore be configured to store highly concentrated medicines, harvest body fluids, such as water, to admix with said medicines, as well as in some cases monitor drug levels and mix/disperse medicines to maintain desired drug levels over a prolonged period. This may be of benefit to those living in remote areas, those too ill to care for themselves, for example, mentally ill patients.

System 8100 in the vicinity of the unitary coil 8114 may comprise space 8110, connecting segment adapter/connector 8173, and one or more directional valves 8170*v*. System 8100 in the vicinity of segmentation pods 8171*a*/8171*b* may comprise connecting segments 8172*a*/8172*b*/8172*c* as well as bladder implant coupling 8180. System 8100 in the vicinity of bladder-like compressible implant 8101 may comprise superstructure 8151 and, in one or more portions, such as the upper half (when viewed from the edge) of the depicted embodiment, complete and/or partial bound stretch resisting form maintaining partitions (BSRFMP) 8191*u*. One or more other portions, such as the lower half below the complete and/or partial (BSRFMP) 8191L, may comprise an electronics assembly 8120, which may comprise, for example, inductance coil 8121, battery 8122, printed circuit board/CPU 8123, antenna 8102*b*, and capacitor 8126. These elements may be delivered through the skin via entrance incision 8160. System 8100 may be remotely programmed/controlled by CPU 8198 with attendant software and associated antenna 8199. Some contemplated embodiments may comprise multiple internal antennas.

FIG. 81*b* depicts a cross-sectional view of spiral implant 8114 taken from FIG. 81*a* along the line and arrow depicted therein. The lower portion of spiral implant 8114, as shown in this figure, may comprise (EMI) suppression element 8132, which may comprise planar shielding. This portion of implant 8114 may further comprise inductance coil 8121, battery 8122, printed circuit board/CPU 8123, antenna 8102*b*, capacitor 8126, data storage 8127, lab-on-a-chip 8129, ancillary electronics 8124 (such as a heating elements, thin film resistors, etc.) and protective inner layer 8125*i*, which may be positioned adjacent to protective outer layer 81250, which may comprise, for example, a sheath or portion of a sheath or an outer laminate. Polymeric protective inner layer 8125*i*, which again may comprise, for example, a sheath or portion or a sheath or an inner laminate, may be attached and divided into portions by one or more partitions, such as the 'Y-shaped' partition with upper limbs 8162*b*, 8162*c* and lower limb 8162*a* shown in the figure, which further subdivides the upper half of the cross sectional view of the spiral coil implant 8114 into multiple chambers comprising central upper chamber 8161*b* and lateral chambers 8161*a* and 8161*c*. Lab-on-a-chip 8129 may receive information from biosensor 8197 to assess drug/drug-moiety/chemical presence(s)/concentration(s). In some embodiments, biosensors may comprise optical fibers, electrochemical, nanomechanical and the like. It should be understood that any number of chambers/partitions may be provided as desired. For example, in some embodiments, only a single partition may be provided to separate a portion of the hollow inner core of spiral implant 8114 into just two chambers rather than three.

FIG. 81*c* depicts a cross-sectional view of bladder-like compressible implant 8101 taken from FIG. 81*a* along the line and arrow depicted therein. Superstructure 8151 may be used to provide rigidity to the implant 8101 and/or to bind the upper half lamination 8101*u* with lower half lamination 8101L as well as midlayer 8101*m*. The upper BSRFMP 8191*u* may also bind the upper half lamination 8101*u* with midlayer 8101*m*. The lower half BSRFMP 8191L may also bind the lower half lamination 8101L with midlayer 8101*m* which may house, protect and retain the midlayer electronics group 8120. In some embodiments, BSRFMP may facilitate disc-like shape maintenance of implant 8101 by preventing spherical inflation and/or by maintaining intraluminal pressure which may facilitate drug passage through porous lower half lamination 8101L membrane. The comparatively large size and/or surface areas of the spiral implant and/or the relatively flattened compressible implant may facilitate fluid collection and/or medicine/chemical administration without vascular catheterization/cannulation/penetration. In some embodiments, priming one or more parts of the system with a desired solvent(s) may facilitate operation. Bladder-like compressible implant 8101 may comprise pores 8101*p*, for example, nanoscale agents responsive to stimuli, as previously discussed.

FIG. 81*d* depicts a further enlarged cross-sectional view of spiral implant 8114 of that partially seen in FIG. 81*b* including polymeric protective inner layer 8125*i*, outer layer 81250. 'Y-shaped' partition upper limbs 8162*b*, 8162*c* and lower limb 8162*a*, central upper chamber 8161*b*, upper lateral chambers 8161*a* and 8161*c*. One or more gates 8138 may be positioned along the exterior of implant 8114 to selectively allow chemical/molecular passage into one or more of the chambers defined therein. These gates may, for example, comprise electrically actuatable smart nanoporous membranes (as per Langer, Wireless on-Demand Drug Delivery, Nature Electronics, 2021). Biosensor 8197 may be present inside or exterior to any of the displayed chambers as well as extending external to the implant to assess drug/drug-moiety/chemical presence(s)/concentration(s). Internalized partition gates 8130 may also be positioned along one or more of the internal partitions, which may be configured to selectively allow chemical/molecular passage. These internal gates 8130 may, for example, comprise electrically actuatable smart nanoporous membranes.

Spiral implant 8114 may be configured to collect body fluids including but not limited to saline and desalinated water. For example, body fluid may be drawn into lateral chamber 8161*a* through pore 8125*p*, which may be of a desired average diameter to allow passage of molecules of a desired number of Dalton molecular weight. The incoming fluid may be further filtered by porous membrane 8136, which is shown only extending adjacent to pore 8125*p* but may, in some embodiments, extend about the entire perimeter of implant 8114, or at least the portion of the implant adjacent to a particular storage chamber with which the pore 8125*p* is functionally associated. Porous membrane 8136 may comprise, for example, a polymeric and/or nano-enhanced membrane for reverse osmosis. A negative internal pressure may be assisted by microfluidic pump 8139, which may comprise, for example, a piezoelectric microfluidic pump/microdiaphragm pump or the like. Internal pressure accumulation may be balanced elsewhere within or external to the system via tube 8195, which may comprise directional valves if desired. Thus, implant 8114 may be configured to draw in filtered water from a patient's body fluids into chamber 8161$a$. Such water may be distributed elsewhere within the system 8100 via micropumps and tubes for admixing with concentrated drugs for controlled expulsion into a patient's tissues surrounding the implant, which may be vascularized due to the new or foreign nature of the implant and/or added to by virtue of exogenous chemicals/hormones discussed elsewhere within.

Spiral implant 8114 may collect body fluids including but not limited to saline and desalinated water. For example, fluid may be drawn into lateral chamber 8161$c$ through pore 8125$p$, which may be of a desired average diameter to allow passage of molecules of a desired number of Dalton molecular weight upon which the fluid may be further drawn in by, for example, an electro-osmotic-pump, which may comprising, for example, an outer electrically charged porous membrane 8131, through electro-osmotic filter sandwich layer 8132 toward and through outer electrically charged porous membrane 8133. Again, although structures 8131, 8132, and 8133 are shown only extending adjacent to pore 8125$p$, this is for ease of illustration and these structures may extend about the entire periphery of chamber 8161$c$ if desired. Thus, filtered water may accumulate in chamber 8161$c$. Such water may be distributed elsewhere within the system via, for example, micropumps and tubes for admixing with concentrated drugs for controlled expulsion into a patient's tissues surrounding the implant which may be vascularized due to the new or foreign nature of the implant and/or added to by virtue of exogenous chemicals/hormones discussed elsewhere within. Piezoelectric element 8170 may facilitate mixing and/or heating and/or cleaning.

As shown in the perspective view of FIG. 81$e$, implant system 8100 may further comprise, for example, auxiliary implant 8108$a$, which may comprise CPU/printed-circuit-board 8183, battery 8184, memory/data storage element 8185, antenna 8182$b$, capacitor 8186, electronic heart rate sensor 8188, and/or lab-on-a-chip 8187.

FIG. 81$f$ is an enlarged view of a powder mixing/distributing segmentation pod 8171$a$, which may further comprise fluidic tubing 8178, fluidic tubing 8179, which may be configured to deliver fluids in the directions to/opposite directions from tubings and/or storage bays such as 8177$f$. Such storage bays may house drugs, fluids, powders, etc. and may be coupled with means for distributing a drug, preferably in a dry form, such as screw drives 8195 and 8194 or, for example, a piston or the like. A preferably highly concentrated drug powder may be stored in one or more bays, such as bay 8177$f$. In some embodiments, this drug/powder may be moved/kept movable by piezoelectric element 8170 and/or screw 8195 toward screw 8194 which may facilitate transport of concentrated powder into mixing/storage bay 8177$m$, which may further comprise mixing element 8170$s$, such as a magnetic stirring element, that may be configured to mix a powder with fluid carried by one or more of fluidic tubing(s) 8178/8179, which may be received from spiral implant 8114. Biosensor 8197 may be used to determine the mixed concentration of materials, a signal indicative of which may be relayed to a CPU within an element of the system, which may elicit a desired action. In further contemplated embodiments, micro-pumps/motors may be present between bays and/or tubing.

FIG. 81$g$ depicts another example of a segmentation pod 8171$g$ that may be used in some embodiments, either in place of or in addition to any of the other pods. Pod 8171$g$ may comprise a gas bubble delivery segmentation pod, which may further comprise fluidic tubing 8178, fluidic tubing 8179, which may be configured to deliver fluids in the directions to/opposite directions from tubings and/or storage bays such as 8177$g$, and/or storage bay 8177$gg$ which may house fluids, powders capable of reacting to form a gas on mixing directly and/or in the presence of a catalyst and/or in the presence of energy (heat, light, electricity, etc.) and/or may comprise micro-pumps/motors 8174, which may facilitate transport into mixing/storage bay 8177$m$, which, again, may further comprise magnetic mixing element 8197, which may be configured to mix a powder or a fluid with another fluid carried by one or more of fluidic tubing(s) 8178/8179. Again, a biosensor 8197 may be used to determine the mixed concentration of materials, which may be relayed by way of a signal to a CPU within an element of the system for a desired action. The highly concentrated chemical solution and/or powder present in bay(s) 8177$h$, and/or storage bay 8177$hh$ may be moved/kept movable by piezoelectric element 8170 and/or a stirring element or the like. An example of chemical pairs that may possibly be used to provide a nontoxic, relatively inert gas source is sodium bicarbonate (baking soda) and acetic acid reacting to form carbon dioxide. In some embodiments, the gas bubble delivery segmentation pod 8171$g$ may be placed in an advantageous location, such as adjacent to the spiral implant 8114, to drive the system by gas contribution. In other embodiments, gas bubble(s) 8187$g$ may be used to separate various liquid aliquots of various components and/or concentrations which may be analyzed at any point along their paths via biosensors.

FIG. 81$h$ depicts another example of a possible modular segmentation pod, namely, a liquid mixing/distributing segmentation pod 8171$b$, which may further comprise fluidic tubing 8178, fluidic tubing 8179, which may be configured to deliver fluids in the directions to/opposite directions from tubings and/or storage bays, such as storage bay 8177$h$ and/or storage bay 8177$hh$, one or both of which may house drugs, fluids, powders, etc. and/or may comprise micro-pumps/motors 8174 that may facilitate transport into mixing/storage bay 8177$m$. Storage/mixing bay 8177$m$ may optionally comprise a mixing element, such as a magnetic stirring element, which may facilitate mixing powders and/or fluids with fluids carried by one or more of fluidic tubing(s) 8178/8179, which may be coupled to and/or received from spiral implant 8114 and/or one or more adjacent pods. Biosensor 8197 may be used to determine the mixed concentration of materials, which may be relayed via a signal to a CPU or other electrical element within the system, which may be used to trigger a desired action. The highly concentrated drug solution present in bay(s) 8177$h$, and/or storage bay 8177$hh$ may be moved/kept movable by piezoelectric element 8170 and/or a stirring element or the like.

In further contemplated embodiments, a wrapper, such as the wrapper shown in FIG. 46, may be placed overlying the exterior of one or more of the segmentation pods and/or outside of connection segments, which may facilitate sliding the implant into an incision and past tissues. In some embodiments, this wrapper may comprise a shrink wrap or may otherwise be adherent to one or more of the pods, in which case the wrapper may pinch/extend into the space overlying one or more of segments between the pods.

In further implementations, inorganic draw solutes such as, for example, magnesium and/or copper sulfate, may be placed in/about/between laminates and/or compartments to facilitate solvent movement.

In further contemplated embodiments and implementations, a variety of devices may be used in conjunction with those specifically mentioned in connection with the figures, including but not limited to, thermopneumatic micropumps that may transfer heat generated from RF transmission to a pump chamber, resulting in drug flow, and microminiature infusion devices that may comprise, for example, a reservoir for a therapeutic fluid, a driver, and/or one or more electrodes which may be used to deliver therapeutic electrical stimulation. In some instances, the driver may comprise a pump, such as, for example, a diaphragmatic, negative pressure, and/or peristaltic pump. In some embodiments, the driver may be actuated by electromagnetic means. Nanoscale agents may be used that may be configured to respond to stimuli such as light, magnetic fields, ultrasound, radio frequency, and/or x-ray, which may allow for selective actuation from outside of the user/patient's body. Magnetic fields may be used for magnetoporation and magnetic field drug targeting. Electric current and/or voltage may be used for electroporation and iontophoresis. Ultrasound may be used for sonodynamic therapy and sonoporation. Pulsed light may be used for optoporation and drug release. Temperatures may be influenced for thermoporation.

In some embodiments, self-sustained carbon nanotube hollow fiber scaffold supported polyamide thin film composite (CNT TFC-FO) membranes may be used for forward osmosis. Such membranes may be preferable due to their high porosity, good hydrophilicity, excellent electro-conductivity, and great electrically assisted resistance to organic and microbial fouling. In some instances, the complete TFC-FO hollow fiber membrane may comprise a salt-rejecting polyamide active layer interfacially polymerized on the outer surface of the CNT hollow fiber. The membrane may comprise an active layer facing the feed solution and a support layer facing the draw solution. Additional details regarding the disclosed membrane may be found in 'Highly Permeable Thin-Film Composite Forward Osmosis Membrane Based on Carbon Nanotube Hollow Fiber Scaffold with Electrically Enhanced Fouling Resistance', Fan, Environ. Sci. Technol., 2018, which is hereby incorporated in its entirety by reference.

In some instances, graphene, graphene oxide, zeolites, carbon nanotubes, silica, silver, and/or titanium dioxide nanoparticles may be used to increase membrane water permeability. In some embodiments, silica may be used to improve hydrophilicity of osmotic membranes. In some instances, silver and titanium dioxide may be used to reduce biofouling. In some embodiments, polymeric membranes, such as cellulose acetate and polyamide, may be integrated with other polymers or nanoparticles to form reverse osmotic membranes. In some instances, integration of nanoparticles with polymer-based membranes may improve antifouling properties of RO membranes. Additional details regarding such osmotic membranes may be found in 'A Critical Review on Recent Polymeric and Nano-Enhanced Membranes for Reverse Osmosis', Giwa, RSC Advances, Issue 10, 2016, which is hereby incorporated in its entirety by reference.

For membranes used in forward osmosis (FO), it may be preferable to utilize thinner support layers to lessen the concentration polarization impact on the FO process (higher concentration polarization can lead to a decrease in water flux); however, in some instances, thinner support layers may also compromise mechanical strength. In some embodiments, carbon-based nanomaterials (such as carbon nanotubes, graphene, and/or graphene oxide) may be used to enhance water flux, fouling propensity, and/or mechanical strength of FO membranes. In some instances, hydrophilic nanomaterials may be incorporated into FO membranes to increase membrane porosity and hydrophilicity while decreasing the tortuosity of the support layer, alleviating the effects of internal concentration polarization. In some instances, graphene oxide derivatives may be used to, for example, enhance selectivity, performance, and/or productivity of such FO membranes. In some embodiments, polymeric asymmetric membranes may be covered in functionalized carbon materials. In a preferred embodiment, an asymmetric FO membrane may comprise a dense, thin selective layer for solute rejection and a porous substrate layer to provide mechanical stability to the membrane. Synthetic polymers used for the fabrication of supporting layers of FO membranes may include, for example, cellulose derivatives, polyethersulfone and polysulfone, polyacrylonitrile, hydrophobic polyvinylidene fluoride, and the like. In some embodiments, FO membranes may comprise flat sheet FO membranes, hollow fiber FO membranes, and/or tubular FO membranes. In some instances, conductive FO membranes may be modified with a material (such as a metal, carbon, etc.) that may act as a negative electrode. Applying external voltages to FO membranes may result in an increased resistance to fouling. In a specific embodiment, anti-fouling double-skinned FO membranes may be used that may contain a polyamide salt-rejection layer and a zwitterionic brush-decorated, multiwalled carbon nanotube (MWCNT) foulant-resistant layer. Materials used to improve FO membrane performance may include, for example, carbon nanotubes, graphene, graphene oxide, zeolites, metal-organic framework, titanium dioxide, and the like. In some embodiments, active layers may comprise polymeric active layers, which may comprise polymers such as polyamide. In some instances, supporting substrates may comprise nanocomposite substrates, porous substrates, and the like. In certain embodiments, FO membranes may comprise nanomaterial interlayers in between the active layer and the supporting layer. Additional details regarding such FO membranes may be found in 'Recent Developments in Forward Osmosis Membranes Using Carbon-Based Nanomaterials', Yadav, ScienceDirect, Desalination 482 (2020), 114375, which is hereby incorporated in its entirety by reference.

In some embodiments, stimuli-responsive hydrogels may be used as draw solutes in FO membranes. Stimuli-responsive hydrogels may be preferred as they may be easily regenerated. In preferred embodiments, draw solutes may possess high osmotic pressure, be nontoxic, exhibit low reverse flux, and be easily/rapidly regenerated. In some instances, polyelectrolyte hydrogels, such as thermos-responsive poly(ionic liquid) hydrogels, may be used as draw agents as they produce high osmotic pressure. Such hydrogels may comprise, for example, P(MTxEOy). In some instances, water flux may be enhanced via composite hydrogels and/or reduced-size hydrogels. In some instances, the dewatering rate may be enhanced by changing the network structure of the hydrogel. It may be preferable to have a heterogenous hydrogel as internal microstructures may contribute to formation of water release channels by grafting linear hydrophilic side chains onto hydrogel networks. Additional details regarding such FO membranes may be found in 'Recent Developments and Future Challenges of Hydrogels as Draw Solutes in Forward Osmosis Process', Wang, MDPI, Water 2020, 12, 692, which is hereby incorporated in its entirety by reference.

In FO membranes, it may be preferable to have, for example: an active layer that is ultra-thin, yet dense enough to have a high solute rejection rate; a support layer that is both thin and able to provide mechanical strength; a high hydrophilicity to increase water flux, anti-fouling properties, and CP alleviation; and a high pH, temperature, and oxidation resistance range. In some embodiments, functionalized carbon nanotubes may be blended into the polyethersulfone support layer to enhance hydrophilicity and water flux. In some instances, thin-film inorganic FO membranes may comprise microporous silica xerogels immobilized onto a stainless steel mesh substrate. In some embodiments, FO membranes may undergo physical/chemical modifications to improve membrane properties. In some embodiments, hydrophilic chemicals may be added to membranes to improve water flux without compromising rejection. Modification methods may include, for example, blending, surface coating, in-situ interfacial polymerization, and the like. In some embodiments, draw solutes may comprise, for example, NaCl, NaNO3, KCl, and the like. Other draw solutes may comprise organics, polymers, hydrogels, ionic liquids, and the like. Additional details regarding FO membranes may be found in 'Research on Forward Osmosis Membrane Technology Still Needs Improvement in Water Recovery and Wastewater Treatment', Li, MDPI, Water 2020, 12, 107, which is hereby incorporated in its entirety by reference.

In some embodiments, thin-film inorganic FO membranes may be used in various implants, which membranes may comprise, for example, micro-porous silica xerogels immobilized onto stainless steel mesh substrates. In some instances, NaCl may be used in draw solutions. In some instances, microporous inorganic silica membranes may be used to remedy issues surrounding the severe internal concentration polarization within the supporting layer of asymmetric structured membranes. In some instances, the mechanically rigid stainless steel mesh allows for the formation of self-supporting thin-film structures, which may eliminate the need for a thick supporting layer, enabling short-distance water permeation with minimal internal polarization. Additional details regarding such FO membranes may be found in 'Forward Osmosis with a Novel Thin-Film Inorganic Membrane', You, Environmental Science and Technology 2013, 47, 8733-8742, which is hereby incorporated in its entirety by reference.

In some instances, ultrasound may be used in FO membranes to mitigate the effects of ICP. In some instances, it may be preferred to use low frequency ultrasound, such as 40 kHz. However, the improvement in water flux may be realized at the expense of increased reverse draw solute flux. In some instances, magnesium sulfate and copper sulfate may be used in draw solutions. Additional details regarding ultrasound in FO may be found in 'Ultrasound-Assisted Forward Osmosis Desalination Using Inorganic Draw Solutes', Qasim, Ultrasonics Sonochemistry, 2019, which is hereby incorporated in its entirety by reference.

In some embodiments, low frequency ultrasonic vibrations may be applied to the porous support structure of an FO membrane to mitigate ICP. Low frequency, such as 20 kHz, may be effective in improving water flux by even factors of 2. It may be preferred to place the support layer against the draw solution and the active layer against the feed solution. Such ultrasonic vibrations may show highly enhanced water flux in membranes such as, for example, a membrane comprising a thin-film composite polyamide on polysulfone with embedded support. In other instances, with membranes comprising, for example, cellulose triacetate cartridges with embedded polyester screen meshes, ultrasonic vibrations may show little change in water flux, due to the membranes "ultrasound transparent" nature. In some instances, sodium sulfate may be used as a draw solution. Additional details regarding the aforementioned ultrasound assisted FO membranes may be found in 'Ultrasound-Assisted Forward Osmosis for Mitigating Internal Concentration Polarization', Heikkinen, Journal of Membrane Science 528 (2017), 147-154, which is hereby incorporated in its entirety by reference.

In some embodiments, piezoelectric pumps may be used that may comprise a piezoelectric stack actuator and two unimorph piezoelectric disk valves acting as inlet and delivery valves. Such pump actuation mechanisms may comprise a pumping chamber and a diaphragm attached to the stack actuator. Such piezoelectric disk valves may aid in suppressing back flow that normally accompanies valve operation. The resulting combination of static and dynamic piezoelectric functionality may aid in maximizing fluid output per stroke. Additional details regarding such piezoelectric pumps may be found in 'Design of a Piezoelectric-Hydraulic Pump with Active Valves', Gun Lee, Journal of Intelligent Material Systems and Structures, Vol. 15, February 2004, pp. 107-115, which is hereby incorporated in its entirety by reference.

In some instances, micropumps may be used that may comprise brushless mechanisms. Additional details regarding such pumps may be found at TCS Micropumps, www.micropumps.co.uk.

In some embodiments, piezoelectric pumps may comprise diaphragm pumps, normally closed valves, and/or normally open valves. Such devices may be fabricated from titanium. The normally closed valve can provide low leakage rates while blocking the fluidic paths opening only when activated, while normally open valves allow pressure release while not actuated. Such piezoelectric actuation allows for energy efficient driving, each piezoelectric device requiring only small amounts of energy. Additional details regarding such piezoelectric pumps may be found in 'Piezoelectric Titanium Based Microfluidic Pump and Valves for Implantable Medical Applications', Beate Bussmann, Sensors and Actuators A 323 (2021) 112649, which is hereby incorporated in its entirety by reference.

In some embodiments, electroosmotic pumps may be used, which may be fabricated from porous nanocrystalline silicone membranes. It may be possible, in some embodiments, to alter the rate of electroosmotic flow via surface modification. Ultrathin porous nanocrystalline silicone membranes operate with high flow rates and low applied voltages thanks to their small electrical resistance and high electrical fields across their thin membrane. Additional details regarding such electroosmotic pumps may be found in 'High-Performance, Low Voltage Electroosmotic Pumps with Molecularly Thin Silicon Nanomembranes', Snyder, PNAS, vol. 110, no. 46, 1825-18430, 2013, which is hereby incorporated in its entirety by reference.

In some instances, it may be possible to vary the flow rate of electro-osmotic pumps by varying the aluminum concentration of the aluminosilicate microparticles. In some embodiments, simple electro-osmotic pumps may comprise aluminosilicate frits and alizarin as an active electrode material. Such electro-osmotic pumps may continue to function until the electro-active material is exhausted. Additional details regarding such osmotic pumps may be found in 'Low Voltage non-gassing Electro-Osmotic Pump with Zeta Potential Tuned Aluminosilicate Frits and Organic Dye Electrode', Lakhotiya, Royal Society of Chemistry, 2014, which is hereby incorporated in its entirety by reference.

In some embodiments, electroosmotic pumps may comprise multiple stages and/or liquid metal electrodes. Injection of liquid metal into a PDMS substrate may create a noncontact electrode for micro electroosmotic flow (EOF) pumps. PDMS may be used to fabricate microchannels of the EOF pump before being bonded with a glass slide via plasma treatment to create a microfluidic chip. Two liquid metal microchannels may be located in parallel with the pumping area, with only a small PDMS gap separating the liquid metal microchannel and the ends of the parallel pumping channels. Five identical straight pumping channels may be placed in parallel to form one stage, with five stages being connected in serial. Both electrode channels may be preferred in a vertical arrangement to the pumping channels to give the maximum potential gradient across the pumping direction. Additional details regarding the disclosed EOF pump may be found in 'Development of a Multi-Stage Electroosmotic Flow Pump Using Liquid Metal Electrodes', Gao, MDPI, Micromachines 2016, 7, 165, which is hereby incorporated in its entirety by reference.

In some embodiments, dispensing devices may be used, which may be powered osmotically. Such devices may comprise an inner wall formed of a collapsible material, with a layer of solute deposited on the wall's outer surface, such that the solute may create an osmotic gradient. The device may comprise an outer wall with shape retaining properties and permeable to water, but impermeable to the solute such that water may flow into the space between both layers. As water flows between both layers, the inner layer may collapse, dispensing an agent through a dispensing pathway. Additional details regarding the disclosed dispensing device may be found in U.S. Pat. No. 3,760,984, titled "Osmotically Powered Agent Dispensing Device with Filling Means", which is hereby incorporated in its entirety by reference.

In some instances, inductive power systems may be used to provide on-demand activation and remote delivery adjustments of implanted pumps. Such power systems may be used to power implanted pumps for prolonged periods of time. Such pumps may comprise an electrochemical actuator consisting of an electrolyte (such as water) encased by a Parylene bellows and a pair of interdigitated platinum electrodes on a rigid glass substrate. The application of an electrical current to the electrodes causes the water to split into hydrogen and oxygen, increasing pressure, deflecting the bellows, activating a one-way check valve, and displacing fluid out of the rigid reservoir, through the outlet catheter. Once the current is removed, the gasses may recombine to form water, allowing the bellows to return to its original state. In some instances, two refill ports may be integrated into the device to facilitate filling and flushing of the reservoir. Such pumps may deliver a range of doses (from microliters to nanoliters) at varying rates for extended durations of time. It may be preferable to have a closed-loop feedback system to enable pump performance monitoring. Additional details regarding such pumps may be found in 'A Wireless Implantable Micropump for Chronic Drug Infusion Against Cancer', Cobo, Sensors and Actuators A, 2016, which is hereby incorporated in its entirety by reference.

In some embodiments, xerogel nanocomposites may be used in the synthesis of ultra-filtration membranes. In some instances, such xerogels may be synthesized by a sol-gel process in which tetramethyl orthosilan and/or tetraethyl orthosilan may be used as precursors. To obtain nano-xerogels, xerogels may be milled at an ambient temperature in a high energy planetary ball mill. In some embodiments, PES may be used as a polymer in the formation of such membranes used in conjunction with nano-xerogels. The addition of nano-xerogels may aid in improving the hydrophilicity of the PES membranes. In some instances, the presence of Silanol groups in the xerogels may increase xerogel hydrophilicity, and therefore membrane water flux. Additional details regarding such composite membranes may be found in 'Preparation and Characterization of PES-Xerogel Nanocomposite Ultra-Filtration Membrane', Shamsodin, Cellulose, 5939-5950, 2018, which is hereby incorporated in its entirety by reference In some embodiments, water-permeable membranes may be made of polyethersulfone (PES) and comprise microfluidic channels and nanoporous membranes. Such membranes allow only for low molecular weight molecules, such as Na, K, Urea, and creatinine to pass through while blocking proteins and larger molecules. Such PES membranes may be formed by the phase inversion method, in which the casting solution can adjust the permeability. In some embodiments the PES membrane may be sandwiched by microchannels. In some instances, nanoporous parylene and fluorinated diamond-like carbon may be deposited onto the membrane surface to alter its properties. In a preferred embodiment, the PED membrane formed from the casting solution may comprise a PES concentration of 17.5%, balancing water permeability and mechanical strength. Additional details may be found in 'Water-Permeable Dialysis Membranes for Multi-Layered Microdialysis System', To, Frontiers in Bioengineering and Biotechnology 3:70, 2015, which is hereby incorporated in its entirety by reference.

In some embodiments, superhydrophilic-hydrophilic self-supported monolayered porous polyethersulfone (PES) membranes with nano/micropores at opposite surfaces may be used for unidirectional liquid (such as water) transport. The volume content of ethanol and water may be controlled to tune the micro/nanopore sizes on each surface. In a preferred embodiment, both sides of the membrane may portray high hydrophilicity. In some embodiments, pores may be formed via the phase transfer method. Additional details regarding the disclosed PES membrane may be found in 'Highly Flexible Monolayered Porous Membrane with Superhydrophilicity-Hydrophilicity for Unidirectional Liquid Penetration', Zhang, ACS Nano, DOI: 10.1021/acsnano.0c02558, 2020, which is hereby incorporated in its entirety by reference.

In some embodiments, optical fibers may comprise chemically sensitive polymeric layers for biosensing applications. In some instances, such coatings may comprise polyelectrolytes, such as, for example, poly(diallyldimethylammoniumchloride), polyethyleneimine, poly(allylamine hydrochloride), and the like. Different polymers may show variations in sensitivity due to their polymeric structure, so it may be beneficial to select polymers based on intended applications. In some embodiments, optical fiber sensor arrays may comprise excitation fibers to guide excitation light and detective fibers to capture the luminescence. In some instances, the detection fibers are placed at a right angle to the excitation fibers. In some instances, optical fibers combined with polymeric layers may not be limited to detection of chemicals, but also may be used to sense physical parameters. In some embodiments, the polymeric matrix may be used as a solid support for the immobilization of a specific chemical transducer, while in other embodiments, the polymeric matrix may be used directly as a chemical transducer. Additional details regarding such fiber optic sensors may be found in 'Optical Fiber Sensors Based on Polymeric Sensitive Coatings', Rivero, MDPI, Polymers 2018, 10, 280, which is hereby incorporated in its entirety by reference.

In some instances, biosensing devices may be used, which may comprise optical biosensors, such as bio-optrode, evanescent field-based sensors; electrochemical sensors, such as, for example, amperometric, potentiometric, field-effect transistor-based, and/or impedimetric sensors; piezoelectric sensors such as quartz crystal microbalance sensors; and/or nanomechanical sensors, such as nanocantilevers. Bio-optrode sensors may comprise fiber-optic devices, while evanescent field-based devices may include SPR-based, surface-enhanced Raman scattering, total internal reflection fluorescence, optical waveguide interferometer, and elipsometric and reflectrometric interference spectroscopy biosensors. Fiber-optic biosensors may comprise a biocatalyzer immobilized at the distal end of a fiber-optic detection device, such that the biocatalyzer mediates between a sensor and an analyte, forming a detectable compound. In some instances, the surfaces of biosensors may comprise a functionalized surface, chosen based on chemical and/or physical properties and/or application. Additional details regarding such biosensors may be found in 'Optical Biosensors for Therapeutic Drug Monitoring', Garzon, MDPI, Biosensors 2019, 9, 132, which is hereby incorporated in its entirety by reference.

In some embodiments, magnetic polymer composites may be used for separating particles in microfluidic devices. Such magnetic polymers may aid in targeting/trapping magnetic microbeads or magnetically labeled cells in microfluidic devices. Magnetic fields used to manipulate magnetic micro/nanoparticles in microfluidic devices may apply repulsive/attractive forces. Magnetic sources in microfluidic systems may generate localized micro-magnetic field gradients via: current carrying micro-coils, microconcentrators made of sof ferromagnets (such as Ni and Fe—Ni alloys) magnetized by an external magnetic field, permanently magnetized micromagnets, comprising hard ferromagnetic materials (such as NdFeB), and the like. In some instances, polymers used to create composite magnetic polymers may comprise elastomers such as, for example, PDMS. Composite polymers based on PDMS may be obtained by mixing soft (Fe, Ni, and alloys thereof) or hard (NdFeB) magnetic powders with a PDMS mixture comprising a base polymer and curing agent. Magnetic PDMS may be integrated into pillars inside microchannels to aid in trapping magnetic targets. Composite magnetic polymers may comprise magnetic micropar-ticles ranging from less than 10% to over 30%. In some instances, ferrofluids may be used to sort cells. An external magnetic field may be used to magnetize the ferrofluid, which creates a gradient field that may be used to attract magnetically tagged cells in side channels. Such ferrofluids may comprise, for example, $Fe_3O_4$ nanoparticles in concentrations as low as 0.01%. Additional details regarding such composite magnetic polymers may be found in 'Magnetic Polymers for Magnetophoretic Separation in Microfluidic Devices', Descamps, MDPI, Magnetochemistry 2021, 7, 100, which is hereby incorporated in its entirety by reference.

The invention claimed is:

1. An implant configured for positioning within an implant pocket, comprising:

an arm extending in a spiral shape from an outer terminus at a periphery of the implant to an inner terminus adjacent to a center of the implant, wherein the arm defines a plurality of adjacent bands, wherein both the outer terminus and the inner terminus are part of the spiral shape, and wherein the implant comprises at least one configuration selected from the group of:

(a) comprising a space defined between adjacent bands; and (b) comprising a flexible material configured to allow for temporary creation of space between adjacent bands so as to facilitate insertion of the implant through a minimally invasive entrance incision;

and wherein the implant is configured to at least substantially maintain the spiral shape both before and after implantation within the implant pocket through a minimally invasive entrance incision; and wherein the implant comprises a source of electromagnetic radiation.

2. The implant of claim 1, wherein the implant is configured to at least substantially maintain the spiral shape during implantation within the implant pocket through the minimally invasive entrance incision and/or wherein the implant pocket comprises a soft tissue and/or subcutaneous implant pocket.

3. The implant of claim 1, wherein the arm of the implant comprises at least 2 turns extending in the spiral shape.

4. A system comprising the implant of claim 1, and further comprising an auxiliary implant electrically coupled with the implant, wherein the auxiliary implant comprises at least one selected from the group of: an antenna, a CPU, a battery, a capacitor, and an inductance coil.

5. The implant of claim 1, wherein the implant further comprises at least one element selected from the group of: a battery, an inductance coil, a capacitor, a data storage element, an EMI suppression element, an antenna, a heating element, a temperature sensor, and a heart rate sensor; and wherein the temperature sensor is configured to reduce or terminate charging from an external wireless inductance coil in response to the temperature sensor detecting a threshold temperature.

6. The implant of claim 1, wherein the source of electromagnetic radiation comprises an LED.

7. The implant of claim 1, wherein the source of electromagnetic radiation comprises at least one selected from the group of: an mLED, an OLED, a multilayer LED stack and an array of LED lights.

8. The implant of claim 1, wherein the source of electromagnetic radiation comprises a light display configured to display at least one selected from the group of: (a) at least one color, (b) images.

9. The implant of claim 1, wherein the source of electromagnetic radiation comprises a therapeutic radiation source.

10. The implant of claim 9, further comprising a heartrate sensor configured to change a light display generated by the source of electromagnetic radiation based upon a heartrate detected by the heartrate sensor.

11. The implant of claim 1, further comprising a barrier layer configured to insulate the electromagnetic source from the biological environment within the implant pocket.

12. The implant of claim 1, further comprising a wireless receiver, wherein the wireless receiver is configured to receive wireless signals for adjusting a source of electromagnetic radiation.

13. A system comprising the implant of claim 1, and an external device comprises at least one selected from the group of: a wristband, an armband, and a smartphone.

14. The implant of claim 1, wherein implant comprises an inductance coil configured to be inductively charged and an electromagnetic radiation source, and wherein power from the inductance coil energizes the electromagnetic radiation source; and/or wherein the implant of claim 1 comprises a spiral-shaped thermoelectric generator.

15. The implant of claim 1, wherein the outer terminus and the inner terminus are at least substantially coplanar.

16. The implant of claim 15, wherein the outer terminus and the inner terminus are coplanar.

17. An implant configured for positioning within an implant pocket, comprising:

an arm extending in a spiral shape from an outer terminus at a periphery of the implant to an inner terminus adjacent to a center of the implant, wherein the arm defines a plurality of adjacent bands, wherein the outer terminus and the inner terminus are at least substantially coplanar, and wherein the implant comprises at least one configuration selected from the group of:

(c) comprising a space defined between adjacent bands; and (d) comprising a flexible material configured to allow for temporary creation of space between adjacent bands so as to facilitate insertion of the implant through a minimally invasive entrance incision;

and wherein the implant is configured to at least substantially maintain the spiral shape both before and after implantation within the implant pocket through a minimally invasive entrance incision; and wherein the implant comprises a source of electromagnetic radiation.

18. The implant of claim 17, wherein both the outer terminus and the inner terminus are part of the spiral shape.

19. The implant of claim 17, wherein the outer terminus and the inner terminus are coplanar.

\* \* \* \* \*